United States Patent
Zheng et al.

(10) Patent No.: US 11,795,196 B2
(45) Date of Patent: Oct. 24, 2023

(54) MITOCHONDRIA-TARGETING PEPTIDES

(71) Applicant: Stealth BioTherapeutics Corp., Grand Cayman (KY)

(72) Inventors: Guozhu Zheng, Lexington, MA (US); Mark J. Bamberger, South Glastonbury, CT (US); Inese Smukste, Weston, MA (US)

(73) Assignee: Stealth BioTherapeutics Inc., Needham, MA (US)

( * ) Notice: Subject to any disclaimer, the term of this patent is extended or adjusted under 35 U.S.C. 154(b) by 663 days.

(21) Appl. No.: 16/771,970

(22) PCT Filed: Dec. 14, 2018

(86) PCT No.: PCT/US2018/065755
§ 371 (c)(1),
(2) Date: Jun. 11, 2020

(87) PCT Pub. No.: WO2019/118878
PCT Pub. Date: Jun. 20, 2019

(65) Prior Publication Data
US 2023/0146515 A1   May 11, 2023

Related U.S. Application Data

(60) Provisional application No. 62/741,334, filed on Oct. 4, 2018, provisional application No. 62/599,175, filed on Dec. 15, 2017.

(51) Int. Cl.
*C07K 5/09* (2006.01)
*C07D 271/06* (2006.01)
*C07K 5/072* (2006.01)
*C07D 413/06* (2006.01)

(52) U.S. Cl.
CPC .......... *C07K 5/0817* (2013.01); *C07D 271/06* (2013.01); *C07D 413/06* (2013.01); *C07K 5/06095* (2013.01); *C07K 5/0815* (2013.01); *C07B 2200/05* (2013.01)

(58) Field of Classification Search
CPC . C07K 5/0817; C07K 5/06095; C07D 271/06
See application file for complete search history.

(56) References Cited

U.S. PATENT DOCUMENTS

| | | |
|---|---|---|
| 9,345,738 B2 | 5/2016 | Wilson et al. |
| 2007/0293530 A1 | 12/2007 | Smil et al. |
| 2014/0235529 A1 | 8/2014 | Wilson et al. |
| 2015/0239937 A1 | 8/2015 | Verdine et al. |
| 2017/0087204 A1 | 3/2017 | Wilson et al. |
| 2017/0129920 A1 | 5/2017 | Zhao et al. |

FOREIGN PATENT DOCUMENTS

| | | | |
|---|---|---|---|
| WO | WO-99/47529 A1 | | 9/1999 |
| WO | WO-2004/091502 A2 | | 10/2004 |
| WO | WO 2012109164 | * | 8/2012 |

OTHER PUBLICATIONS

Buchanan et al., "Structure-activity relationships of a novel class of Src SH2 inhibitors," Bioorganic & Medicinal Chemistry Letters, 9(16): 2359-2364 (1999).
International Search Report and Written Opinion for International Application No. PCT/US2018/065755 dated May 23, 2019.
Vu et al., "Discovery of Potent and Selective SH2 Inhibitors of the Tyrosine Kinase ZAP-70," JMedChem, 42(20):4088-4098 (1999).
Birk et al., "Targeting mitochondrial cardiolipin and the cytochrome c/cardiolipin complex to promote electron transport and optimize mitochondrial ATP synthesis," British Journal of Pharmacology, 171:2017-2028 (2014).
Extended European Search Report for EP Application No. EP 18888579 dated Aug. 20, 2021.
International Preliminary Report on Patentability for International Application No. PCT/US2018/065755 dated Jun. 25, 2020.
Zhen et al., "The discovery of mitochondria-targeted antioxidant SS-31 (H-D-Arg-Dmt-Lys-Phe-NH2) and its research progress," Chinese Journal of New Drugs, 26(12):1382-1389 (2017).

* cited by examiner

*Primary Examiner* — Noble E Jarrell
(74) *Attorney, Agent, or Firm* — Dana M. Gordon; Laura A. Wzorek; Foley Hoag LLP

(57) ABSTRACT

Disclosed are non-natural peptides useful for the treatment and prevention of ischemia-reperfusion injury (e.g., cardiac ischemia-reperfusion injury) or myocardial infarction.

18 Claims, 25 Drawing Sheets

Figure 1 (Cont'd)

| R4 | R3 | R2a | X | R1 | R2b | R7 | R8 | Binding assay A: >0.1, <0.5 μM; B: >0.5, <1 μM |
|---|---|---|---|---|---|---|---|---|
| D-Arg | DMT | "Lys" | 1,2,4-oxadiazole | 4-tBubenzyl | H | H | H | A |
| D-Arg | DMT | "D-Lys" | 1,2,4-oxadiazole | 4-tBubenzyl | H | H | H | A |
| D-Arg | DMT | "Lys" | 1,2,4-oxadiazole | 4'-Trifluoromethylbenzyl | H | H | H | |
| D-Arg | DMT | "Lys" | 1,2,4-oxadiazole | 4-Phenylbenzyl | H | H | H | A |
| D-Arg | DMT | "Lys" | 1,2,4-oxadiazole | 4'-Cyclohexylbenzyl | H | H | H | |

Figure 1 (Cont'd)

| R4 | R3 | R2a | X | R1 | R2b | R7 | R8 | Binding assay A:>0.1, <0.5 µM; B: >0.5, <1 µM |
|---|---|---|---|---|---|---|---|---|
| D-Arg | DMT | "Lys" | 1,2,4-oxadiazole | Phenethyl | H | H | H | A |
| D-Arg | DMT | "Lys" | 1,2,4-oxadiazole | Cyclopentylmethyl | H | H | H | |
| D-Arg | DMT | "Lys" | 1,2,4-oxadiazole | Cyclohexylmethyl | H | H | H | A |
| D-Arg | DMT | "Lys" | 1,2,4-oxadiazole | Cycloheptylmethyl | H | H | H | |
| D-Arg | DMT | "Lys" | 1,2,4-oxadiazole | Bicyclo[2.2.2]pentan-1-yl | H | H | H | |

Figure 1 (Cont'd)

| R4 | R3 | R2a | X | R1 | R2b | R7 | R8 | Binding assay A: >0.1, <0.5 μM; B: >0.5, <1 μM |
|---|---|---|---|---|---|---|---|---|
| D-Arg | DMT | "Lys" | 1,2,4-oxadiazole | Bicyclo[2.2.2]octan-1-yl | H | H | H | |
| D-Arg | DMT | "Lys" | 1,2,4-oxadiazole | Admantyl | H | H | H | A |
| D-Arg | DMT | "D-Lys" | 1,2,4-oxadiazole | Admantyl | H | H | H | B |
| D-Arg | DMT | "Lys" | 1,2,4-oxadiazole | Admantylmethyl | H | H | H | A |
| D-Arg | DMT | "His" | 1,2,4-oxadiazole | Phenyl | H | H | H | B |

Figure 1 (Cont'd)

| R4 | R3 | R2a | X | R1 | R2b | R7 | R8 | Binding assay A:>0.1, <0.5 μM; B: >0.5, <1 μM |
|---|---|---|---|---|---|---|---|---|
| D-Arg | DMT | "His" | 1,2,4-oxadiazole | Benzyl | H | H | H | |
| D-Arg | DMT | "His" | 1,2,4-oxadiazole | Phenethyl | H | H | H | B |
| D-Arg | DMT | "His" | 1,2,4-oxadiazole | Cyclopentylmethyl | H | H | H | |
| D-Arg | DMT | "His" | 1,2,4-oxadiazole | Cyclohexylmethyl | H | H | H | |
| D-Arg | DMT | "τ-Me-His" | 1,2,4-oxadiazole | Cyclohexylmethyl | H | H | H | |

Figure 1 (Cont'd)

| R4 | R3 | R2a | X | R1 | R2b | R7 | R8 | Binding assay A:>0.1, <0.5 μM; B: >0.5, <1 μM |
|---|---|---|---|---|---|---|---|---|
| D-Arg | DMT | "π-Me-His" | 1,2,4-oxadiazole | Cyclohexylmethyl | H | H | H | |
| D-Arg | DMT | "His" | 1,2,4-oxadiazole | Cycloheptylmethyl | H | H | H | |
| D-Arg | DMT | "His" | 1,2,4-oxadiazole | Bicyclo[2,2,2]pentan-1-yl | H | H | H | |
| D-Arg | DMT | "His" | 1,2,4-oxadiazole | Bicyclo[2,2,2]octan-1-yl | H | H | H | |
| D-Arg | DMT | "His" | 1,2,4-oxadiazole | Admantyl | H | H | H | |

Figure 1 (Cont'd)

| R4 | R3 | R2a | X | R1 | R2b | R7 | R8 | Binding assay A: >0.1, <0.5 μM; B: >0.5, <1 μM |
|---|---|---|---|---|---|---|---|---|
| D-Arg | DMT | "His" | 1,2,4-oxadiazole | Adamantylmethyl | H | H | H | |
| D-Arg | DMT | "Trp" | 1,2,4-oxadiazole | Benzyl | H | H | H | B |
| D-Arg | DMT | "(4N)-Pal" | 1,2,4-oxadiazole | Adamantylmethyl | H | H | H | B |
| D-Agb | DMT | "Lys" | 1,2,4-oxadiazole | Benzyl | H | H | H | B |
| D-Agb | DMT | "Orn" | 1,2,4-oxadiazole | Benzyl | H | H | H | B |

Figure 1 (Cont'd)

| R4 | R3 | R2a | X | R1 | R2b | R7 | R8 | Binding assay A: >0.1, <0.5 µM; B: >0.5, <1 µM |
|---|---|---|---|---|---|---|---|---|
| D-Agb | DMT | "N5,N5-diMe-Orn" | 1,2,4-oxadiazole | Benzyl | H | H | H | |
| D-Agb | DMT | "His" | 1,2,4-oxadiazole | Admantylmethyl | H | H | H | A |
| D-Agb | DMT | "His" | 1,2,4-oxadiazole | Admantyl | H | Me | Me | A |
| D-Agb | DMT | "Trp" | 1,2,4-oxadiazole | Benzyl | H | H | H | B |
| D-Agb | DMT | "trp" | 1,2,4-oxadiazole | Admantyl | H | H | H | B |

Figure 1 (Cont'd)

| R4 | R3 | R2a | X | R1 | R2b | R7 | R8 | Binding assay A:>0.1, <0.5 μM; B: >0.5, <1 μM |
|---|---|---|---|---|---|---|---|---|
| (imidazole) | DMT | "Dab" | 1,2,4-oxadiazole | Benzyl | H | H | H | A |
| (imidazole) | DMT | "Orn" | 1,2,4-oxadiazole | Cyclohexylmethyl | H | H | H | A |
| (imidazole) | DMT | "Orn" | 1,2,4-oxadiazole | Admantyl | H | H | H | A |
| (imidazole) | DMT | "Orn" | 1,2,4-oxadiazole | Admantylmethyl | H | H | H | A |
| (imidazole) | DMT | "D-Orn" | 1,2,4-oxadiazole | Admantyl | H | H | H | A |

Figure 1 (Cont'd)

| R4 | R3 | R2a | X | R1 | R2b | R7 | R8 | Binding assay A:>0.1, <0.5 µM; B: >0.5, <1 µM |
|---|---|---|---|---|---|---|---|---|
| | DMT | "Orn" | 1,2,4-oxadiazole | (bicyclo[2.2.2]octan-1-ylmethyl) | H | H | H | A |
| | DMT | "N5,N5-diMe-Orn" | 1,2,4-oxadiazole | Admantyl | H | H | H | |
| | DMT | "Lys" | 1,2,4-oxadiazole | Cyclohexylmethyl | H | H | H | A |
| | DMT | "Lys" | 1,2,4-oxadiazole | Cyclohexylmethyl | H | H | H | A |
| | DMT | "His" | 1,2,4-oxadiazole | Benzyl | H | H | H | |

Figure 1 (Cont'd)

| R4 | R3 | R2a | X | R1 | R2b | R7 | R8 | Binding assay A: >0.1, <0.5 µM; B: >0.5, <1 µM |
|---|---|---|---|---|---|---|---|---|
| | DMT | "His" | 1,2,4-oxadiazole | 4-Phenylbenzyl | H | H | H | A |
| | DMT | "His" | 1,2,4-oxadiazole | Cyclopentylmethyl | H | H | H | |
| | DMT | "His" | 1,2,4-oxadiazole | Cyclohexylmethyl | H | H | H | |
| | DMT | "His" | 1,2,4-oxadiazole | Cycloheptylmethyl | H | H | H | |
| | DMT | "τ-Me-His" | 1,2,4-oxadiazole | Cyclohexylmethyl | H | H | H | |

Figure 1 (Cont'd)

| R4 | R3 | R2a | X | R1 | R2b | R7 | R8 | Binding assay A:>0.1, <0.5 μM; B: >0.5, <1 μM |
|---|---|---|---|---|---|---|---|---|
| pyrrole-ethyl | DMT | "His" | 1,2,4-oxadiazole | bicyclopentyl-ethyl | H | H | H | |
| pyrrole-ethyl | DMT | "His" | 1,2,4-oxadiazole | Cyclohexylmethyl | H | H | H | B |
| pyrrole-ethyl | DMT | "His" | 1,2,4-oxadiazole | Admantyl | H | H | H | B |
| pyrrole-ethyl | DMT | "Trp" | 1,2,4-oxadiazole | Admantyl | H | H | H | A |
| pyrrole-ethyl | DMT | "1-Me-Trp" | 1,2,4-oxadiazole | 4-Phenylbenzyl | H | H | H | B |
| pyrrole-ethyl | DMT | | 1,2,4-oxadiazole | 4-Phenylbenzyl | H | H | H | B |

Figure 1 (Cont'd)

| R4 | R3 | R2a | X | R1 | R2b | R7 | R8 | Binding assay A:>0.1, <0.5 μM; B: >0.5, <1 μM |
|---|---|---|---|---|---|---|---|---|
|  | DMT | "Trp" | 1,2,4-oxadiazole | Admantylmethyl | H | H | H | B |
|  | DMT | "6-Fluoro-Trp" | 1,2,4-oxadiazole | Admantylmethyl | H | H | H | B |
|  | DMT | "1-methyl-Trp" | 1,2,4-oxadiazole | Admantylmethyl | H | H | H | B |
|  | (O-Me)-DMT | "His" | 1,2,4-oxadiazole | 4-Phenylbenzyl | H | H | H | A |
|  | (O-Me)-DMT | "1-methylHis" | 1,2,4-oxadiazole | 4-Phenylbenzyl | H | H | H | B |

Figure 1 (Cont'd)

| R4 | R3 | R2a | X | R1 | R2b | R7 | R8 | Binding assay A:>0.1, <0.5 µM; B: >0.5, <1 µM |
|---|---|---|---|---|---|---|---|---|
| D-Dab | DMT | "Lys" | 1,2,4-oxadiazole | Benzyl | H | carbamimidoyl | H | A |
| D-Dab | DMT | "Lys" | 1,2,4-oxadiazole | Benzyl | H | carbamimidoyl | H | A |
| D-Agb | DMT | "His" | 1,2,4-oxadiazole | Adamantylmethyl | H | carbamimidoyl | H | A |
| D-Arg | DMT | "His" | 1,3,4-oxadiazole | Benzyl | H | H | H | |
| D-Arg | DMT | "Lys" | 1,3-oxazole | Benzyl | H | H | H | |

Figure 1 (Cont'd)

| R4 | R3 | R2a | X | R1 | R2b | R7 | R8 | Binding assay A:>0.1, <0.5 µM; B: >0.5, <1 µM |
|---|---|---|---|---|---|---|---|---|
| D-Arg | DMT | "Lys" | 1,3-oxazole | Benzyl | H | H | H | |
| D-Arg | DMT | "Lys" | 1,3-thiazole | Benzyl | H | H | H | |
| D-Arg | DMT | "Lys" | 1,3-thiazole | Benzyl | H | H | H | |
| D-Arg | DMT | "Lys" | 1,3-thiazole | Benzyl | H | H | H | |
| D-Arg | DMT | "Lys" | furan | Benzyl | H | H | H | |
| D-Arg | DMT | "Lys" | furan | Benzyl | H | H | H | |

Figure 1 (Cont'd)

| R4 | R3 | R2a | X | R1 | R2b | R7 | R8 | Binding assay A:>0.1, <0.5 µM; B: >0.5, <1 µM |
|---|---|---|---|---|---|---|---|---|
| D-Arg | DMT | "Lys" | Benzene | Phenoxy | H | H | H | A |
| D-Arg | DMT | "Lys" | Benzene | Phenoxy | H | H | H | B |
| D-Arg | DMT | "Lys" | Pyridine | Phenoxy | H | H | H | |
| D-Arg | DMT | "Lys" | Pyridine | Phenoxy | H | H | H | |
| D-Arg | DMT | "Lys" | Pyridine | Phenoxy | H | H | H | |
| D-Arg | DMT | "Lys" | Pyridine | Benzyl | | | | |

Figure 1 (Cont'd)

| R4 | R3 | R2a | X | R1 | R2b | R7 | R8 | Binding assay A: >0.1, <0.5 μM; B: >0.5, <1 μM |
|---|---|---|---|---|---|---|---|---|
| D-Arg | DMT | "Lys" | Pyrimidine | Benzyl | H | H | H | |

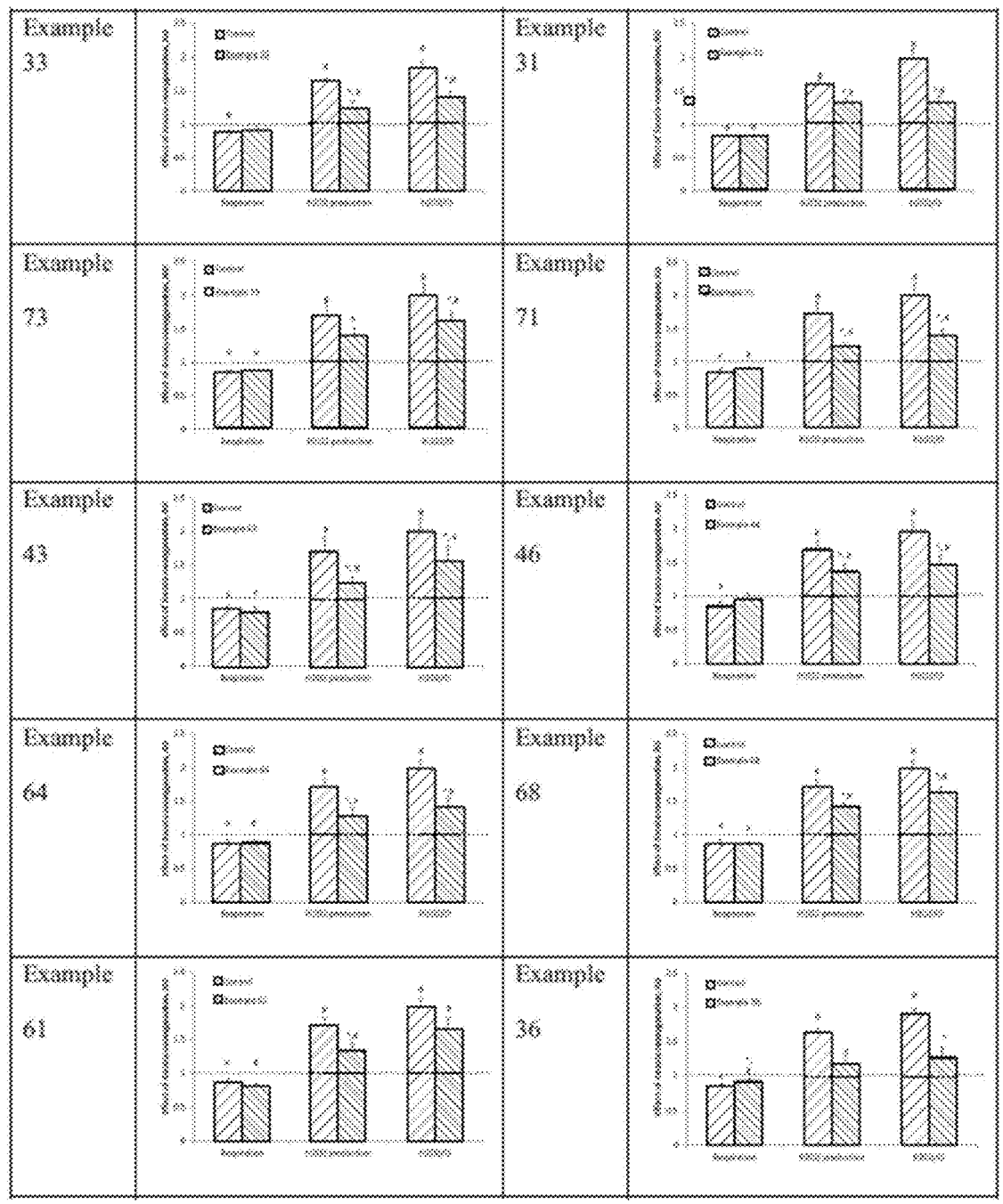
Figure 7, continued

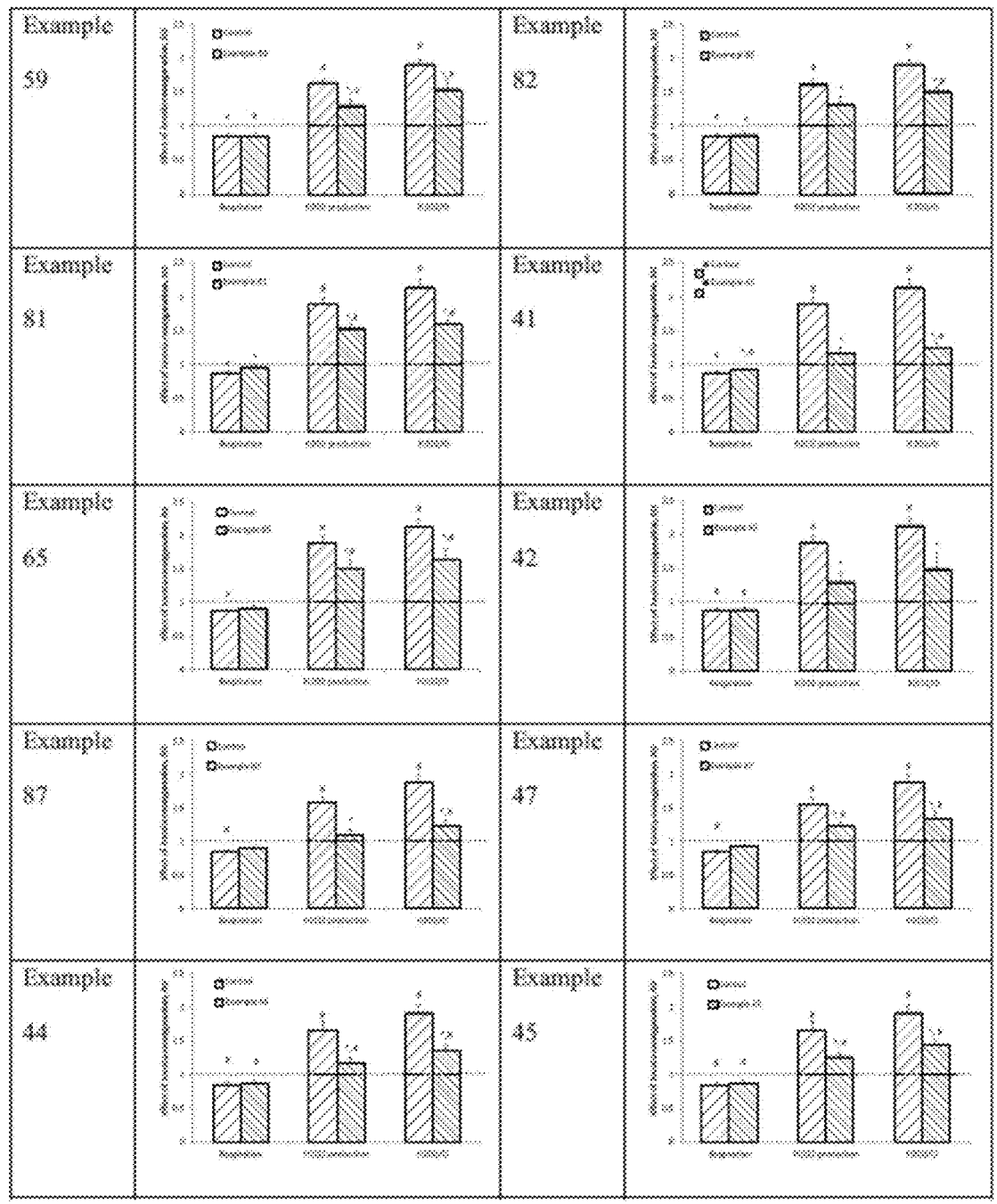
Figure 7, continued

MITOCHONDRIA-TARGETING PEPTIDES

RELATED APPLICATIONS

This application is a U.S. National Stage Application of International Application No. PCT/US18/65755, filed Dec. 14, 2018; which claims the benefit of priority to U.S. Provisional Patent Application No. 62/599,175, filed Dec. 15, 2017; and U.S. Provisional Patent Application No. 62/741,334, filed Oct. 4, 2018.

BACKGROUND OF THE INVENTION

Mitochondria-targeting peptide compounds have shown therapeutic potential for treating diseases associated with mitochondrial dysfunction. Because of the potential therapeutic applications of these compounds, there exists a need to develop novel compounds with improved efficacy and therapeutic profiles.

SUMMARY OF THE INVENTION

The present application provides mitochondria-targeting peptides. In some aspects, of the invention, the peptides are useful for the treatment and prevention of ischemia-reperfusion injury (e.g., cardiac ischemia-reperfusion injury) or myocardial infarction.

More specifically, the invention provides compounds of formula (I), or pharmaceutically acceptable salts thereof:

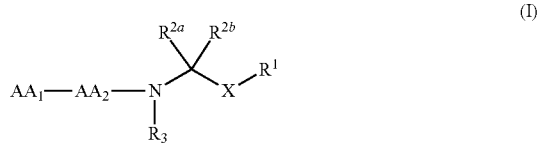

wherein
AA$_1$ is selected from

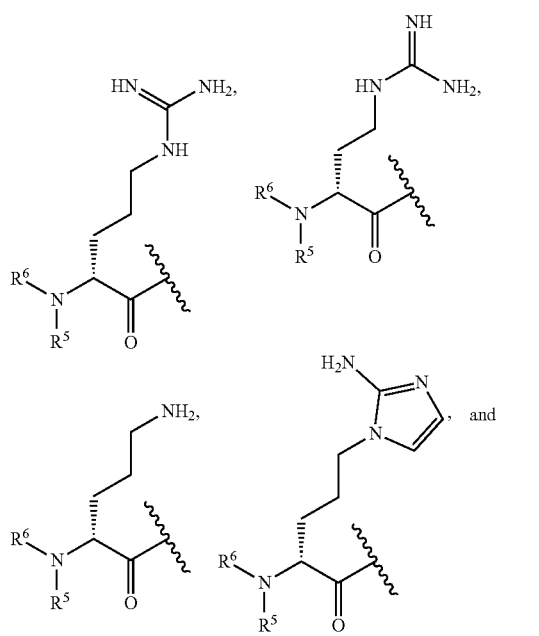

AA$_2$ is selected from

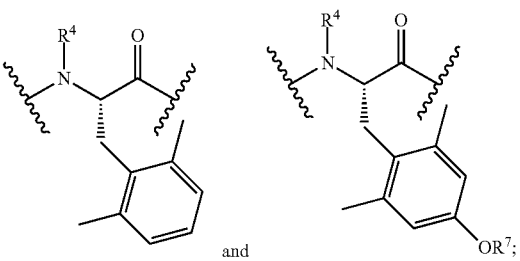

R$^1$ is selected from

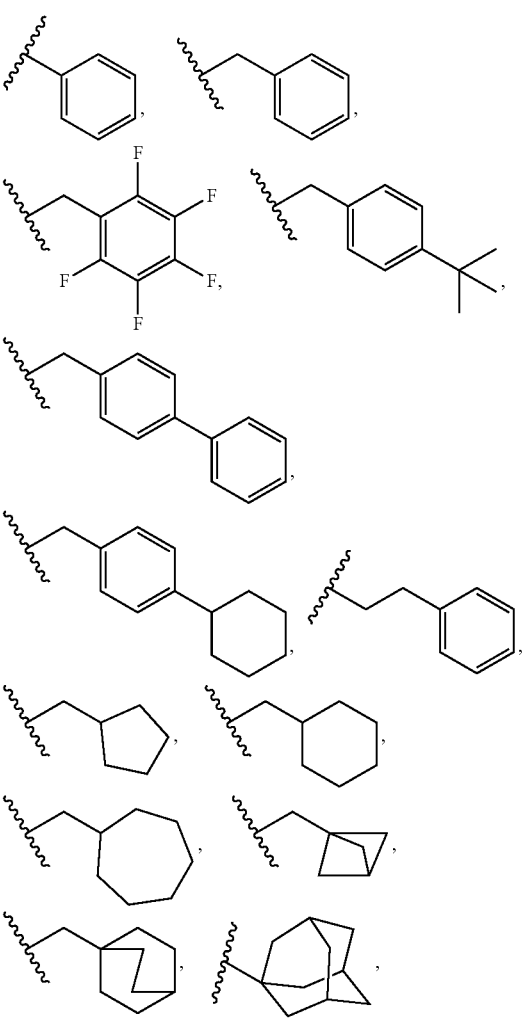

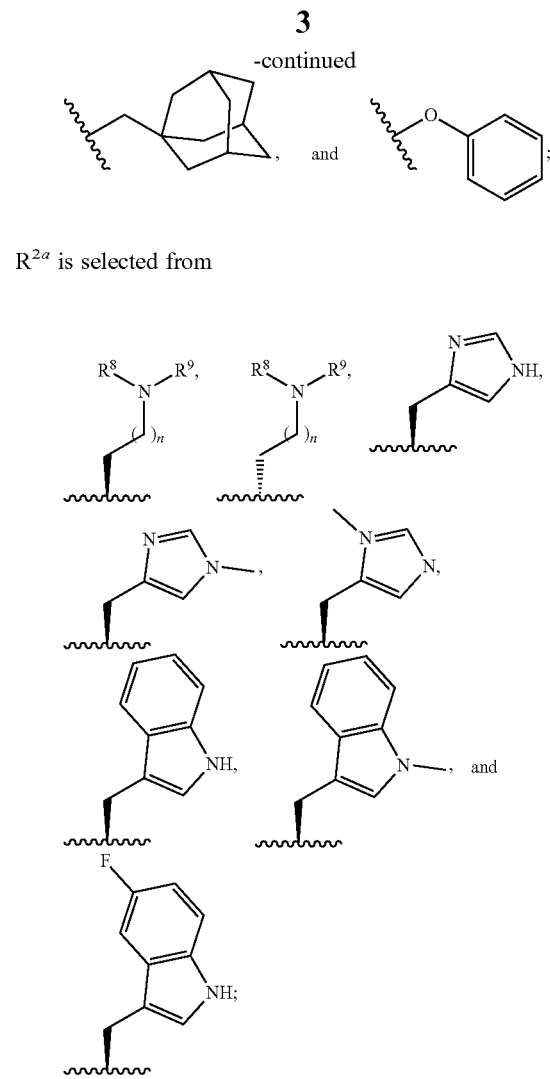

$R^{2a}$ is selected from

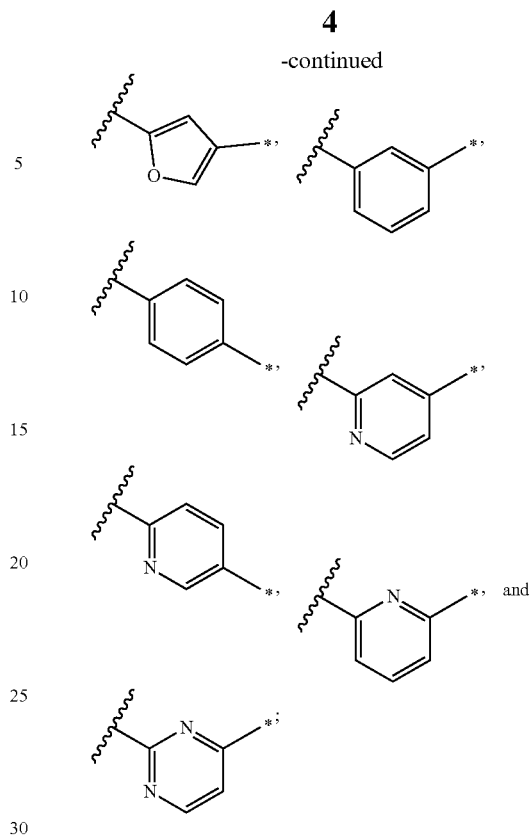

and

* denotes the point of attachment of X to $R^1$.

Another aspect of the invention is a pharmaceutical composition, comprising a compound of the invention, and a pharmaceutically acceptable carrier.

The invention also provides methods of treating or preventing ischemia-reperfusion injury, comprising administering to a subject in need thereof a therapeutically effective amount of a compound of the invention.

The invention also provides methods of treating or preventing myocardial infarction, comprising administering to a subject in need thereof a therapeutically effective amount of a compound of the invention.

The invention also provides methods of treating or preventing hind limb or critical limb ischemia, comprising administering to a subject in need thereof a therapeutically effective amount of a compound of the invention.

$R^{2b}$ is H or Me;

$R^3$ and $R^4$ are independently selected from H and (C1-C6)alkyl;

$R^5$ and $R^6$ are independently H, methyl, ethyl, propyl, cyclopropyl, or cyclobutyl; or $R^5$ and $R^6$ together with the N atom to which they are attached form a 4-6-membered heterocyclyl;

$R^7$ is selected from H, (C1-C6)alkyl, cycloalkyl, and aryl;

$R^8$ and $R^9$ are independently selected from H, (C1-C6) alkyl, cycloalkyl, and aryl; or $R^8$ and $R^9$ together with the N atom to which they are attached form a 4-6-membered heterocyclyl;

n is 1, 2, or 3;

X is selected from

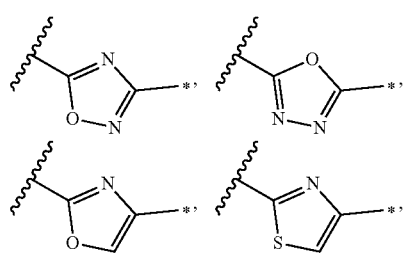

DETAILED DESCRIPTION OF THE INVENTION

Figure 1:
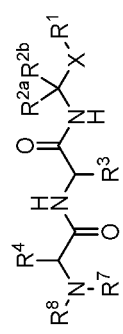
FIG. 1 tabulates exemplary compounds of Formula (I).
Figure 2:
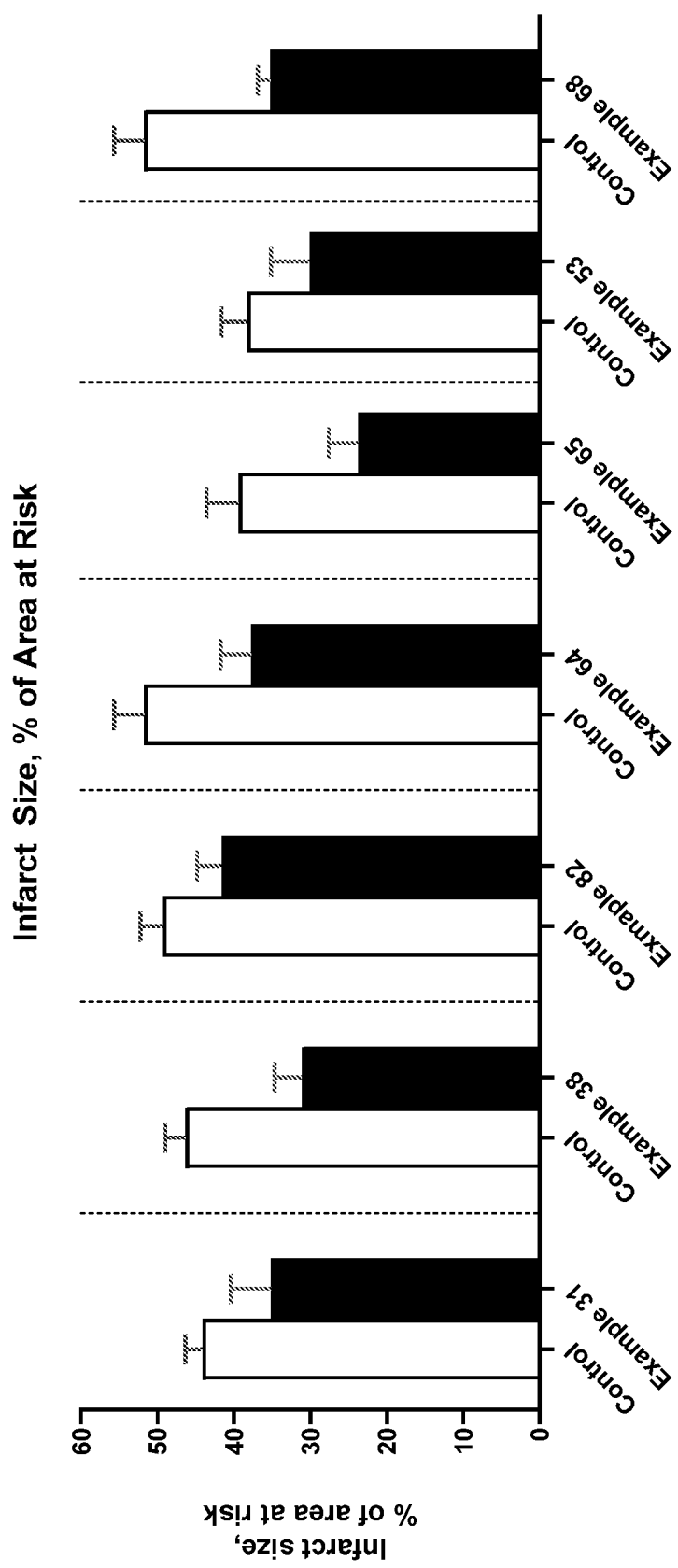
FIG. 2 is a graphic representing the infarct size versus % of area at risk (mean values with standard error of the mean (SEM)), using compounds of the invention.
Figure 3:
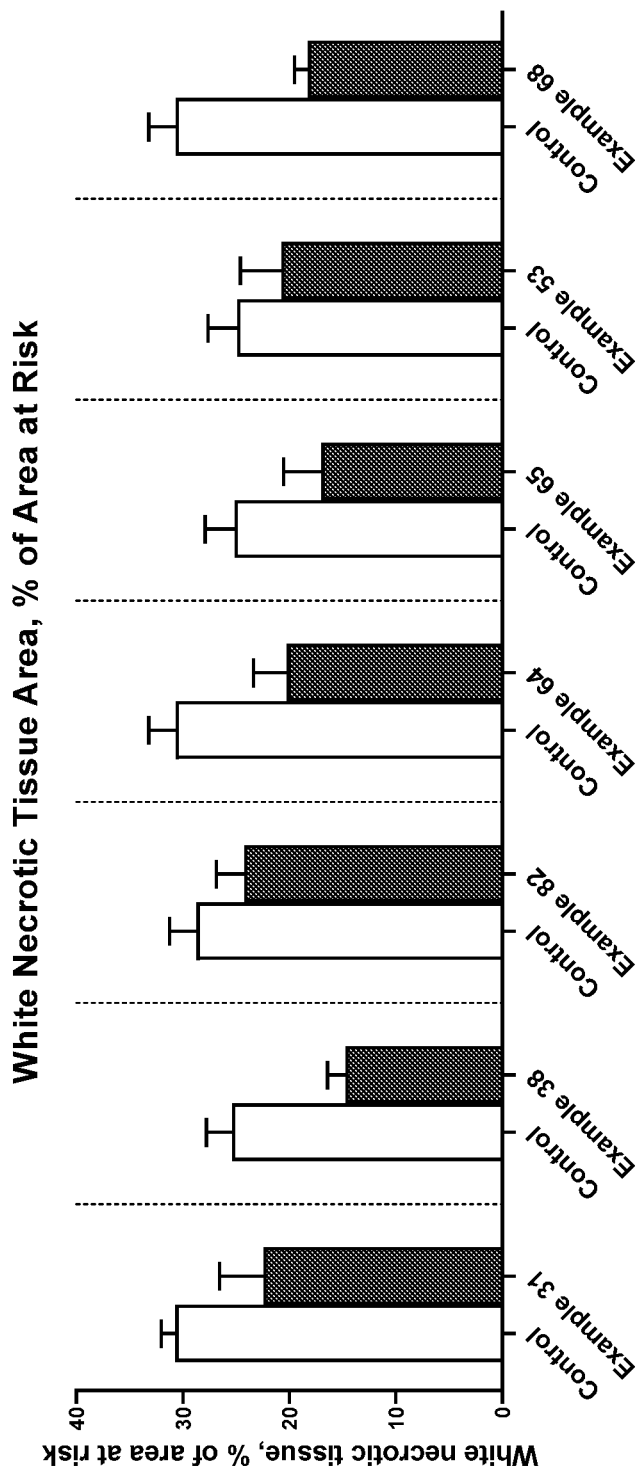
FIG. 3 is a graphic representing white necrotic tissue area versus % of area at risk, using compounds of the invention. NB: Only the area of the white necrotic tissue is used in the analysis; mean values with SEM.
Figure 4:
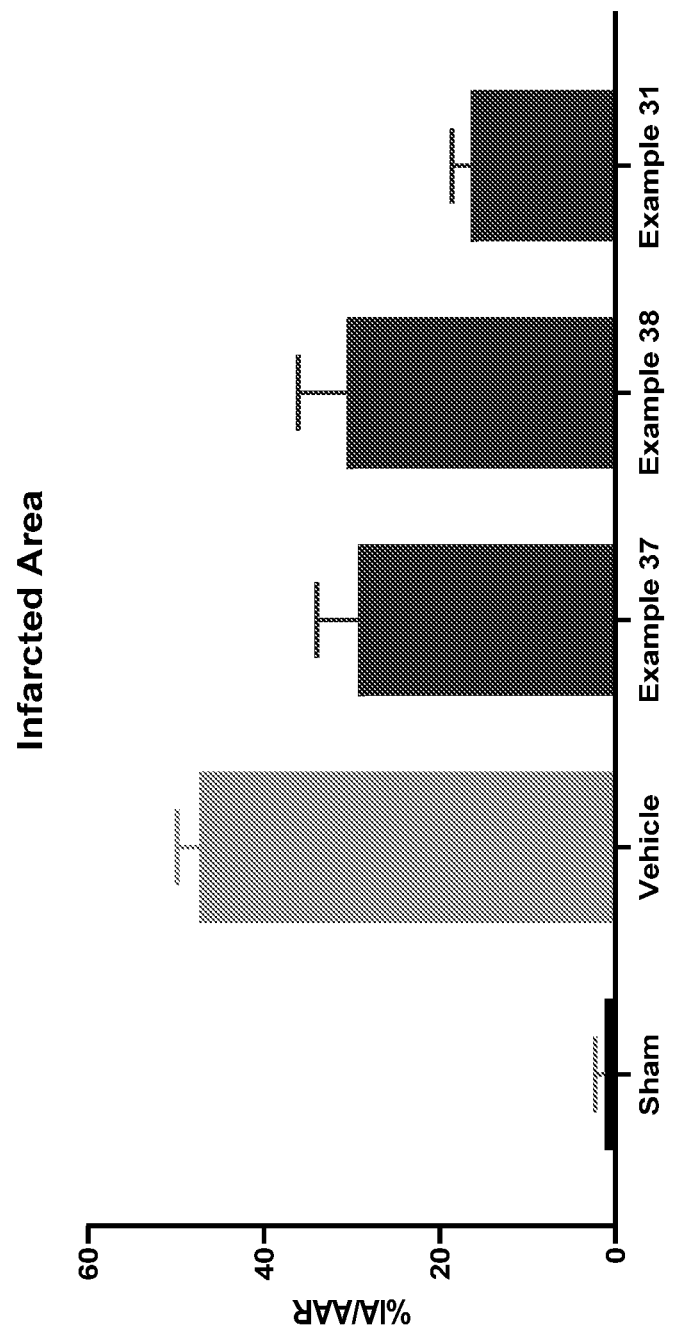
FIG. 4 is a graphic representing infarct size (%), using compounds of the invention.
Figure 5:
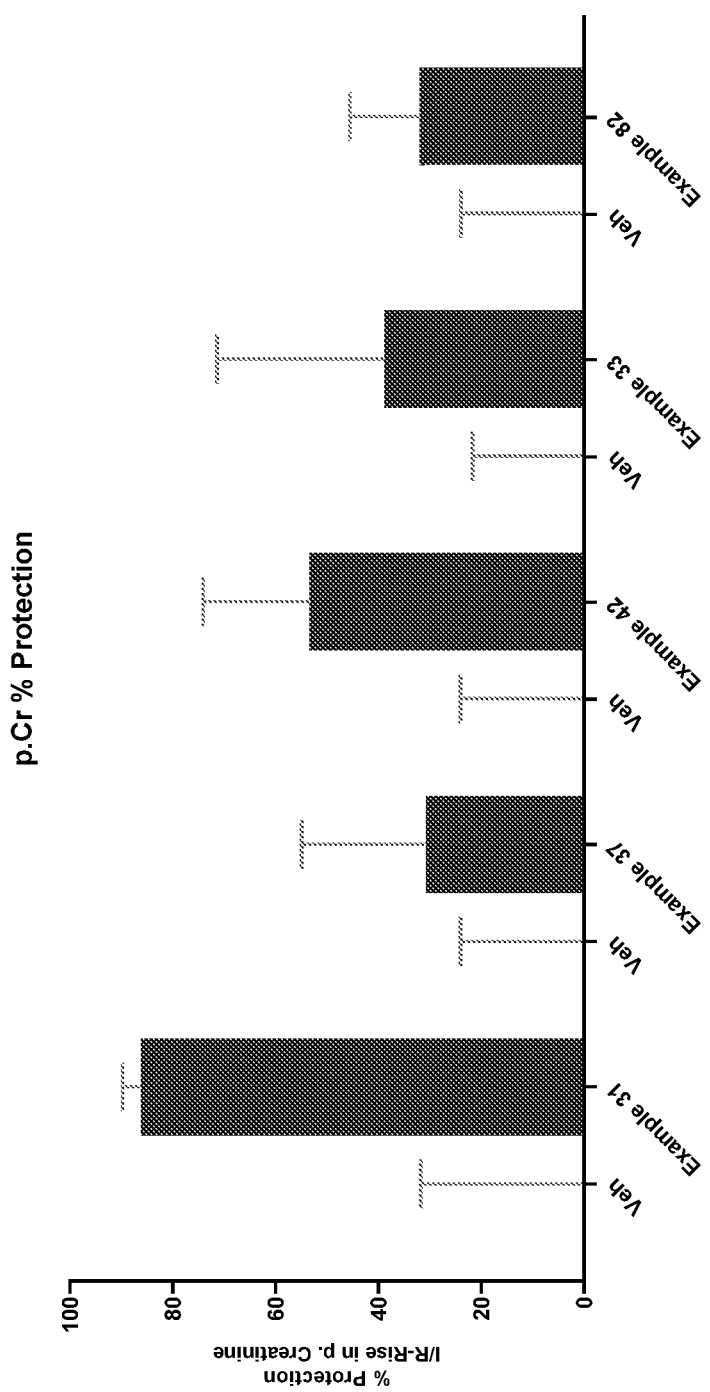
FIG. 5 is a graphic representing plasma crearinine versus % protection, using compounds of the invention.
Figure 6:
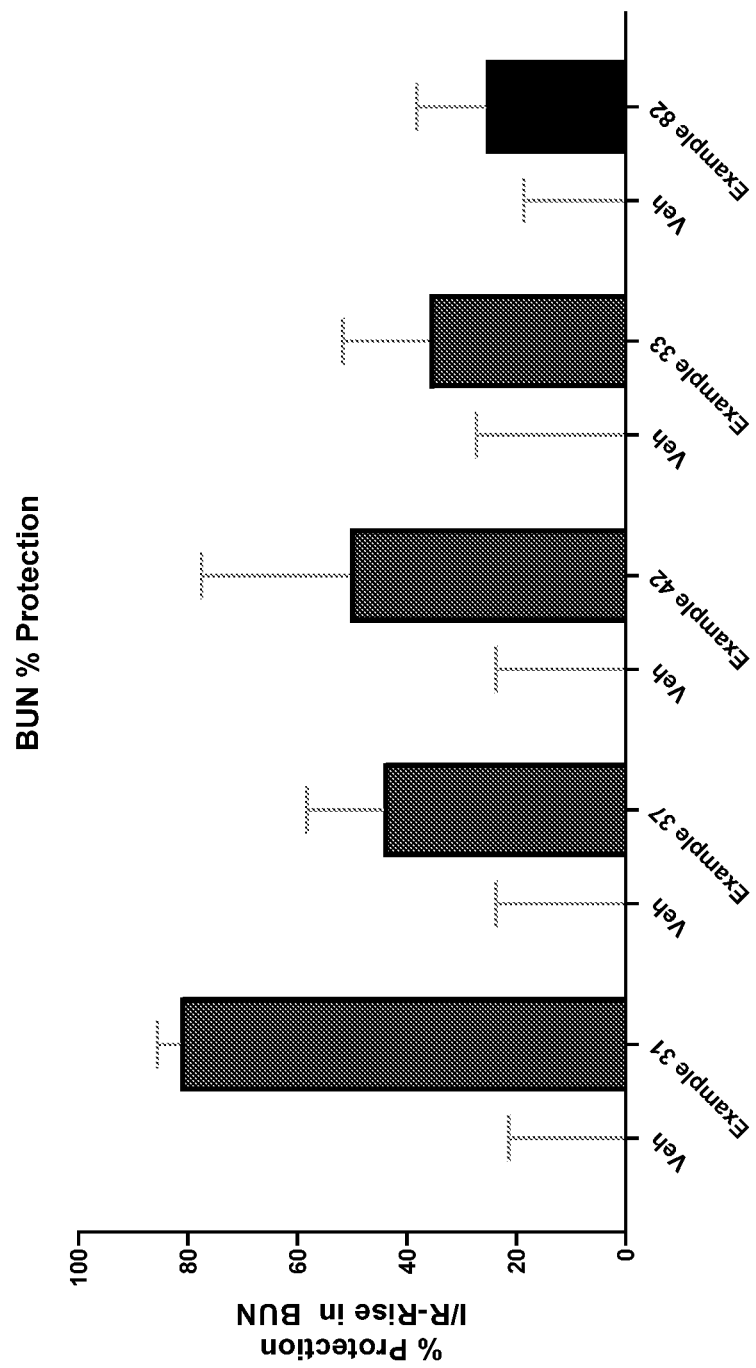
FIG. 6 is a graphic representing blood urea nitrogen (BUN) versus % protection, using compounds of the invention.

In certain embodiments, the invention provides a compound of formula (I), or a pharmaceutically acceptable salt thereof:

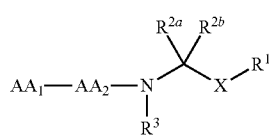

(I)

wherein
$AA_1$ is selected from

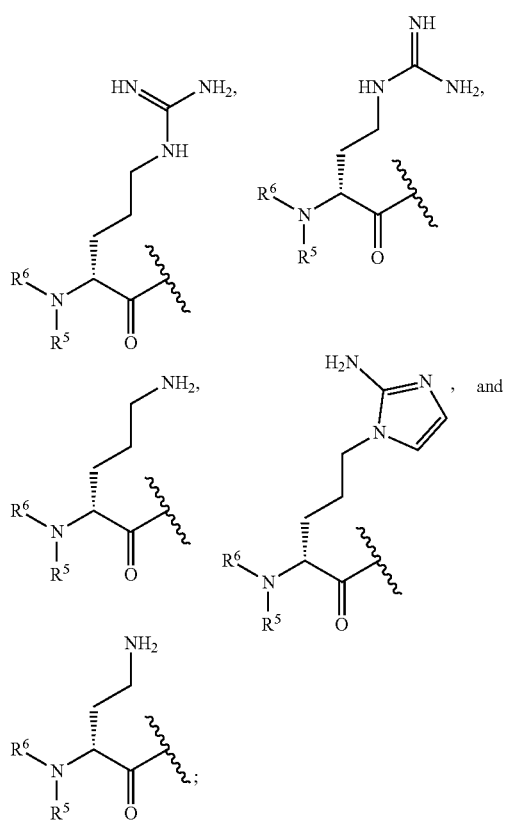

$AA_2$ is selected from

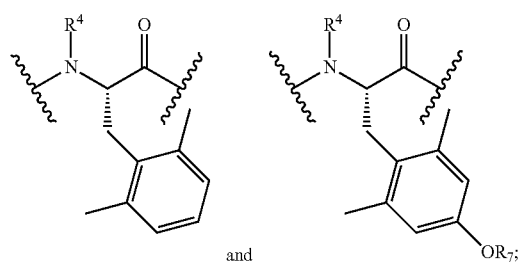

$R^1$ is selected from

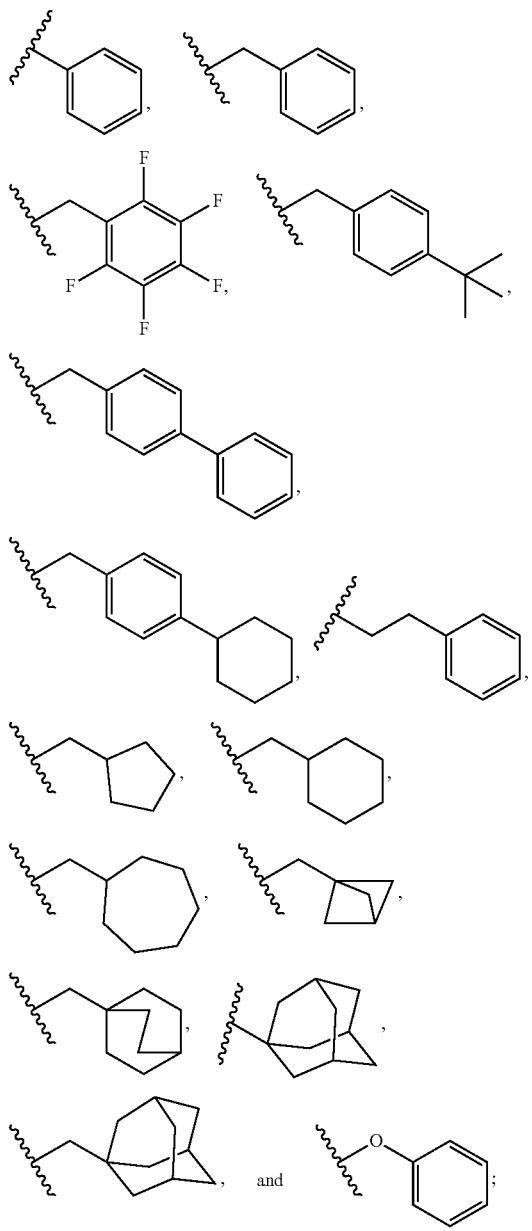

$R^{2a}$ is selected from

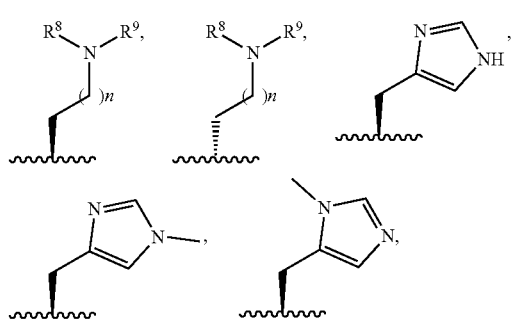

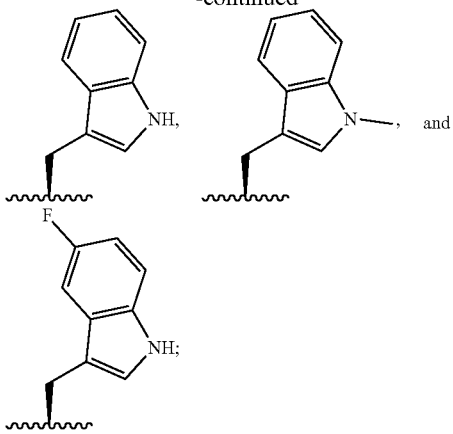

$R^{2b}$ is H or Me;
$R^3$ and $R^4$ are independently selected from H and (C1-C6)alkyl;
$R^5$ and $R^6$ are independently H, methyl, ethyl, propyl, cyclopropyl, or cyclobutyl; or $R^5$ and $R^6$ together with the N atom to which they are attached form a 4-6-membered heterocyclyl;
$R^7$ is selected from H, (C1-C6)alkyl, cycloalkyl, and aryl;
$R^8$ and $R^9$ are independently selected from H, (C1-C6) alkyl, cycloalkyl, and aryl; or $R^8$ and $R^9$ together with the N atom to which they are attached form a 4-6-membered heterocyclyl;
n is 1, 2, or 3;
X is selected from

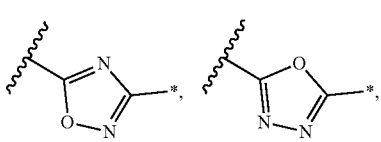
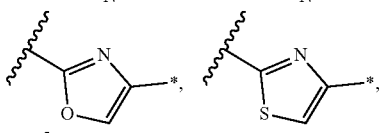
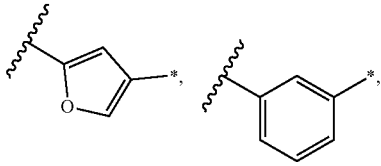
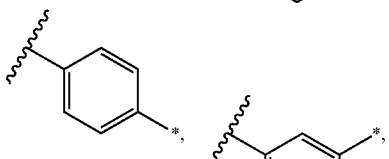
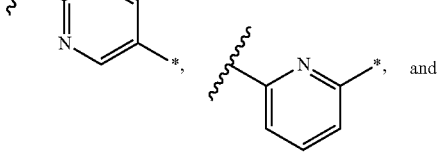

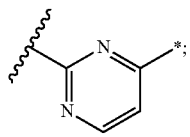

and
\* denotes the point of attachment of X to $R^1$.
In some embodiments, $AA_1$ is

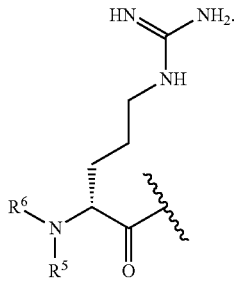

In some embodiments $AA_1$ is

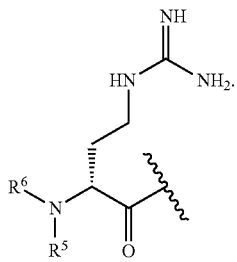

In some embodiments, $AA_1$ is

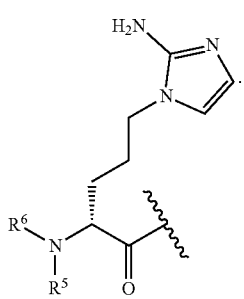

In some embodiments, $AA_1$ is

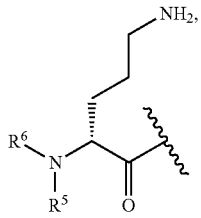

In some embodiments, AA$_1$ is
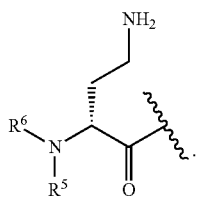
In some embodiments, AA$_2$ is
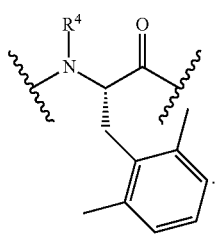
In some embodiments, AA$_2$ is
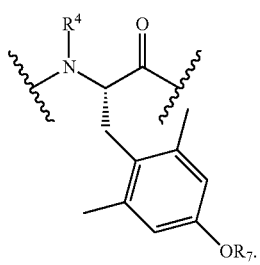
In some embodiments, R$^1$ is
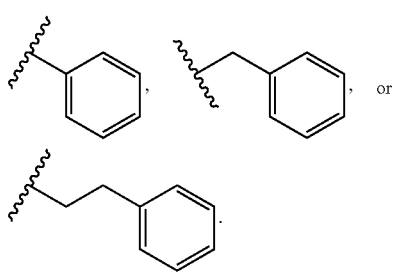, or
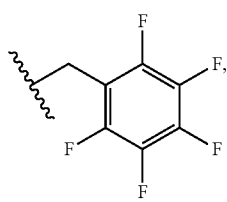 [SMILES: *Cc1c(F)c(F)c(F)c(F)c1F]
In some embodiments, R$^1$ is
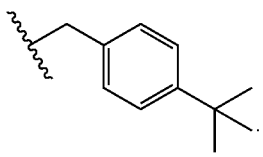 [SMILES: *Cc1ccc(C(C)(C)C)cc1]
In some embodiments, R$^1$ is
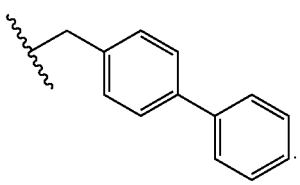 [SMILES: *Cc1ccc(-c2ccccc2)cc1]
In some embodiments, R$^1$ is
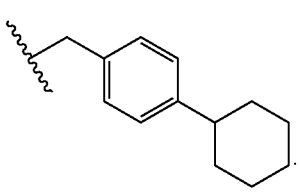 [SMILES: *Cc1ccc(C2CCCCC2)cc1]
In some embodiments, R$^1$ is
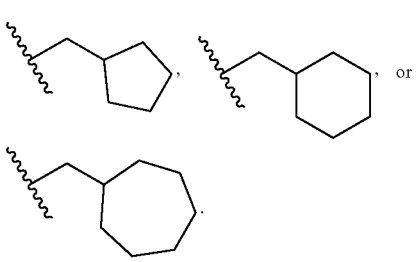
In some embodiments, R$^1$ is
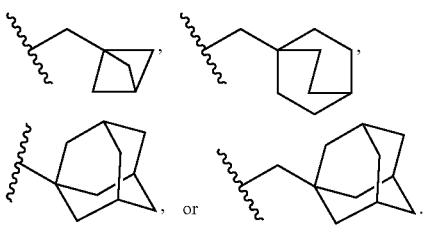
In some embodiments, R$^1$ is
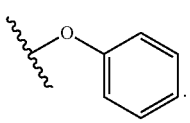

In some embodiments, $R^{2a}$ is

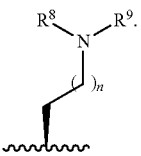

In some embodiments, $R^{2a}$ is

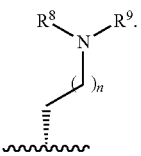

In some embodiments, $R^{2a}$ is

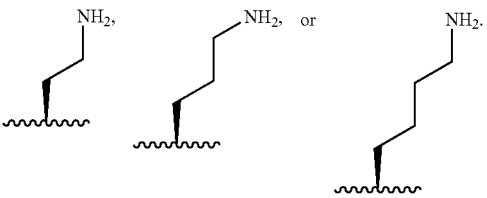

In some embodiments, $R^{2a}$ is

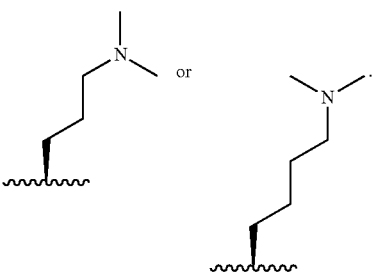

In some embodiments, $R^{2a}$ is

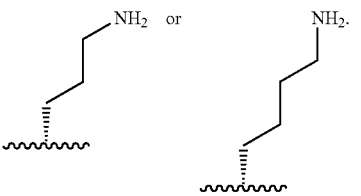

In some embodiments, $R^{2a}$ is

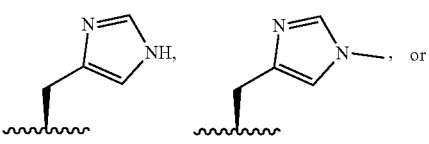

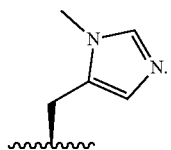

In some embodiments, $R^{2a}$ is

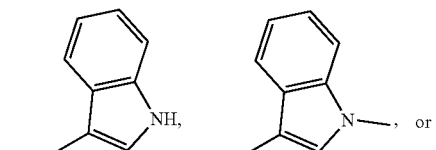

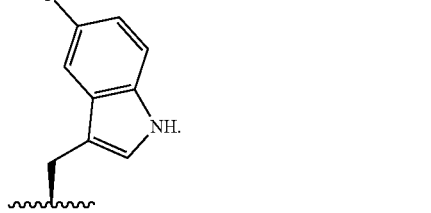

In some embodiments, $R^{2b}$ is H. In some embodiments, $R^{2b}$ is methyl.

In some embodiments, $R^3$ is H. In some embodiments, $R^3$ is (C1-C6)alkyl. In some embodiments, $R^3$ is methyl, ethyl, n-propyl, i-propyl, n-butyl, i-butyl, or t-butyl. In some embodiments, $R^3$ is methyl. In some embodiments, $R^3$ is ethyl.

In some embodiments, $R^4$ is H. In some embodiments, $R^4$ is (C1-C6)alkyl. In some embodiments, $R^4$ is methyl, ethyl, n-propyl, i-propyl, n-butyl, i-butyl, or t-butyl. In some embodiments, $R^4$ is methyl. In some embodiments, $R^4$ is ethyl.

In some embodiments, $R^3$ and $R^4$ are the same. In some embodiments, $R^3$ and $R^4$ are different.

In some embodiments, $R^5$ is H. In some embodiments, $R^5$ is methyl.

In some embodiments, $R^6$ is H. In some embodiments, $R^6$ is methyl.

In some embodiments, $R^5$ and $R^6$ are the same. In some embodiments, $R^5$ and $R^6$ are different.

In some embodiments, $R^5$ and $R^6$ together with the N atom to which they are attached form a 4-6-membered heterocyclyl. In some embodiments, the heterocyclyl is a 4-6 membered ring. In some embodiments, the heterocyclyl is azetidinyl, pyrrolidinyl, or piperidinyl.

In some embodiments, $R^7$ is H. In some embodiments, $R^7$ is (C1-C6)alkyl. In some embodiments, $R^7$ is methyl, ethyl, n-propyl, i-propyl, n-butyl, i-butyl, or t-butyl. In some embodiments, $R^7$ is methyl.

In some embodiments, $R^7$ is cycloalkyl. In some embodiments, $R^7$ is cyclopropyl, cyclobutyl, cyclopropyl, or cyclohexyl. In some embodiments, $R^7$ is aryl. In some embodiments, $R^7$ is phenyl.

In some embodiments, $R^8$ is H. In some embodiments, $R^8$ is (C1-C6)alkyl. In some embodiments, $R^8$ is methyl, ethyl, n-propyl, i-propyl, n-butyl, i-butyl, or t-butyl. In some embodiments, $R^8$ is methyl.

In some embodiments, R[8] is cycloalkyl. In some embodiments, R[8] is cyclopropyl, cyclobutyl, cyclopropyl, or cyclohexyl. In some embodiments, R[8] is aryl. In some embodiments, R[8] is phenyl.

In some embodiments, R[9] is cycloalkyl. In some embodiments, R[9] is cyclopropyl, cyclobutyl, cyclopropyl, or cyclohexyl. In some embodiments, R[9] is aryl. In some embodiments, R[9] is phenyl.

In some embodiments, R[8] and R[9] are the same. In some embodiments, R[8] and R[9] are different.

In some embodiments, R[8] and R[9] together with the N atom to which they are attached form a 4-6-membered heterocyclyl. In some embodiments, the heterocyclyl is a 4-6 membered ring. In some embodiments, the heterocyclyl is azetidinyl, pyrrolidinyl, or piperidinyl.

In some embodiments, X is

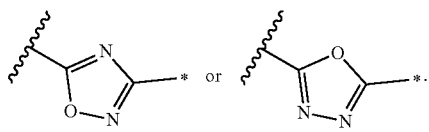

In some embodiments, X is

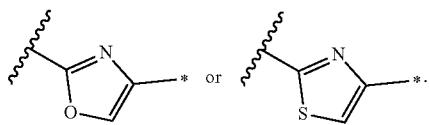

In some embodiments, X is

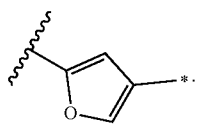 [SMILES: *c1cc(C)co1]

In some embodiments, X is

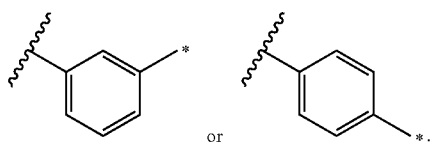

In some embodiments, X is

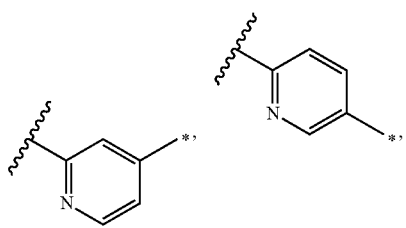

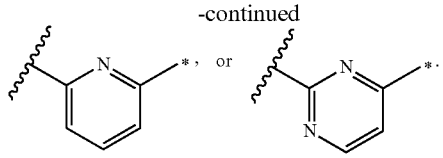

In some embodiments, n is 1. In some embodiments, n is 2. In some embodiments, n is 3.

In some embodiments, the compound is selected from:
D-Arg-DMT-(5-((S)-1',5'-diaminopent-1'-yl)-3-benzyl)-1,2,4-oxadiazole;
D-Arg-DMT-(5-((R)-1',5'-diaminopent-1'-yl)-3-benzyl)-1,2,4-oxadiazole;
D-Arg-DMT-(5-((S)-2',6'-diaminohex-2'-yl)-3-benzyl)-1,2,4-oxadiazole;
D-Arg-DMT-(5-((S)-5'-di methylamino-1'-aminopent-1'-yl)-3-benzyl)-1,2,4-oxadiazole;
D-Arg-DMT-(5-((R)-1',5'-diaminopent-1'-yl)-3-(2',3',4',5',6'-pentafluorobenzyl)-1,2,4-oxadiazole;
D-Arg-DMT-(5-((S)-1',5'-diaminopent-1'-yl)-3-(4-tert-butylbenzyl)-1,2,4-oxzdiazole;
D-Arg-DMT-(5-((R)-1',5'-diaminopent-1'-yl)-3-(4-tert-butylbenzyl)-1,2,4-oxzdiazole;
D-Arg-DMT-(5-((S)-1',5'-diaminopent-1'-yl)-3-(4'-trifluoromethylbenzyl)-1,2,4-oxadiazole;
D-Arg-DMT-(5-((S)-1',5'-diaminopent-1'-yl)-3-(4-phenylbenzyl))-1,2,4-oxadiazole;
D-Arg-DMT-(5-((S)-1',5'-diaminopent-1'-yl)-3-(4'-cyclohexylbenzyl))-1,2,4-oxadiazole;
D-Arg-DMT-(5-((S)-1',5'-diaminopent-1'-yl)-3-phenethyl))-1,2,4-oxadiazole;
D-Arg-DMT-(5-((S)-1',5'-diaminopent-1'-yl)-3-cyclohexyl-methyl)-1,2,4-oxadiazole;
D-Arg-DMT-(5-((S)-1',5'-diaminopent-1'-yl)-3-cyclohexyl-methyl)-1,2,4-oxadiazole;
D-Arg-DMT-(5-((S)-1',5'-diaminopent-1'-yl)-3-cycloheptyl-mathyl)-1,2,4-oxadiazole;
D-Arg-DMT-(5-((S)-1',5'-diaminopent-1'-yl)-3-bicyclo[2,2,2]pentanylmethyl)-1,2,4-oxadiazole;
D-Arg-DMT-(5-((S)-1',5'-diaminopent-1'-yl)-3-bicyclo[2,2,2]octanylmethyl)-1,2,4-oxadiazole;
D-Arg-DMT-(5-((1 S)-(5-(1',5'-diaminopent-1'-yl-3-adamant-1'-yl)-1,2,4-oxadiazole;
D-Arg-DMT-(5-((1R)-(5-(1',5'-diaminopent-1'-yl-3-adamant-1'-yl)-1,2,4-oxadiazole;
D-Arg-DMT-(5-((S)-1',5'-diaminopent-1'-yl)-3-admantylmethyl)-1,2,4-oxzadiazole;
D-Arg-DMT-(5-(α-(S)-histamine)-3-phenyl)-1,2,4-oxadiazole;
D-Arg-DMT-(5-(α-(S)-histamine)-3-benzyl)-1,2,4-oxadiazole;
D-Arg-DMT-(5-(α-(S)-histamine)-3-phenethyl)-1,2,4-oxadiazole;
D-Arg-DMT-(5-(α-(S)-histamine)-3-cyclopentylmethyl)-1,2,4-oxadiazole;
D-Arg-DMT-(5-(α-(S)-histamine)-3-cyclohexylmethyl)-1,2,4-oxadiazole;
D-Arg-DMT-(5-(α-(S)-t-methylhistamine)-3-cyclohexylmethyl)-1,2,4-oxadiazole;
D-Arg-DMT-(5-(α-(S)-p-methylhistamine)-3-cyclohexylmethyl)-1,2,4-oxadiazole;
D-Arg-DMT-(5-(α-(S)-histamine)-3-cycloheptylmethyl)-1,2,4-oxadiazole;
D-Arg-DMT-(5-(α-(S)-histamine)-3-bicyclo[2,2,2]pentanylmethyl)-1,2,4-oxadiazole;

D-Arg-DMT-(5-(α-(S)-histamine)-3-bicyclo[2,2,2]octanyl-methyl)-1,2,4-oxadiazole;
D-Arg-DMT-(5-(α-(S)-histamine)-3-admantyl)-1,2,4-oxadiazole;
D-Arg-DMT-(5-(α-(S)-histamine)-3-admantylmethyl)-1,2,4-oxadiazole;
D-Arg-DMT-(5-((S)-(2-(1H-indol-3-ye-1-aminoethyl)-3-benzyl)-1,2,4-oxadiazole;
D-Arg-DMT-(5-((1 S)-2-(pyridin-4-yl)-1-aminoethyl-3-admantylmethyl)-1,2,4-oxadiazole;
D-Agb-DMT-(5-((S)-1',5'-diaminopent-1'-yl)-3-benzyl)-1,2,4-oxadiazole;
D-Agb-DMT-(5-((S)-1',4'-diaminobut-1'-yl)-3-benzyl)-1,2,4-oxadiazole;
D-Agb-DMT-(5-((S)-4'-dimethylamino-1'-aminobut-1'-yl)-3-benzyl)-1,2,4-oxadiazole;
D-Agb-DMT-(5-(2'-(S)-4-histamine)-3-admantylmethyl)-1,2,4-oxadiazole;
(N,N-diMe)-D-Agb-DMT-(5-(2'-(S)-4-histamine)-3-admantyl)-1,2,4-oxadiazole;
D-Agb-DMT-(5-((S)-(2-(1H-indol-3-yl)-1-aminoethyl)-3-benzyl)-1,2,4-oxadiazole;
D-Agb-DMT-(5-((S)-(2-(1H-indol-3-yl)-1-aminoethyl)-3-admantylmethyl)-1,2,4-oxadiazole;
D-(δ-2-amino-1H-imidazol-1-yl)-Nva-DMT-(5-((S)-1',4'-diaminopropan-1'-yl)-3-benzyl)-1,2,4-oxadiazole;
D-(δ-2-amino-1H-imidazol-1-yl)-Nva-DMT-(5-((S)-1',4'-diaminobut-1'-yl)-3-cyclohexylmethyl)-1,2,4-oxadiazole;
D-(δ-2-amino-1H-imidazol-1-yl)-Nva-DMT-(5-((S)-1',4'-diaminobut-1'-yl)-3-admantyl)-1,2,4-oxadiazole;
D-(δ-2-amino-1H-imidazol-1-yl)-Nva-DMT-(5-((S)-1',4'-diaminobut-1'-yl)-3-admantylmethyl)-1,2,4-oxadiazole;
D-(δ-2-amino-1H-imidazol-1-yl)-Nva-DMT-(5-((R)-1',4'-diaminobut-1'-yl)-3-admantylmethyl)-1,2,4-oxadiazole;
D-(δ-2-amino-1H-imidazol-1-yl)-Nva-DMT-(5-((R)-1',4'-diaminobut-1'-yl)-3-(bicyclo[2.2.2]octanylmethyl)-1,2,4-oxadiazole;
D-(δ-amino-1H-imidazol-1-yl)-Nva-DMT-(5-((S)-4'-dimethylamino-1'-aminobut-1'-yl)-3-admantylmethyl)-1,2,4-oxadiazole;
D-(δ-2-amino-1H-imidazol-1-yl)-Nva-DMT-(5-((S)-1',5'-diaminopent-1'-yl)-3-cyclohexylmethyl)-1,2,4-oxadiazole;
D-(δ-2-amino-1H-imidazol-1-yl)-Nva-DMT-(5-((S)-5'-dimethyl amino-1'-aminopent-1'-yl)-3-cyclohexylmethyl)-1,2,4-oxadiazole;
D-(δ-2-amino-1H-imidazol-1-yl)-Nva-DMT-(5-(α-(S)-histamine)-3-benzyl)-1,2,4-oxadiazole;
D-(δ-2-amino-1H-imidazol-1-yl)-Nva-DMT-(5-(α-(S)-histamine)-3-(4-phenylbenzyl))-1,2,4-oxadiazole;
D-(δ-2-amino-1H-imidazol-1-yl)-Nva-DMT-(5-(α-(S)-histamine)-3-cyclopentylmethyl)-1,2,4-oxadiazole;
D-(δ-2-amino-1H-imidazol-1-yl)-Nva-DMT-(5-(α-(S)-histamine)-3-cyclohexylmethyl)-1,2,4-oxadiazole;
D-(δ-2-amino-1H-imidazol-1-yl)-Nva-DMT-(5-(α-(S)-histamine)-3-cycloheptylmethyl)-1,2,4-oxadiazole;
D-(δ-2-amino-1H-imidazol-1-yl)-Nva-DMT-(5-(α-(S)-t-methylhistamine)-3-cyclohexylmethyl)-1,2,4-oxadiazole;
D-(δ-2-amino-1H-imidazol-1-yl)-Nva-DMT-(5-(α-(S)-histamine)-3-cyclohexylmethyl)-1,2,4-oxadiazole;
D-(δ-2-amino-1H-imidazol-1-yl)-Nva-DMT-(5-(α-(S)-histamine)-3-admantylmethyl)-1,2,4-oxadiazole;
D-(δ-2-amino-1H-imidazol-1-yl)-Nva-DMT-(5-(α-(S)-t-methylhistamine)-3-admantylmethyl)-1,2,4-oxadiazole;
D-(δ-2-amino-1H-imidazol-1-yl)-Nva-DMT-(5-((1 S)-(2-(1H-indol-3-yl)-1-aminoethyl)-3-(4-phenylbenzyl))-1,2,4-oxadiazole;
D-(δ-2-amino-1H-imidazol-1-yl)-Nva-DMT-(5-((1S)-(2-(1-methyl-indol-3-yl)-1-aminoethyl)-3-(4-phenylbenzyl))-1,2,4-oxadiazole;
D-(δ-2-amino-1H-imidazol-1-yl)-Nva-DMT-(5-((1S)-(2-(1H-indol-3-yl)ethyl)-3-admantylmethyl)-1,2,4-oxadiazole;
D-(δ-2-amino-1H-imidazol-1-yl)-Nva-DMT-(5-((1 S)-(2-(6-fluoro-1H-indol-3-yl)ethyl)-3-admantylmethyl)-1,2,4-oxadiazole;
D-(δ-2-amino-1H-imidazol-1-yl)-Nva-DMT-(5-((1S)-(2-(1-methyl-indol-3-yl)-1-aminoethyl)-3-admantylmethyl)-1,2,4-oxadiazole;
D-(δ-2-amino-1H-imidazol-1-yl)-Nva-(O-Me)-DMT-(5-(α-histamine)-3-(4-phenylbenzyl))-1,2,4-oxadiazole;
D-(δ-2-amino-1H-imidazol-1-yl)-Nva-(O-Me)-DMT-(5-(α-(S)-t-methylhistamine)-3-(4-phenylbenzyl))-1,2,4-oxadiazole (Carbamimidoyl)-D-Dab-DMT-(5-((S)-1',5'-diaminopent-1'-yl)-3-benzyl)-1,2,4-oxadiazole;
(Carbamimidoyl)-D-Dab-DMT-(5-((S)-1',5'-diaminobutan-1'-yl)-3-benzyl)-1,2,4-oxadiazole;
(Carbamimidoyl)-D-Dab-DMT-(5-(2'-(S)-4-histamine)-3-admantylmethyl)-1,2,4-oxadiazole;
D-Arg-DMT-(5-(α-histimine))-3-benzyl)-1,3,4-oxadiazole;
D-Arg-DMT-(2-((S)-1',5'-diaminopent-1'-yl)-4-benzyl)-1,3-oxazole;
D-Arg-DMT-(2-((S)-1',5'-diaminopent-1'-yl)-5-benzyl)-1,3-oxazole;
D-Arg-DMT-(2-((S)-1',5'-diaminopent-1'-yl)-4-benzyl)-1,3-thiazole;
D-Arg-DMT-(2-((S)-1',5'-diaminopent-1'-yl)-5-benzyl)-1,3-thiazole;
D-Arg-DMT-(2-((S)-1',5'-diaminopent-1'-yl)-4-benzyl)-furan;
D-Arg-DMT-(2-((S)-1',5'-diaminopent-1'-yl)-5-benzyl)-furan;
D-Arg-DMT-(1-((S)-1',5'-diaminopent-1'-yl)-3-phenoxy)-benzene;
D-Arg-DMT-(1-((5)-1',5'-diaminopent-1'-yl)-4-phenoxy)-benzene;
D-Arg-DMT-(2-((S)-1',5'-diaminopent-1'-yl)-4-phenoxy)-pyridine;
D-Arg-DMT-(2-((S)-1',5'-di aminopent-1'-yl)-5-phenoxy)-pyridine;
D-Arg-DMT-(2-((S)-1',5'-diaminopent-1'-yl)-6-benzyl)-pyridine; and
D-Arg-DMT-(2-((S)-1',5'-diaminopent-1'-yl)-4-benzyl)-pyrimidine.

Peptide Synthesis

The peptidic compounds of the invention may be prepared using a peptide synthesis method, such as conventional liquid-phase peptide synthesis or solid-phase peptide synthesis, or by peptide synthesis by means of an automated peptide synthesizer (Kelley et al., Genetics Engineering Principles and Methods, Setlow, J. K. eds., Plenum Press NY. (1990) Vol. 12, pp. 1 to 19; Stewart et al., Solid-Phase Peptide Synthesis (1989) W. H.; Houghten, Proc. Natl. Acad. Sci. USA (1985) 82: p.5132). The peptide thus produced can be collected or purified by a routine method, for example, chromatography, such as gel filtration chromatography, ion exchange column chromatography, affinity chromatography, reverse phase column chromatography, and HPLC, ammonium sulfate fractionation, ultrafiltration, and immunoadsorption.

In a solid-phase peptide synthesis, peptides are typically synthesized from the carbonyl group side (C-terminus) to amino group side (N-terminus) of the amino acid chain. In certain embodiments, an amino-protected amino acid is covalently bound to a solid support material through the carboxyl group of the amino acid, typically via an ester or amido bond and optionally via a linking group. The amino group may be deprotected and reacted with (i.e., "coupled" with) the carbonyl group of a second amino-protected amino acid using a coupling reagent, yielding a dipeptide bound to a solid support. These steps (i.e., deprotection, coupling) may be repeated to form the desired peptide chain. Once the desired peptide chain is complete, the peptide may be cleaved from the solid support.

In certain embodiments, the protecting groups used on the amino groups of the amino acid residues include 9-fluorenylmethyloxycarbonyl group (Fmoc) and t-butyloxycarbonyl (Boc). The Fmoc group is removed from the amino terminus with base while the Boc group is removed with acid. In alternative embodiments, the amino protecting group may be formyl, acrylyl (Acr), benzoyl (Bz), acetyl (Ac), trifluoroacetyl, substituted or unsubstituted groups of aralkyloxycarbonyl type, such as the benzyloxycarbonyl (Z), p-chlorobenzyloxycarbonyl, p-bromobenzyloxycarbonyl, p-nitrobenzyloxycarbonyl, p-methoxybenzyloxycarbonyl, benzhydryloxycarbonyl, 2(p-biphenylyl)isopropyloxycarbonyl, 2-(3,5-dimethoxyphenyl)isopropyloxycarbonyl, p-phenylazobenzyloxycarbonyl, triphenylphosphonoethyloxycarbonyl or 9-fluorenylmethyloxycarbonyl group (Fmoc), substituted or unsubstituted groups of alkyloxycarbonyl type, such as the tert-butyloxycarbonyl (BOC), tert-amyloxycarbonyl, diisopropylmethyloxycarbonyl, isopropyloxycarbonyl, ethyloxycarbonyl, allyloxycarbonyl, 2 methylsulphonylethyloxycarbonyl or 2,2,2-trichloroethyloxycarbonyl group, groups of cycloalkyloxycarbonyl type, such as the cyclopentyloxycarbonyl, cyclohexyloxycarbonyl, adamantyloxycarbonyl or isobornyloxycarbonyl group, and groups containing a hetero atom, such as the benzenesulphonyl, p-toluenesulphonyl, mesitylenesulphonyl, methoxytrimethylphenylsulphonyl, 2-nitrobenzenesulfonyl, 2-nitrobenzenesulfenyl, 4-nitrobenzenesulfonyl or 4-nitrobenzenesulfenyl group.

Many amino acids bear reactive functional groups in the side chain. In certain embodiments, such functional groups are protected in order to prevent the functional groups from reacting with the incoming amino acid. The protecting groups used with these functional groups must be stable to the conditions of peptide synthesis, but may be removed before, after, or concomitantly with cleavage of the peptide from the solid support.

In certain embodiments, the solid support material used in the solid-phase peptide synthesis method is a gel-type support such as polystyrene, polyacrylamide, or polyethylene glycol. Alternatively, materials such as pore glass, cellulose fibers, or polystyrene may be functionalized at their surface to provide a solid support for peptide synthesis.

Coupling reagents that may be used in the solid-phase peptide synthesis described herein are typically carbodiimide reagents. Examples of carbodiimide reagents include, but are not limited to, N,N'-dicyclohexylcarbodiimide (DCC), 1-(3-dimethylaminopropyl)-3-ethylcarbodiimide (EDC), N-cyclohexyl-N'-isopropylcarbodiimide (CIC), N,N'-diisopropylcarbodiimide (DIC), N-tert-butyl-N'-methylcarbodiimide (BMC), N-tert-butyl-N'-ethylcarbodiimide (BEC), bis[[4-(2,2-dimethyl-1,3-dioxolyl)]-methyl]carbodiimide (BDDC), and N,N-dicyclopentylcarbodiimide. DCC is a preferred coupling reagent.

In certain exemplary embodiments, linear compounds 1 are synthesized in a convergent fashion, according to the solid phase synthesis depicted in Scheme 1.

For reference in the following schemes,

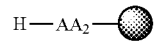

indicates

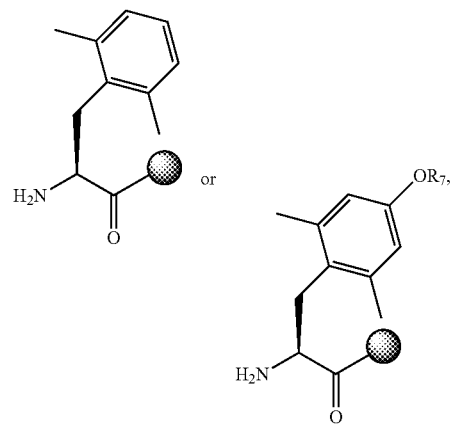

wherein

represents a solid support and optionally a linking group.

Scheme 1

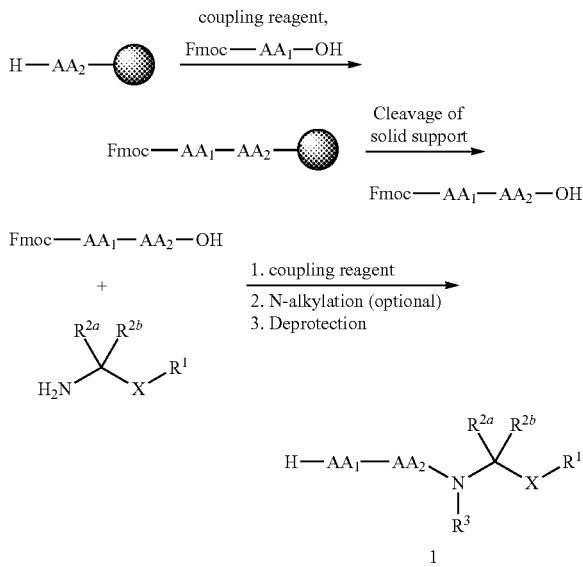

For example, the compound pictured below may be synthesized in such a fashion, as illustrated in Scheme 2.

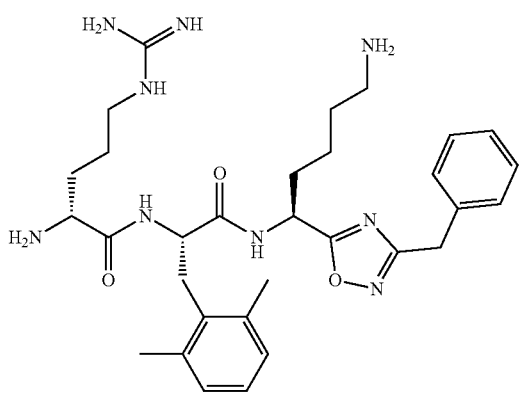 [SMILES: Cc1cccc(C)c1C[C@H](NC(=O)[C@H](N)CCCNC(=N)N)C(=O)N[C@@H](CCCCN)c1nc(Cc2ccccc2)no1]

For reference in the following schemes,

indicates

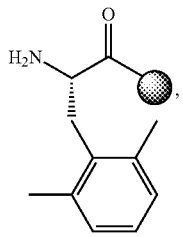

wherein

○ represents a solid support and optionally a linking group.

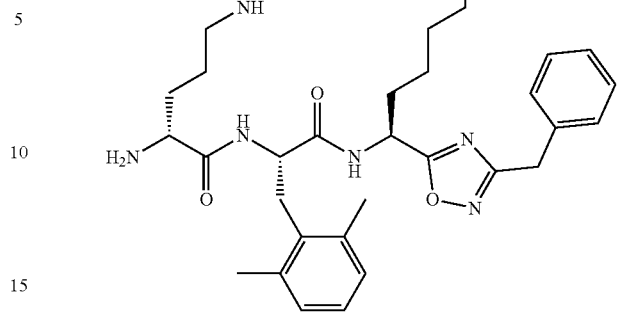

The compounds of the invention (1) may also be synthesized according to conventional liquid-phase peptide synthetic routes, e.g., according to Scheme 3.

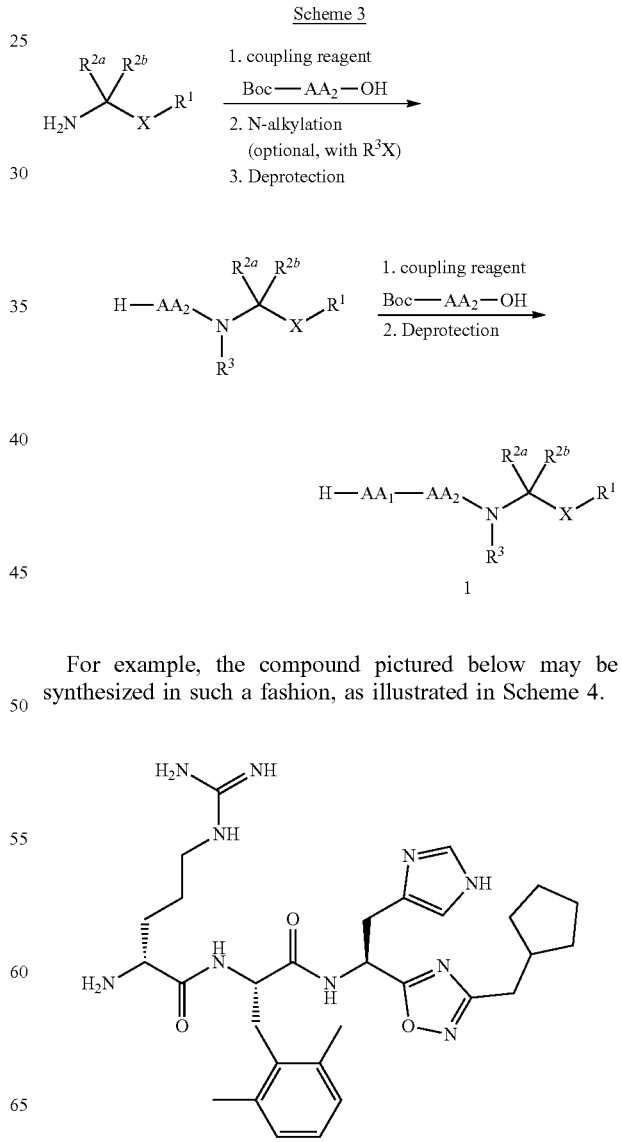

For example, the compound pictured below may be synthesized in such a fashion, as illustrated in Scheme 4.

21
-continued
Scheme 4

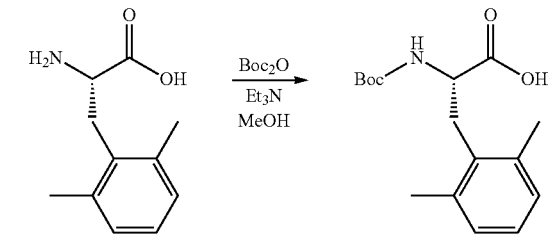

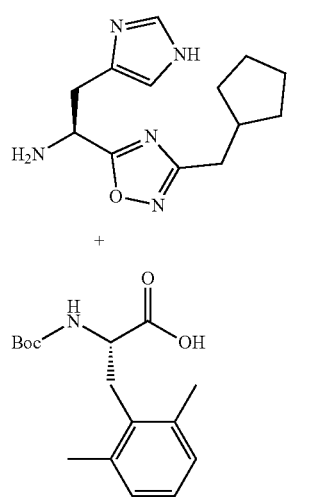

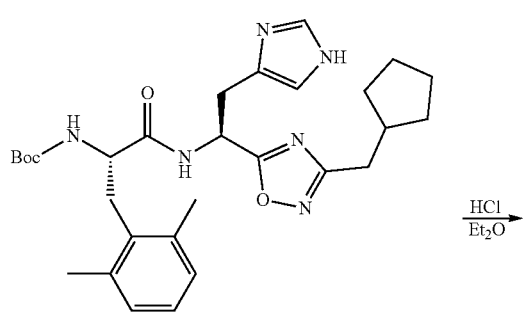

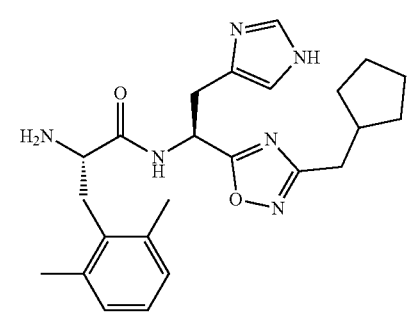

22
-continued

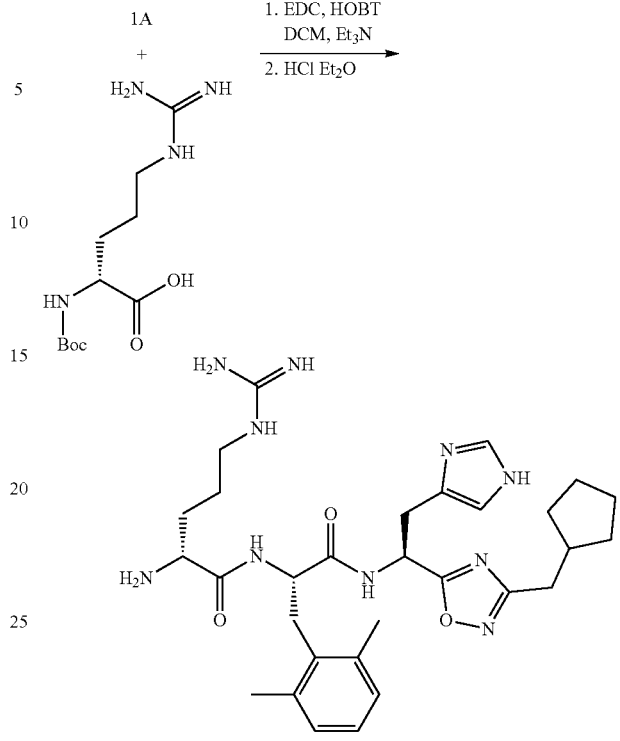

Definitions

The nomenclature used to define the peptide compounds described herein is that typically used in the art wherein the amino group at the N-terminus appears to the left and the carboxyl group at the C-terminus appears to the right.

As used herein, the term "amino acid" includes both a naturally occurring amino acid and a non-natural amino acid. The term "amino acid," unless otherwise indicated, includes both isolated amino acid molecules (i.e., molecules that include both, an amino-attached hydrogen and a carbonyl carbon-attached hydroxyl) and residues of amino acids (i.e., molecules in which either one or both an amino-attached hydrogen or a carbonyl carbon-attached hydroxyl are removed). The amino group can be alpha-amino group, beta-amino group, etc. For example, the term "amino acid alanine" can refer either to an isolated alanine H-Ala-OH or to any one of the alanine residues H-Ala-, -Ala-OH, or -Ala-. Unless otherwise indicated, all amino acids found in the compounds described herein can be either in D or L configuration. An amino acid that is in D configuration may be written such that "D" precedes the amino acid abbreviation. For example, "D-Arg" represents arginine in the D configuration. The term "amino acid" includes salts thereof, including pharmaceutically acceptable salts. Any amino acid can be protected or unprotected. Protecting groups can be attached to an amino group (for example alpha-amino group), the backbone carboxyl group, or any functionality of the side chain. As an example, phenylalanine protected by a benzyloxycarbonyl group (Z) on the alpha-amino group would be represented as Z-Phe-OH.

With the exception of the N-terminal amino acid, all abbreviations of amino acids (for example, Phe) in this disclosure stand for the structure of —NH—C(R)(R')—CO—, wherein R and R' each is, independently, hydrogen or the side chain of an amino acid (e.g., R═ benzyl and R'═H for Phe). Accordingly, phenylalanine is H-Phe-OH. The designation "OH" for these amino acids, or for peptides (e.g., Lys-Val-Leu-OH) indicates that the C-terminus is the free acid. The designation "NH$_2$" in, for example, Phe-D-Arg-Phe-Lys-NH$_2$ indicates that the C-terminus of the protected peptide fragment is amidated. Further, certain R and R', separately, or in combination as a ring structure, can include functional groups that require protection during the liquid phase synthesis.

Where the amino acid has isomeric forms, it is the L form of the amino acid that is represented unless otherwise explicitly indicated as D form, for example, D-Arg. Notably, many amino acid residues are commercially available in both D- and L-form. For example, D-Arg is a commercially available D-amino acid.

A capital letter "D" used in conjunction with an abbreviation for an amino acid residue refers to the D-form of the amino acid residue.

As used herein, the term "peptide" refers to two or more amino acids covalently linked by at least one amide bond (i.e., a bond between an amino group of one amino acid and a carboxyl group of another amino acid selected from the amino acids of the peptide fragment). The term "peptide" includes salts thereof, including pharmaceutically acceptable salts.

The term "DMT" refers to 2,6-di(methyl)tyrosine (e.g., 2,6-dimethyl-L-tyrosine; CAS 123715-02-6).

The term "Nva" refers to norvaline, a/k/a 2-aminopentanoic acid (CAS 6600-40-4). Norvaline has two enantiomeric forms, which may be termed D- and L-norvaline. Additionally, and for example, the name "8-(substituent)-Nva" or "5-(substituent)-Nva" refers to a norvaline in which the designated substituent replaces a hydrogen atom on the δ- or 5-carbon of norvaline. Other substitution patterns are possible, which are named in a similar fashion.

The term "Agb" refers to 2-amino-4-guanidino-butyric acid (e.g., 2-amino-4-guanidino-D-butyric acid), a homologue of Arg.

The articles "a" and "an" are used herein to refer to one or to more than one (i.e., to at least one) of the grammatical object of the article. By way of example, "an element" means one element or more than one element.

The invention also provides salts of the compounds of the invention.

The term "pharmaceutically acceptable salt" as used herein includes salts derived from inorganic or organic acids including, for example, hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2-sulfonic, and other acids. Pharmaceutically acceptable salt forms can include forms wherein the ratio of molecules comprising the salt is not 1:1. For example, the salt may comprise more than one inorganic or organic acid molecule per molecule of base, such as two hydrochloric acid molecules per molecule of compound. As another example, the salt may comprise less than one inorganic or organic acid molecule per molecule of base, such as two molecules of compound per molecule of tartaric acid.

The terms "carrier" and "pharmaceutically acceptable carrier" as used herein refer to a diluent, adjuvant, excipient, or vehicle with which a compound is administered or formulated for administration. Non-limiting examples of such pharmaceutically acceptable carriers include liquids, such as water, saline, and oils; and solids, such as gum acacia, gelatin, starch paste, talc, keratin, colloidal silica, urea, and the like. In addition, auxiliary, stabilizing, thickening, lubricating, flavoring, and coloring agents may be used. Other examples of suitable pharmaceutical carriers are described in Remington's Pharmaceutical Sciences by E. W. Martin, herein incorporated by reference in its entirety.

As used herein, "inhibit" or "inhibiting" means reduce by an objectively measureable amount or degree compared to control. In one embodiment, inhibit or inhibiting means reduce by at least a statistically significant amount compared to control. In one embodiment, inhibit or inhibiting means reduce by at least 5 percent compared to control. In various individual embodiments, inhibit or inhibiting means reduce by at least 10, 15, 20, 25, 30, 33, 40, 50, 60, 67, 70, 75, 80, 90, 95, or 99 percent compared to control.

As used herein, the terms "treating" and "treat" refer to performing an intervention that results in (a) preventing a condition or disease from occurring in a subject that may be at risk of developing or predisposed to having the condition or disease but has not yet been diagnosed as having it; (b) inhibiting a condition or disease, e.g., slowing or arresting its development or progression; or (c) relieving or ameliorating a condition or disease, e.g., causing regression of the condition or disease. In one embodiment the terms "treating" and "treat" refer to performing an intervention that results in (a) inhibiting a condition or disease, e.g., slowing or arresting its development; or (b) relieving or ameliorating a condition or disease, e.g., causing regression of the condition or disease.

As used herein, a "subject" refers to a living animal. In various embodiments, a subject is a mammal. In various embodiments, a subject is a non-human mammal, including, without limitation, a mouse, rat, hamster, guinea pig, rabbit, sheep, goat, cat, dog, pig, horse, cow, or non-human primate. In certain embodiments, the subject is a human.

As used herein, "administering" has its usual meaning and encompasses administering by any suitable route of administration, including, without limitation, intravenous, intramuscular, intraperitoneal, subcutaneous, direct injection, mucosal, inhalation, oral, and topical.

As used herein, the phrase "effective amount" refers to any amount that is sufficient to achieve a desired biological effect. A "therapeutically effective amount" is an amount that is sufficient to achieve a desired therapeutic effect, e.g., to treat ischemia-reperfusion injury.

Compounds of the invention and the salts thereof can be combined with other therapeutic agents. The compounds of the invention and other therapeutic agent may be administered simultaneously or sequentially. When the other therapeutic agents are administered simultaneously, they can be administered in the same or separate formulations, but they are administered substantially at the same time. The other therapeutic agents are administered sequentially with one another and with compounds of the invention, when the administration of the other therapeutic agents and the compound of the invention is temporally separated. The separation in time between the administration of these compounds may be a matter of minutes or it may be longer.

Pharmaceutical Compositions, Routes of Administration, and Dosing

In certain embodiments, the invention is directed to a pharmaceutical composition, comprising a compound of the invention and a pharmaceutically acceptable carrier. In certain embodiments, the pharmaceutical composition comprises a plurality of compounds of the invention and a pharmaceutically acceptable carrier.

In certain embodiments, a pharmaceutical composition of the invention further comprises at least one additional pharmaceutically active agent other than a compound of the invention. The at least one additional pharmaceutically active agent can be an agent useful in the treatment of ischemia-reperfusion injury.

Pharmaceutical compositions of the invention can be prepared by combining one or more compounds of the invention with a pharmaceutically acceptable carrier and, optionally, one or more additional pharmaceutically active agents.

As stated above, an "effective amount" refers to any amount that is sufficient to achieve a desired biological effect. Combined with the teachings provided herein, by choosing among the various active compounds and weighing factors such as potency, relative bioavailability, patient body weight, severity of adverse side-effects and mode of administration, an effective prophylactic or therapeutic treatment regimen can be planned which does not cause substantial unwanted toxicity and yet is effective to treat the particular subject. The effective amount for any particular application can vary depending on such factors as the disease or condition being treated, the particular compound of the invention being administered, the size of the subject, or the severity of the disease or condition. One of ordinary skill in the art can empirically determine the effective amount of a particular compound of the invention and/or other therapeutic agent without necessitating undue experimentation. A maximum dose may be used, that is, the highest safe dose according to some medical judgment. Multiple doses per day may be contemplated to achieve appropriate systemic levels of compounds. Appropriate systemic levels can be determined by, for example, measurement of the patient's peak or sustained plasma level of the drug. "Dose" and "dosage" are used interchangeably herein.

In certain embodiments, intravenous administration of a compound may typically be from 0.1 mg/kg/day to 20 mg/kg/day. In one embodiment, intravenous administration of a compound may typically be from 0.1 mg/kg/day to 2 mg/kg/day. In one embodiment, intravenous administration of a compound may typically be from 0.5 mg/kg/day to 5 mg/kg/day. In one embodiment, intravenous administration of a compound may typically be from 1 mg/kg/day to 20 mg/kg/day. In one embodiment, intravenous administration of a compound may typically be from 1 mg/kg/day to 10 mg/kg/day.

Generally, daily oral doses of a compound will be, for human subjects, from about 0.01 milligrams/kg per day to 1000 milligrams/kg per day. It is expected that oral doses in the range of 0.5 to 50 milligrams/kg, in one or more administrations per day, will yield therapeutic results. Dosage may be adjusted appropriately to achieve desired drug levels, local or systemic, depending upon the mode of administration. For example, it is expected that intravenous administration would be from one order to several orders of magnitude lower dose per day. In the event that the response in a subject is insufficient at such doses, even higher doses (or effective higher doses by a different, more localized delivery route) may be employed to the extent that patient tolerance permits. Multiple doses per day are contemplated to achieve appropriate systemic levels of the compound.

For any compound described herein the therapeutically effective amount can be initially determined from animal models. A therapeutically effective dose can also be determined from human data for compounds which have been tested in humans and for compounds which are known to exhibit similar pharmacological activities, such as other related active agents. Higher doses may be required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

The formulations of the invention can be administered in pharmaceutically acceptable solutions, which may routinely contain pharmaceutically acceptable concentrations of salt, buffering agents, preservatives, compatible carriers, adjuvants, and optionally other therapeutic ingredients.

For use in therapy, an effective amount of the compound can be administered to a subject by any mode that delivers the compound to the desired surface. Administering a pharmaceutical composition may be accomplished by any means known to the skilled artisan. Routes of administration include but are not limited to intravenous, intramuscular, intraperitoneal, intravesical (urinary bladder), oral, subcutaneous, direct injection (for example, into a tumor or abscess), mucosal (e.g., topical to eye), inhalation, and topical.

For intravenous and other parenteral routes of administration, a compound of the invention can be formulated as a lyophilized preparation, as a lyophilized preparation of liposome-intercalated or -encapsulated active compound, as a lipid complex in aqueous suspension, or as a salt complex. Lyophilized formulations are generally reconstituted in suitable aqueous solution, e.g., in sterile water or saline, shortly prior to administration.

For oral administration, the compounds can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, e.g., EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of acid hydrolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, "Soluble Polymer-Enzyme Adducts", In: Enzymes as Drugs, Hocenberg and Roberts, eds., Wiley-Interscience, New York, N.Y., pp. 367-383 (1981); Newmark et al., J Appl Biochem 4:185-9 (1982). Other polymers that could be used are poly-1,3-dioxolane and poly-1,3,6-tioxocane. For pharmaceutical usage, as indicated above, polyethylene glycol moieties are suitable.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the compound of the invention (or derivative) or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic (e.g., powder); for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the compound of the invention (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, α-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Ho, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents which can be used and can include benzalkonium chloride and benzethonium chloride. Potential non-ionic detergents that could be included in the formulation as surfactants include lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the compound of the invention or derivative either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For topical administration, the compound may be formulated as solutions, gels, ointments, creams, suspensions, etc. as are well-known in the art. Systemic formulations include those designed for administration by injection, e.g., subcutaneous, intravenous, intramuscular, intrathecal or intraperitoneal injection, as well as those designed for transdermal, transmucosal oral or pulmonary administration.

For administration by inhalation, compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

Also contemplated herein is pulmonary delivery of the compounds disclosed herein (or salts thereof). The compound is delivered to the lungs of a mammal while inhaling and traverses across the lung epithelial lining to the blood stream. Other reports of inhaled molecules include Adjei et al., *Pharm Res* 7:565-569 (1990); Adjei et al., *Int J Pharmaceutics* 63:135-144 (1990) (leuprolide acetate); Braquet et al., *J Cardiovasc Pharmacol* 13 (suppl. 5):143-146 (1989) (endothelin-1); Hubbard et al., *Annal Int Med* 3:206-212 (1989) (al-antitrypsin); Smith et al., 1989, *J Clin Invest* 84:1145-1146 (a-1-proteinase); Oswein et al., 1990, "Aerosolization of Proteins", Proceedings of Symposium on Respiratory Drug Delivery II, Keystone, Colo., March, (recombinant human growth hormone); Debs et al., 1988, *J Immunol* 140:3482-3488 (interferon-gamma and tumor necrosis factor alpha) and Platz et al., U.S. Pat. No. 5,284,656 (granulocyte colony stimulating factor; incorporated by reference). A method and composition for pulmonary delivery of drugs for systemic effect is described in U.S. Pat. No. 5,451,569 (incorporated by reference), issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, North Carolina; and the Spinhaler powder inhaler, manufactured by Fisons Corp., Bedford, Mass.

All such devices require the use of formulations suitable for the dispensing of the compounds of the invention. Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified compound of the invention may also be prepared in different formulations depending on the type of chemical modification or the type of device employed.

Formulations suitable for use with a nebulizer, either jet or ultrasonic, will typically comprise a compound of the invention (or derivative) dissolved in water at a concentration of about 0.1 to 25 mg of biologically active compound of the invention per ml_of solution. The formulation may also include a buffer and a simple sugar (e.g., for inhibitor stabilization and regulation of osmotic pressure). The nebulizer formulation may also contain a surfactant, to reduce or prevent surface induced aggregation of the compound of the invention caused by atomization of the solution in forming the aerosol.

Formulations for use with a metered-dose inhaler device will generally comprise a finely divided powder containing the compound of the invention (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing compound of the invention (or derivative) and may also include a bulking agent, such as lactose, sorbitol, sucrose, or mannitol in amounts which facilitate dispersal of the powder from the device, e.g., 50 to 90% by weight of the formulation. The compound of the invention (or derivative) should advantageously be prepared in particulate form with an average particle size of less than 10 micrometers (µm), most preferably 0.5 to 5 µm, for most effective delivery to the deep lung.

Nasal delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethylcellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described above, a compound may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer R, *Science* 249:1527-33 (1990).

The compound of the invention and optionally other therapeutics may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

Pharmaceutical compositions of the invention contain an effective amount of a compound as described herein and optionally therapeutic agents included in a pharmaceutically acceptable carrier. The term "pharmaceutically acceptable carrier" means one or more compatible solid or liquid filler, diluents or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

The therapeutic agent(s), including specifically but not limited to a compound of the invention, may be provided in particles. Particles as used herein means nanoparticles or microparticles (or in some instances larger particles) which can consist in whole or in part of the compound of the invention or the other therapeutic agent(s) as described herein. The particles may contain the therapeutic agent(s) in a core surrounded by a coating, including, but not limited to, an enteric coating. The therapeutic agent(s) also may be dispersed throughout the particles. The therapeutic agent(s) also may be adsorbed into the particles. The particles may be of any order release kinetics, including zero-order release, first-order release, second-order release, delayed release, sustained release, immediate release, and any combination thereof, etc. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules which contain the compound of the invention in a solution or in a semi-solid state. The particles may be of virtually any shape.

Both non-biodegradable and biodegradable polymeric materials can be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels described in Sawhney H S et al. (1993) *Macromolecules* 26:581-7, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) may be contained in controlled release systems. The term "controlled release" is intended to refer to any drug-containing formulation in which the manner and profile of drug release from the formulation are controlled. This refers to immediate as well as non-immediate release formulations, with non-immediate release formulations including but not limited to sustained release and delayed release formulations. The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the drug there from. "Delayed release" may or may not involve gradual release of drug over an extended period of time, and thus may or may not be "sustained release."

Use of a long-term sustained release implant may be particularly suitable for treatment of chronic conditions. "Long-term" release, as used herein, means that the implant is constructed and arranged to deliver therapeutic levels of the active ingredient for at least 7 days, and preferably 30-60 days. Long-term sustained release implants are well-known to those of ordinary skill in the art and include some of the release systems described above.

It will be understood by one of ordinary skill in the relevant arts that other suitable modifications and adaptations to the compositions and methods described herein are readily apparent from the description of the invention contained herein in view of information known to the ordinarily skilled artisan, and may be made without departing from the scope of the invention or any embodiment thereof. Having now described the present invention in detail, the same will be more clearly understood by reference to the following examples, which are included herewith for purposes of illustration only and are not intended to be limiting of the invention.

Methods of Use

The present invention provides non-natural tripeptide compounds that are useful for treating or preventing ischemia-reperfusion injury or myocardial infarction, or injury associated with myocardial infarction.

Accordingly, in certain embodiments, the invention is directed to a method of treating or preventing ischemia-reperfusion injury, comprising administering to a subject in need thereof a therapeutically effective amount of a compound of formula (I), described herein, or a pharmaceutically acceptable salt thereof. In certain such embodiments, the ischemia-reperfusion injury is cardiac ischemia-reperfusion injury. In some embodiments, the compound is administered orally, topically, systemically, intravenously, subcutaneously, intraperitoneally, or intramuscularly.

In other embodiments, the present invention provides a method for treating or preventing a myocardial infarction, comprising administering to a subject in need thereof a therapeutically effective amount of compound of formula (I), or a pharmaceutically acceptable salt thereof. Such methods may prevent injury to the heart upon reperfusion by preventing the initiation or progression of the infarction. In some embodiments, the compound is administered orally, topically, systemically, intravenously, subcutaneously, intraperitoneally, or intramuscularly.

Ischemia is reduction or decrease in blood supply to a tissue or an organ and has many different causes. Ischemia may be local, e.g., caused by thrombus or embolus, or more global, e.g., due to low perfusion pressure. An ischemic event can lead to hypoxia (reduced oxygen) and/or anoxia (absence of oxygen).

Ischemia in a tissue or organ of a mammal is a multifaceted pathological condition that is caused by oxygen deprivation (hypoxia) and/or glucose (e.g., substrate) deprivation. Oxygen and/or glucose deprivation in cells of a tissue or organ leads to a reduction or total loss of energy generating capacity and consequent loss of function of active ion transport across the cell membranes. Oxygen and/or glucose deprivation also leads to pathological changes in other cell membranes, including permeability transition in the mitochondrial membranes. In addition, other molecules, such as apoptotic proteins normally compartmentalized within the mitochondria, may leak out into the cytoplasm and cause apoptotic cell death. Profound ischemia can lead to necrotic cell death.

Ischemia or hypoxia in a particular tissue or organ may be caused by a loss or severe reduction in blood supply to the tissue or organ. The loss or severe reduction in blood supply may, for example, be due to thromboembolic stroke, coronary atherosclerosis, or peripheral vascular disease. The tissue affected by ischemia or hypoxia is typically muscle, such as cardiac, skeletal, or smooth muscle.

The organ affected by ischemia or hypoxia may be any organ that is subject to ischemia or hypoxia. By way of example, but not by way of limitation, cardiac muscle ischemia or hypoxia is commonly caused by atherosclerotic or thrombotic blockages, which lead to the reduction or loss of oxygen delivery to the cardiac tissues by the cardiac arterial and capillary blood supply. Such cardiac ischemia or hypoxia may cause pain and necrosis of the affected cardiac muscle, and ultimately may lead to cardiac failure.

Reperfusion is the restoration of blood flow to any organ or tissue in which the flow of blood is decreased or blocked. For example, blood flow can be restored to any organ or tissue affected by ischemia. The restoration of blood flow (reperfusion) can occur by any method known to those in the art. For instance, reperfusion of ischemic cardiac tissues may arise from angioplasty, coronary artery bypass graft, or the use of thrombolytic drugs.

Ischemia-reperfusion injury is the cellular or tissue damage caused when blood supply returns to the affected area after a period of ischemia. The lack of oxygen and nutrients during ischemia creates a condition in which the restoration of circulation results damage to the tissues. By way of example, but not by way of limitation, forms of myocardial reperfusion injury including reperfusion-induced arrhythmias, myocardial stunning, microvascular obstruction manifesting in sluggish coronary blood flow, and lethal myocardial reperfusion injury (i.e., reperfusion-induced death of cardiomyocytes that were viable at the end of the index ischemic event). Studies have suggested that lethal myocardial reperfusion injury accounts for about 50% of the final myocardial infarct size.

In certain embodiments, the peptide is administered orally, intravenously, or parenterally.

In certain embodiments, the subject is a human.

A non-natural tripeptide compound of the invention, or a pharmaceutically acceptable salt thereof, such as acetate, tartrate, or trifluoroacetate salt, may be administered to a subject suspected of, or already suffering from ischemic injury in an amount sufficient to cure, or at least partially arrest, the symptoms of the disease, including its complications and intermediate pathological phenotypes in development of the disease. Subjects suffering from ischemic injury can be identified by any or a combination of diagnostic or prognostic assays known in the art. By way of example, but not by way of limitation, in some embodiments, the ischemic injury is related to cardiac ischemia, brain ischemia, renal ischemia, cerebral ischemia, intestinal ischemia, hepatic ischemia, or myocardial infarction.

By way of example, but not by way of limitation, typical symptoms of cardiac ischemia include, but are not limited to, angina (e.g., chest pain and pressure), shortness of breath, palpitations, weakness, dizziness, nausea, sweating, rapid heartbeat, and fatigue.

In some embodiments, treatment of subjects diagnosed with cardiac ischemia with at least one peptide disclosed herein ameliorates or eliminates of one or more of the following symptoms of cardiac ischemia: angina (e.g., chest pain and pressure), shortness of breath, palpitations, weakness, dizziness, nausea, sweating, rapid heartbeat, and fatigue.

By way of example, but not by way of limitation, typical symptoms of renal ischemia include, but are not limited to, uremia (i.e., high blood levels of protein by-products, such as, e.g., urea), acute episodes of dyspnea (labored or difficult breathing) caused by sudden accumulation of fluid in the lungs, hypertension, pain felt near the kidneys, weakness, hypertension, nausea, a history of leg pain, a stride that reflects compromised circulation to the legs, and bruits (sound or murmurs heard with a stethoscope) caused by turbulent blood flow within the arteries may be detected in the neck (e.g., carotid artery bruit), abdomen (which may reflect narrowing of the renal artery), and groin (femoral artery bruit).

In some embodiments, treatment of subjects diagnosed with renal ischemia with at least one peptide disclosed herein ameliorates or eliminates of one or more of the following symptoms of renal ischemia: uremia (i.e., high blood levels of protein by-products, such as, e.g., urea), acute episodes of dyspnea (labored or difficult breathing) caused by sudden accumulation of fluid in the lungs, hypertension, pain felt near the kidneys, weakness, hypertension, nausea, a history of leg pain, a stride that reflects compromised circulation to the legs, and bruits (sound or murmurs heard with a stethoscope) caused by turbulent blood flow within the arteries may be detected in the neck (e.g., carotid artery bruit), abdomen (which may reflect narrowing of the renal artery), and groin (femoral artery bruit).

By way of example, but not by way of limitation, typical symptoms of cerebral (or brain) ischemia include, but are not limited to, blindness in one eye, weakness in one arm or leg, weakness in one entire side of the body, dizziness, vertigo, double vision, weakness on both sides of the body, difficulty speaking, slurred speech, and the loss of coordination.

In some embodiments, treatment of subjects diagnosed with cerebral (or brain) ischemia with at least one peptide disclosed herein ameliorates or eliminates of one or more of the following symptoms of cerebral (or brain) ischemia: blindness in one eye, weakness in one arm or leg, weakness in one entire side of the body, dizziness, vertigo, double vision, weakness on both sides of the body, difficulty speaking, slurred speech, and the loss of coordination.

In another aspect, the present invention relates to methods of treating ischemia reperfusion injury and/or side effects associated with existing therapeutics against ischemia reperfusion injury. In therapeutic applications, a composition or medicament comprising at least one compound of the invention, or a pharmaceutically acceptable salt thereof, such as acetate, tartrate or trifluoroacetate, is administered to a subject suspected of, or already suffering from ischemic reperfusion injury in an amount sufficient to cure, or at least partially arrest, the symptoms of the disease, including its complications and intermediate pathological phenotypes in development of the disease. Subjects suffering from ischemic-reperfusion injury can be identified by any or a combination of diagnostic or prognostic assays known in the art. In some embodiments, the ischemia-reperfusion injury is related to cardiac ischemia, brain ischemia, renal ischemia, cerebral ischemia, intestinal ischemia, and hepatic ischemia. In some embodiments, the compounds disclosed herein are useful in the treatment of cardiac ischemia-reperfusion injury.

In some embodiments, the cyclic peptide compounds disclosed herein are useful in treating myocardial infarction in a subject to prevent injury to the heart upon reperfusion. In some embodiments, the invention relates to methods of coronary revascularization, comprising administering to a mammalian subject a therapeutically effective amount of a compound of the invention, or a pharmaceutically acceptable salt thereof, and performing a coronary artery bypass graft (CABG) procedure on the subject.

In some embodiments, treatment of myocardial infarction with the compounds disclosed herein reduces infarct size, increases LVDP, and increases maximal rates of contraction and relaxation (±dP/dt).

In still yet further embodiments, the invention provides a method for treating or preventing hind limb or critical limb ischemia in a subject in need thereof, comprising administering to the subject a therapeutically effective amount of a compound of the invention.

In any of the foregoing embodiments, the compound of the invention may be administered orally, topically, systemically, intravenously, subcutaneously, intraperitoneally, or intramuscularly.

Prophylactic Methods

In some embodiments, the present invention provides methods for preventing or delaying the onset of ischemic injury or symptoms of ischemic injury in a subject at risk of having ischemia injury. In some embodiments, the present technology provides methods for preventing or reducing the symptoms of ischemic injury in a subject at risk of having ischemia injury.

In some embodiments, the present invention provides methods for preventing or delaying the onset of ischemia-reperfusion injury or symptoms of ischemia-reperfusion injury in a subject at risk of having ischemia-reperfusion injury. In some embodiments, the present invention provides methods for preventing or reducing the symptoms of ischemia reperfusion injury in a subject at risk of having ischemia-reperfusion injury.

In some embodiments, the ischemic injury, the ischemia-reperfusion injury, or symptoms of ischemic or ischemia-reperfusion injury is related to cardiac ischemia, brain ischemia, renal ischemia, cerebral ischemia, intestinal ischemia, and hepatic ischemia. In some embodiments, the ischemic injury is myocardial infarction.

In some embodiments, the cyclic peptide compounds disclosed herein are useful in the treatment or prevention of cardiac ischemia-reperfusion injury. In some embodiments, the compounds disclosed herein are useful in the prevention of cardiac ischemia-reperfusion injury.

Subjects at risk for ischemic injury or ischemia-reperfusion injury can be identified by, e.g., any or a combination of diagnostic or prognostic assays known in the art. In prophylactic applications, a pharmaceutical composition or medicament of a compound of the invention, or a pharmaceutically acceptable salt thereof, such as acetate, tartrate, or trifluoroacetate salt, is administered to a subject susceptible to, or otherwise at risk of for ischemic injury or ischemia reperfusion injury in an amount sufficient to eliminate, reduce the risk, or delay the onset of the disease, including biochemical, histologic and/or behavioral symptoms of the disease, its complications and intermediate pathological phenotypes presenting during development of the disease or reduce the symptoms and/or complications and intermediate pathological phenotypes presenting during development of the disease. Administration of a prophylactic peptide can occur prior to the manifestation of symptoms characteristic of the disease or disorder, such that the disease or disorder is prevented, delayed in its progression, or the severity of the symptoms or side effects of the disease or disorder are reduced.

By way of example, in some embodiments, subjects may be at risk for cardiac ischemia if they have coronary artery disease (atherosclerosis), blood clots, or coronary artery spasm.

By way of example, but not by way of limitation, in some embodiments, subjects may be at risk for renal ischemia if they have kidney injury (e.g., acute kidney injury) and/or injuries or complications from surgeries in which the kidneys are deprived of normal blood flow for extended periods of time (e.g., heart-bypass surgery).

By way of example, but not by way of limitation, in some embodiments, subjects may be at risk for cerebral ischemia if they have sickle cell anemia, compressed blood vessels, ventricular tachycardia, plaque buildup in the arteries, blood clots, extremely low blood pressure as a result of heart attack, had a stroke, or congenital heart defects.

For therapeutic and/or prophylactic applications, a composition comprising at least one cyclic peptide compound described herein, or a pharmaceutically acceptable salt thereof, such as acetate, tartrate, or trifluoroacetate salt, is administered to a subject in need thereof. In some embodiments, the peptide composition is administered one, two, three, four, or five times per day. In some embodiments, the peptide composition is administered more than five times per day. Additionally or alternatively, in some embodiments, the peptide composition is administered every day, every other day, every third day, every fourth day, every fifth day, or every sixth day. In some embodiments, the peptide composition is administered weekly, bi-weekly, tri-weekly, or monthly. In some embodiments, the peptide composition is administered for a period of one, two, three, four, or five weeks. In some embodiments, the peptide is administered for six weeks or more. In some embodiments, the peptide is administered for twelve weeks or more. In some embodiments, the peptide is administered for a period of less than one year. In some embodiments, the peptide is administered for a period of more than one year. In some embodiments, treatment with at least one peptide disclosed herein will prevent or delay the onset of one or more of the following symptoms of cardiac ischemia: angina (e.g., chest pain and pressure), shortness of breath, palpitations, weakness, dizziness, nausea, sweating, rapid heartbeat, and fatigue.

In some embodiments, treatment with at least one peptide disclosed herein will prevent or delay the onset of one or more of the following symptoms of renal ischemia: uremia (i.e., high blood levels of protein by-products, such as, e.g., urea), acute episodes of dyspnea (labored or difficult breathing) caused by sudden accumulation of fluid in the lungs, hypertension, pain felt near the kidneys, weakness, hypertension, nausea, a history of leg pain, a stride that reflects compromised circulation to the legs, and bruits (sound or murmurs heard with a stethoscope) caused by turbulent blood flow within the arteries may be detected in the neck (e.g., carotid artery bruit), abdomen (which may reflect narrowing of the renal artery), and groin (femoral artery bruit).

In some embodiments, treatment with at least one peptide disclosed herein will prevent or delay the onset of one or more of the following symptoms of cerebral (or brain) ischemia: blindness in one eye, weakness in one arm or leg, weakness in one entire side of the body, dizziness, vertigo, double vision, weakness on both sides of the body, difficulty speaking, slurred speech, and the loss of coordination.

EXAMPLES

General Procedures for Synthesis of Peptidomimetics

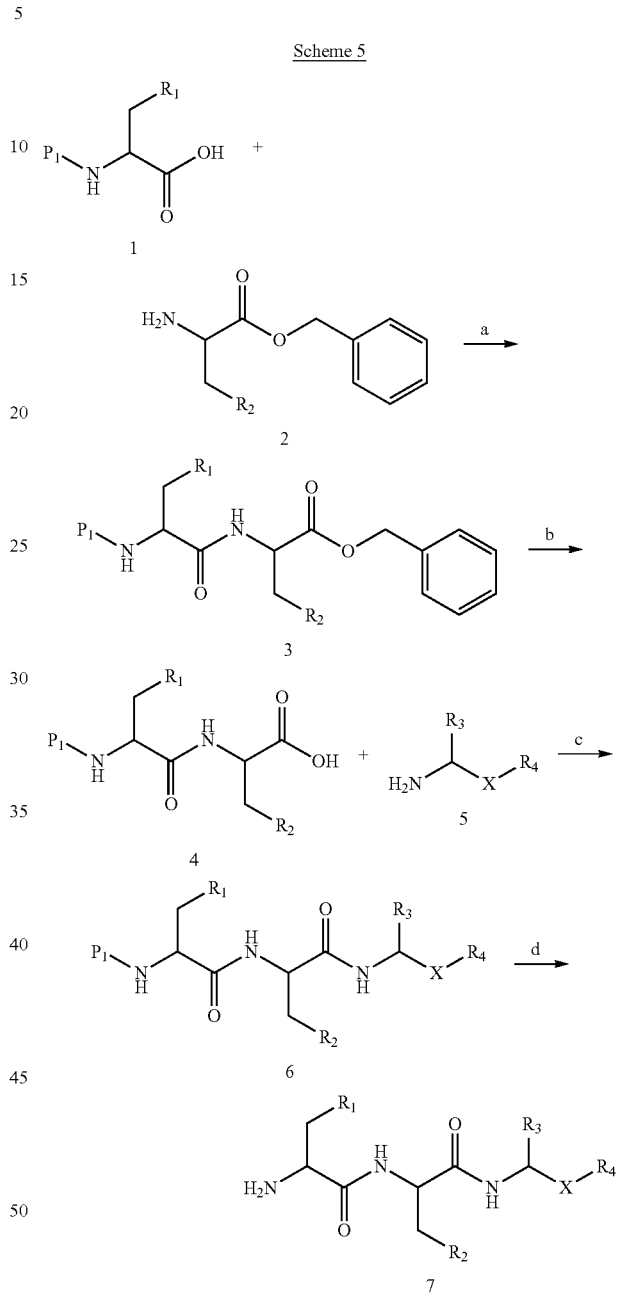

General Procedure for Synthesis of 1,2,4-Oxadiazole Components

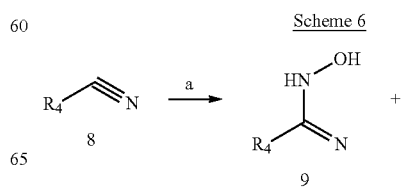

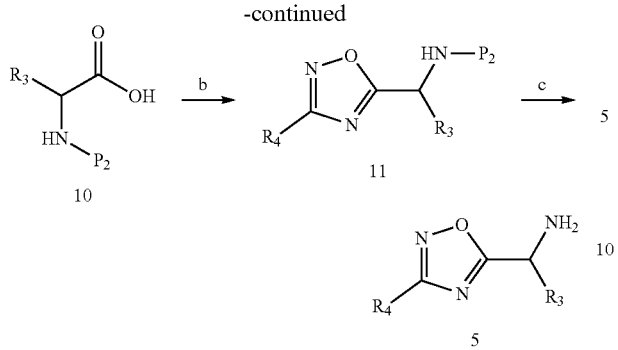

a) HONH$_2$; b) T$_3$P/NaHCO$_3$; c) TEA

1) Step a: Synthesis of N-hydroxyimidamide 9:

To a solution of nitrile 8 (1.0 mol) in EtOH (1.2 L) was added NH$_2$OH (50% aqueous solution, 130 g, 2.0 mol), the solution was heated to reflux and stirred for 12 hrs. After completion, the reaction mixture was concentrated under reduced pressure. The resulting residue was re-dissolved in EtOH (350 mL) and concentrated under reduced pressure again (this procedure was repeated three times). The resulting solid was triturated in hexane (350 mL), filtered and washed with hexane (100 mL), dried to give the desired product 9 as white solid.

2) Step b: Cyclization of 1,2,4-oxadiazole heterocycle 11:

To a solution of protected enantiomerically pure amino-acid 10 (0.50 mol) and hydroxyimidamide 9 (0.55 mol, 1.1 equiv.) in ethyl acetate (2.30 L) was added NaHCO$_3$ (1.5 mol, 3.0 equiv.). The mixture was stirred at 25° C. for 20 min, Propane phosphonic acid anhydride (T$_3$P, 50% solution in ethyl acetate, 1.5 mol, 3.0 equiv.) was added and then the reaction mixture was heated to 80° C. and stirred for 4 hr (about 60% conversion of compound 10 based on HPLC). Then compound 9 (0.55 mol, 1.1 equiv.) was added and the reaction mixture was stirred at 80° C. for another 20 hr (about 10% compound 10 remained). The reaction mixture was cooled to room temperature, saturated aqueous NaHCO$_3$ (2.0 L) was added, extracted with ethyl acetate (3×1.0 L), the combined organic layers were washed with brine (1 L), dried over anhydrous Na$_2$SO$_4$. Filtered and concentrated to give a crude residue, which was purified by silica gel column chromatography (PE: EtOAc=5:1) to give compound 11.

Step c: Deprotection to Produce the Final 1,2,4-Oxadiazole:

To a solution of compound 11 in ACN (0.4 mol) was added TEA (1.0 mol). The mixture was kept stirring with mechanical stirrer at 20~25° C. for 15 h. The reaction mixture was diluted by tap water and MTBE. Separated, aqueous layer was extracted by MTBE for one time. Both MTBE layers were combined, and then washed by NH$_4$Cl and NH$_4$Cl. Then anhydrous Na$_2$SO$_4$ was added and that solution stirred for least 2 h, then filtered and washed with MTBE to afford 5.

References:

a) Moussebois, Claude; Heremans, Joseph F.; Merenyi, Robert; Rennerts, Walthere: *Synthesis of two new phenolic amino acids containing the 1,2,4-oxadiazole ring*, Helvetica Chimica Acta Vol. 60(1), 237-42, 1977;

b) Borg, Susanna; Estenne-Bouhtou, Genevieve; Luthman, Kristina; Csoeregh, Ingeborg; Hesselink, Willy; Hacksell, Uli: *Synthesis of 1,2,4-Oxadiazole-, 1,3,4-Oxadiazole-, and 1,2,4-Triazole-Derived Dipeptidomimetics*, Journal of Organic Chemistry, Vol. 60(10), 3112-20, 1995;

Example 1: Synthesis of (S)-1-(3-Benzyl-1,2,4-oxadiazol-5-yl)-5-((tert-Butoxycarbonyl)amino)pentan-1-Aminium 4-Methylbenzenesulfonate (12a)

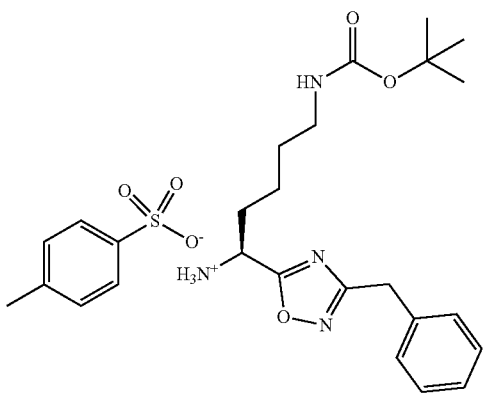

Compound 12a

Scheme 7

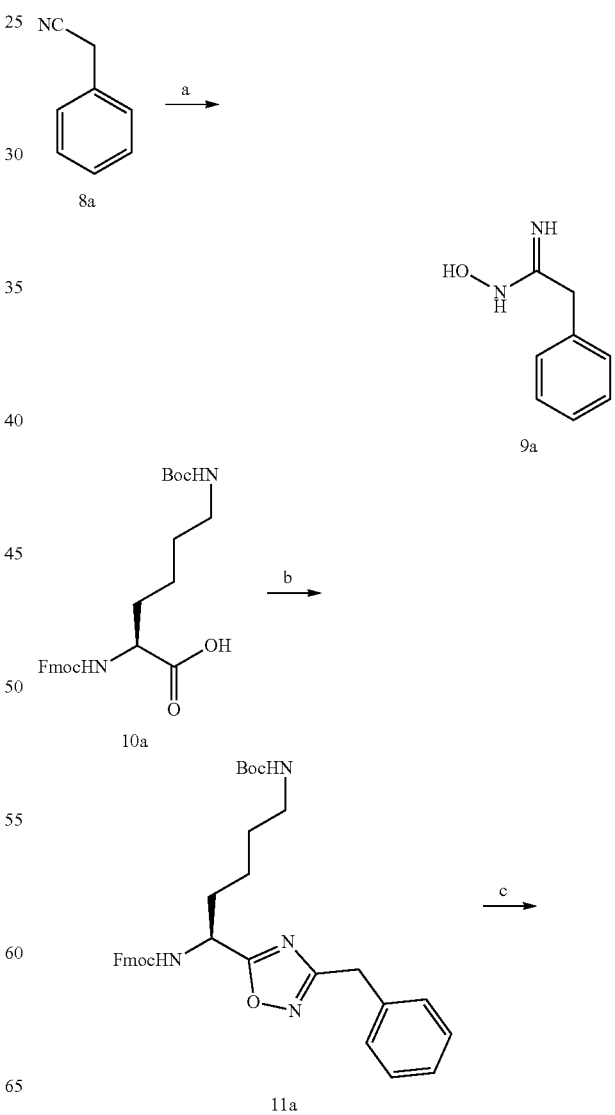

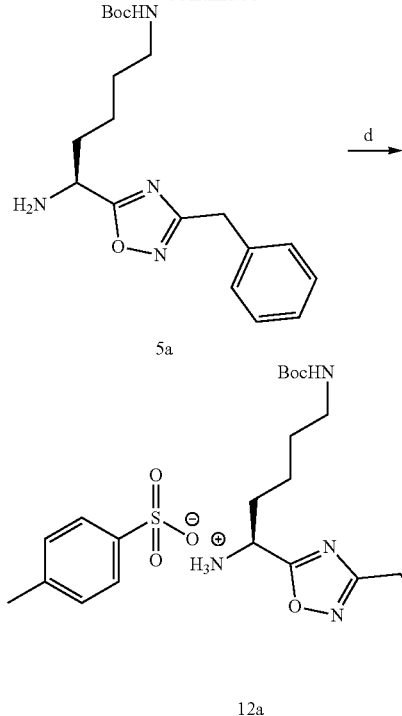

5a

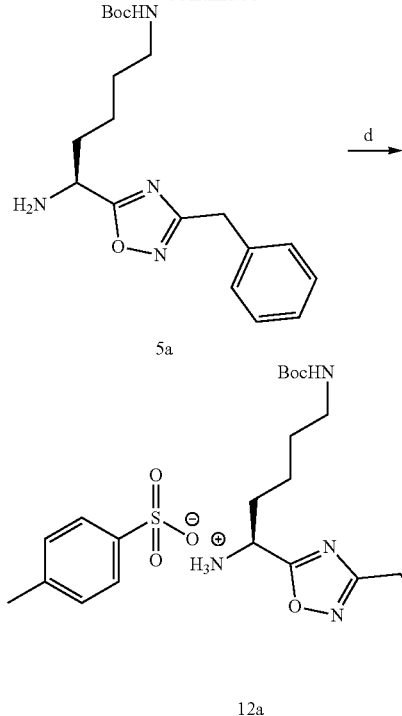

12a

1) Step a: NH₂OH; Step b: T₃P, NaHCO₃; Step c: TEA; Step d: PTSA

1) Step a: Synthesis of N-hydroxy-2-phenylacetimidamide (9a)

The same procedure as described in general procedure of Scheme 6 using 2-phenylacetonitrile (8a, 2 kg, 17.1 mol) to afford a solution of intermediate N-hydroxy-2-phenylacetimidamide (9a) in IPAC (10.5 kg; KF=1295) with good results (purity by HPLC, >98.9 A %; Assay=22.2 w %, yield=91%).

$^1$H NMR (300 MHz, DMSO-$d_6$): δ8.90 (s, 1H), 7.28-7.18 (m, 5H), 5.40 (s, 2H), 3.25 (s, 2H) ppm. MS: (M+H)$^+$: m/z=151.1

2) Step b: Synthesis of (9H-Fluoren-9-yl)methyl tert-Butyl (1-(3-Benzyl-1,2,4-oxadiazol-5-yl)pentane-1,5-diyl) (S)-Dicarbamate (11a)

The same procedure as described in Scheme 6 by using N2-(((9H-fluoren-9-yl)methoxy)carbonyl)-N6-(tert-butoxycarbonyl)-L-lysine (10a, 4.31 kg, 9.2 mol) to gain crude product, (9H-fluoren-9-yl)methyl tert-butyl (1-(3-benzyl-1,2,4-oxadiazol-5-yl)pentane-1,5-diyl) (S)-dicarbamate (11a), solution in ACN (19.7 kg, assay=20%, chiral HPLC purity=99.12 A %, yield=73%).

$^1$H NMR (300 MHz, CDCl₃): δ7.78 (d, J=7.5 Hz, 2H), 7.61 (d, J=6.3 Hz, 2H), 7.42 (t, J=7.5 Hz, 2H), 7.35-7.30 (m, 7H), 5.52 (br, 1H), 5.09-5.05 (m, 1H), 4.56-4.37 (m, 3H), 4.22 (t, J=6.6 Hz, 1H), 4.08 (s, 2H), 1.95-1.86 (m, 2H), 1.48-1.42 (m, 11H) ppm. MS: (M-100+H)$^+$: m/z=483.2.

3) Step c: Synthesis of tert-Butyl (S)-(5-Amino-5-(3-Benzyl-1,2,4-oxadiazol-5-yl)pentyl)-carbamate (5a)

The same procedure as described in Scheme 6 by using compound (9H-fluoren-9-yl)methyl tert-butyl (1-(3-benzyl-1,2,4-oxadiazol-5-yl)pentane-1,5-diyl) (S)-dicarbamate (11a) to afford crude tert-butyl (S)-(5-amino-5-(3-benzyl-1,2,4-oxadiazol-5-yl)pentyl)-carbamate (5) solution in MTBE (32.9 kg, assay=6.5%, yield=88%).

$^1$H NMR (300 MHz, DMSO-$d_6$): 7.33-7.25 (m, 5H), 6.78 (br, 1H), 5.09-5.05 (m, 1H), 4.56-4.37 (m, 3H), 4.06 (s, 2H), 3.98 (t, J=6.6 Hz, 1H), 2.87-2.84 (m, 2H), 2.10 (s, 2H), 1.38-1.34 (m, 2H), 1.24 (s, 9H), 1.20-1.15 (m, 2H) ppm. MS: (M+H)$^+$: m/z=361.1.

4) Step d: Synthesis of (S)-1-(3-Benzyl-1,2,4-oxadiazol-5-yl)-5-((tert-Butoxycarbonyl)-amino)pentan-1-Aminium 4-Methylbenzenesulfonate (12a)

The same procedure as described in Scheme 6 by using a solution of crude tert-butyl (S)-(5-amino-5-(3-benzyl-1,2,4-oxadiazol-5-yl)pentyl)-carbamate (5a) and PTSA (1.07 kg, 5.63 mol) to afford (S)-1-(3-benzyl-1,2,4-oxadiazol-5-yl)-5-((tert-butoxycarbonyl)amino)pentan-1-aminium 4-methylbenzenesulfonate (12a) (2.7 kg, yield=85%, HPLC purity>99%, ee>99%) as white solid.

$^1$H NMR (400 MHz, DMSO-$d_6$): δ8.74 (br, 3H), 7.48 (d, J=8.0 Hz, 2H), 7.37-7.26 (m, 5H), 7.11 (d, J=8.0 Hz, 2H), 6.77 (t, J=5.2 Hz, 1H), 4.82 (t, J=6.8 Hz, 1H), 4,17 (s, 2H), 2.90-2.86 (m, 2H), 2.29 (s, 3H), 1.39-1.36 (m, 11H), 1.35-1.28 (m, 2H) ppm. MS: (M-172+H)$^+$: m/z=361.1.

Example 2: Synthesis of (S)-tert-butyl (5-(3-([1,1'-biphenyl]-4-ylmethyl)-1,2,4-oxadiazol-5-yl)-5-aminopentyl)carbamate acetate (12b)

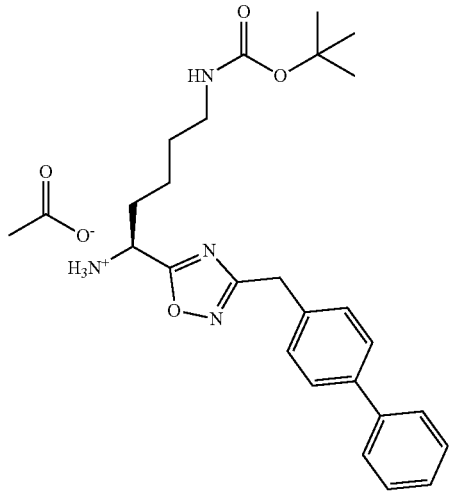

Compound 12b

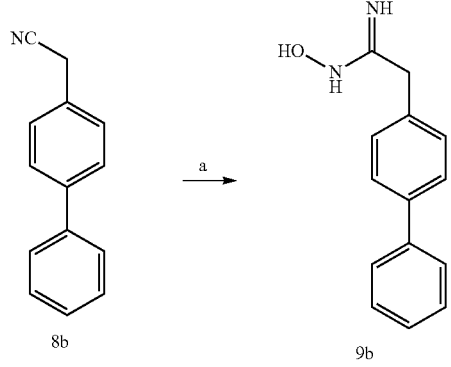

Scheme 8

8b        9b

-continued

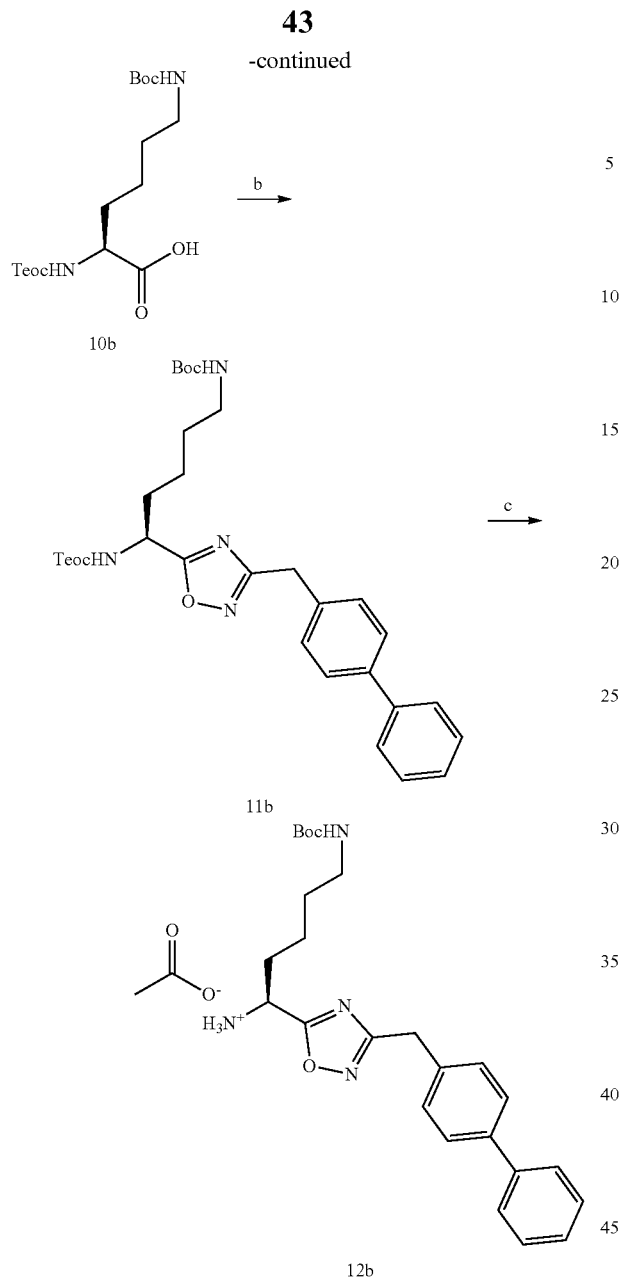

1) Step a: Synthesis of 2-([1,1'-biphenyl]-4-yl)-N'-hydroxyacetimidamide (9b)
The same procedure as described in general procedure of Scheme 6 using 2-([1,1'-biphenyl]-4-yl)acetonitrile (8b, 3.00 g, 15.5 mmol) to afford 2-([1,1'-biphenyl]-4-yl)-N-hydroxyacetimidamide (9a) (2.4 g) in 68% yield.

$^1$H NMR (DMSO-$d_6$, 300 MHz): δ=9.10 (br s, 1H), 7.67-7.54 (m, 4H), 7.49-7.41 (m, 2H), 7.41-7.30 (m, 3H), 5.76 ppm (br s, 2H).

2) Step b: Synthesis of (S)-tert-butyl (2-(trimethylsilyl)ethyl) (1-(3-([1,1'-biphenyl]-4-ylmethyl)-1,2,4-oxadiazol-5-yl)pentane-1,5-diyl)dicarbamate (11b)
The same procedure as described in Scheme 6 by using (S)-6-((tert-butoxycarbonyl)amino)-2-(((2-(trimethylsilyl)ethoxy)carbonyl)amino)hexanoic acid (10b, 391 mg, 1.0 mmol) to gain crude product, (S)-tert-butyl (2-(trimethylsilyl)ethyl) (1-(3-([1,1'-biphenyl]-4-ylmethyl)-1,2,4-oxadiazol-5-yl)pentane-1,5-diyl)dicarbamate (11b, 295 mg, 51%) as colorless glass-like solid.

$^1$H NMR (CDCl$_3$, 300 MHz): δ=7.61-7.52 (m, 4H), 7.47-7.30 (m, 5H), 5.33-5.20 (m, 1H), 5.12-4.98 (m, 1H), 4.52 (br s, 1H), 4.21-4.12 (m, 2H), 4.10 (s, 2H), 3.16-3.00 (m, 2H), 2.02-1.77 (m, 2H), 1.54-1.33 (m, 4H), 1.43 (s, 9H), 1.02-0.92 (m, 2H), 0.02 ppm (s, 9H).

3) Step c: Synthesis of (S)-tert-butyl (5-(3-([1,1'-biphenyl]-4-ylmethyl)-1,2,4-oxadiazol-5-yl)-5-aminopentyl)carbamate acetate (12b)

To a solution of (S)-tert-butyl (2-(trimethylsilyl)ethyl) (1-(3-([1,1'-biphenyl]-4-ylmethyl)-1,2,4-oxadiazol-5-yl)pentane-1,5-diyl)dicarbamate (11b, 290 mg, 0.508 mmol) in dry THF (10 mL) (cooled in ice/water bath) TBAF (1 M in THF, 0.76 mL, 0.762 mmol) was added dropwise and the reaction mixture was stirred at r.t. for 20 h. The reaction mixture was cooled in ice/water bath and additional TBAF (1 M in THF, 0.25 mL, 0.254 mmol) was added dropwise. The resulting mixture was stirred at r.t. for 6 h and quenched with solution of AcOH (0.2 mL) in THF (30 mL) while cooled in ice bath. The volatile matters were removed under reduced pressure and the crude product was purified by reversed phase flash chromatography using a mixture of MeOH and 0.1% solution of AcOH in water as an eluent. The product came out of the column at 70% of MeOH to give desired product 12b (221 mg) in 88% yield.

$^1$H NMR (CD$_3$OD, 300 MHz): δ=7.61-7.52 (m, 4H), 7.46-7.27 (m, 5H), 4.41-4.30 (m, 1H), 4.13 (s, 2H), 3.01 (t, 2H, $^3J_{(H,H)}$=6.6 Hz), 1.98-1.83 (m, 2H), 1.54-1.27 (m, 4H), 1.41 ppm (s, 9H).

Example 3: Synthesis of (S)-tert-butyl (5-amino-5-(3-(4-(tert-butyl)benzyl)-1,2,4-oxadiazol-5-yl)pentyl)carbamate (5c)

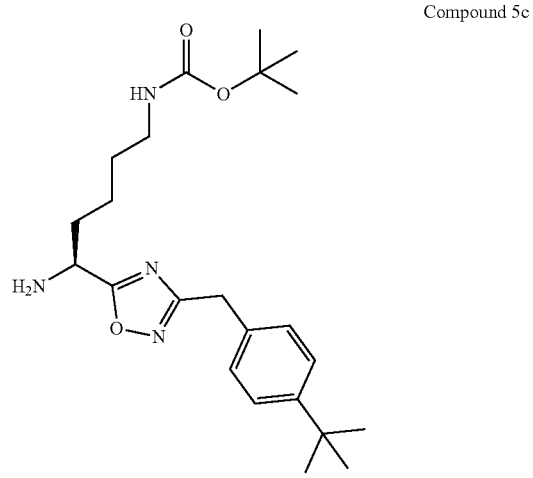

Compound 5c

Scheme 9

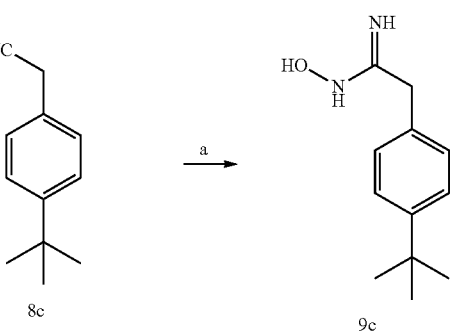

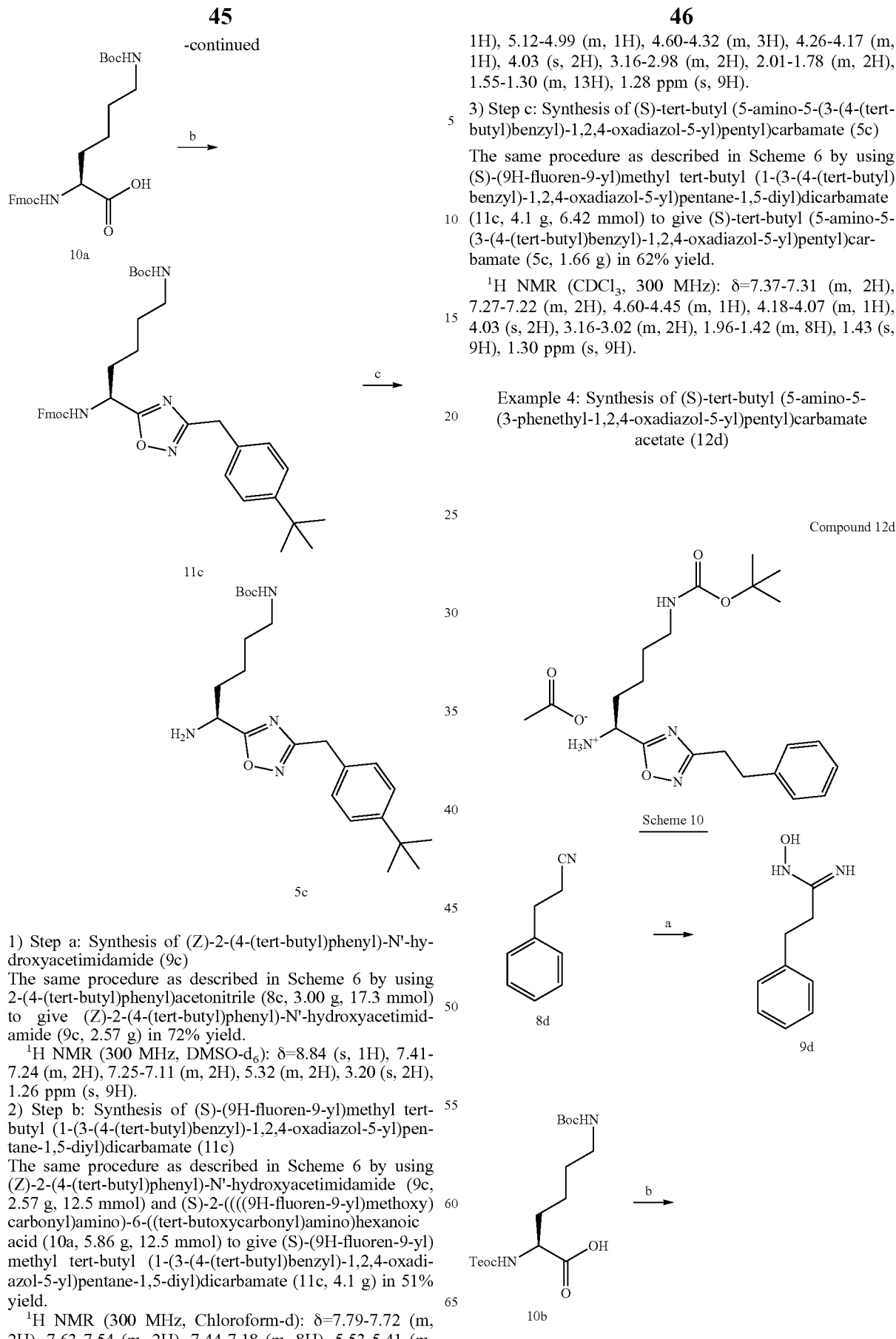

1H), 5.12-4.99 (m, 1H), 4.60-4.32 (m, 3H), 4.26-4.17 (m, 1H), 4.03 (s, 2H), 3.16-2.98 (m, 2H), 2.01-1.78 (m, 2H), 1.55-1.30 (m, 13H), 1.28 ppm (s, 9H).

3) Step c: Synthesis of (S)-tert-butyl (5-amino-5-(3-(4-(tert-butyl)benzyl)-1,2,4-oxadiazol-5-yl)pentyl)carbamate (5c)

The same procedure as described in Scheme 6 by using (S)-(9H-fluoren-9-yl)methyl tert-butyl (1-(3-(4-(tert-butyl)benzyl)-1,2,4-oxadiazol-5-yl)pentane-1,5-diyl)dicarbamate (11c, 4.1 g, 6.42 mmol) to give (S)-tert-butyl (5-amino-5-(3-(4-(tert-butyl)benzyl)-1,2,4-oxadiazol-5-yl)pentyl)carbamate (5c, 1.66 g) in 62% yield.

$^1$H NMR (CDCl$_3$, 300 MHz): δ=7.37-7.31 (m, 2H), 7.27-7.22 (m, 2H), 4.60-4.45 (m, 1H), 4.18-4.07 (m, 1H), 4.03 (s, 2H), 3.16-3.02 (m, 2H), 1.96-1.42 (m, 8H), 1.43 (s, 9H), 1.30 ppm (s, 9H).

Example 4: Synthesis of (S)-tert-butyl (5-amino-5-(3-phenethyl-1,2,4-oxadiazol-5-yl)pentyl)carbamate acetate (12d)

1) Step a: Synthesis of (Z)-2-(4-(tert-butyl)phenyl)-N'-hydroxyacetimidamide (9c)

The same procedure as described in Scheme 6 by using 2-(4-(tert-butyl)phenyl)acetonitrile (8c, 3.00 g, 17.3 mmol) to give (Z)-2-(4-(tert-butyl)phenyl)-N'-hydroxyacetimidamide (9c, 2.57 g) in 72% yield.

$^1$H NMR (300 MHz, DMSO-d$_6$): δ=8.84 (s, 1H), 7.41-7.24 (m, 2H), 7.25-7.11 (m, 2H), 5.32 (m, 2H), 3.20 (s, 2H), 1.26 ppm (s, 9H).

2) Step b: Synthesis of (S)-(9H-fluoren-9-yl)methyl tert-butyl (1-(3-(4-(tert-butyl)benzyl)-1,2,4-oxadiazol-5-yl)pentane-1,5-diyl)dicarbamate (11c)

The same procedure as described in Scheme 6 by using (Z)-2-(4-(tert-butyl)phenyl)-N'-hydroxyacetimidamide (9c, 2.57 g, 12.5 mmol) and (S)-2-((((9H-fluoren-9-yl)methoxy)carbonyl)amino)-6-((tert-butoxycarbonyl)amino)hexanoic acid (10a, 5.86 g, 12.5 mmol) to give (S)-(9H-fluoren-9-yl)methyl tert-butyl (1-(3-(4-(tert-butyl)benzyl)-1,2,4-oxadiazol-5-yl)pentane-1,5-diyl)dicarbamate (11c, 4.1 g) in 51% yield.

$^1$H NMR (300 MHz, Chloroform-d): δ=7.79-7.72 (m, 2H), 7.63-7.54 (m, 2H), 7.44-7.18 (m, 8H), 5.53-5.41 (m, -continued

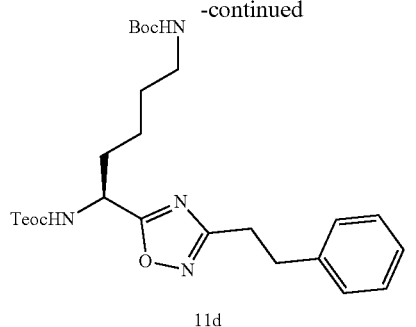

11d

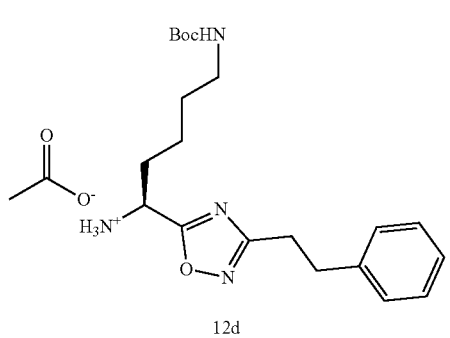

12d

1) Step a: Synthesis of (Z)-N'-hydroxy-3-phenylpropanimidamide (9d)

The same procedure as described in Scheme 6 by using 3-phenylpropanenitrile (8d, 2.00 g, 15.2 mmol) to give N-hydroxy-3-phenylpropanimidamide (9d, 1.9 g) in 76% yield.

$^1$H NMR (DMSO-d$_6$, 300 MHz): δ=8.72 (br s, 1H), 7.30-7.13 (m, 5H), 5.41 (br s, 2H), 2.83-2.74 (m, 2H), 2.28-2.19 (m, 2H).

2) Step b: Synthesis of (S)-tert-butyl (2-(trimethylsilyl)ethyl) (1-(3-phenethyl-1,2,4-oxadiazol-5-yl)pentane-1,5-diyl)dicarbamate (11d)

The same procedure as described in Scheme 6 by using (Z)-N-hydroxy-3-phenylpropanimidamide (9d, 391 mg, 1.0 mmol) to give (S)-tert-butyl (2-(trimethylsilyl)ethyl) (1-(3-phenethyl-1,2,4-oxadiazol-5-yl)pentane-1,5-diyl)dicarbamate (10b, 328 mg) in 63% yield as colorless sticky oil.

$^1$H NMR (CDCl$_3$, 300 MHz): δ=7.33-7.17 (m, 5H), 5.34-5.21 (m, 1H), 5.11-4.98 (m, 1H), 4.59-4.47 (m, 1H), 4.23-4.13 (m, 2H), 3.18-2.96 (m, 6H), 2.01-1.79 (m, 2H), 1.61-1.31 (m, 6H), 1.44 (s, 9H), 1.04-0.94 (m, 2H), 0.04 (s, 9H).

3) Step c: Synthesis of (S)-tert-butyl (5-amino-5-(3-phenethyl-1,2,4-oxadiazol-5-yl)pentyl)carbamate acetate (12d)

The same procedure as described in Scheme 6 by using (S)-tert-butyl (2-(trimethylsilyl)ethyl) (1-(3-phenethyl-1,2,4-oxadiazol-5-yl)pentane-1,5-diyl)dicarbamate (11d, 320 mg, 0.617 mmol) and TBAF (1 M in THF, 0.95 mL, 0.925 mmol) to give (S)-tert-butyl (5-amino-5-(3-phenethyl-1,2,4-oxadiazol-5-yl)pentyl)carbamate acetate (12d, 191 mg) in 71% yield.

$^1$H NMR (CD$_3$OD, 300 MHz): δ=7.30-7.13 (m, 5H), 4.49-4.37 (m, 1H), 3.10-2.98 (m, 6H), 2.02-1.89 (m, 2H), 1.56-1.27 (m, 4H), 1.42 (s, 9H).

Example 5: Synthesis of tert-butyl (S)-(5-amino-5-(3-(cyclohexylmethyl)-1,2,4-oxadiazol-5-yl)pentyl)carbamate (5e)

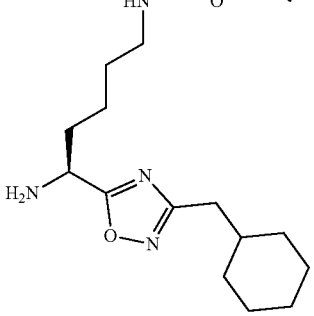

Compound 5e

Scheme 11

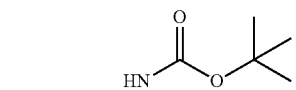  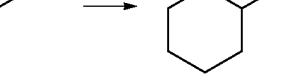 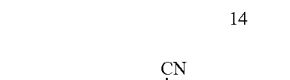 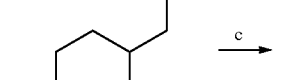 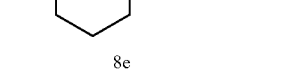   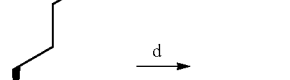    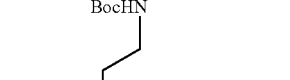  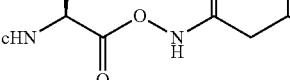 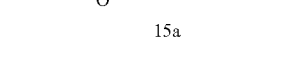 

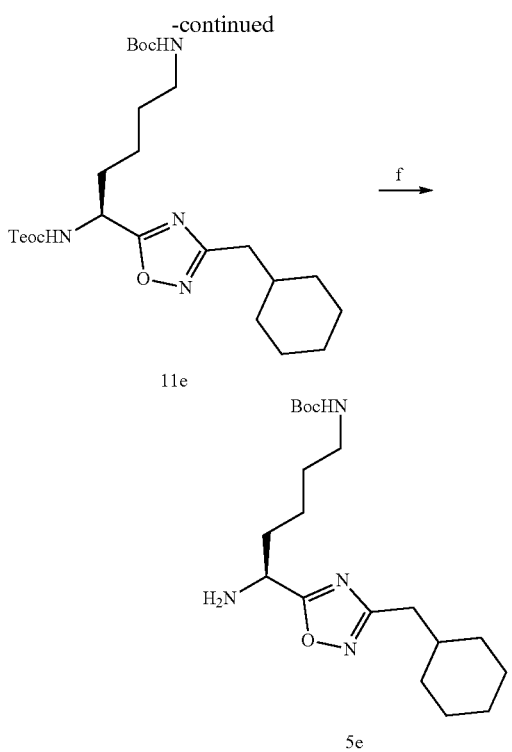

1) Step a: Synthesis of cyclohexylmethyl methanesulfonate (14)
To a solution of cycloxehylmethanol (13, 43.79 mmol, 5.00 g, 1.0 eq.) in anhydrous DCM (80 mL) methanesulfonyl chloride (48.17 mmol, 5.51 g, 1.10 eq.) and triethyamine (6.9 mL) were added under argon at 0° C. The reaction mixture was stirred at 0° C. for 30 min, washed with $H_2O$ (3×40 mL), 1N HCl (2×30 mL) and brine, dried over $Na_2SO_4$ and concentrated under reduced pressure to give crude product as a yellow oil cyclohexylmethyl methanesulfonate (14, 12 g, 96%). Product used further without additional purification.

2) Step b: Synthesis of 2-cyclohexylacetonitrile (8e) A mixture of cyclohexylmethyl methanesulfonate (14, 30.16 mmol, 5.80 g, 1.00 eq.) and KCN (66.36 mmol, 4.32 g, 2.20 eq.) in DMF (30 mL) was stirred at 90° C. for 16 h. After cooling to room temperature, the reaction mixture was poured into $H_2O$ (100 mL). The aqueous layer was extracted with $Et_2O$ (3×100 mL). The combined organic layers were washed with brine (2×100 mL), dried over $Na_2SO_4$ and concentrated under reduced pressure. The crude product 2-cyclohexylacetonitrile (8e, 4.13 g, 111%) used further without additional purification.

3) Step c: Synthesis of (Z)-2-cyclohexyl-N'-hydroxyacetimidamide (9e)
The same procedure as described in Scheme 6 by using 2-cyclohexylacetonitrile (8e, 4.10 g, 33.28 mmol) and hydroxylamine hydrochloride (3.47 g, 49.92 mmol) to yield product (Z)-2-cyclohexyl-N'-hydroxyacetimidamide (9e, 2.3 g, 44%) as a white solid.
$^1$H NMR (400 MHz, Chloroform-d) δ6.89 (s, 1H), 4.50 (s, 2H), 2.00 (d, J=7.2 Hz, 2H), 1.80-1.59 (m, 5H), 1.60-1.48 (m, 1H), 1.31-1.08 (m, 3H), 1.01-0.88 (m, 2H).

4) Step d: Synthesis of tert-butyl (2-trimethylsilylethyl) (6-((2-cyclohexylacetimidamido)oxy)-6-oxohexane-1,5-diyl)(S)-dicarbamate (15a)
To a solution of compound 10b (101.2 g, 0.26 mmol, 1.5 eq) in DMF (300 mL) was added HOBT (23.49 g, 0.26 mol, 1.5 eq), EDC.HCl (28.31 g, 0.22 mol, 1.3 eq) and compound 9e (27.0 g, 0.17 mol) and then stirred for overnight at rt. After completion, water was added, extracted with EA, washed with $NaCl_{(aq)}$, dried over $Na_2SO_4$. Filtered and concentrated to give yellow liquid (15a, 32.0 g, crude) which was used into next step without purification.

5) Step e: Synthesis of tert-butyl (2-trimethylsilylethyl) (1-(3-(cyclohexylmethyl)-1,2,4-oxadiazol-5-yl)pentane-1,5-diyl)(S)-dicarbamate (11e)
To a solution of compound 15a (32.0 g, crude) in pyridine (320 mL) was refluxed for overnight. After completion, Cooling to room temperature, water (500 mL) was added, extracted with EA (300 mL*3), washed with $NaCl_{(aq)}$, dried over $Na_2SO_4$. Filtered and concentrated to get crude which was purified by silica column to give yellow liquid (11e, 18 g).

6) Step f: Synthesis of tert-butyl (S)-(3-amino-3-(3-benzyl-1,2,4-oxadiazol-5-yl)propyl)carbamate (5e)
Compound 11e (24 g, 46.99 mmol) was dissolved in THF (450 mL) was added TBAF (24.6 g, 93.9 mol, 2 eq) and stirred at 35° C. for overnight, After LCMS indicated completion, water (500 mL) was added, extracted with EA (300 mL*3), washed with $NaCl_{(aq)}$, dried over $Na_2SO_4$. Filtered and concentrated to get crude which was purified by silica column to give yellow liquid as mixture which was purified by chiral HPLC to give a pure product 5e (11 g, 100%, 98.6% ee).
1H NMR (CDCl$_3$, MHz 300): d=4.55 (s(br), 1H); 4.15 (m, 1H); 3.12 (m, 2H); 2.61 (m, 2H); 1.90 (m, 6H); 1.75 (m, 4H); 1.55 (m, 2H); 1.45 (s, 9H); 1.30 (m, 4H). MS (M+1): 367.1.

Example 6: Synthesis of tert-butyl (S)-5-(3-(adamantan-1-yl)methyl-1,2,4-oxadiazol-5-yl)-5-aminopentylcarbamate (5f)

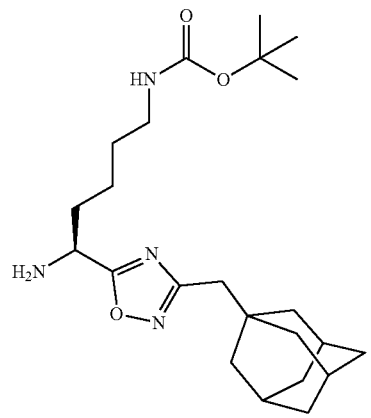

Scheme 12

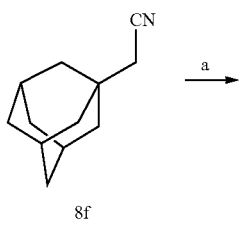

-continued

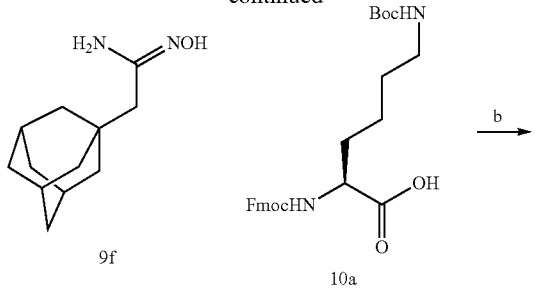

yl-methyl-1,2,4-oxadiazol-5-yl)pentane-1,5-diyldicarbamate (11f, 2.5 g, 3.90 mmol) to give tert-butyl (S)-5-(3-adamantan-1-yl-methyl-1,2,4-oxadiazol-5-yl)-5-aminopentylcarbamate (5f, 820 mg, 50%).

¹H-NMR (400 MHz, Methanol-d₄) δ4.15 (t, J=6.9 Hz, 1H), 3.02 (t, J=6.9 Hz, 2H), 2.48 (s, 2H), 1.96-1.80 (m, 5H), 1.76-1.74 (m, 3H), 1.66-1.61 (m, 10H), 1.51-1.34 (m, 12H).

Example 7: Synthesis of tert-butyl (S)-5-(3-(adamantan-1-yl)-1,2,4-oxadiazol-5-yl)-5-aminopentylcarbamate (5g)

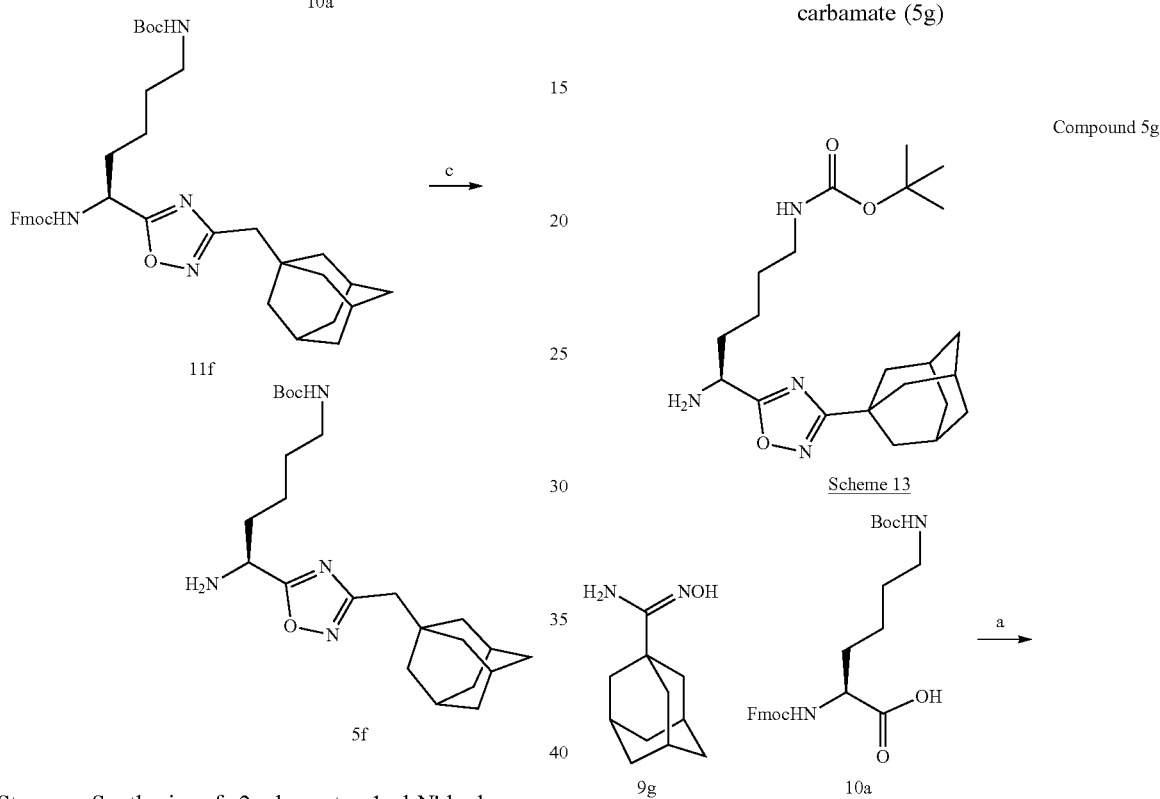

1) Step a: Synthesis of 2-adamantan-1-yl-N'-hydroxyacetimidamide (90

The same procedure as described in Scheme 6 by using 2-Adamantan-1-yl-acetonitrile (8f, 1.0 g, 5.705 mmol) to give 2-adamantan-1-yl-N'-hydroxyacetimidamide (9f, 665 mg, 56%) as white powder.

¹H-NMR (300 MHz, Methanol-d₄) δ1.98-1.93 (m, 3H), 1.87 (s, 2H), 1.77-1.61 (m, 12H).

2) Step b: Synthesis of (9H-fluoren-9-yl)methyl tert-butyl (S)-1-(3-(adamantan-1-yl)methyl-1,2,4-oxadiazol-5-yl)pentane-1,5-diyldicarbamate (11f).

The same procedure as described in Scheme 6 by using 2-adamantan-1-yl-N'-hydroxyacetimidamide (9f, 1.30 g, 6.27 mmol) to yield 2.21 g (11f, 52%) of (9H-fluoren-9-yl) methyl tert-butyl (S)-1-(3-adamantan-1-ylmethyl-1,2,4-oxadiazol-5-yl)pentane-1,5-diyl) dicarbamate.

¹H-NMR (300 MHz, Methanol-d₄) δ7.79 (d, J=7.5 Hz, 2H), 7.67 (t, J=8.1 Hz, 2H), 7.34 (dt, J=25.2, 7.3 Hz, 4H), 4.90 (dd, J=8.7, 6.2 Hz, 1H), 4.44 (dd, J=10.2, 6.5 Hz, 1H), 4.31 (dd, J=10.2, 7.3 Hz, 1H), 4.22 (t, J=6.8 Hz, 1H), 3.03 (t, J=6.1 Hz, 2H), 2.45 (s, 2H), 1.98-1.88 (m, 5H), 1.66-1.42 (m, 23 Hz).

3) Step c: Synthesis of tert-butyl (S)-5-(3-(adamantan-1-yl)methyl-1,2,4-oxadiazol-5-yl)-5-aminopentylcarbamate (5f)

The same procedure as described in Scheme 6 by using (9H-fluoren-9-yl)methyl tert-butyl (S)-1-(3-adamantan-1-

1) Step a: Synthesis of (9H-fluoren-9-yl)methyl tert-butyl (1S)-1-(3-(adamantan-1-yl)-1,2,4-oxadiazol-5-yl)pentane-1,5-diyldicarbamate (11g)

The same procedure as described in Scheme 6 by using N'-hydroxyadamantane-1-carboximidamide (9g, 1.0 g, 5.15 mmol) to give (9H-fluoren-9-yl)methyl tert-butyl (1S)-1-(3-adamantan-1-yl-1,2,4-oxadiazol-5-yl)pentane-1,5-diyldicarbamate (11g, 1.75 g, 62%) as a white powder.

$^1$H-NMR (300 MHz, Methanol-$d_4$) δ7.79 (d, J=7.5 Hz, 2H), 7.67 (dd, J=16.3, 7.5 Hz, 2H), 7.41-7.35 (m, 2H), 7.30 (t, J=7.5 Hz, 2H), 4.93 (dd, J=9.3, 5.5 Hz, 1H), 4.43 (dd, J=10.4, 6.8 Hz, 1H), 4.34 (d, J=17.6 Hz, 1H), 4.23 (t, J=6.8 Hz, 1H), 3.08 (dt, J=7.9, 4.0 Hz, 2H), 2.05-1.97 (m, 10H), 1.85-1.74 (m, 7H), 1.56-1.51 (m, 2H), 1.43 (s, 9H).

2) Step b: Synthesis of tert-butyl (5S)-5-(3-(adamantan-1-yl)-1,2,4-oxadiazol-5-yl)-5-aminopentylcarbamate (5g)

The same procedure as described in Scheme 6 by using (9H-fluoren-9-yl)methyl tert-butyl (1S)-1-(3-adamantan-1-yl-1,2,4-oxadiazol-5-yl)pentane-1,5-diyldicarbamate (11g, 1.75 g, 2.86 mmol) to yield a desired product tert-butyl (S)-5-(3-adamantan-1-yl-1,2,4-oxadiazol-5-yl)-5-aminopentylcarbamate as a white foam (5g, 0.89 g, 80%).

$^1$H-NMR (400 MHz, Methanol-$d_4$) δ4.15 (t, J=6.9 Hz, 1H), 3.06 (t, J=6.9 Hz, 2H), 2.07 (s, 3H), 2.02 (d, J=2.8 Hz, 6H), 1.91-1.75 (m, 8H), 1.55-1.48 (m, 2H), 1.43 (s, 9H).

Example 8: Synthesis of tert-butyl (S)-(3-amino-3-(3-benzyl-1,2,4-oxadiazol-5-yl)propyl)carbamate (5h)

Compound 5h

Scheme 14

1) Step a: Synthesis of 2,5-dioxopyrrolidin-1-yl (2-(trimethylsilyl)ethyl) carbonate (18)

To a solution of compound 16 (22.2 mL, 0.156 mol, 1.0 eq) in CH$_3$CN (780 mL) was added Et$_3$N (65.7 mL, 0.468 mol, 3.0 eq) and compound 17 (60 g, 0.234 mmol, 1.5 eq) at room temperature and stirred for overnight. After completion, concentrated and EA (500 mL) was added, washed with saturated NaHCO$_3$ (200 mL), NaCl (200 mL*3), dried over Na$_2$SO$_4$. Filtered and concentrated to give yellow liquid (18, 54.2 g, crude) which was used into next step without purification.

2) Step b: Synthesis of (S)-4-((tert-butoxycarbonyl)amino)-2-(((2-(trimethylsilyl)ethoxy)-carbonyl)amino)butanoic acid (10c)

To a solution of compound 19a (25 g, 0.114 mol, 1.0 eq) in 1,4-dioxane (180 mL) and H$_2$O (180 mL) was added NaHCO₃ (23.2 g, 0.228 mol, 2.0 eq) and the solution of compound 2,5-dioxopyrrolidin-1-yl (2-(trimethylsilyl)ethyl) carbonate (18, 32.7 g, 0.12 mmol, 1.1 eq) in 1,4-dioxane (100 mL) was added drop wise at room temperature and stirred for overnight. After completion, the remainder was added water (200 mL) and adjusted pH=3-4 with 2N HC at 0° C., extracted with DCM:MeOH=10:1 (100 mL*5), dried over Na₂SO₄. Filtered and concentrated to give yellow liquid (10c, 43.6 g, crude) which was used into next step without purification. MS: (m−H)⁺: 361.1.

3) Step c: Synthesis of tert-butyl (2-(trimethylsilyl)ethyl) (4-oxo-4-((2-phenylacetimida-mido)oxy)butane-1,3-diyl) (S)-dicarbamate (15b)

To a solution of compound 10c (43.6 g, crude, 0.12 mmol, 1.5 eq) in DMF (300 mL) was added HOBT (16.26 g, 0.18 mol, 1.5 eq), EDC.HCl (19.98 g, 0.156 mol, 1.3 eq) and compound 9a (12.04 g, 0.08 mol, 1 eq) and then stirred for overnight at rt. After completion, water (500 mL) was added, extracted with EA (300 mL*3), washed with NaCl$_{(aq)}$, dried over Na₂SO₄. Filtered and concentrated to give yellow liquid (15b, 53.3 g, crude) which was used into next step without purification. MS: (m+H)⁺: 495.2.

4) Step d: Synthesis of tert-butyl (2-(trimethylsilyl)ethyl) (1-(3-benzyl-1,2,4-oxadiazol-5-yl)propane-1,3-diyl)(S)-dicarbamate (11h)

To a solution of compound 15b (53.3 g, crude) in pyridine (533 mL) was refluxed for overnight. After completion, Cooling to room temperature, water (500 mL) was added, extracted with EA (300 mL*3), washed with NaCl$_{(aq)}$, dried over Na₂SO₄. Filtered and concentrated to get crude which was purified by silica column to give yellow liquid (11h, 23 g). MS: (m+H)⁺: 476.1.

5) Step e: Synthesis of tert-butyl (S)-(3-amino-3-(3-benzyl-1,2,4-oxadiazol-5-yl)propyl)carbamate (5h)

Compound 11h (22 g, 46.22 mmol) was dissolved in THF (440 mL) was added TBAF (24.2 g, 92.4 mol, 2 eq) and stirred at 35° C. for overnight, After LCMS indicated completion, water (500 mL) was added, extracted with EA (300 mL*3), washed with NaCl$_{(aq)}$, dried over Na₂SO₄. Filtered and concentrated to get crude which was purified by silica column to give yellow liquid (14 g) as mixture which was purified by chiral HPLC to give a pure product 5h (96%, 97% ee).

1H NMR (CDCl₃, MHz 300): d=7.31 (m, 5H); 4.20 (m, 1H); 4.17 (s, 2H); 3.43 (m, 1H); 3.27 (m, 1H); 2.06 (m, 1H); 1.92 (m, 1H); 1.83 (s(br), 2H (NH)); 1.44 (s, 9H). MS (M+1): 333.2.

Example 9: Synthesis of tert-butyl (S)-(4-amino-4-(3-benzyl-1,2,4-oxadiazol-5-yl)butyl)carbamate (5i)

Compound 5i

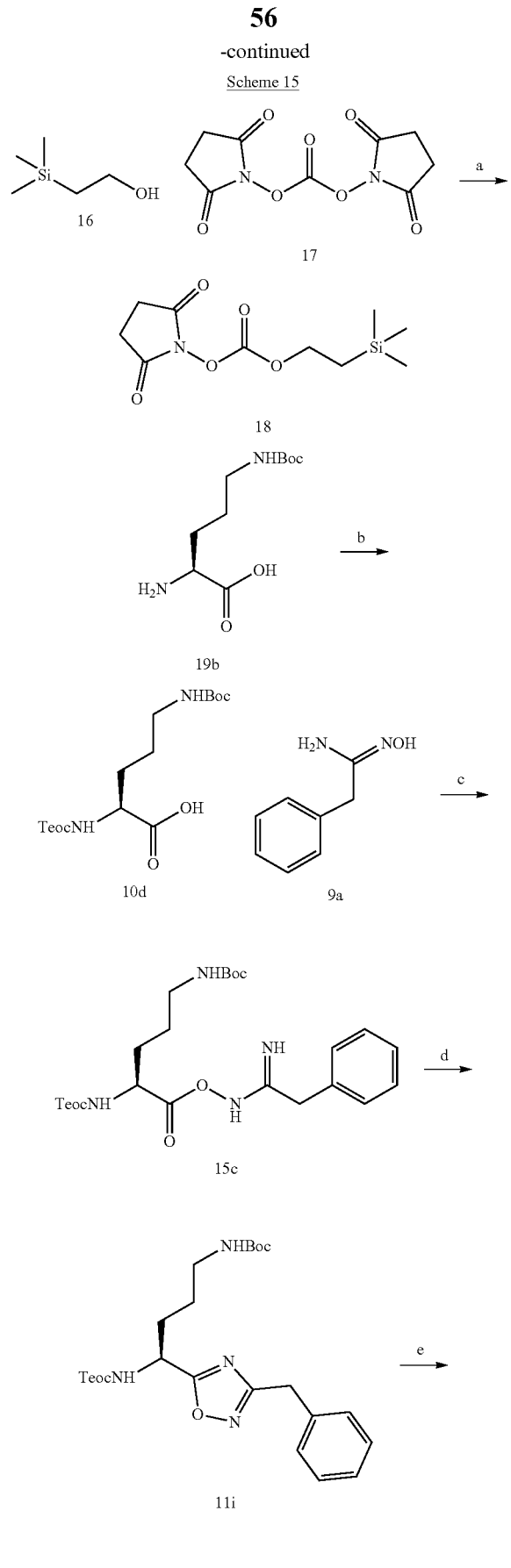

Scheme 15

-continued

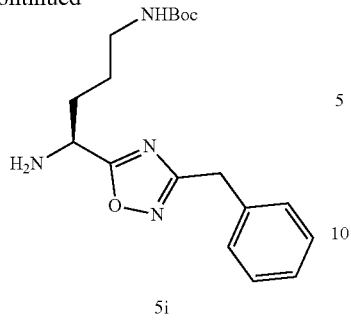

5i

1) Step a: Synthesis of 2,5-dioxopyrrolidin-1-yl (2-(trimethylsilyl)ethyl) carbonate (18)

The same procedure as described in Scheme 14.

2) Step b: Synthesis of (S)-5-((tert-butoxycarbonyl)amino)-2-(((2-trimethylsilylethoxy)-carbonyl)amino)pentanoic acid (10d)

The same procedure as described in Scheme 14 by using compound 19b (25 g, 0.108 mol) in 1,4-dioxane (180 mL) and H$_2$O (180 mL) was added NaHCO$_3$ (23.2 g, 0.228 mol, 2.0 eq) to give a yellow liquid product (10d). MS: (m–H)$^+$: 376.1.

3) Step c: Synthesis of tert-butyl (2-trimethylsilylethyl) (5-oxo-5-((2-phenylacetimidamido)-oxy)pentane-1,4-diyl) (S)-dicarbamate (15c)

The same procedure as described in Scheme 14 by using compound 10d (52.8 g, 0.14 mol) to give yellow liquid (15c, 65.3 g). MS (M+H): 509.3.

4) Step d: Synthesis of tert-butyl (2-trimethylsilylethyl) (1-(3-benzyl-1,2,4-oxadiazol-5-yl)butane-1,4-diyl)(S)-dicarbamate (11i)

The same procedure as described in Scheme 14 by using compound 15c to give a yellow liquid (11i, 23 g). MS: (m+H)$^+$: 489.2.

5) Step e: Synthesis of tert-butyl (S)-(4-amino-4-(3-benzyl-1,2,4-oxadiazol-5-yl)butyl)carbamate (5i)

The same procedure as described in Scheme 14 by using compound 11i (23 g, 46.87 mmol) to give a yellow liquid (14 g) as racemic mixture, which was purified by chiral separation to give a pure product 5i (98%, 97% ee).

1H NMR (CDCl$_3$, MHz 300): d=7.33 (m, 5H); 4.68 (s(br), 1H); 4.15 (m, 1H); 4.08 (s, 2H); 3.16 (m, 2H); 1.92 (m, 1H); 1.83 (m, 3H); 1.74 (m, 2H); 1.45 (s, 9H). MS (M+Na$^+$): 369.2.

Example 10: Synthesis of (S)-4-((tert-butoxycarbonyl)amino)-1-(3-(cyclohexylmethyl)-1,2,4-oxadiazol-5-yl)butan-1-aminium acetate (12j)

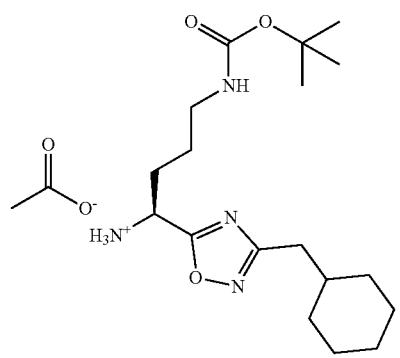

Compound 12j

-continued
Scheme 16

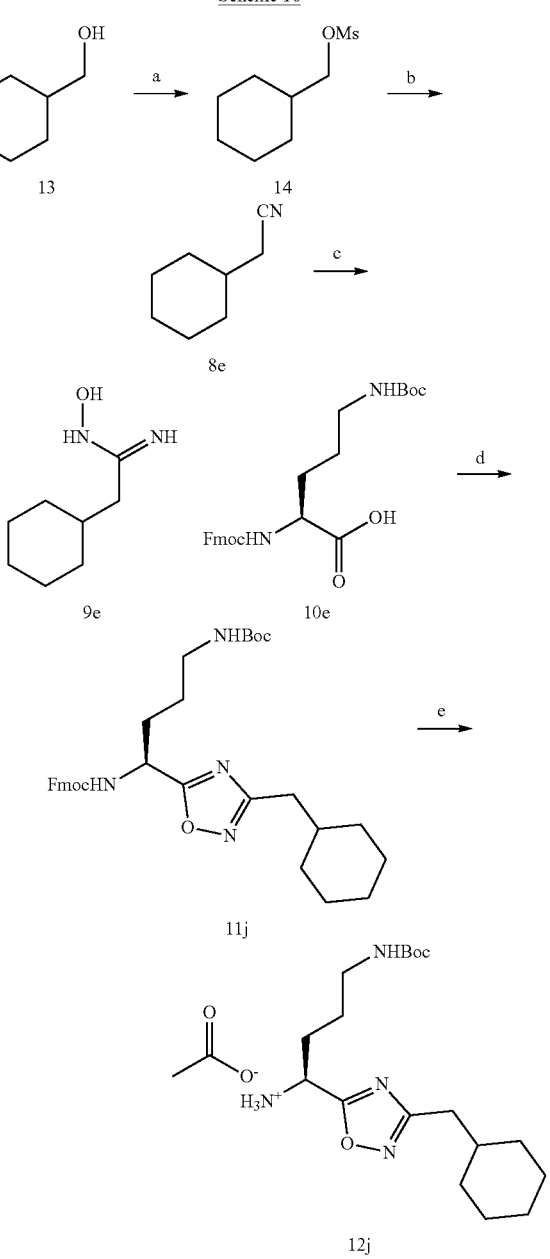

1) Step a: Synthesis of cyclohexylmethyl methanesulfonate (14)

The same procedure as described in Scheme 11.

2) Step b: Synthesis of 2-cyclohexylacetonitrile (8e)

The same procedure as described in Scheme 11.

3) Step c: Synthesis of (Z)-2-cyclohexyl-N'-hydroxyacetimidamide (9e)

The same procedure as described in Scheme 11 by using 2-cyclohexylacetonitrile (8e, 4.10 g, 33.28 mmol) and hydroxylamine hydrochloride (3.47 g, 49.92 mmol) to yield product (Z)-2-cyclohexyl-N'-hydroxyacetimidamide (9e, 2.3 g, 44%) as a white solid.

$^1$H NMR (400 MHz, Chloroform-d) δ6.89 (s, 1H), 4.50 (s, 2H), 2.00 (d, J=7.2 Hz, 2H), 1.80-1.59 (m, 5H), 1.60-1.48 (m, 1H), 1.31-1.08 (m, 3H), 1.01-0.88 (m, 2H).

4) Step d: Synthesis of (9H-fluoren-9-yl) methyl tert-butyl (1-(3-(cyclohexylmethyl)-1,2,4-oxadiazol-5-yl)butane-1,4-diyl)dicarbamate (11j)

The same procedure as described in Scheme 6 by using (Z)-2-cyclohexyl-N'-hydroxyacetimidamide (9e, 2.30 g, 14.72 mmol) and N2-(((9H-fluoren-9-yl)methoxy)carbonyl)-N6-(tert-butoxycarbonyl)-L-lysine (10e, 6.08 g, 13.38 mmol) to give of (9H-fluoren-9-yl) methyl tert-butyl (1-(3-(cyclohexylmethyl)-1,2,4-oxadiazol-5-yl)butane-1,4-diyl)dicarbamate (11j, 1.57 g, 20%) as white solid.

$^1$H NMR (400 MHz, Methanol-$d_4$) δ7.79 (d, J=7.5 Hz, 2H), 7.67 (dd, J=11.8, 7.6 Hz, 2H), 7.39 (t, J=7.5 Hz, 2H), 7.30 (t, J=7.5 Hz, 2H), 4.93 (dd, J=9.2, 5.6 Hz, 1H), 4.42 (dd, J=10.4, 6.9 Hz, 1H), 4.34 (dd, J=10.5, 7.0 Hz, 1H), 4.22 (t, J=6.9 Hz, 1H), 3.08 (t, J=6.2 Hz, 2H), 2.56 (d, J=7.0 Hz, 2H), 2.00-1.93 (m, 1H), 1.92-1.82 (m, 1H), 1.80-1.72 (m, 1H), 1.72-1.51 (m, 7H), 1.43 (s, 9H), 1.22-1.12 (m, 3H), 1.05-0.93 (m, 2H).

5) Step e: Synthesis of (S)-4-((tert-butoxycarbonyl)amino)-1-(3-(cyclohexylmethyl)-1,2,4-oxadiazol-5-yl)butan-1-aminium acetate (12j)

The same procedure as described in Scheme 6 by using (9H-fluoren-9-yl) methyl tert-butyl (1-(3-(cyclohexylmethyl)-1,2,4-oxadiazol-5-yl)butane-1,4-diyl)dicarbamate (11j, 1.50 g, 2.61 mmol) to give (S)-4-((tert-butoxycarbonyl)amino)-1-(3-(cyclohexylmethyl)-1,2,4-oxadiazol-5-yl)butan-1-aminium acetate (12j, 750 mg, 81%) as yellow viscous oil.

$^1$H NMR (400 MHz, Methanol-$d_4$) δ4.22 (t, J=5.3 Hz, 1H), 3.06 (t, J=6.8 Hz, 2H), 2.59 (d, J=7.0 Hz, 2H), 1.95-1.77 (m, 3H), 1.76-1.63 (m, 5H), 1.60-1.47 (m, 2H), 1.43 (s, 9H), 1.34-1.14 (m, 3H), 1.09-0.96 (m, 2H).

Example 11: Synthesis of tert-butyl (S)-(4-amino-4-(3-(bicyclo[2.2.2]octan-1-ylmethyl)-1,2,4-oxadiazol-5-yl)butyl)carbamate (5k)

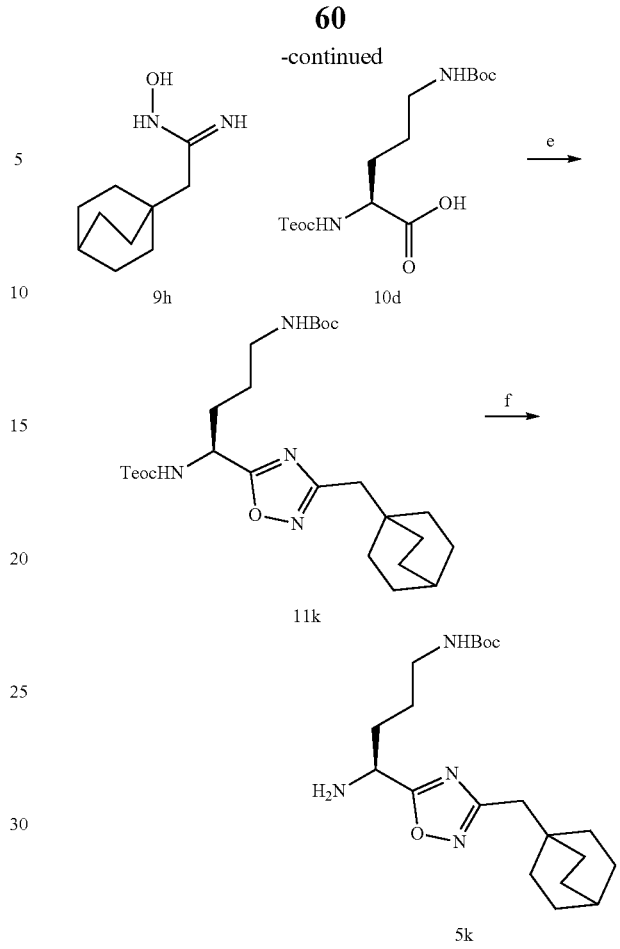

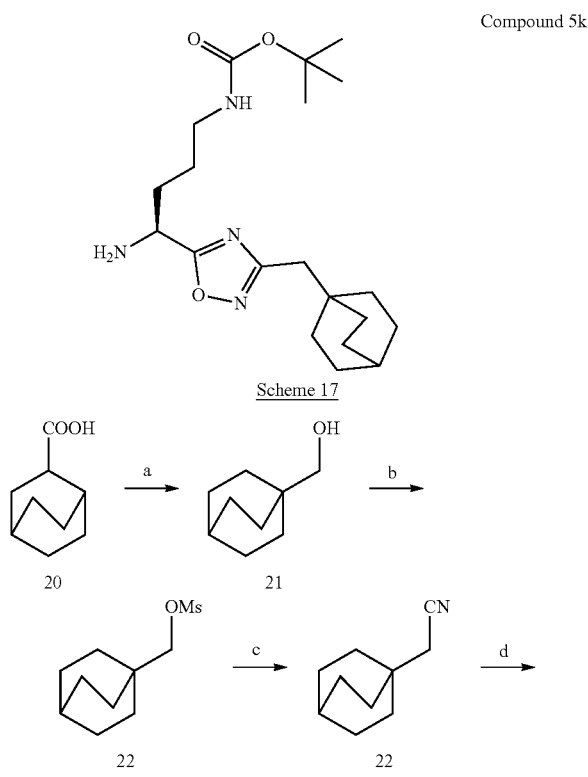

1) Step a: Synthesis of bicyclo[2.2.2]octan-1-ylmethanol (21)

Bicyclo[2.2.2]octane-1-carboxylic acid (20, 1.00 g; 6.5 mmol) was dissolved in dry THF (10 mL) at 0° C. $BH_3$ (1M THF solution; 15 mL) was added dropwise. Reaction mixture was stirred overnight at ambient temperature. Reaction was quenched with dry MeOH (15 mL) and volatiles were removed under reduced pressure. Residue was dissolved in dry MeOH (50 mL) and evaporated three more times. Bicyclo[2.2.2]octan-1-ylmethanol (21, 930 mg, quantitative) was obtained. Product was used in the next step without further purification.

$^1$H NMR (300 MHz, Chloroform-d) δ3.14 (d, J=6.1 Hz, 2H), 1.57-1.40 (multiple peaks, 7H), 1.36-1.23 (multiple peaks, 6H), 1.19 (t, J=6.1 Hz, 1H).

2) Step b: Synthesis of bicyclo[2.2.2]octan-1-ylmethyl methanesulfonate (22)

Bicyclo[2.2.2]octan-1-ylmethanol (21, 897 mg; 6.4 mmol) and DIPEA (1.75 mL; 10.0 mmol) were dissolved in dry DCM (30 mL) at 0° C. MsCl (0.70 mL; 9.0 mmol) was added dropwise. Reaction progress was monitored by TLC. After complete conversion (~4 h) reaction mixture was partitioned between EtOAc (150 mL) and aq $KHSO_4$ (5%; 100 mL). Organic phase was washed with sat. aq $NaHCO_3$ (100 mL) and brine (150 mL), dried ($MgSO_4$) and evaporated under reduced pressure. Bicyclo[2.2.2]octan-1-ylmethyl methanesulfonate (22, 1.45 g, ~100%) of yellowish oil was obtained. Product was used in the next step without further purification.

$^1$H NMR (300 MHz, Chloroform-d) δ3.74 (s, 2H), 2.91 (s, 3H), 1.60-1.43 (multiple peaks, 7H), 1.43-1.23 (multiple peaks, 6H).

Step c: Synthesis of 2-(Bicyclo[2.2.2]octan-1-yl)acetonitrile (8g)

Bicyclo[2.2.2]octan-1-ylmethyl methanesulfonate (22, 1.40 g; 6.4 mmol), KCN (1.30 g; 20 mmol) and KI (830 mg; 5.0 mmol) were heated in DMF (10 mL) and HMPA (3 mL) to 100° C. for ~6 h. Reaction progress was monitored by GC-MS. Upon full conversion reaction mixture was partitioned between EtOAc (150 mL) and water (200 mL). Organic phase was washed with water (4×100 mL) and brine (100 mL), dried (MgSO$_4$) and evaporated under reduced pressure. Residue was dissolved in minimal amounts of DCM/hexanes (¼) and filtered through a pad of silica gel. Fractions containing product were evaporated under reduced pressure. 2-(Bicyclo[2.2.2]octan-1-yl)acetonitrile (8g, 770 mg, 80%) of a white solid was obtained. Product was used in the next step without further characterization.

3) Step d: Synthesis of 2-(Bicyclo[2.2.2]octan-1-yl)-N'-hydroxyacetimidamide (9h)

The same procedure as described in Scheme 6 by using 2-(Bicyclo[2.2.2]octan-1-yl)acetonitrile (8g, 770 mg; 5.16 mmol) to give 2-(Bicyclo[2.2.2]octan-1-yl)-N'-hydroxyacetimidamide (9h, 585 mg, 62%) of white solid was obtained after drying in vacuum. LC-MS analysis showed single peak with [M+H]+=183. Product was used in the next step without further characterization.

4) Step e: Synthesis of tert-Butyl (2-(trimethylsilyl)ethyl) (1-(3-(bicyclo[2.2.2]octan-1-ylmethyl)-1,2,4-oxadiazol-5-yl)butane-1,4-diyl)(S)-dicarbamate (11k)

The same procedure as described in Scheme 6 by using 2-(bicyclo[2.2.2]octan-1-yl)-Ar-hydroxyacetimidamide (9h, 585 mg; 3.2 mmol) and (S)-tert-butyl (2-(trimethylsilyl) ethyl) (1-(3-phenethyl-1,2,4-oxadiazol-5-yl)pentane-1,5-diyl)dicarbamate (10d, 328 mg) to give 740 mg (44%) of tert-Butyl (2-(trimethylsilyl)ethyl)(1-(3-(bicyclo[2.2.2]octan-1-ylmethyl)-1,2,4-oxadiazol-5-yl)butane-1,4-diyl)(S)-dicarbamate (11k) as a form of amorphous solid.

$^1$H NMR (300 MHz, Methanol-d$_4$) δ4.85 (dd, J=8.8, 5.7 Hz, 1H), 4.12 (t, J=8.2 Hz, 2H), 3.03 (t, J=6.8 Hz, 2H), 2.40 (s, 2H), 1.97-1.68 (m, 2H), 1.61-1.30 (m, 24H), 0.96 (t, J=8.2 Hz, 2H), 0.00 (s, 9H).

5) Step f: Synthesis of tert-Butyl (S)-(4-amino-4-(3-(bicyclo [2.2.2]octan-1-ylmethyl)-1,2,4-oxadiazol-5-yl)butyl)carbamate (5k)

The same procedure as described in Scheme 6 by using tert-butyl (2-(trimethylsilyl)ethyl)(1-(3-(bicyclo[2.2.2]octan-1-ylmethyl)-1,2,4-oxadiazol-5-yl)butane-1,4-diyl)(S)-dicarbamate (11k, 740 mg; 1.42 mmol) to give 520 mg (97%) of amorphous product (5k). Product was used in the next step without characterization.

Example 12: Synthesis of tert-butyl (S)-4-(3-(adamantan-1-yl)methyl-1,2,4-oxadiazol-5-yl)-4-aminobutylcarbamate (5l)

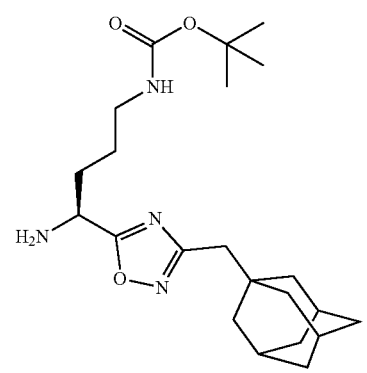

Compound 5l

Compound 5l was synthesis with the same procedures as described in Scheme 12 by using 10d to give the desired product (95% HPLC, 95% ee).

Example 13: Synthesis of tert-butyl (S)-4-(3-(adamantan-1-yl)-1,2,4-oxadiazol-5-yl)-4-aminobutylcarbamate (5m)

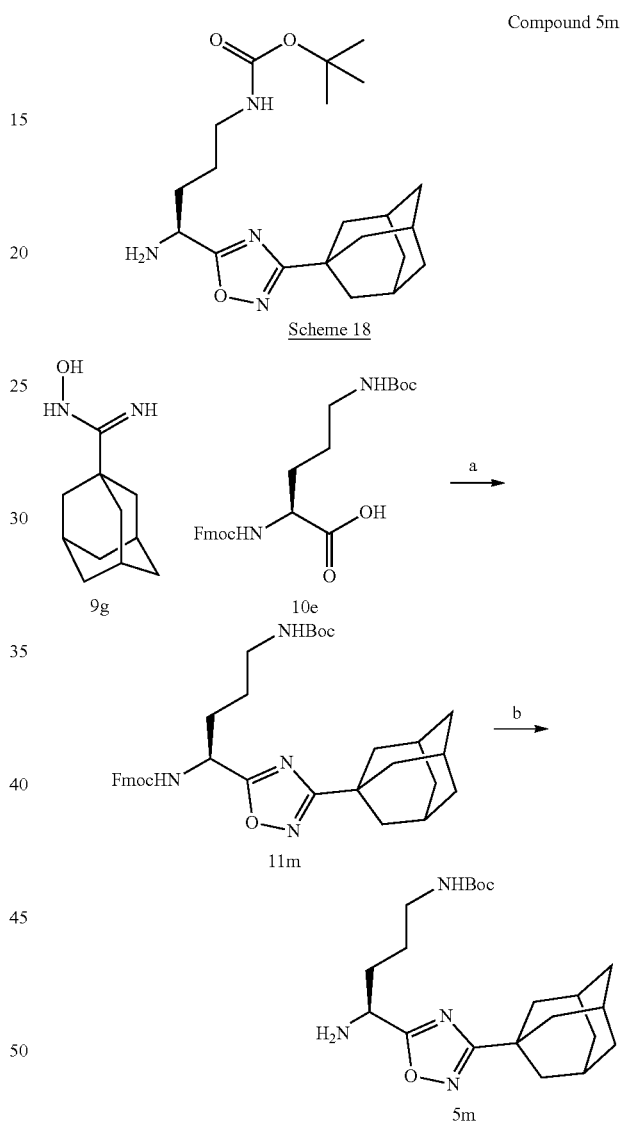

Scheme 18

1) Step a: Synthesis of (9H-fluoren-9-yl)methyl tert-butyl (1S)-1-(3-(adamantan-1-yl)-1,2,4-oxadiazol-5-yl)butane-1, 4-diyldicarbamate (11m)

The same procedure as described in Scheme 13 by using 9g (1.0 g, 5.15 mmol) and 10e (2.11 g, 4.633 mmol) to give 1.75 g (62%) of 11m as a white powder.

$^1$H-NMR (300 MHz, Methanol-d$_4$) δ7.79 (d, J=7.5 Hz, 2H), 7.67 (dd, J=16.3, 7.5 Hz, 2H), 7.41-7.35 (m, 2H), 7.30 (t, J=7.5 Hz, 2H), 4.93 (dd, J=9.3, 5.5 Hz, 1H), 4.43 (dd, J=10.4, 6.8 Hz, 1H), 4.34 (d, J=17.6 Hz, 1H), 4.23 (t, J=6.8 Hz, 1H), 3.08 (dt, J=7.9, 4.0 Hz, 2H), 2.05-1.97 (m, 10H), 1.85-1.74 (m, 7H), 1.56-1.51 (m, 2H), 1.43 (s, 9H).

2) Step b: Synthesis of tert-butyl (S)-4-(3-(adamantan-1-yl)-1,2,4-oxadiazol-5-yl)-4-aminobutylcarbamate (5m)

The same procedure as described in Scheme 13 by using 11m (1.75 g, 2.86 mmol) to yield product 5m as a white foam (0.89 g, 80%).

$^1$H-NMR (400 MHz, Methanol-$d_4$) δ4.15 (t, J=6.9 Hz, 1H), 3.06 (t, J=6.9 Hz, 2H), 2.07 (s, 3H), 2.02 (d, J=2.8 Hz, 6H), 1.91-1.75 (m, 8H), 1.55-1.48 (m, 2H), 1.43 (s, 9H).

Example 14: Synthesis of (S)-1-(3-(adamantan-1-yl)-1,2,4-oxadiazol-5-yl)-N5,N5-dimethylpentane-1,5-diaminium 2,2,2-trifluoroacetate (12n)

1) Step a: Synthesis of tert-butyl (S)-1-(3-(adamantan-1-yl)-1,2,4-oxadiazol-5-yl)-5-(dimethylamino)pentylcarbamate (11n)

The same procedure as described in Scheme 13 by using 9g (330 mg, 1.70 mmol) and 10f (424 mg, 1.54 mmol) to yield product as a colourless oil (11n, 360 mg, 54%).

$^1$H NMR (300 MHz, CD$_3$OD) δ: 2.38 (t, J=7.6 Hz, 2H), 2.28 (s, 6H), 2.07 (br s, 3H), 2.01 (br s, 6H), 1.97-1.75 (m, 8H), 1.61-1.49 (m, 2H), 1.45 (s, 9H), 1.49-1.28 (m, 2H).

2) Step b: Synthesis of tert-butyl (S)-4-(3-(adamantan-1-yl)-1,2,4-oxadiazol-5-yl)-4-aminobutylcarbamate (12n)

11n (360 mg, 0.832 mmol) dissolved in DCM (13 mL) and cooled to 0° C., TFA (1.27 mL, 16.64 mmol) added dropwise and the solution allowed stirring at 0° C. for 5 h. Then DCM was evaporated (at 0-5° C.) yielding product 12n as amorphous solid 435 mg (99%).

$^1$H NMR (300 MHz, CD$_3$OD) δ: 4.82 (t, J=7.0 Hz, 1H), 3.13 (t, J=8.1 Hz, 2H), 2.88 (s, 6H), 2.19-2.00 (m, 11H), 1.93-1.72 (m, 8H), 1.59-1.43 (m, 2H).

Example 15: Synthesis of tert-butyl (R)-(5-amino-5-(3-benzyl-1,2,4-oxadiazol-5-yl)pentyl)carbamate (5o)

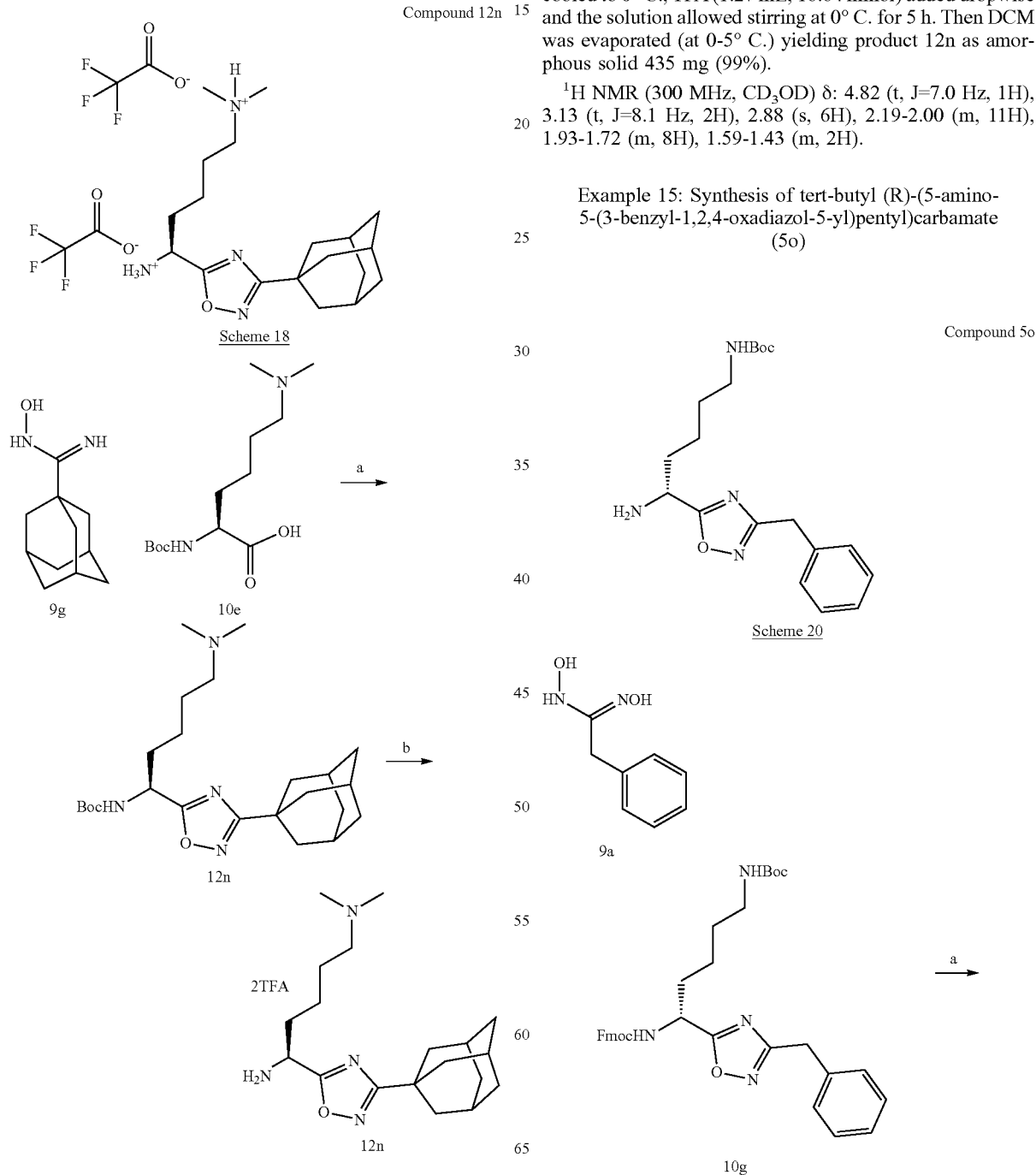

65

-continued

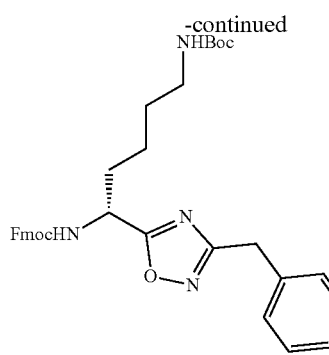

11o

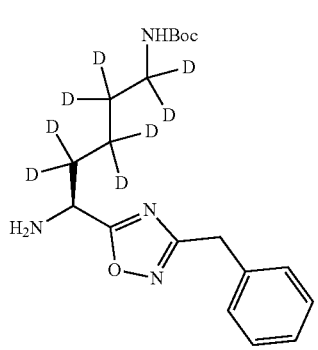

5o

1) Step a: Synthesis of (9H-fluoren-9-yl)methyl tert-butyl (R)-(1-(3-benzyl-1,2,4-oxadiazol-5-yl)pentane-1,5-diyl)dicarbamate (11o)
The same procedure as described in Scheme 7 by using 9a (3.0 g; 20.0 mmol) and 10f (7.0 g; 14.9 mmol) to yield 5.4 g (62%) of product was obtained in a form of amorphous solid. Reaction product was used in the next step without characterization.

2) Step b: Synthesis of tert-butyl (S)-4-(3-adamantan-1-yl-1,2,4-oxadiazol-5-yl)-4-aminobutylcarbamate (12n)
The same procedure as described in Scheme 7 by using 11o (5.4 g; 9.3 mmol) to give 2.54 g (62%) of yellowish oil 5o.
$^1$H NMR (400 MHz, Methanol-$d_4$) δ 7.29-7.26 (m, 4H), 7.25-7.18 (m, 1H), 4.09 (t, J=6.9 Hz, 1H), 4.04 (s, 2H), 2.98 (t, J=6.8 Hz, 2H), 1.90-1.70 (m, 2H), 1.50-1.24 (m, 13H).

Example 16: Synthesis of tert-butyl (S)-(5-amino-5-(3-benzyl-1,2,4-oxadiazol-5-yl)pentyl-1,1,2,2,3,3,4,4-d8)carbamate (5p)

Compound 5p

66

-continued

Scheme 21

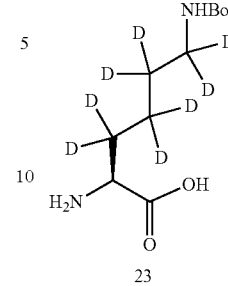

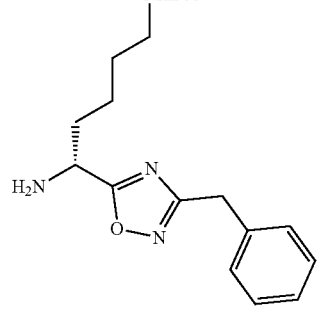

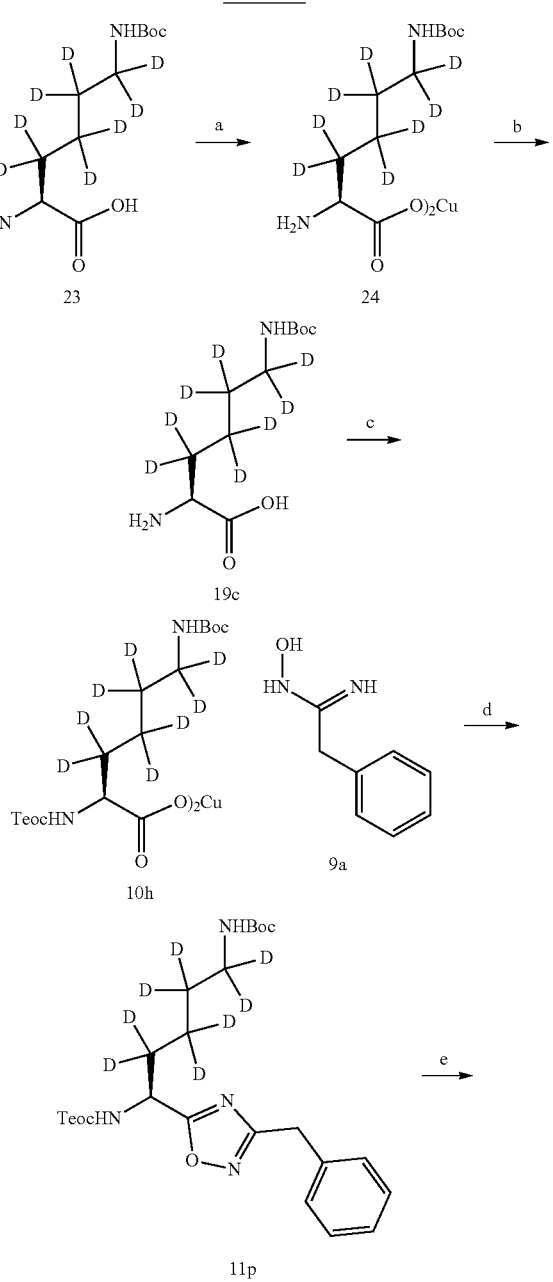

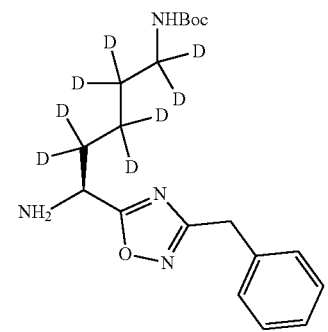

5p

1) Step a: Synthesis of copper(II) bis(N6-(tert-butoxycarbonyl)-L-lysinate-3,3,4,4,5,5,6,6-d8) (24)

Lysine(D8)·2HCl (23, 1.50 g, 7.87 mmol) was dissolved in 2M NaHCO$_3$ (7.80 mL, 15.72 mmol, 1.32 g), to which a solution of CuSO$_4$·5H$_2$O (0.982 g, 3.94 mmol) in H$_2$O (7.8 mL) was added. An additional NaHCO$_3$ (0.66 g, 7.89 mmol) was added, followed by ditertbutyldicarbonate (2.75 g, 12.59 mmol) dissolved in 9.6 mL acetone. The mixture stirred 24 hours. Methanol (3 mL) was added to the solution and stirring continued 14 hours. To reaction mixture H$_2$O (3 mL) is added and the product was subsequently filtered, washed with H$_2$O (6×3 mL) and dried to give 2.24 g (99% yield) of Cu[lys(D8)$^\varepsilon$(Boc)]$_2$ (24) as pale blue solid.

2) Step b: Synthesis of N6-(tert-butoxycarbonyl)-L-lysine-3,3,4,4,5,5,6,6-d$_8$ (19c)

To remove the copper of 24, the Cu-chelate (2.19 g, 3.84 mmol) was suspended in H$_2$O (80 mL). Thereafter, 8-quinolinol (1.45 g, 9.98 mmol) was added, and the mixture stirred 18 hours (pale salad green precipitate formation). The suspension was filtered, precipitates washed with H$_2$O (3×25 mL) and the filtrate washed with EtOAc (3×50 mL). The aqueous layer was evaporated to yield 2.00 g (99% yield) of Lys(ε-Boc)(D8)-OH (19c) as a white solid.

$^1$H NMR (300 MHz, D$_2$O) δ: 3.72 (s, 1H), 1.44 (s, 9H).

3) Step c: Synthesis of N6-(tert-butoxycarbonyl)-L-lysine-3,3,4,4,5,5,6,6-d8 (10h)

NaHCO$_3$ (3.30 g, 39.3 mmol) was suspended in water (31 mL), then 19c (1.00 g, 3.93 mmol), THF (31 mL) and teocOnsu (1.43 g, 5.50 mmol) was added. Biphasic mixture was allowed to vigorously stir at r.t. for 20 h. Then reaction mixture was evaporated from THF and additional water (50 mL) was added and reaction mixture was washed with Et$_2$O (2×20 mL). To aqueous layer was added citric acid to pH 3-4 and product was extracted with DCM (4×50 mL). Organic layers were combined and dried on Na$_2$SO$_4$, filtered and evaporated to give product as a colorless oil (1.52, 97%).

$^1$H NMR (300 MHz, MeOD-d$_4$) δ: 4.15 (t, J=8.1 Hz, 2H), 4.09 (s, 1H), 1.43 (s, 9H), 1.00 (t, J=8.4 Hz, 2H), 0.05 (s, 9H).

4) Step d: Synthesis of tert-butyl (2-trimethylsilylethyl) (1-(3-benzyl-1,2,4-oxadiazol-5-yl)pentane-1,5-diyl-2,2,3,3,4,4,5,5-d8)(S)-dicarbamate (11p)

The same procedure as described in Scheme 6 by using 10h (1.52 g, 3.81 mmol) and 9a (1.14 g, 7.62 mmol) to yield product 11p as a colorless oil (1.21 g, 62%).

$^1$H NMR (300 MHz, MeOD-d$_4$) δ: 7.34-7.19 (m, 5H), 4.14 (t, J=8.3 Hz, 2H), 4.05 (s, 2H), 1.42 (s, 9H), 0.99 (t, J=8.3 Hz, 2H), 0.04 (s, 9H).

5) Step e: Synthesis of tert-butyl (S)-(5-amino-5-(3-benzyl-1,2,4-oxadiazol-5-yl)pentyl-1,1,2,2,3,3,4,4-d8)carbamate (5p)

The same procedure as described in Scheme 6 by using 11p (1.21 mg, 2.36 mmol) to yield product 5p as a yellowish oil (835 mg, 96%).

$^1$H NMR (300 MHz, MeOD-d$_4$) δ: 7.33-7.20 (m, 5H), 4.10 (s, 1H), 4.06 (s, 2H), 1.42 (s, 9H).

Example 17: Synthesis of (S)-2-(1H-imidazol-4-yl)-1-(3-phenyl-1,2,4-oxadiazol-5 yl)ethan-1-aminium 2,2,2-trifluoroacetate (12q)

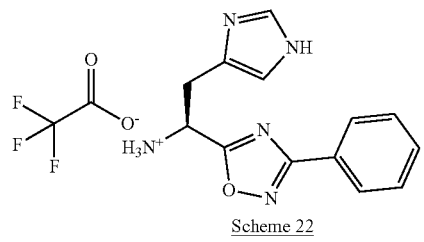

Compound 12q

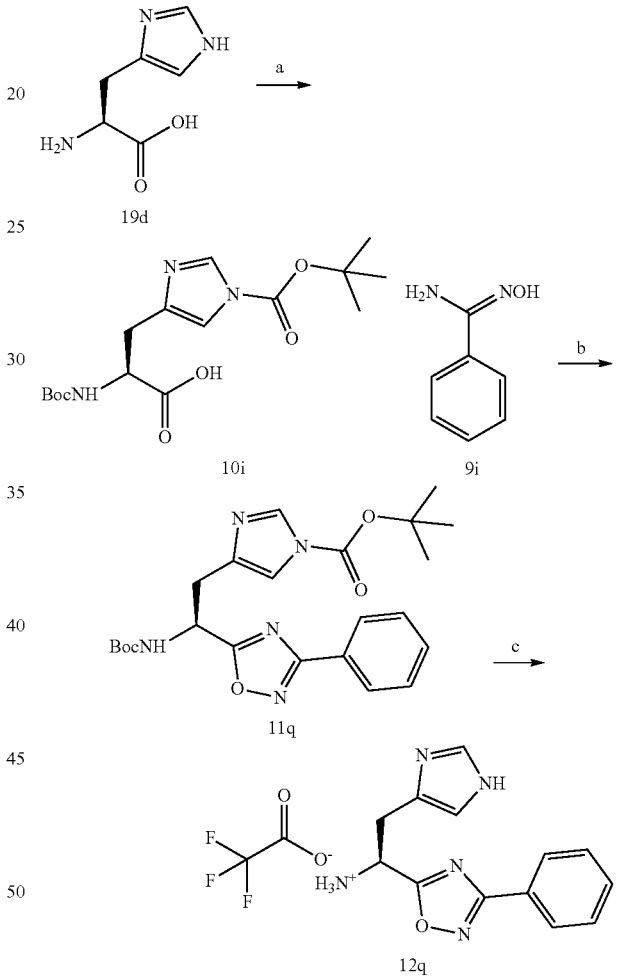

Scheme 22

1) Step a: Synthesis of N$^\alpha$,N$^\tau$-bis(tert-butoxycarbonyl)-L-histidine (10i)

To a solution of L-histidine (19d, 2.00 g, 12.9 mmol) in dioxane (16 mL) and water (16 mL) was added NaOH (1.03 g, 25.8 mmol) at 0° C. and the reaction mixture was stirred 5 min, then Boc$_2$O (7.03 g, 32.2 mmol) was added in portions. The reaction mixture was stirred 4 h at room temperature, then organic solvent was evaporated. The residue was extracted with Et$_2$O (2×). The water layer was carefully acidified with potassium bisulfate to pH 3 and then extracted with EtOAc (3×). The EtOAc extract was separated, dried over anh. Na$_2$SO$_4$, filtered and evaporated. 4.0 g (87%) of N$^\alpha$,N$^\tau$-bis(tert-butoxycarbonyl)-L-histidine (10i) were isolated and used in the next step without further purification.

2) Step b: Synthesis of tert-butyl (S)-4-(2-((tert-butoxycarbonyl)amino)-2-(3-phenyl-1,2,4-oxadiazol-5-yl)ethyl)-1H-imidazole-1-carboxylate (11q)

The same procedure as described in Scheme 6 by using compound 110i (1000 mg, 2.81 mmol) and 9i (383 mg, 2.81 mmol) to give 884 mg (69%) of 11q.

3) Step c: Synthesis of (S)-2-(1H-imidazol-4-yl)-1-(3-phenyl-1,2,4-oxadiazol-5-yl)ethan-1-aminium 2,2,2-trifluoroacetate (12q)

To a solution of 11q (165 mg, 0.362 mmol) in DCM (6 mL) was added TFA (3 mL) at 0° C. After 5 min ice bath was removed and the reaction mixture was stirred 30 min at ambient temperature. The volatiles were evaporated, then crude product 12q was evaporated with toluene and used in the next step without purification.

Example 18: Synthesis of (S)-1-(3-benzyl-1,2,4-oxadiazol-5-yl)-2-(1H-imidazol-4-yl)ethan-1-aminium 2,2,2-trifluoroacetate (12r)

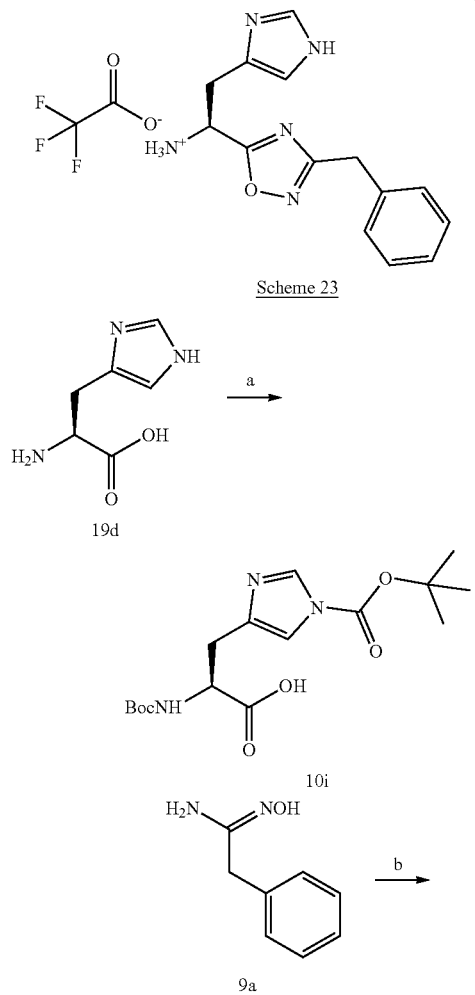

Scheme 23

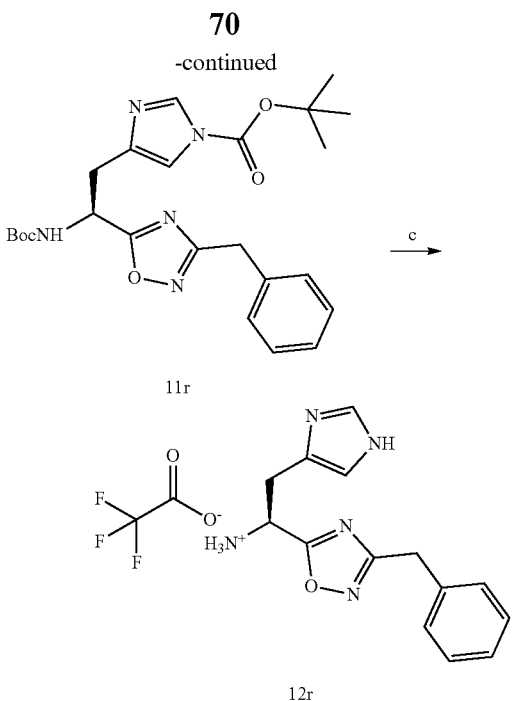

1) Step a: Synthesis of N$^\alpha$,N$^\tau$-bis(tert-butoxycarbonyl)-L-histidine (10i)

The same procedure as described in Scheme 22 to give a product of N$^\alpha$,N$^\tau$-bis(tert-butoxycarbonyl)-L-histidine (10i).

2) Step b: Synthesis of tert-butyl (S)-4-(2-(3-benzyl-1,2,4-oxadiazol-5-yl)-2-((tert-butoxycarbonyl)amino)ethyl)-1H-imidazole-1-carboxylate (11r)

The same procedure as described in Scheme 22 by using 10i (1000 mg, 2.81 mmol) and 9a (422 mg, 2.81 mmol) to give tert-butyl (S)-4-(2-(3-benzyl-1,2,4-oxadiazol-5-yl)-2-((tert-butoxycarbonyl)amino)ethyl)-1H-imidazole-1-carboxylate (11r, 615 mg, 46%).

$^1$H NMR (400 MHz, Methanol-d$_4$) b: 7.93 (s, 1H), 7.34-7.23 (m, 5H), 7.04 (s, 1H), 6.09 (d, J=8 Hz, 1H), 5.31 (d, J=8 Hz, 1H), 4.04 (s, 2H), 3.17-3.11 (m, 2H), 1.60 (s, 9H), 1.53 (s, 9H).

3) Step c: Synthesis of (S)-1-(3-benzyl-1,2,4-oxadiazol-5-yl)-2-(1H-imidazol-4-yl)ethan-1-aminium 2,2,2-trifluoroacetate (12r)

The same procedure as described in Scheme 22 by using 11r (75 mg, 0.160 mmol) to give the desired product without purification.

Example 19: Synthesis of (S)-2-(1H-imidazol-4 yl)-1-(3 phenethyl-1,2,4-oxadiazol-5-yl)ethan-1-aminium 2,2,2-trifluoroacetate (12s)

Scheme 24

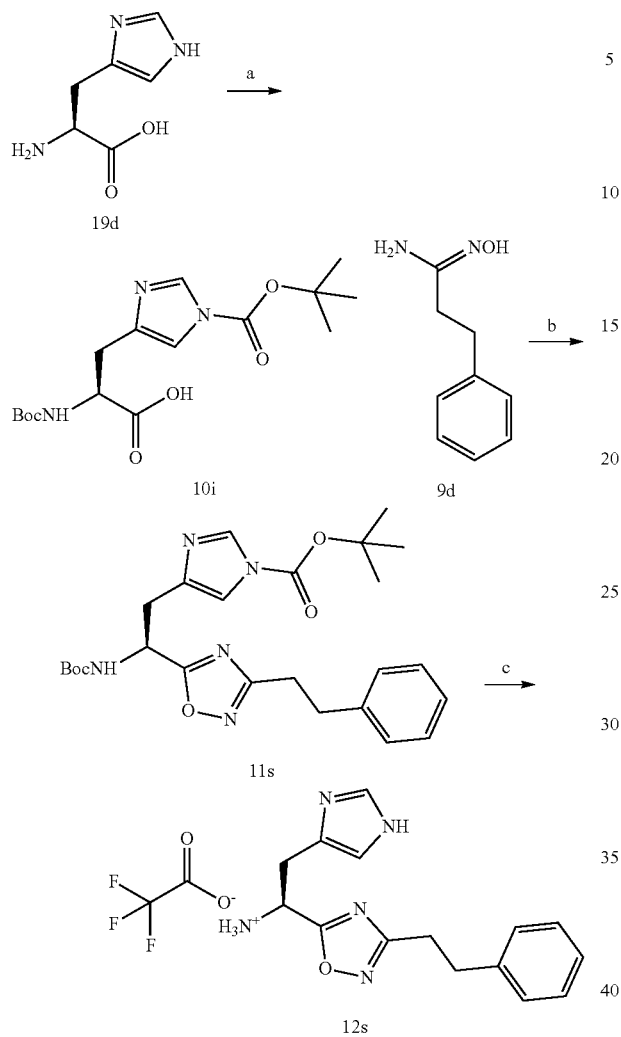

1) Step a: Synthesis of N^α,N^τ-bis(tert-butoxycarbonyl)-L-histidine (10i)

The same procedure as described in Scheme 22 to give a product of N^α,N^τ-bis(tert-butoxycarbonyl)-L-histidine (10i).

2) Step b: Synthesis of tert-butyl (S)-4-(2-((tert-butoxycarbonyl)amino)-2-(3-phenethyl-1,2,4-oxadiazol-5-yl)ethyl)-1H-imidazole-1-carboxylate (11s)

The same procedure as described in Scheme 22 by using 10i (960 mg, 2.70 mmol) and 9d (444 mg, 2.70 mmol) to give tert-butyl (S)-4-(2-((tert-butoxycarbonyl)amino)-2-(3-phenethyl-1,2,4-oxadiazol-5-yl)ethyl)-1H-imidazole-1-carboxylate (11s, 600 mg, 46%).

$^1$H NMR (400 MHz, Methanol-$d_4$) δ: 7.97 (s, 1H), 7.30-7.17 (m, 5H), 7.08 (s, 1H), 6.15 (d, J=8.8 Hz, 1H), 5.32 (d, J=8.8 Hz, 1H), 3.20-3.18 (m, 2H), 3.05-2.94 (m, 4H), 1.58 (s, 9H), 1.45 (s, 9H).

3) Step c: Synthesis of (S)-1-(3-benzyl-1,2,4-oxadiazol-5-yl)-2-(1H-imidazol-4-yl)ethan-1-aminium 2,2,2-trifluoroacetate (12s)

The same procedure as described in Scheme 22 by using 11s (190 mg, 0.393 mmol) to give he desired product without purification.

Example 20: Synthesis of (S)-1-(3-([1,1'-biphenyl]-4-ylmethyl)-1,2,4-oxadiazol-5-yl)-2-(1H-imidazol-4-yl)ethan-1-aminium 2,2,2-trifluoroacetate (12t)

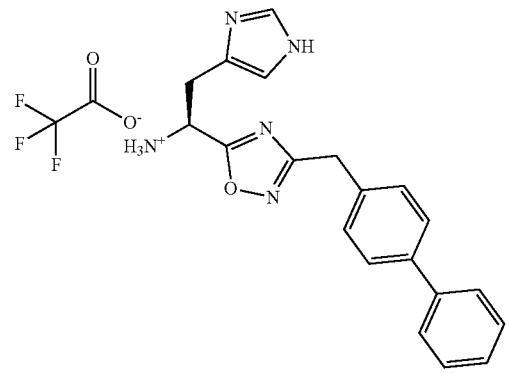

Compound 12t

Scheme 25

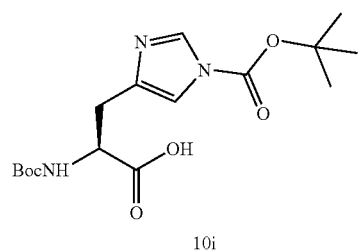

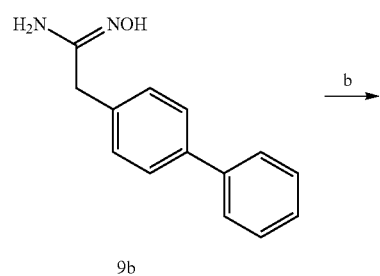

74

Example 21: Synthesis of (S)-1-(3-(adamantan-1-yl)methyl-1,2,4-oxadiazol-5-yl)-2-(1H-imidazol-4-yl)ethan-1-aminium 2,2,2-trifluoroacetate (12u)

Compound 12u

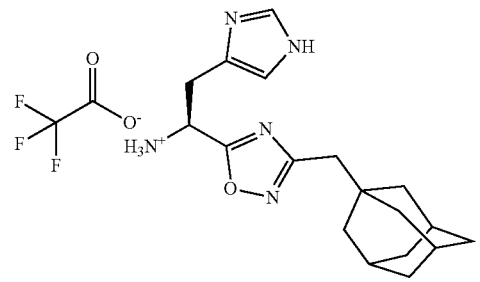

Scheme 26

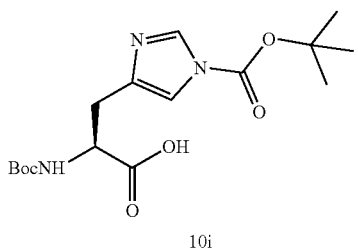

19d

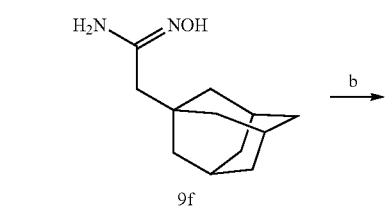

10i

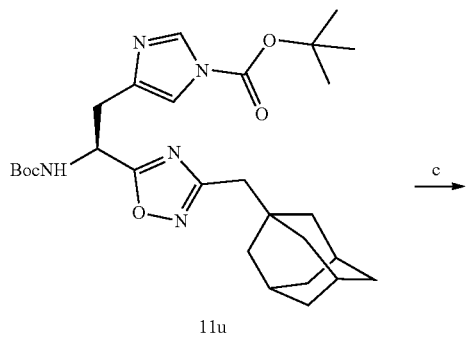

---

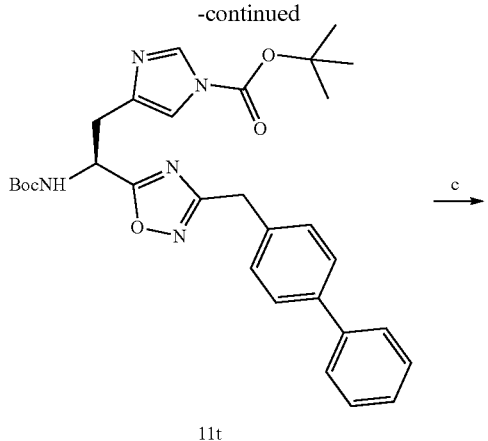

11t

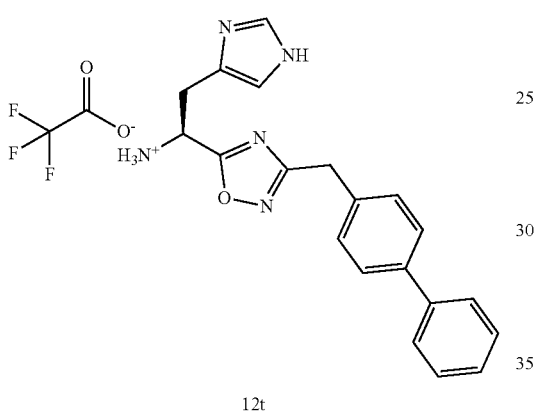

12t

1) Step a: Synthesis of N$^\alpha$,N$^\tau$-bis(tert-butoxycarbonyl)-L-histidine (10i)

The same procedure as described in Scheme 22 to give a product of N$^\alpha$,N$^\tau$-bis(tert-butoxycarbonyl)-L-histidine (10i).

2) Step b: Synthesis of tert-butyl (S)-4-(2-(3-([1,1'-biphenyl]-4-ylmethyl)-1,2,4-oxadiazol-5-yl)-2-((tert-butoxycarbonyl)amino)ethyl)-1H-imidazole-1-carboxylate (11t)

The same procedure as described in Scheme 22 by using 10i (0.432 g, 1.217 mmol) and 9b (0.275 g, 1.217 mmol) to give a yellowish solid (S)-4-(2-(3-([1,1'-biphenyl]-4-ylmethyl)-1,2,4-oxadiazol-5-yl)-2-((tert-butoxycarbonyl)amino)ethyl)-1H-imidazole-1-carboxylate (11t, 0.35 g).

$^1$H NMR (400 MHz, Methanol-d$_4$) δ8.06 (s, 1H), 7.58-7.52 (m, 4H), 7.41-7.37 (m, 2H), 7.33-7.27 (m, 3H), 7.24 (s, 1H), 5.18-5.14 (m, 1H), 4.08 (s, 2H), 3.17 (dd, J=14.8, 5.8 Hz, 1H), 3.07 (dd, J=14.8, 8.7 Hz, 1H), 1.56 (s, 9H), 1.37 (s, 9H).

3) Step c: Synthesis of (S)-1-(3-([1,1'-biphenyl]-4-ylmethyl)-1,2,4-oxadiazol-5-yl)-2-(1H-imidazol-4-yl)ethan-1-aminium 2,2,2-trifluoroacetate (12t)

The same procedure as described in Scheme 22 by using 11t (0.3 g, 0.55 mmol) to give a yellowish solid (12t, 0.185 g).

$^1$H NMR (400 MHz, Methanol-d$_4$) δ8.91 (d, J=1.3 Hz, 1H), 7.60-7.57 (m, 4H), 7.50-7.48 (m, 1H), 7.45-7.38 (m, 4H), 7.36-7.31 (m, 1H), 5.24 (t, J=7.3 Hz, 1H), 4.19 (s, 2H), 3.60 (d, J=7.3 Hz, 2H).

-continued

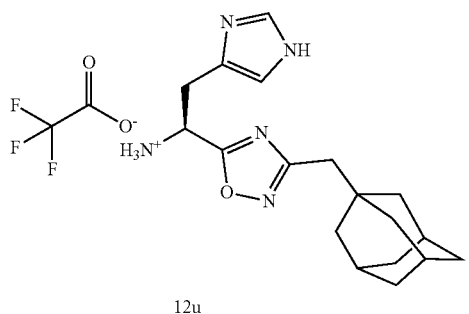

12u

1) Step a: Synthesis of N$^\alpha$,N$^\tau$-bis(tert-butoxycarbonyl)-L-histidine (10i)

The same procedure as described in Scheme 22 to give a product of N$^\alpha$,N$^\tau$-bis(tert-butoxycarbonyl)-L-histidine (10i).

2) Step b: Synthesis of tert-butyl 4-((S)-2-(3-(adamantan-1-yl)methyl-1,2,4-oxadiazol-5-yl)-2-((tert-butoxycarbonyl)amino)ethyl)-1H-imidazole-1-carboxylate (11u)

The same procedure as described in Scheme 22 by using 10i (1.28 g; 3.6 mmol) and 9f (660 mg; 3.17 mmol) to give 635 mg (38%) of product 11u as an amorphous solid.

$^1$H NMR (300 MHz, Chloroform-d) δ7.88 (s, 1H), 7.01 (s, 1H), 6.09 (d, J=8.4 Hz, 1H), 5.26 (q, J=5.4 Hz, 1H), 3.24-3.01 (multiple peaks, 2H), 2.38 (s, 2H), 1.91-1.81 (bs, 3H), 1.66-1.56 (multiple peaks, 3H), 1.52 (multiple peaks, 12H), 1.49-1.42 (multiple peaks, 6H), 1.38 (s, 9H).

3) Step c: Synthesis of (S)-1-(3-(adamantan-1-yl)methyl-1,2,4-oxadiazol-5-yl)-2-(1H-imidazol-4-yl)ethan-1-aminium 2,2,2-trifluoroacetate (12u)

The same procedure as described in Scheme 22 by using 11u (635 mg; 1.49 mmol) to give 835 mg (~100%) of 12u as an amorphous solid.

$^1$H NMR (300 MHz, Methanol-d$_4$) δ8.94 (s, 1H), 7.49 (s, 1H), 5.27 (t, J=7.4 Hz, 1H), 3.64 (multiple peaks, 2H), 2.56 (s, 2H), 1.98 (bs, 3H), 1.82-1.72 (multiple peaks, 3H), 1.71-1.51 (multiple peaks, 9H).

Example 22: Synthesis of (S)-1-(3-(adamantan-1-yl)methyl-1,2,4-oxadiazol-5-yl)-2-(1-methyl-1H-imidazol-4-yl)ethan-1-aminium chloride (12v)

Compound 12v

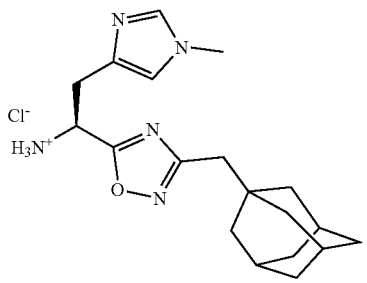

Scheme 27

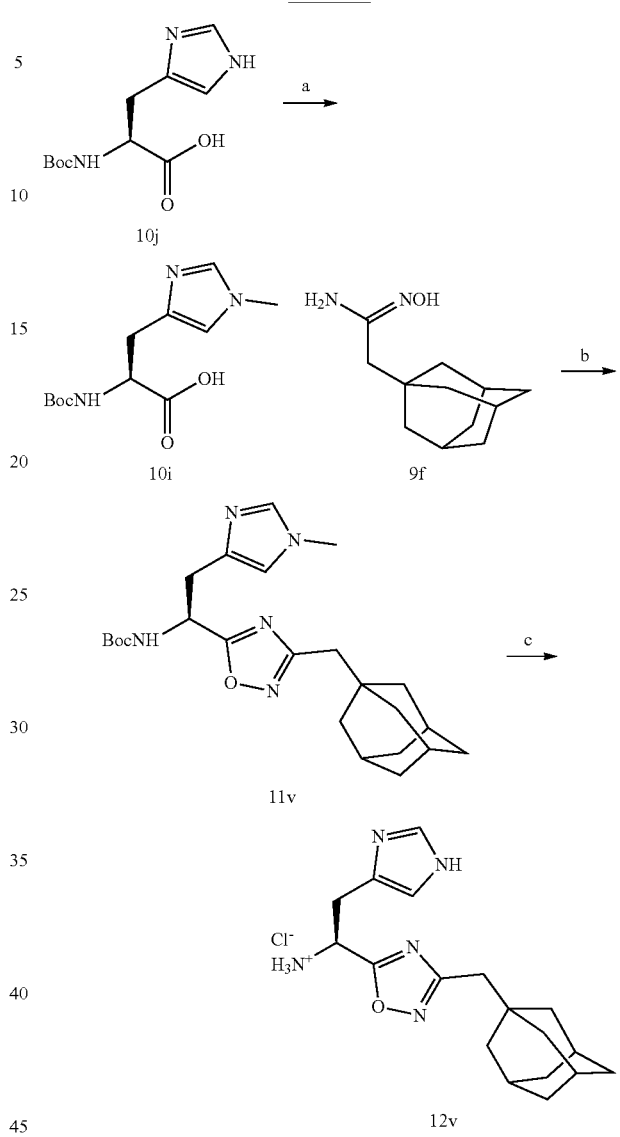

1) Step a: Synthesis of N$^\alpha$-(tert-butoxycarbonyl)-N$^\tau$-methyl-L-histidine (10k)

To a cooled (−15° C.) and stirred suspension of 10j (1.00 g, 3.92 mmol) in dry MeCN (20 mL) under argon atmosphere sodium hydride (60% suspension in mineral oil, 548 mg, 13.7 mmol) was added portion-wise. After complete addition of NaH, the resulting mixture was stirred at the same temperature for 30 min. Then, methyl iodide (0.13 mL, 4.31 mmol) was added dropwise and the reaction mixture was stirred at −5° C. for 4 h. The reaction mixture was quenched with MeOH (15 mL) and evaporated under reduced pressure at r.t. Dry petroleum ether (50 mL) was added to the solid residue and the flask was closed by CaCl$_2$ tube, because the crude mixture is extremely hygroscopic. The mixture was stirred at r.t. for 10 min and the petroleum ether was decanted. Then, the resulting white amorphous solid was extracted with chloroform (3×50 mL) and the combined liquid phases were evaporated to give crude 10k which was used to carry out next step reaction.

2) Step b: Synthesis of tert-butyl ((S)-1-(3-(adamantan-1-yl)methyl-1,2,4-oxadiazol-5-yl)-2-(1-methyl-1H-imidazol-4-yl)ethyl)carbamate (11v)

The same procedure as described in Scheme 22 by using 10k from previous step and 9f (817 mg, 3.92 mmol) to give 11v (0.51 g, 29%).

$^1$H NMR (300 MHz, CDCl$_3$): δ=7.30 (s, 1H), 6.52 (s, 1H), 6.40-6.31 (m, 1H), 5.32-5.21 (m, 1H), 3.56 (s, 3H), 3.26-3.06 (m, 2H), 2.45 (s, 2H), 2.02-1.88 (m, 4H), 1.79-1.17 ppm (m, 20H).

3) Step c: Synthesis of (S)-1-(3-(adamantan-1-yl)methyl-1,2,4-oxadiazol-5-yl)-2-(1-methyl-1H-imidazol-4-yl)ethan-1-aminium chloride (12v)

The same procedure as described in Scheme 22 by using 11v (635 mg; 1.49 mmol) to give 12v (350 mg, 87%).

$^1$H NMR (300 MHz, Methanol-d$_4$): δ=8.65-8.48 (m, 1H), 7.35 (s, 1H), 5.16-5.09 (m, 1H), 3.85 (s, 3H), 3.54-3.42 (m, 2H), 2.54 (s, 2H), 2.01-1.91 (s, 3H), 1.84-1.51 (m, 12H).

Example 23: Synthesis of (S)-1-(3-([1,1'-biphenyl]-4 ylmethyl)-1,2,4-oxadiazol-5-yl)-2-(1-methyl-1H-imidazol-4-yl)ethan-1-aminium chloride (12w)

Compound 12w

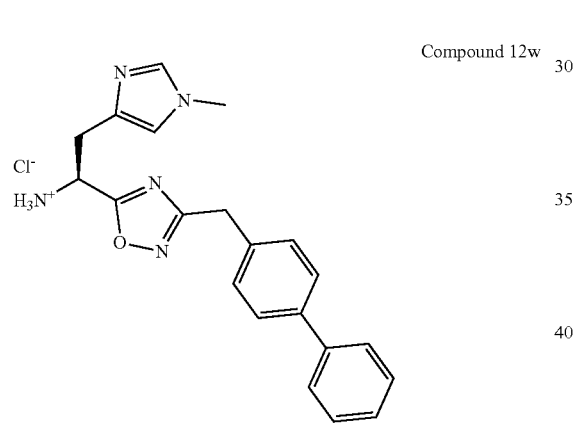

Scheme 28

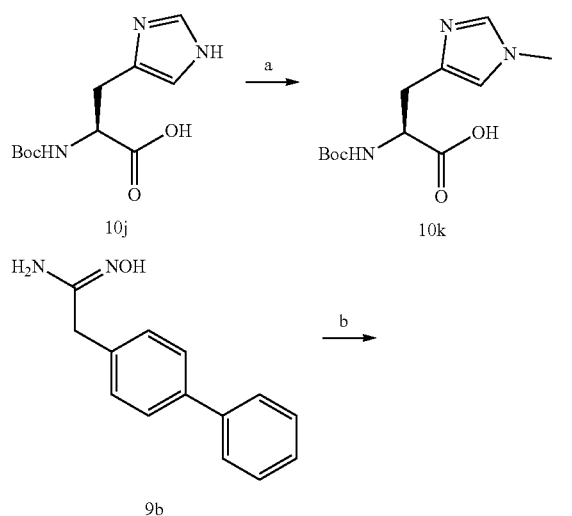

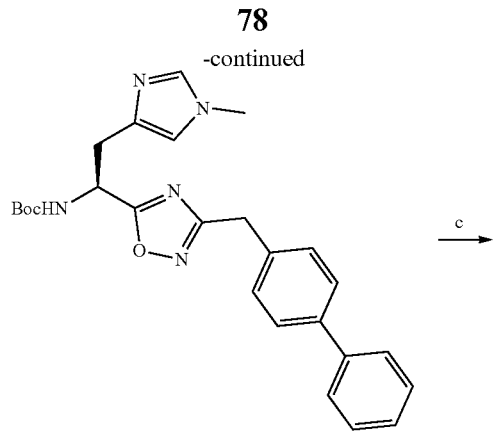

11w

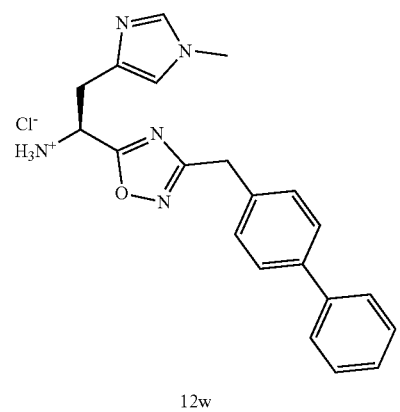

12w

1) Step a: Synthesis of N$^α$-(tert-butoxycarbonyl)-N$^τ$-methyl-L-histidine (10k)

The same procedure as described in Scheme 27.

2) Step b: Synthesis of tert-butyl (S)-(1-(3-([1,1'-biphenyl]-4-ylmethyl)-1,2,4-oxadiazol-5-yl)-2-(1-methyl-1H-imidazol-4-yl)ethyl)carbamate (11w)

The same procedure as described in Scheme 22 by using 10k from previous step and 9b (267 mg, 1.18 mmol) to give 11w (136 mg, 25%).

$^1$H NMR (300 MHz, CDCl$_3$): δ=7.61-7.30 (m, 9H), 6.46-6.38 (m, 1H), 6.36-6.25 (m, 1H), 5.33-5.21 (m, 1H), 4.07 (s, 2H), 3.50 (s, 3H), 3.26-3.05 (m, 2H), 1.53-1.28 ppm (m, 9H).

3) Step c: Synthesis of (S)-1-(3-([1,1'-biphenyl]-4-ylmethyl)-1,2,4-oxadiazol-5-yl)-2-(1-methyl-1H-imidazol-4-yl)ethan-1-aminium chloride (12w)

The same procedure as described in Scheme 22 by using 11q (635 mg; 1.49 mmol) to give 12q (76 mg) in 65% yield as a white amorphous solid.

$^1$H NMR (300 MHz, Methanol-d$_4$): =8.56 (s, 1H), 7.64-7.54 (m, 4H), 7.49-7.24 (m, 6H), 5.14-5.06 (m, 1H), 4.18 (s, 2H), 3.80 (s, 3H), 3.55-3.39 ppm (m, 2H).

Example 24: Synthesis of (S)-1-(3-benzyl-1,2,4-oxadiazol-5-yl)-2-(1H-indol-3 yl)ethan-1-amine (5x)

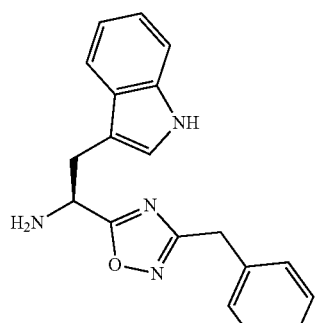

Scheme 29

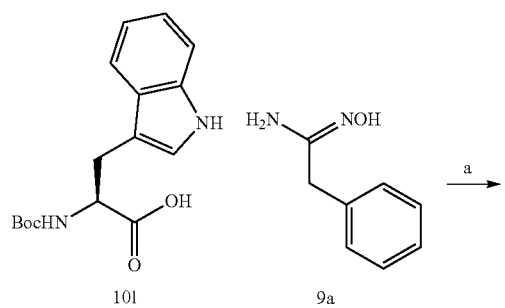

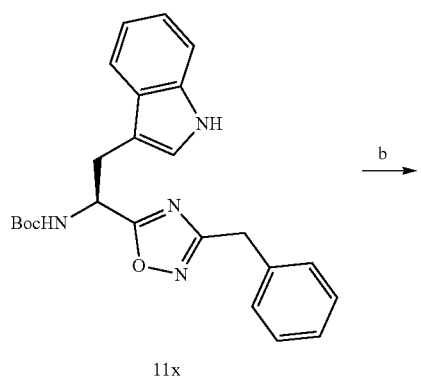

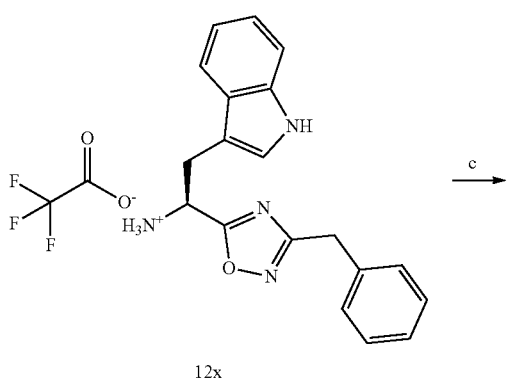

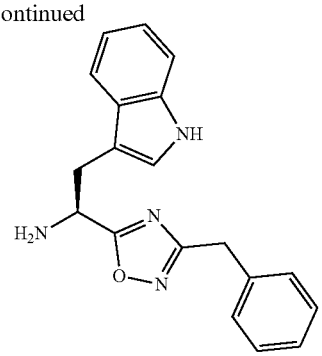

5x

1) Step a: Synthesis of tert-butyl (S)-(1-(3-benzyl-1,2,4-oxadiazol-5-yl)-2-(1H-indol-3-yl)ethyl)carbamate (11x)

The same procedure as described in Scheme 6 by using 10l (788 mg, 2.59 mmol) and 9a (389 mg, 2.59 mmol) to give a yellowish oil product of tert-butyl (S)-(1-(3-benzyl-1,2,4-oxadiazol-5-yl)-2-(1H-indol-3-yl)ethyl)carbamate (11x, 560 mg, 52%).

$^{1H}$ NMR (300 MHz, CDCl$_3$) δ: 7.96 (s, 1H), 7.45-7.13 (m, 8H), 7.05 (t, J=7.5 Hz, 1H), 6.77 (s, 1H), 5.35 (s, 1H), 5.18 (s, 1H), 4.01 (s, 2H), 3.40 (d, J=4.9 Hz, 2H), 1.41 (s, 9H).

2) Step b: Synthesis of (S)-1-(3-benzyl-1,2,4-oxadiazol-5-yl)-2-(1H-indol-3-yl)ethan-1-aminium 2,2,2-trifluoroacetate (12x)

The same procedure as described in Scheme 22 by using 11x (560 mg, 1.34 mmol) to give he desired product which was used for the subsequent reaction.

3) Step c: Synthesis of (S)-1-(3-benzyl-1,2,4-oxadiazol-5-yl)-2-(1H-indol-3-yl)ethan-1-amine (5x)

The above product was dissolved in DCM (20 mL), then 5% NaHCO$_3$ (20 mL) water solution was added and after stirring for 30 min organic phase with product was separated, dried over anh. Na$_2$SO$_4$, filtered and evaporated. The crude product was purified by flash column chromatography (SiO$_2$, EtOAc (100%, R$_f$(PR) 0.3)) to yield product as a yellowish oil 305 mg product (5x, 72%).

$^1$H NMR (400 MHz, CDCl$_3$) δ: 8.16 (s, 1H), 7.49 (d, J=8.0 Hz, 1H), 7.34-7.20 (m, 5H), 7.16 (dd, J=11.3, 3.9 Hz, 1H), 7.07 (ddd, J=7.1, 0.9, 0.5 Hz, 1H), 6.86 (d, J=2.3 Hz, 1H), 4.48 (dd, J=7.5, 5.3 Hz, 1H), 4.03 (s, 2H), 3.29 (ddd, J=21.9, 14.4, 6.2 Hz, 2H), 1.72 (s, 2H).

Example 25: Synthesis of (S)-1-(3-([1,1'-biphenyl]-4 ylmethyl)-1,2,4-oxadiazol-5-yl)-2-(1H-indol-3-yl)ethan-1-aminium chloride (12y)

Compound 12y

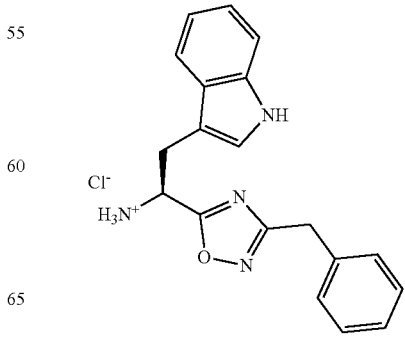

-continued
Scheme 30

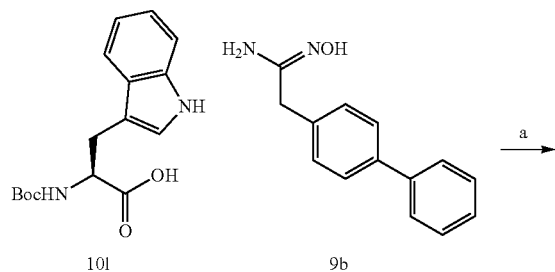

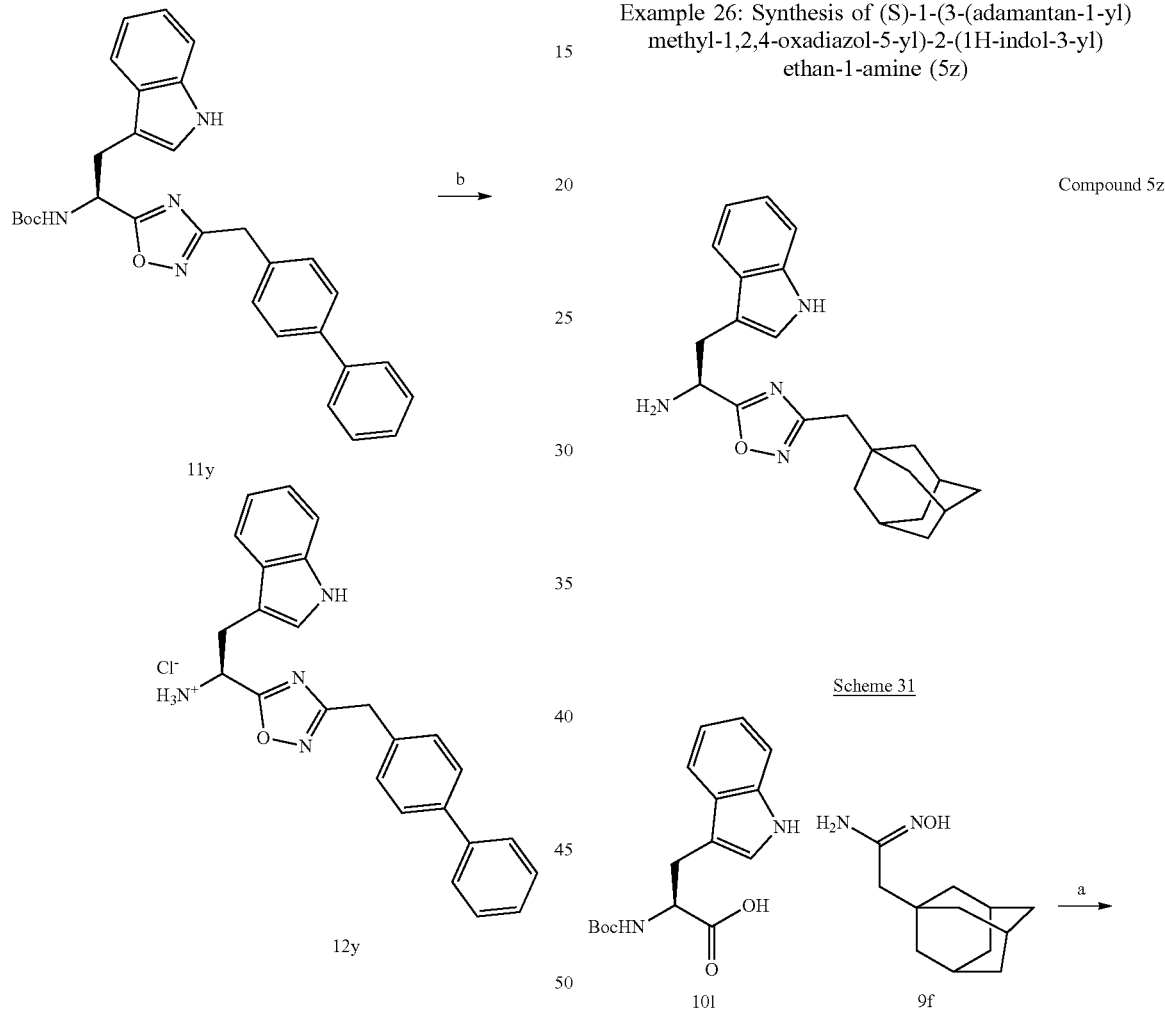

1) Step a: Synthesis of tert-butyl (S)-(1-(3-([1,1'-biphenyl]-4-ylmethyl)-1,2,4-oxadiazol-5-yl)-2-(1H-indol-3-yl)ethyl)carbamate (11y)

The same procedure as described in Scheme 6 by using 10l (1.086 g, 3.568 mmol) and 9b (0.807 g, 3.568 mmol) to give the product (S)-(1-(3-([1,1'-biphenyl]-4-ylmethyl)-1,2,4-oxadiazol-5-yl)-2-(1H-indol-3-yl)ethyl)carbamate (11y, 0.905 g) as brown solid.

$^1$H NMR (400 MHz, DMSO-$d_6$) δ10.87 (s, 1H), 7.74 (d, J=7.9 Hz, 1H), 7.63 (m, 4H), 7.47 (m, 3H), 7.34 (dt, J=17.2, 8.0 Hz, 4H), 7.10 (d, J=1.9 Hz, 1H), 7.06 (t, J=7.5 Hz, 1H), 6.95 (t, J=7.5 Hz, 1H), 5.00 (q, J=7.6 Hz, 1H), 4.10 (s, 2H), 3.29-3.22 (m, 2H), 1.31 (s, 9H).

2) Step b: Synthesis of (5)-1-(3-([1,1'-biphenyl]-4-ylmethyl)-1,2,4-oxadiazol-5-yl)-2-(1H-indol-3-yl)ethan-1-aminium chloride (12y)

The same procedure as described in Scheme 22 by using 11y (0.68 g, 1.375 mmol) to give 0.55 g of desired product 12y.

$^1$H NMR (400 MHz, Methanol-$d_4$) δ7.58-7.50 (m, 4H), 7.43 (m, 2H), 7.38-7.31 (m, 3H), 7.26-7.24 (m, 2H), 7.14-7.09 (m, 2H), 6.99 (ddd, J=8.0, 7.1, 0.9 Hz, 1H), 5.07 (t, J=6.7 Hz, 1H), 4.10 (d, J=3.0 Hz, 2H), 3.56 (d, J=6.7 Hz, 2H).

Example 26: Synthesis of (S)-1-(3-(adamantan-1-yl)methyl-1,2,4-oxadiazol-5-yl)-2-(1H-indol-3-yl)ethan-1-amine (5z)

Compound 5z

Scheme 31

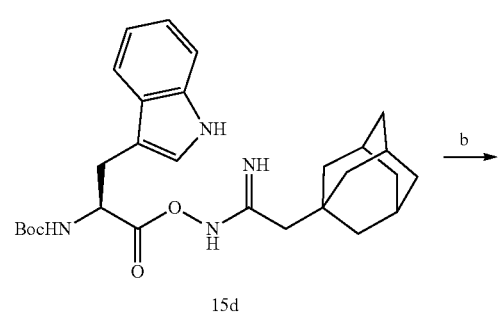

-continued

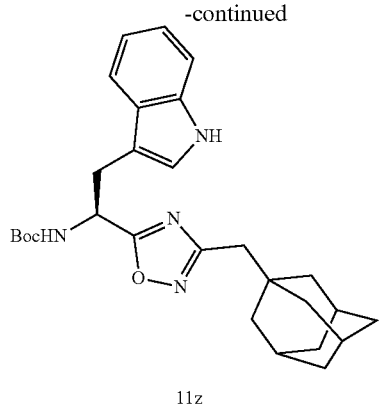

11z

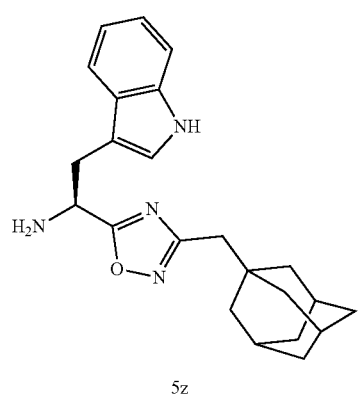

5z

1) Step a: Synthesis of tert-butyl (S)-1-(2-(adamantan-1-yl) acetimidamidooxy)-3-(1H-indol-3-yl)-1-oxopropan-2-yl-carbamate (15d)
The same procedure as described in Scheme 11 by using 10l (61.32 g, 0.20 mol) and 9f (35 g, 0.17 mmol) to give yellow solid (15d, 40 g, 48%).

2) Step b: Synthesis of tert-butyl (S)-1-(3-(adamantan-1-yl) methyl-1,2,4-oxadiazol-5-yl)-2-(1H-indol-3-yl)ethylcarbamate (11z)
The same procedure as described in Scheme 11 by using 15d (40 g) to give to get white solid (11z, 15 g, 39%) which dried and used in next step directly.

3) Step c: Synthesis of (S)-1-(3-(adamantan-1-yl)methyl-1, 2,4-oxadiazol-5-yl)-2-(1H-indol-3-yl)ethan-1-amine (5z)
The same procedure as described in Scheme 11 by using 11z (15 g) to give a yellow liquid (5z, 5.5 g, 99.35% HPLC, 47%).

$^1$H NMR (CDCl$_3$, 300 MHz): δ=8.10 (s(br), 1H), 7.60 (d, J=7.8 Hz, 1H), 7.37 (d, J=7.8 Hz, 1H), 7.18 (m, 2H), 7.04 (s, 1H), 4.56 (m, 1H), 3.45 (m, 1H), 3.33 (m, 1H), 2.49 (s, 2H), 1.50-2.10 (m, 15H).

Example 27: Synthesis of (S)-1-(3-(adamantan-1-yl) methyl-1,2,4-oxadiazol-5-yl)-2-(1-methyl-1H-in-dol-3 yl)ethan-1-aminium 2,2,2-trifluoroacetate (12aa)

Compound 12aa

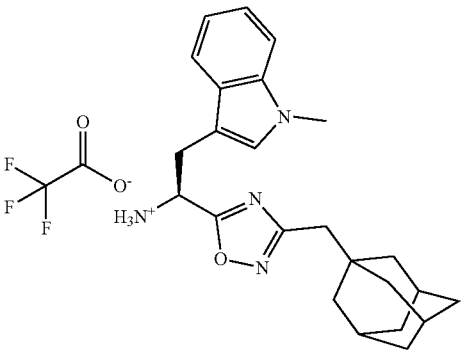

Scheme 32

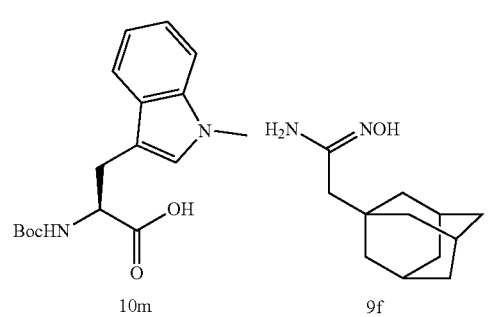

10m       9f

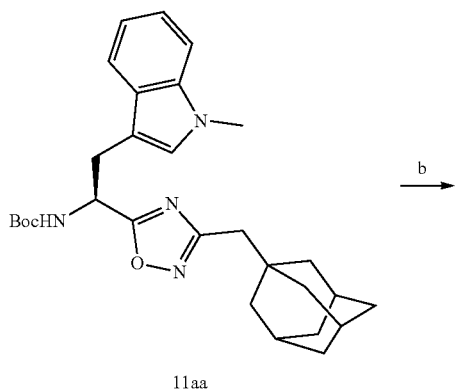

11aa

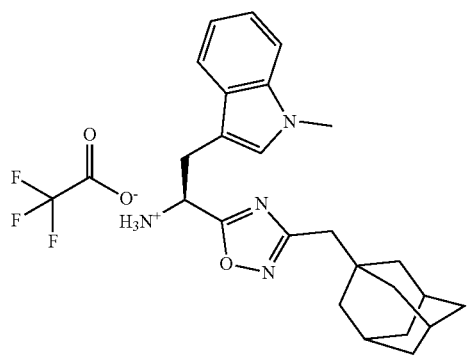

12aa

1) Step a: Synthesis of tert-butyl ((S)-1-(3-(adamantan-1-yl)methyl-1,2,4-oxadiazol-5-yl)-2-(1-methyl-1H-indol-3-yl)ethyl)carbamate (11aa)

The same procedure as described in Scheme 11 by using 10l (500 mg; 1.6 mmol) and 9f (270 mg; 1.3 mmol) to give 219 mg (34%) of 11aa as an amorphous solid.

$^1$H NMR (300 MHz, Chloroform-d) δ 7.37 (d, J=7.9 Hz, 1H), 7.19 (d, J=8.1 Hz, 1H), 7.13 (m, 1H), 7.01 (m, 1H), 6.66 (bs, 1H), 5.36-5.20 (m, 1H), 5.18-5.00 (m, 1H), 3.63 (s, 3H), 3.35 (m, 2H), 2.38 (s, 2H), 1.87 (bs, 3H), 1.61 (bd, J=12.0 Hz, 3H), 1.55-1.40 (m, 9H), 1.36 (s, 9H).

2) Step b: Synthesis of (S)-1-(3-(adamantan-1-yl)methyl-1,2,4-oxadiazol-5-yl)-2-(1-methyl-1H-indol-3-yl)ethan-1-aminium 2,2,2-trifluoroacetate (12aa)

The same procedure as described in Scheme 11 by using 11aa (219 mg; 0.45 mmol) to give 195 mg (~100%) of 12aa as an amorphous solid.

$^1$H NMR (400 MHz, Methanol-d$_4$) δ 7.37 (dt, J=8.0, 0.9 Hz, 1H), 7.32 (d, J=8.3 Hz, 1H), 7.15 (ddd, J=8.2, 7.1, 1.1 Hz, 1H), 7.05-6.98 (m, 2H), 5.06 (t, J=6.8 Hz, 1H), 3.74 (s, 3H), 3.55 (m, 2H), 2.42 (s, 2H), 1.88 (bs, 3H), 1.69 (bd, J=12.1 Hz, 3H), 1.56 (bd, J=11.3 Hz, 3H), 1.46 (m, 6H).

Example 28: Synthesis of (S)-1-(3-(adamantan-1-yl)methyl-1,2,4-oxadiazol-5-yl)-2-(5-fluoro-1H-indol-3-yl)ethan-1-aminium 2,2,2-trifluoroacetate (12ab)

Compound 12ab

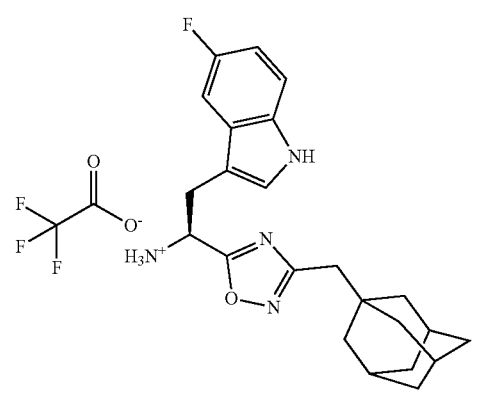

Scheme 33

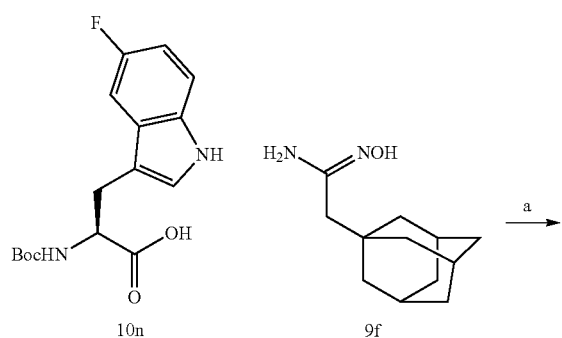

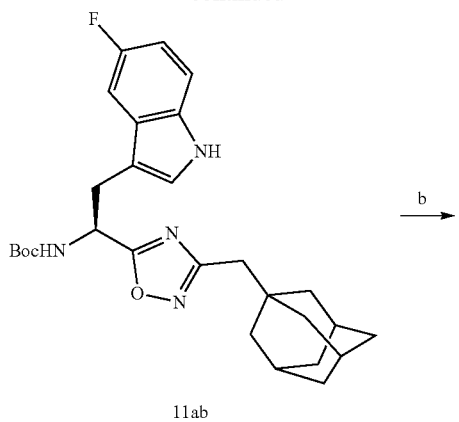

11ab

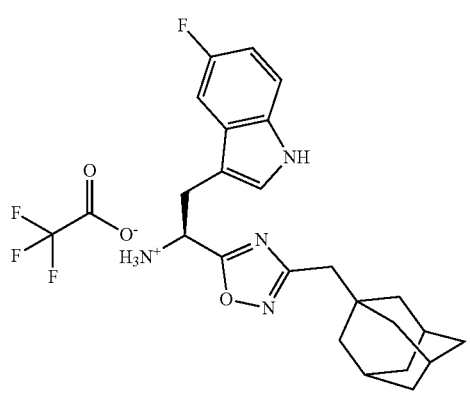

12ab

1) Step a: Synthesis of tert-butyl ((S)-1-(3-(adamantan-1-yl)methyl-1,2,4-oxadiazol-5-yl)-2-(5-fluoro-1H-indol-3-yl)ethyl)carbamate (11ab)

The same procedure as described in Scheme 11 by using 10n (676 mg; 2.1 mmol) and 9f (625 mg; 3.0 mmol) to give 220 mg (21%) of 11ab was obtained in a form of amorphous solid. Product was used in the next step without characterization.

2) Step b: Synthesis of (5)-1-(3-(adamantan-1-yl)methyl-1,2,4-oxadiazol-5-yl)-2-(5-fluoro-1H-indol-3-yl)ethan-1-aminium 2,2,2-trifluoroacetate (12ab)

The same procedure as described in Scheme 11 by using flab (219 mg; 0.45 mmol) to give 234 mg (~100%) of 12ab was isolated as an amorphous solid. Product was used in the next step without characterization.

87

Example 29: Synthesis of (S)-1-(3-([1,1'-biphenyl]-4-ylmethyl)-1,2,4-oxadiazol-5-yl)-2-(1-methyl-1H-indol-3 yl)ethan-1-aminium 2,2,2-trifluoroacetate (12ac)

Compound 12ac

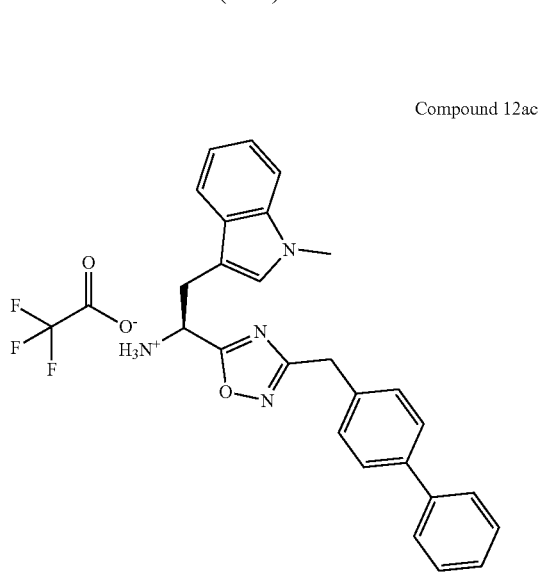

Scheme 34

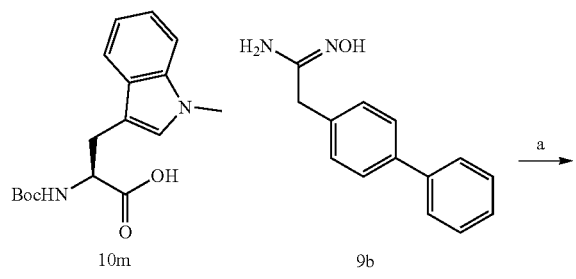

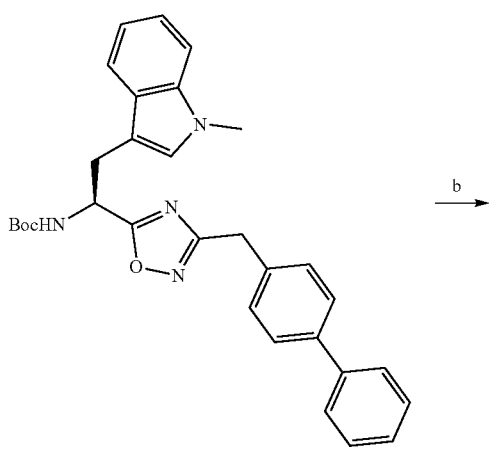

11ac

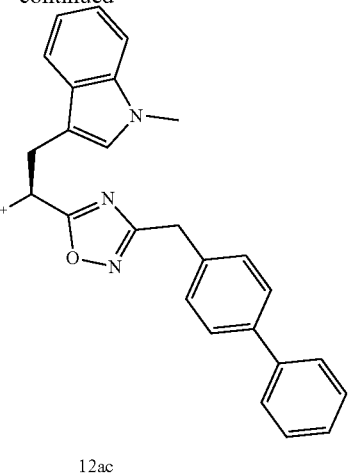

12ac

1) Step a: Synthesis of tert-butyl (S)-(1-(3-([1,1'-biphenyl]-4-ylmethyl)-1,2,4-oxadiazol-5-yl)-2-(1-methyl-1H-indol-3-yl)ethyl)carbamate (11ac)

The same procedure as described in Scheme 11 by using 10m (950 mg; 3.0 mmol) and 9b (700 mg; 3.1 mmol) to give 75 mg (49%) of 11-ad as a form of amorphous solid.

$^1$H NMR (300 MHz, Chloroform-d) δ7.75-7.63 (m, 4H), 7.62-7.53 (m, 2H), 7.53-7.41 (m, 4H), 7.38-7.29 (ms, 2H), 7.23-7.11 (td, J=7.2, 2.2 Hz 1H), 6.76 (bs, 1H), 5.48 (bs, 1H), 5.30 (d, J=7.9 Hz, 1H), 4.20 (s, 2H), 3.76 (s, 3H), 3.54 (m, 2H), 1.55 (s, 9H).

2) Step b: Synthesis of (S)-1-(3-([1,1'-biphenyl]-4-ylmethyl)-1,2,4-oxadiazol-5-yl)-2-(1-methyl-1H-indol-3-yl)ethan-1-aminium 2,2,2-trifluoroacetate (12ac)

The same procedure as described in Scheme 11 by using 11ac (219 mg; 0.45 mmol) to give 605 mg (~79%) of 12ac as a white crystalline solid.

$^1$H NMR (400 MHz, Methanol-d$_4$) δ7.55 (m, 2H), 7.50 (m, 2H), 7.41 (m, 2H), 7.34-7.27 (m, 3H), 7.24 (d, J=8.3 Hz, 2H), 7.16 (ddd, J=8.2, 7.1, 1.1 Hz, 1H), 6.99 (ddd, J=7.9, 7.1, 0.9 Hz, 1H), 6.94 (s, 1H), 5.02 (t, J=6.6 Hz, 1H), 4.10 (d, J=15.3 Hz, 1H), 4.05 (d, J=15.3 Hz, 1H), 3.68 (s, 3H), 3.51 (m, 2H).

Example 30: Synthesis of 4-((S)-2-(3-(adamantan-1-yl)methyl-1,2,4-oxadiazol-5-yl)-2-ammonioethyl)pyridin-1-ium 2,2,2-trifluoroacetate (12ad)

Compound 12ad

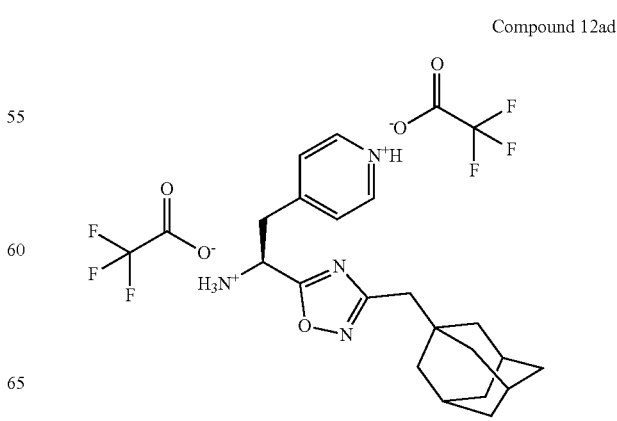

89

-continued
Scheme 35

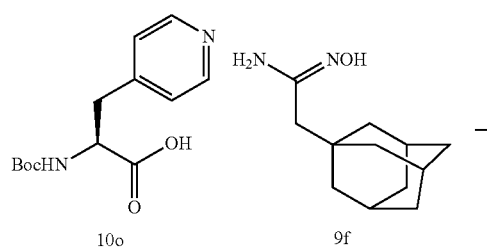

10o    9f

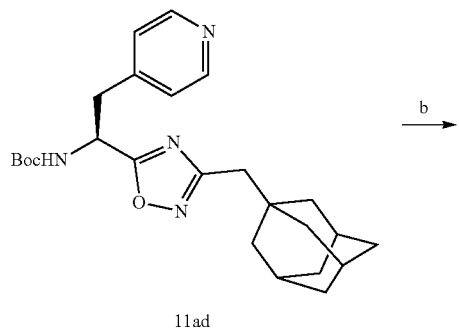

11ad

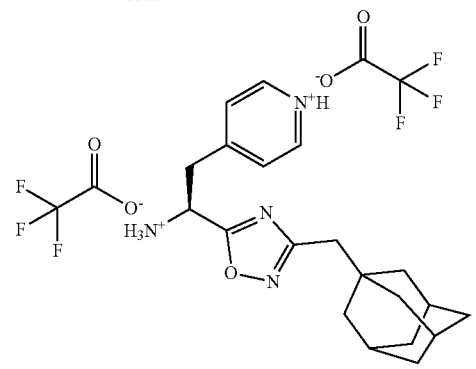

12ad

1) Step a: Synthesis of tert-butyl ((S)-1-(3-(adamantan-1-yl)methyl-1,2,4-oxadiazol-5-yl)-2-(pyridin-4-yl)ethyl)carbamate (11ad)

The same procedure as described in Scheme 11 by using 10o (0.384 g, 1.44 mmol) and 9f (0.3 g, 1.44 mmol) to yield product 11ad (220 mg, 45%).

$^1$H-NMR (300 MHz, CDCl$_3$) δ8.46 (d, J=5.5 Hz, 2H), 7.01 (d, J=5.5 Hz, 2H), 5.34 (s, 2H), 3.34-3.11 (m, 2H), 2.44 (s, 2H), 1.97-1.89 (m, 3H), 1.72-1.52 (m, 6H), 1.51-1.45 (m, 6H), 1.40 (s, 9H).

2) Step b: Synthesis of 4-((S)-2-(3-(adamantan-1-yl)methyl-1,2,4-oxadiazol-5-yl)-2-ammonioethyl)pyridin-1-ium 2,2,2-trifluoroacetate (12ad)

The same procedure as described in Scheme 11 by using 11ad (219 mg; 0.45 mmol) to give 605 mg (~79%) of 12ad as a white crystalline solid.

$^1$H NMR (400 MHz, Methanol-d$_4$) δ7.55 (m, 2H), 7.50 (m, 2H), 7.41 (m, 2H), 7.34-7.27 (m, 3H), 7.24 (d, J=8.3 Hz, 2H), 7.16 (ddd, J=8.2, 7.1, 1.1 Hz, 1H), 6.99 (ddd, J=7.9, 7.1, 0.9 Hz, 1H), 6.94 (s, 1H), 5.02 (t, J=6.6 Hz, 1H), 4.10 (d, J=15.3 Hz, 1H), 4.05 (d, J=15.3 Hz, 1H), 3.68 (s, 3H), 3.51 (m, 2H).

90

Example 31: Synthesis of (R)-2-amino-N-((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (D-Arg-DMT-NH((S)-5-amino-1-(3-benzyl-1,2,4-oxadiazol-5-yl)pent-1-yl), 7a)

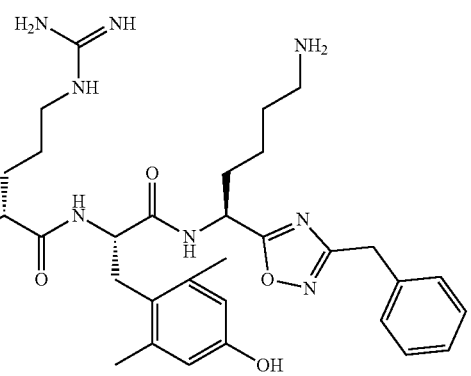

Compound 7a

Scheme 36

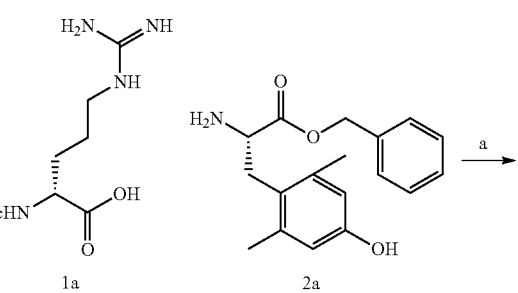

1a    2a

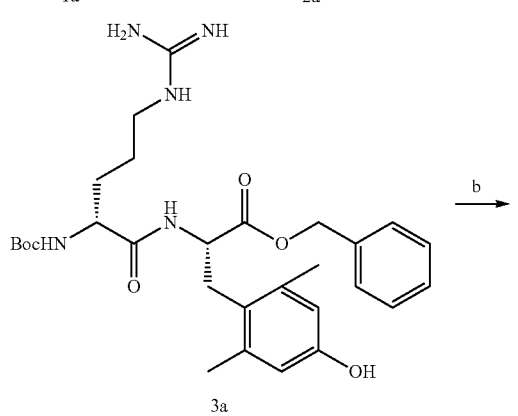

3a

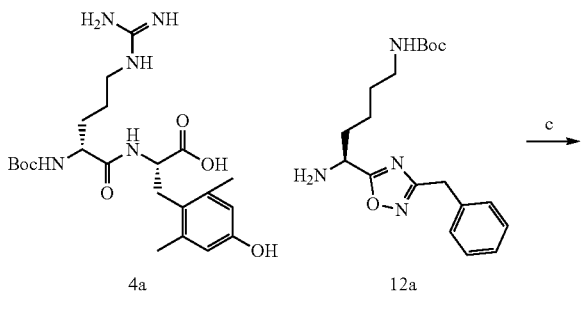

4a    12a

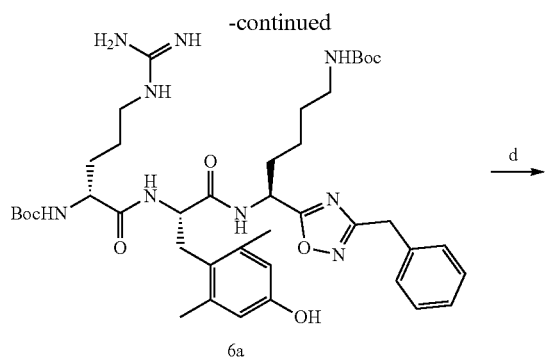

6a

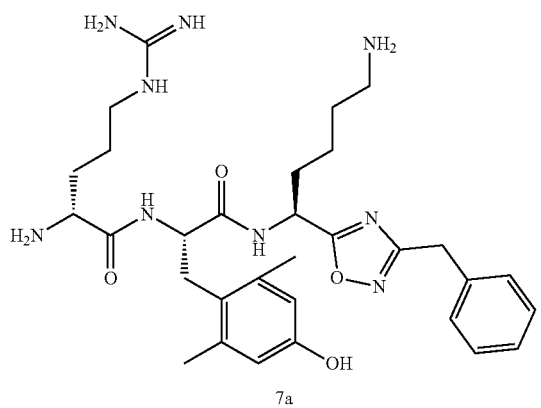

7a

1) Step a: Synthesis of benzyl (S)-2-((R)-2-((tert-butoxycarbonyl)amino)-5-guanidinopentanamido)-3-(4-hydroxy-2,6-dimethylphenyl)propanoate (3a)

To a suspension of DMT-OBn×HCl (2a, 45.0 g, 134 mmol) in MeCN (800 mL) NMM (32.7 mL, 298 mmol) was added at 0° C. The reaction mixture was stirred until reaction mixture became transparent. Then Boc-D-Arg-OH×HCl (1a, 46.3 g, 149 mmol) and HOBt*H$_2$O (9.11 g, 59.5 mmol) were added to reaction mixture and stirred for 15 min. Finally, EDC*HCl (38.5 g, 201 mmol) was added and mixture was stirred at 0° C. for 4 h. Then EtOAc (450 mL) and 1N HCl in brine (300 mL) were added. The combined organic extracts were washed with 1N HCl in brine (7×150 mL), NaHCO$_3$/brine (300 mL and until pH of aqueous layer is about pH=δ=7), dried over Na$_2$SO$_4$ and concentrated. 86.0 g (97%) of Boc-D-Arg-DMT-OBn (3a) were obtained and used without further purification.

$^1$H NMR (400 MHz, Methanol-d$_4$) δ7.33-7.18 (m, 5H), 6.43 (s, 2H), 5.06 (s, 2H) 4.71 (t, J=7.8 Hz, 1H), 4.07 (t, J=6.7 Hz, 1H), 3.19-3.09 (m, 3H), 3.03-2.97 (m, 1H), 2.23 (s, 6H), 1.72-1.65 (m, 1H), 1.54-1.43 (m, 3H), 1.45 (s, 9H).

2) Step b: Synthesis of (S)-2-((R)-2-((tert-butoxycarbonyl)amino)-5-guanidinopentanamido)-3-(4-hydroxy-2,6-dimethylphenyl)propanoic acid (4a)

To a solution of Boc-D-Arg-DM-Tyr-OBn (3a, 84.0 g, 142 mmol) in MeOH (1000 mL) Pd/C (10% w/w, 14.0 g) was added. The hydrogen was purged in reaction mixture at room temperature for 4 h. Then reaction mixture was filtrated through filter paper and washed with MeOH (150 mL). The solvent was removed by evaporation. White foam product 4a was obtained (74.0 g, 93%) and used without further purification.

$^1$H NMR (400 MHz, Methanol-d$_4$) δ6.44 (s, 2H), 4.68 (t, J=7.2 Hz, 1H), 4.04 (t, J=6.8 Hz, 1H), 3.15-3.09 (m, 3H), 3.02-2.94 (m, 1H), 2.29 (s, 6H), 1.74-1.59 (m, 1H), 1.54-1.43 (m, 1H), 1.45 (s, 9H).

3) Step c: Synthesis of tert-butyl ((6R,9S,12S)-1-amino-12-(3-benzyl-1,2,4-oxadiazol-5-yl)-9-(4-hydroxy-2,6-dimethylbenzyl)-1-imino-20,20-dimethyl-7,10,18-trioxo-19-oxa-2,8,11,17-tetraazahenicosan-6-yl)carbamate (6a)

DMF (200 mL) was added to 4a (11.17 g, 24 mmol) and stirred at r.t. for 15 min. To the resulting suspension, 12a (10.65 g, 20 mmol) was added and stirred at r.t. for 20 min. After addition of HOBt (612 mg, 4.00 mmol), the suspension was cooled in ice bath. EDC HCl (5.38 g, 28 mmol) was added in one portion, and the reaction mixture was stirred while cooled in ice bath for 2.5 h and, then, for 4.5 h at r.t. The nearly homogeneous reaction mixture was quenched with EtOAc (1500 mL) and the resulting solution was washed for 10 times with brine/aq. 0.5 M HCl (1:1; 400 mL). During the 6th and 9th washings, gel in the aqueous phase was formed. After addition of iPrOH (40 mL in each case) and repeated shaking the layers went clear again. Afterwards, the organic phase was washed for 6 times with brine/sat. aq. NaHCO$_3$ (9:1; 400 mL). During the 4th washing, gel in the aqueous phase was formed. After addition of iPrOH (40 mL) and repeated shaking the layers were separated easily. The organic phase was washed with brine (200 mL) and water (100 mL) and the solvent was removed under reduced pressure. No vigorous shaking was performed upon washing with water to avoid difficulties in phase separation. As a result, 16.8 g of the crude product were obtained (6a, 97.0% purity by HPLC, white amorphous solid).

$^1$H NMR (300 MHz, Methanol-d$_4$) ppm: δ=7.33-7.16 (m, 5H), 6.38 (s, 2H), 5.18-5.07 (m, 1H), 4.64-4.55 (m, 1H), 4.10-3.92 (m, 3H), 3.18-2.77 (m, 6H), 2.20 (s, 6H), 1.97-1.76 (m, 2H), 1.75-1.14 (m, 8H), 1.43 (s, 9H), 1.41 (s, 9H).

4) Step d: Synthesis of (R)-2-amino-N-((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (7a)

6a (16.8 g) was dissolved in DCM (100 mL) and cooled to 0° C., TFA (20 mL) was added dropwise and the solution was allowed to stir at 0° C. for 10 min, and then at rt for 3 h (LC/MS shows no starting material). Then reaction mixture was evaporated (at 0-5° C.) and additionally re-evaporated from DCM (100 mL, at 0-5° C.). The purification by flash chromatography on reverse phase (cartridge C-18, 120G) was performed divided crude material in 4 parts. Then all solvents were evaporated at reduced pressure at <40° C. White foam was dissolved in isopropanol (100 mL) and 5 mL of HCl in isopropanol (5-6M) was added at 0° C. and evaporated under reduced pressure. This step was repeated 3 times. Additionally, 100 mL of MeCN was added and suspension was evaporated one more time. As a result, white powder of 7a was obtained as hydrochloride salt.

$^1$H NMR (300 MHz, Methanol-d$_4$) δ7.36-7.14 (m, 5H), 6.40 (s, 2H), 5.15 (dd, J=8.5, 6.3 Hz, 1H), 4.68 (dd, J=8.7, 7.5 Hz, 1H), 4.07 (s, 2H), 3.97 (t, J=6.3 Hz, 1H), 3.18 (t, J=6.9 Hz, 2H), 3.11 (dd, J=14.2, 8.8 Hz, 1H), 2.95-2.84 (m, 3H), 2.22 (s, 6H), 2.02-1.59 (m, 6H), 1.57-1.28 (m, 4H). MS: EI-MS: m/z 608.4 [M+1].

Example 32: Synthesis of (R)-N-((S)-1-(((S)-1-(3-([1,1'-biphenyl]-4 ylmethyl)-1,2,4-oxadiazol-5 yl)-5-aminopentyl)amino)-3-(4-hydroxy-2,6-dimethylphenyl)-1-oxopropan-2-yl)-2-amino-5-guanidinopentanamide (D-Arg-DMT-NH((S)-5-amino-1-(3-(1,1'-biphenyl-4 yl)methyl-1,2,4-oxadiazol-5-yl)pent-1-yl), 7b)
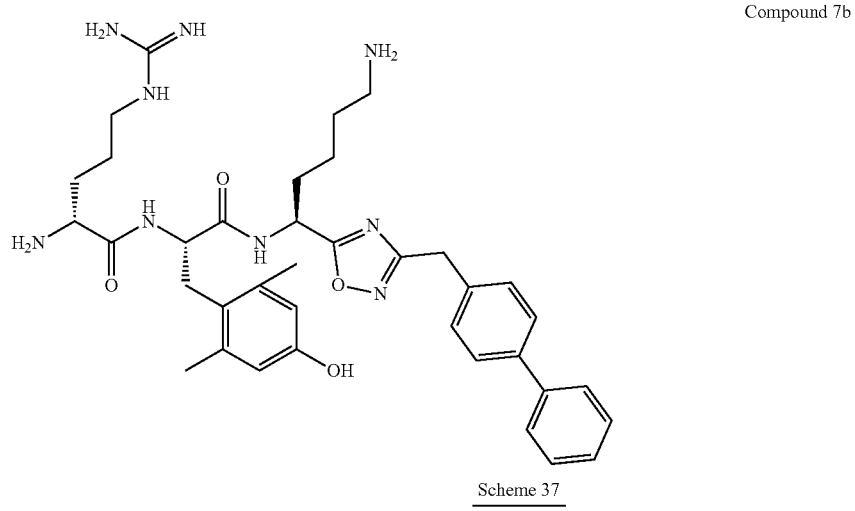
Compound 7b
Scheme 37
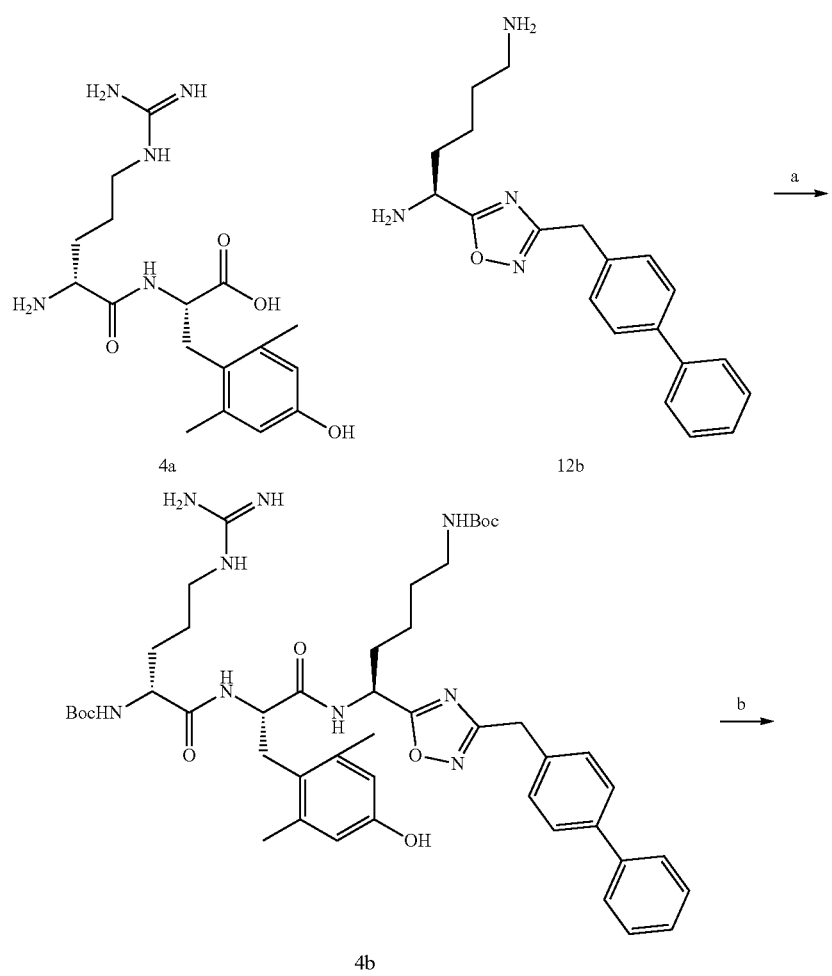

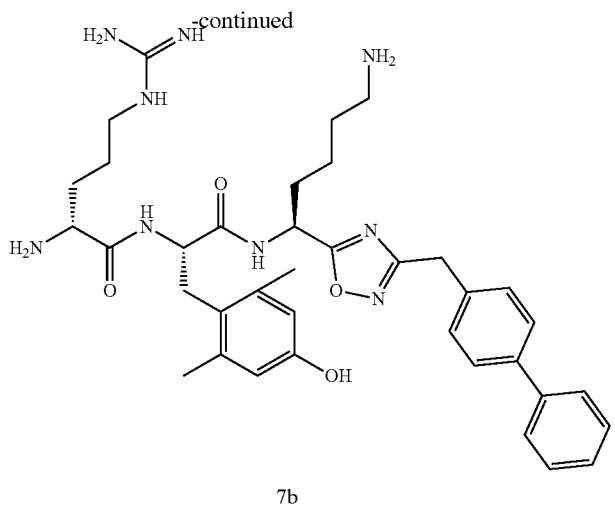

7b

1) Step a: Synthesis of tert-butyl ((6R,9S,12S)-12-(3-([1,1'-biphenyl]-4-ylmethyl)-1,2,4-oxadiazol-5-yl)-1-amino-9-(4-hydroxy-2,6-dimethylbenzyl)-1-imino-20,20-dimethyl-7,10,18-trioxo-19-oxa-2,8,11,17-tetraazahenicosan-6-yl) carbamate (6b)

The same procedure as described in Scheme 36 by using 4a (11.17 g, 24 mmol) and 12b (221 mg, 0.445 mmol) to give 6b (300 mg) as an acetate salt in 78% yield.

$^1$H NMR (CD$_3$OD, 300 MHz): δ=7.61-7.50 (m, 4H), 7.46-7.29 (m, 5H), 6.39 (s, 2H), 5.19-5.10 (m, 1H), 4.67-4.56 (m, 1H), 4.10 (s, 2H), 3.99-3.90 (m, 1H), 3.16-2.77 (m, 7H), 2.20 (s, 6H), 2.02-1.82 (m, 2H), 1.67-1.05 (m, 25H).

2) Step b: Synthesis of (R)-N-((S)-1-(((S)-1-(3-([1,1'-biphenyl]-4-ylmethyl)-1,2,4-oxadiazol-5-yl)-5-aminopentyl)amino)-3-(4-hydroxy-2,6-dimethylphenyl)-1-oxopropan-2-yl)-2-amino-5-guanidinopentanamide (7b)

The same procedure as described in Scheme 36 by using 6b (300 mg, 0.318 mmol) to give 7b TFA salt (68 mg) in 21% yield as a pale yellow glass-like solid.

$^1$H NMR (CD$_3$OD, 400 MHz): δ=7.57-7.50 (m, 4H), 7.43-7.36 (m, 4H), 7.34-7.29 (m, 1H), 6.39 (s, 2H), 5.15 (dd, 1H, J=6.3 Hz, J=8.7 Hz), 4.69 (dd, 1H, J=7.6 Hz, J=8.7 Hz), 4.12 (s, 2H), 3.92 (t, 1H, J=6.3 Hz), 3.14 (t, 2H, J=6.8 Hz), 3.07 (dd, 1H, J=8.8 Hz, J=14.1 Hz), 2.92-2.80 (m, 3H), 2.20 (s, 6H), 2.01-1.58 (m, 6H), 1.54-1.25 ppm (m, 4H). Molecular formula: C$_{37}$H$_{49}$N$_9$O$_4$·3TFA; Molecular weight: 1025.93; Free base molecular weight: 683.86. EI-MS: m/z 684.5 [M+1].

Example 33: Synthesis of (R)-2-amino-N-((S)-1-(((S)-5-amino-1-(3-(4-(tert-butyl)benzyl)-1,2,4-oxadiazol-5 yl)pentyl)amino)-3-(4-hydroxy-2,6-dimethylphenyl)-1-oxopropan-2-yl)-5-guanidinopentanamide (D-Arg-DMT-NH((S)-5-amino-1-(3-(4-(tert-butyl)benzyl)-1,2,4-oxadiazol-5-yl)pent-1-yl), 7c)

Compound 7c

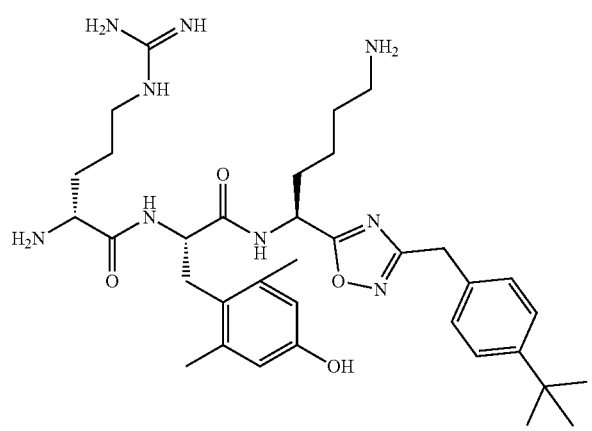

Scheme 38

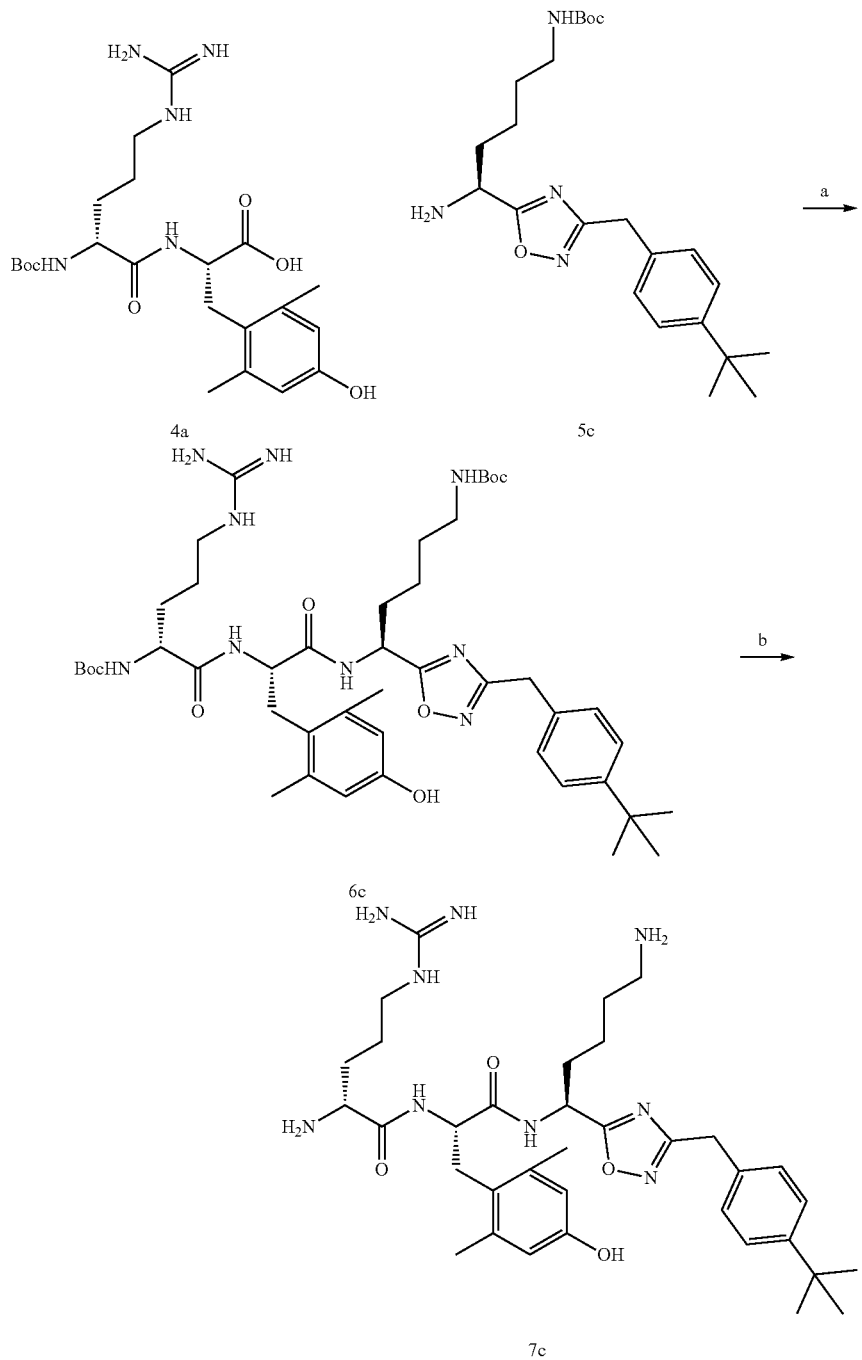

1) Step a: Synthesis of tert-butyl (((6R,9S,12S)-1-amino-12-(3-(4-(tert-butyl)benzyl)-1,2,4-oxadiazol-5-yl)-9-(4-hydroxy-2,6-dimethylbenzyl)-1-imino-20,20-dimethyl-7,10,18-trioxo-19-oxa-2,8,11,17-tetraazahenicosan-6-yl)carbamate (6c) The same procedure as described in Scheme 36 by using 4a (2.0 g, 3.98 mmol) and 5c (1.66 g, 3.98 mmol) to give 6c (1.97 g) in 54% yield, which was used in next step without further purification.

2) Step b: Synthesis of (R)-2-amino-N-((S)-1-(((S)-5-amino-1-(3-(4-(tert-butyl)benzyl)-1,2,4-oxadiazol-5-yl)pentyl)amino)-3-(4-hydroxy-2,6-dimethylphenyl)-1-oxopropan-2-yl)-5-guanidinopentanamide (7c) The same procedure as described in Scheme 36 by using 6c (1.97 g, 2.13 mmol) to give 7c HCl salt (590 mg) in 38% yield as a pale yellow glass-like solid.

$^1$H NMR (400 MHz, Methanol-$d_4$): δ=8.65-8.60 (m, 1H), 7.35-7.30 (m, 2H), 7.24-7.19 (m, 2H), 6.39 (s, 2H), 5.19-5.11 (m, 1H), 4.73-4.66 (t, J=8.2 Hz, 1H), 4.08-3.93 (m, 3H), 3.21-3.05 (m, 3H), 2.94-2.84 (m, 3H), 2.21 (s, 6H), 2.03-1.31 (m, 10H), 1.28 ppm (s, 9H). EI-MS: m/z 664.6 [M+1].

Example 34: Synthesis of (R)-2-amino-N-((S)-1-(((R)-5-amino-1-(3-(4-(tert-butyl)benzyl)-1,2,4-oxadiazol-5 yl)pentyl)amino)-3-(4-hydroxy-2,6-dimethylphenyl)-1-oxopropan-2-yl)-5-guanidinopentanamide (D-Arg-DMT-NH((R)-5-amino-1-(3-(4-(tert-butyl)benzyl)-1,2,4-oxadiazol-5 yl)pent-1-yl), 7d)

Compound 7d was isolated from Scheme 38:

$^1$H NMR (400 MHz, Methanol-$d_4$): δ=7.38 ppm (m, 2H), 7.22 (m, 2H), 6.52 (s, 2H), 5.06 (m, 1H), 4.78 (m, 1H), 4.02 (m, 2H), 3.95 (m, 1H), 3.20 (m, 3H), 2.95 (m, 3H), 2.34 (s, 6H), 1.50-1.90 (m, 8H), 1.33 (s, 9H), 1.10 (m, 2H). EI-MS: m/z 664.5 [M+1].

Compound 7d

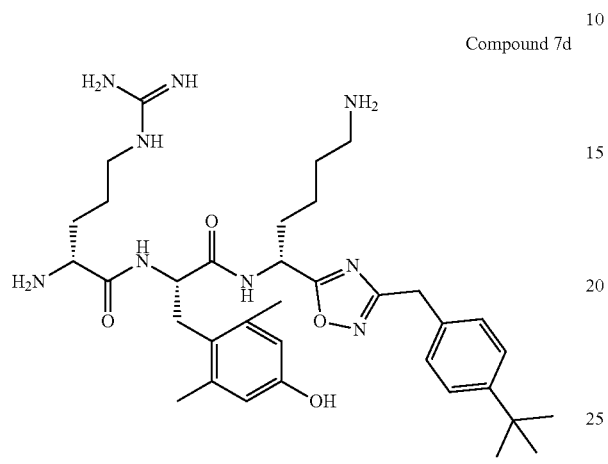

Example 35: Synthesis of (R)-2-amino-N-((S)-1-(((S)-5-amino-1-(3 phenethyl-1,2,4-oxadiazol-5-yl)pentyl)amino)-3-(4-hydroxy-2,6-dimethylphenyl)-1-oxopropan-2-yl)-5-guanidinopentanamide (D-Arg-DMT-NH((S)-5-amino-1-(3 phenethyl-1,2,4-oxadiazol-5-yl)pent-1-yl), 7e)

Compound 7e

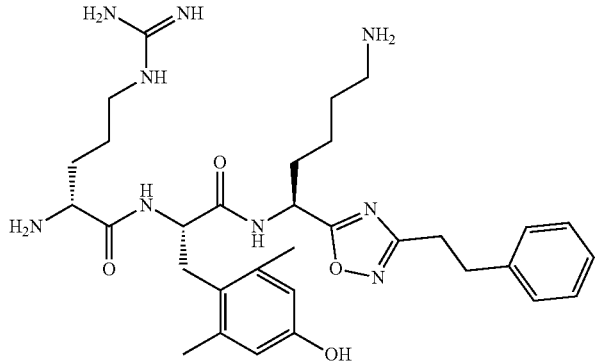

Scheme 39

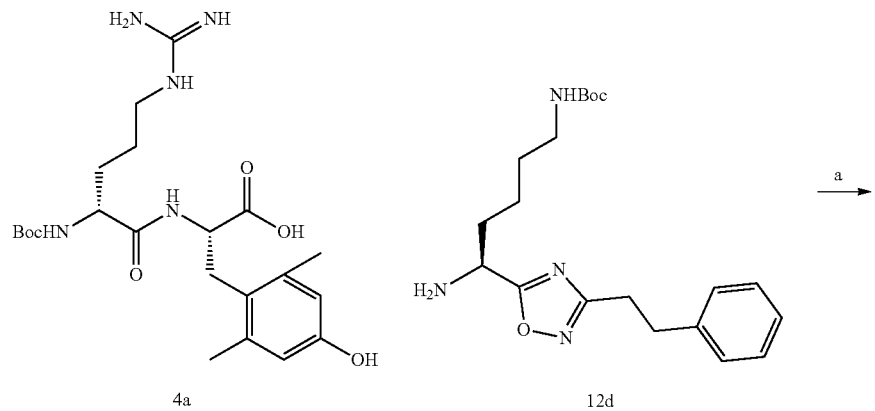

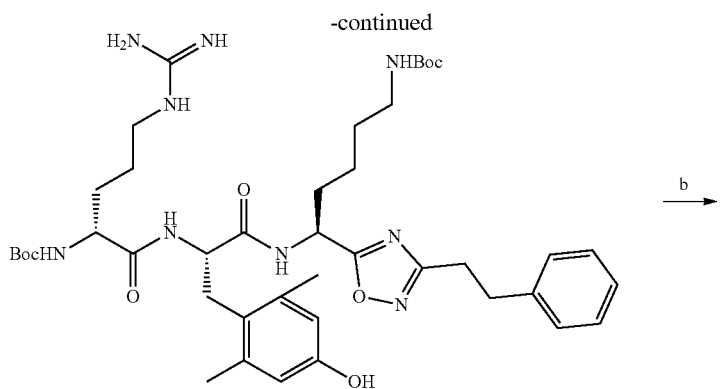

6d

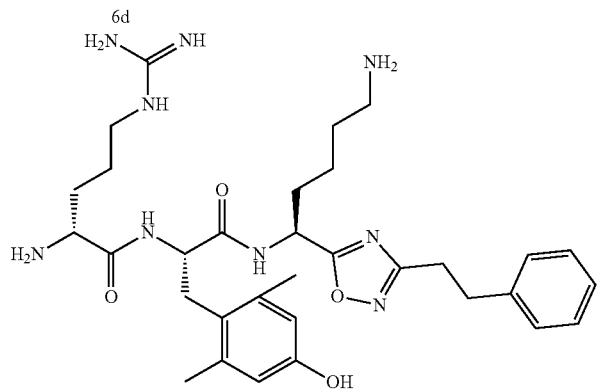

7e

1) Step a: Synthesis of tert-butyl ((6R,9S,12S)-1-amino-9-(4-hydroxy-2,6-dimethylbenzyl)-1-imino-20,20-dimethyl-7,10,18-trioxo-12-(3-phenethyl-1,2,4-oxadiazol-5-yl)-19-oxa-2,8,11,17-tetraazahenicosan-6-yl)carbamate (6d) The same procedure as described in Scheme 36 by using 4a (201 mg, 0.400 mmol) and 12d (191 mg, 0.440 mmol) to give 6d (260 mg) in 74% yield.

$^1$H NMR (CD$_3$OD, 300 MHz): δ=7.31-7.10 (m, 5H), 6.38 (s, 2H), 5.19-5.10 (m, 1H), 4.69-4.57 (m, 1H), 4.03-3.91 (m, 1H), 3.20-2.79 (m, 10H), 2.22 (s, 6H), 2.00-1.83 (m, 2H), 1.72-1.02 (m, 26H).

2) Step b: Synthesis of (R)-2-amino-N-((S)-1-(((S)-5-amino-1-(3-phenethyl-1,2,4-oxadiazol-5-yl)pentyl)amino)-3-(4-hydroxy-2,6-dimethylphenyl)-1-oxopropan-2-yl)-5-guanidinopentanamide (7e)

The same procedure as described in Scheme 36 by using 6d (234 mg, 0.265 mmol) to give 7e TFA salt (140 mg) in 55% yield as a pale yellow glass-like solid.

$^1$H NMR (CD$_3$OD, 400 MHz): δ=7.29-7.14 (m, 5H), 6.37 (s, 2H), 5.15 (dd, 1H, J=6.7 Hz, J=8.4 Hz), 4.69 (dd, 1H, J=7.3 Hz, J=9.1 Hz), 3.93 (t, 1H, J=6.3 Hz), 3.16 (t, 2H, J. 6.9 Hz), 3.11 (dd, 1H, J=9.3 Hz, J=14.1 Hz), 3.07-3.01 (m, 4H), 2.93-2.86 (m, 3H), 2.22 (s, 6H), 2.06-1.61 (m, 6H), 1.57-1.27 ppm (m, 4H). Molecular formula: C$_{32}$H$_{47}$N$_9$O$_4$·3TFA; Molecular weight: 963.86; Free base molecular weight: 621.79. EI-MS: m/z 622.5 [M+1].

Example 36: Synthesis of (R)-2-amino-N-((S)-1-(((S)-5-amino-1-(3-(cyclohexylmethyl)-1,2,4-oxadiazol-5 yl)pentyl)amino)-3-(4-hydroxy-2,6-dimethylphenyl)-1-oxopropan-2-yl)-5-guanidinopentanamide (D-Arg-DMT-NH((S)-5-amino-1-(3-cyclohexylmethyl-1,2,4-oxadiazol-5-yl)pent-1-yl), 7f)

Compound 7f

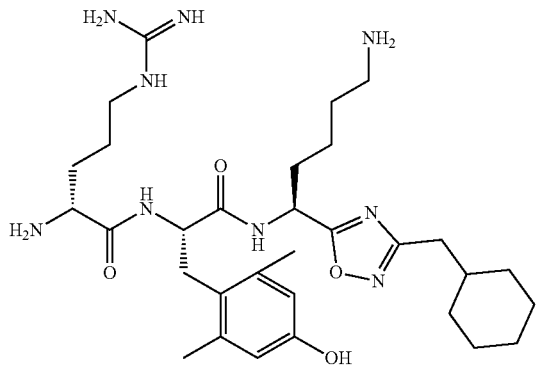

Scheme 40

-continued

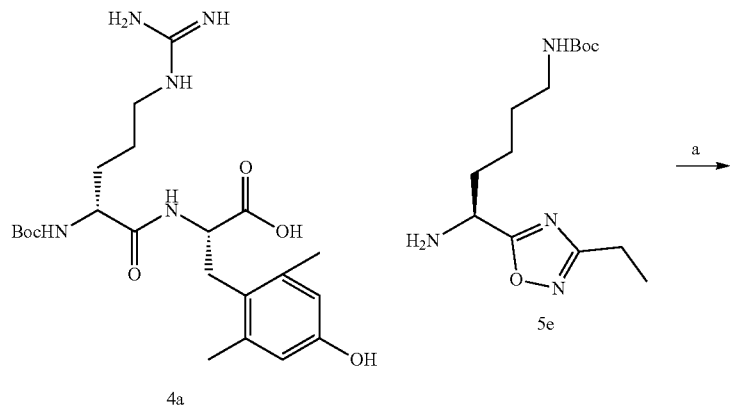

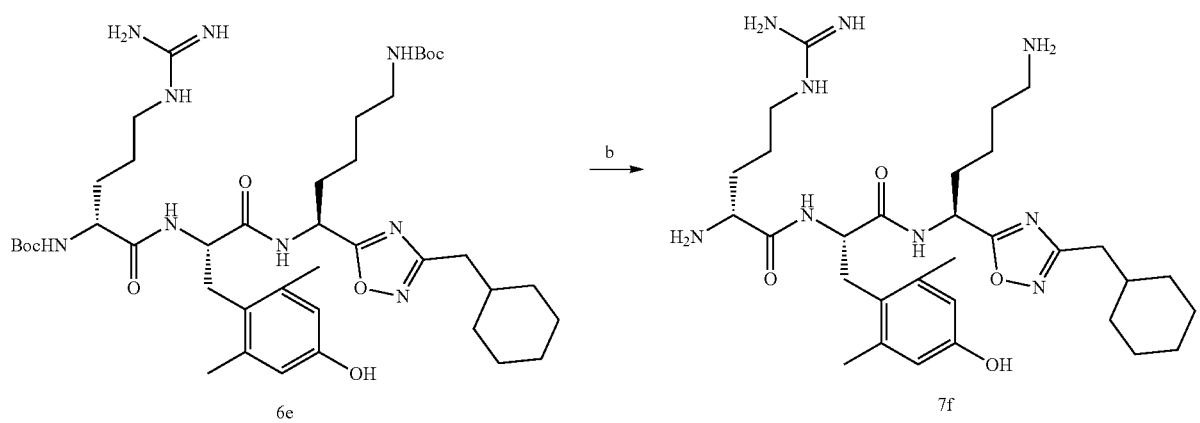

1) Step a: Synthesis of tert-butyl ((6R,9S,12S)-1-amino-12-(3-(cyclohexylmethyl)-1,2,4-oxadiazol-5-yl)-9-(4-hydroxy-2,6-dimethylbenzyl)-1-imino-20,20-dimethyl-7,10,18-trioxo-19-oxa-2,8,11,17-tetraazahenicosan-6-yl)carbamate (6e) The same procedure as described in Scheme 36 by using 4a (1.40 g; 2.80 mmol) and 5e (843 mg; 2.3 mmol) to give 6e 1.22 g (61%) of a white foam.

$^1$H NMR (400 MHz, Methanol-$d_4$) δ6.36 (s, 2H), 5.11 (m, 1H), 4.62 (t, J=7.8 Hz, 1H), 3.95 (m, 1H), 3.18-3.04 (m, 3H), 2.99 (t, J=6.5 Hz, 2H), 2.85 (dd, J=14.1, 8.2 Hz, 1H), 2.56 (d, J=6.9 Hz, 2H), 2.20 (s, 6H), 1.97-1.84 (m, 5H), 1.78-1.59 (multiplepeaks, 8H), 1.56-1.33 (m, 24H), 1.32-1.11 (m, 3H), 1.08-0.92 (m, 2H).

2) Step b: Synthesis of (R)-2-amino-N-((S)-1-(((S)-5-amino-1-(3-phenethyl-1,2,4-oxadiazol-5-yl)pentyl)amino)-3-(4-hydroxy-2,6-dimethylphenyl)-1-oxopropan-2-yl)-5-guanidinopentanamide (7f)

The same procedure as described in Scheme 36 by using 6e (8.28 g; 8.66 mmol) to give 7f HCl salt 6.09 g (97%) as a white solid.

$^1$H NMR (CD$_3$OD): δ6.37 (s, 2H), 5.13 (dd, J=8.7, 6.3 Hz, 1H), 4.71 (t, J=8.1 Hz, 1H), 3.97 (t, J=6.4 Hz, 1H), 3.20-3.06 (m, 3H), 2.96-2.84 (m, 3H), 2.57 (d, J=6.9 Hz, 2H), 2.23 (s, 6H), 2.02-1.87 (m, 2H), 1.84-1.59 (m, 10H), 1.55-1.31 (m, 4H), 1.32-1.13 (m, 3H), 1.01 (m, 2H). MS: EI-MS: m/z 614.6 [M+1].

Example 37: Synthesis of (R)-N-((S)-1-(((S)-1-(3-(adamantan-1-ylmethyl)-1,2,4-oxadiazol-5-yl)-5-aminopentyl)amino)-3-(4-hydroxy-2,6-dimethylphenyl)-1-oxopropan-2-yl)-2-amino-5-guanidinopentanamide (D-Arg-DMT-NH((S)-1-(3-(adamantan-1-ylmethyl)-1,2,4-oxadiazol-5-yl)-5-aminopent-1-yl), 7g)
Compound 7g
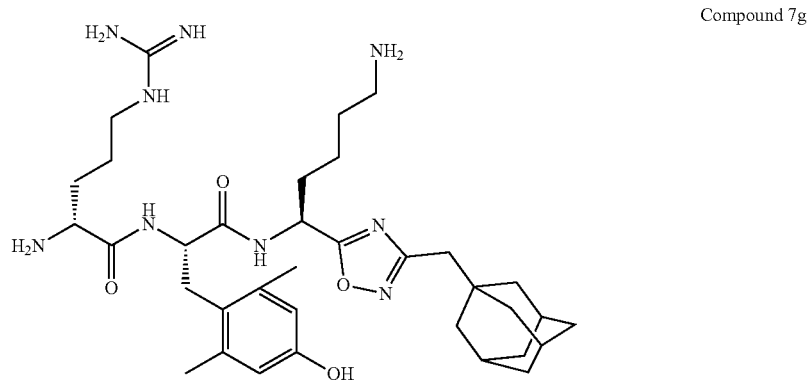
Scheme 41
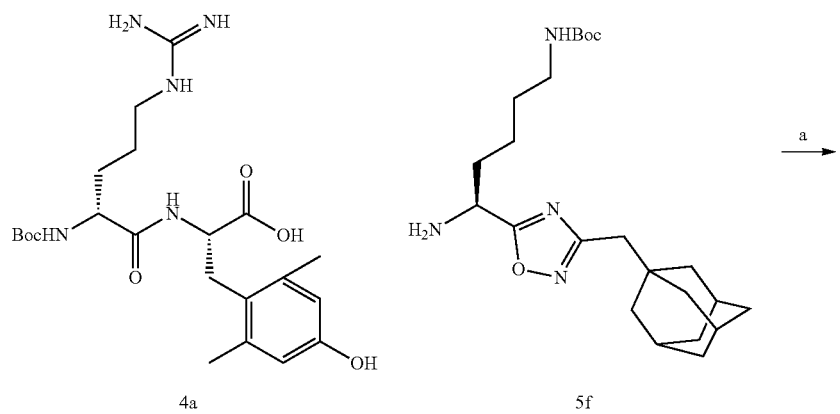
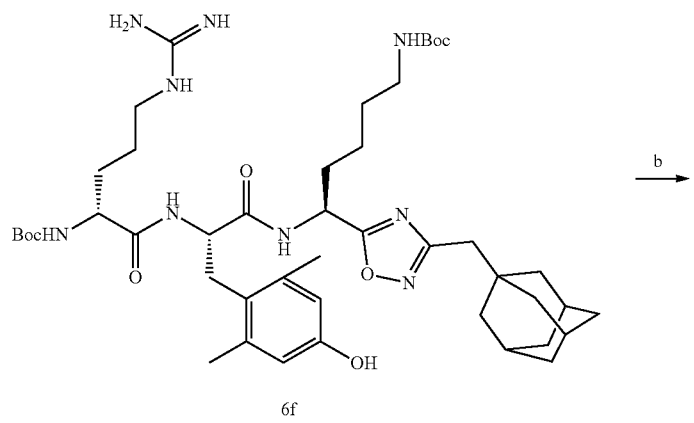

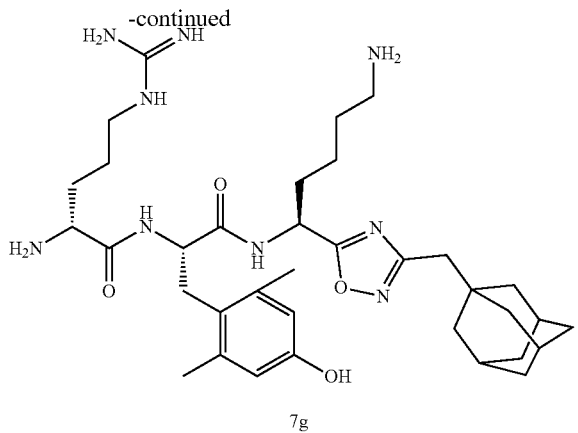

7g

1) Step a: Synthesis of tert-butyl ((6R,9S,12S)-12-(3-(adamantan-1-ylmethyl)-1,2,4-oxadiazol-5-yl)-1-amino-9-(4-hydroxy-2,6-dimethylbenzyl)-1-imino-20,20-dimethyl-7,10,18-trioxo-19-oxa-2,8,11,17-tetraazahenicosan-6-yl)carbamate (60

The same procedure as described in Scheme 36 by using 4a (959 mg, 1.91 mmol) and 5f (800 mg, 1.91 mmol) to give 6f as a white foam (1.04 g, 63%).

$^1$H-NMR (300 MHz, Methanol-d$_4$) δ6.41 (s, 2H), 5.13 (t, J=7.4 Hz, 1H), 4.68 (t, J=7.7 Hz, 1H), 3.95 (t, J=6.9 Hz, 1H), 3.17-3.08 (m, 3H), 3.02 (t, J=6.1 Hz, 2H) 2.94-2.86 (m, 1H), 2.47 (s, 2H), 2.24 (s, 6H), 1.99-1.95 (m, 5H), 1.80-1.53 (m, 16H), 1.49-1.30 (m, 22H).

2) Step b: Synthesis of (R)-N-((S)-1-(((S)-1-(3-(adamantan-1-ylmethyl)-1,2,4-oxadiazol-5-yl)-5-aminopentyl)amino)-3-(4-hydroxy-2,6-dimethylphenyl)-1-oxopropan-2-yl)-2-amino-5-guanidinopentanamide (7g)

The same procedure as described in Scheme 36 by using 6f (8.28 g; 8.66 mmol) to give 7g HCl salt 6.09 g (97%) as a white solid.

$^1$H NMR (CD$_3$OD): δ6.37 (s, 2H), 5.13 (dd, J=8.7, 6.3 Hz, 1H), 4.71 (t, J=8.1 Hz, 1H), 3.97 (t, J=6.4 Hz, 1H), 3.20-3.06 (m, 3H), 2.96-2.84 (m, 3H), 2.57 (d, J=6.9 Hz, 2H), 2.23 (s, 6H), 2.02-1.87 (m, 2H), 1.84-1.59 (m, 10H), 1.55-1.31 (m, 4H), 1.32-1.13 (m, 3H), 1.01 (m, 2H). MS: EI-MS: m/z 614.6 [M+1].

Example 38: Synthesis of (R)-N-((S)-1-(((S)-1-(3-(adamantan-1-ylmethyl)-1,2,4-oxadiazol-yl)-5-aminopentyl)amino)-3-(4-hydroxy-2,6-dimethylphenyl)-1-oxopropan-2-yl)-2-amino-5-guanidinopentanamide (D-Arg-DMT-NH((S)-1-(3-(adamantan-1-yl)-1,2,4-oxadiazol-5-yl)-5-aminopent-1-yl), 7h)

Compound 7h

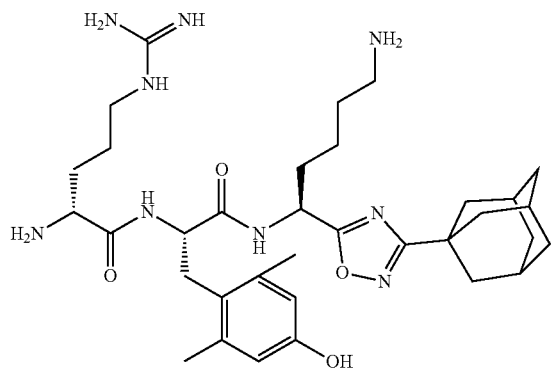

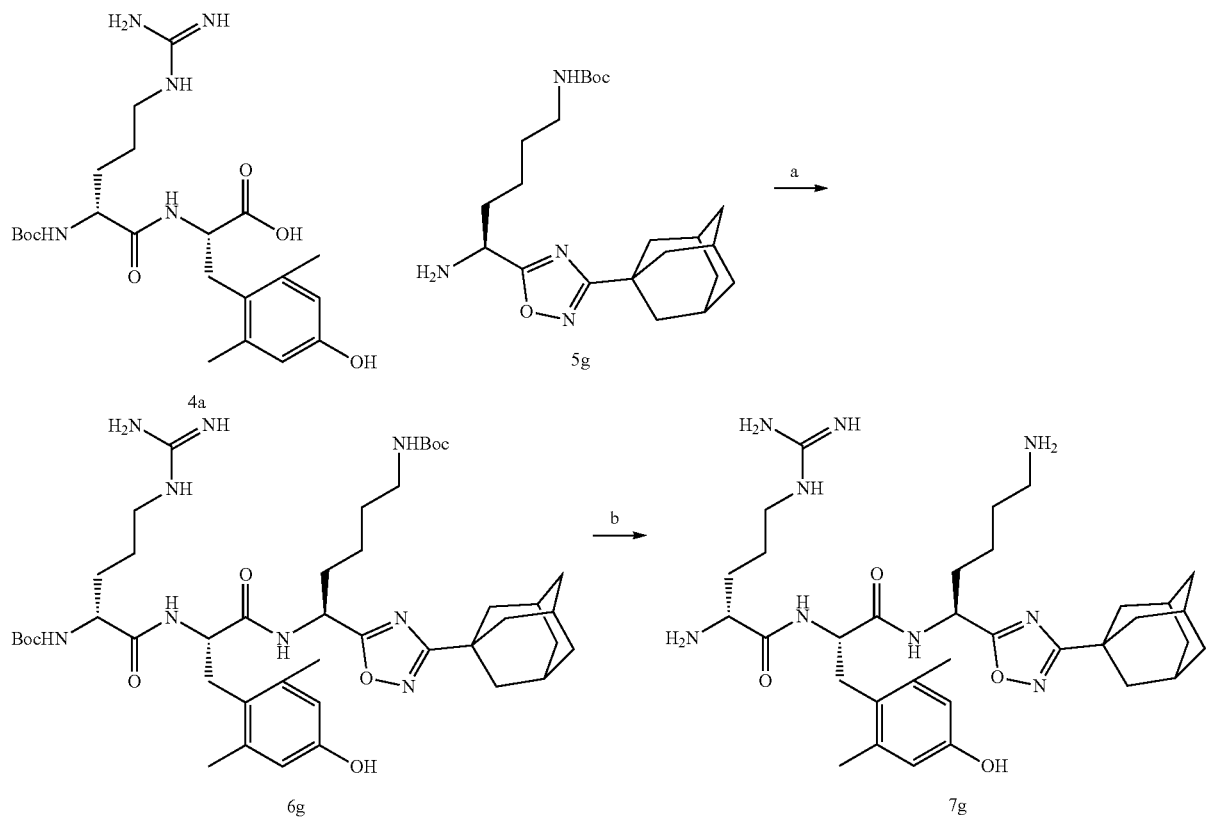

1) Step a: Synthesis of tert-butyl ((6R,9S,12S)-12-(3-(adamantan-1-yl)-1,2,4-oxadiazol-5-yl)-1-amino-9-(4-hydroxy-2,6-dimethylbenzyl)-1-imino-20,20-dimethyl-7,10,18-trioxo-19-oxa-2,8,11,17-tetraazahenicosan-6-yl)carbamate (6g)

The same procedure as described in Scheme 36 by using 4a (950 mg, 1.89 mmol) and 5g (850 mg, 2.10 mmol) to give 6f as white solid (1.15 g).

$^1$H NMR (400 MHz, Methanol-$d_4$) 6.38 (s, 2H), 5.16 (t, J=7.8 Hz, 1H), 4.62 (t, J=8.1 Hz, 1H), 3.98 (t, J=8.2 Hz, 1H), 3.19-3.07 (m, 3H), 3.06-2.96 (m, 2H), 2.92-2.82 (m, 1H), 2.23 (s, 6H), 2.11-1.75 (m, 18H), 1.74-1.60 (m, 2H), 1.58-1.26 (m, 14H).

2) Step b: Synthesis of (R)-N-((S)-1-(((S)-1-(3-(adamantan-1-ylmethyl)-1,2,4-oxadiazol-5-yl)-5-aminopentyl)amino)-3-(4-hydroxy-2,6-dimethylphenyl)-1-oxopropan-2-yl)-2-amino-5-guanidinopentanamide (7g)

The same procedure as described in Scheme 36 by using 6g (1.02 g, 1.19 mmol) to give 7g TFA salt as a white solid (750 mg).

$^1$H NMR (400 MHz, Methanol-$d_4$) δ6.39 (s, 2H), 5.17 (dd, J=8.7, 6.3 Hz, 1H), 4.72 (t, J=8.2 Hz, 1H), 3.98 (t, J=6.2 Hz, 1H), 3.16 (dt, J=14.5, 7.7 Hz, 3H), 2.98-2.86 (m, 3H), 2.24 (s, 6H), 2.07 (s, 3H), 2.04-1.89 (m, 8H), 1.89-1.64 (m, 9H), 1.56-1.28 (m, 4H). Molecular formula: $C_{34}H_{53}N_9O_4 \cdot 3HCl$; MS: EI-MS: m/z 652.6 [M+1].

Example 39: Synthesis of (2R)-N-((2S)-1-(((1R)-1-(3-(adamantan-1-yl)-1,2,4-oxadiazol-5-yl)-5-aminopentyl)amino)-3-(4-hydroxy-2,6-dimethylphenyl)-1-oxopropan-2-yl)-2-amino-5-guanidinopentanamide (D-Arg-DMT-NH((R)-1-(3-(adamantan-1-yl)-1,2,4-oxadiazol-5-yl)-5-aminopent-1-yl), 7i)

Compound 7i

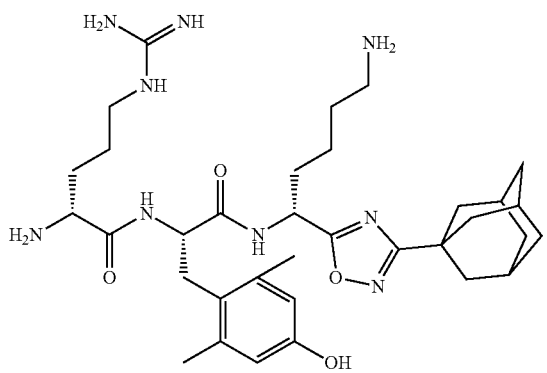

Compound 7i was isolated from previous Scheme 42:

$^1$H NMR (400 MHz, Methanol-$d_4$) δ6.43 (s, 2H), 5.20 (m, 1H), 4.73 (m, 1H), 3.97 (m, 1H), 3.18 (m, 3H), 2.95 (m, 3H), 2.27 (s, 6H), 1.30-2.10 (m, 25H). EI-MS: m/z 652.5 [M+1].

Example 40: Synthesis of (R)-2-amino-N-((S)-1-(((S)-3-amino-1-(3-benzyl-1,2,4-oxadiazol-5-yl)propyl)amino)-3-(4-hydroxy-2,6-dimethylphenyl)-1-oxopropan-2-yl)-5-(2-amino-1H-imidazol-1-yl)pentanamide (D-(δ(2-amino-1H-imidazol-1-yl))-Nva-DMT-NH((S)-3-amino-1-(3-benzyl-1,2,4-oxadiazol-5 yl)prop-1-yl), 7j)
Compound 7j
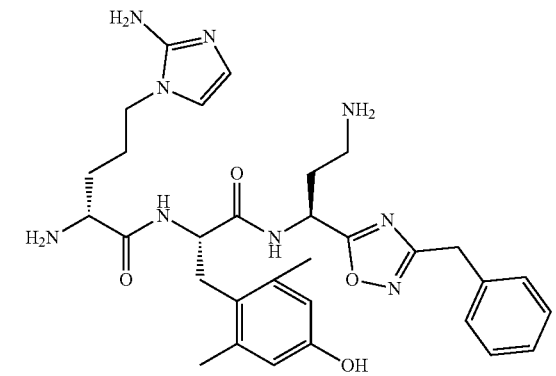
Scheme 43
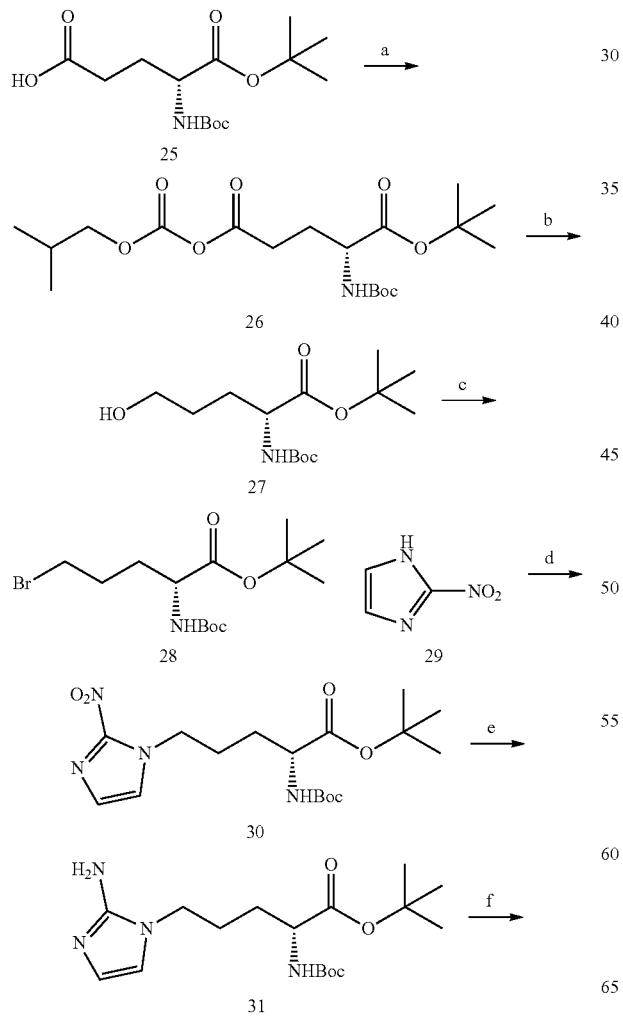
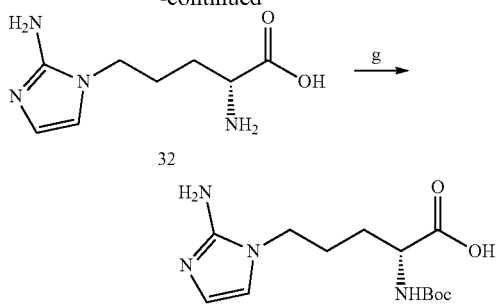
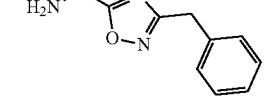
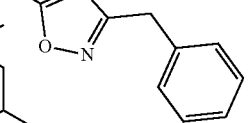
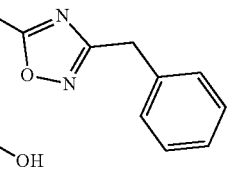

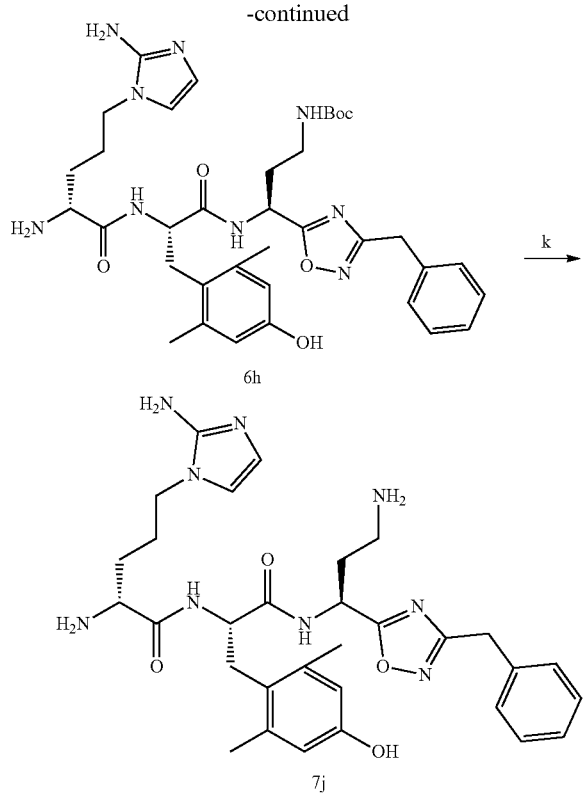

<sup>1</sup>H NMR (300 MHz, CDCl<sub>3</sub>) δ5.08 (m, 1H), 4.22 (m, 1H), 3.43 (m, 2H), 1.93 (m, 4H), 1.48 (s, 9H), 1.45 (s, 9H).

4) Step d: Synthesis of tert-butyl (R)-2-((tert-butoxycarbonyl)amino)-5-(2-nitro-1H-imidazol-1-yl)pentanoate (30)

2-nitro-1H-imidazole (29, 1.0 g, 9.1 mmol) was dissolved in DMF (15 mL), Cs$_2$CO$_3$ (3.0 g, 9.1 mmol) was added in one portion, stirred for 30 min, then the DMF solution (3 mL) of compound 28 (2.0 g, 5.7 mmol) was added dropwise at 0° C., the result solution was stirred for overnight, diluted with EtOAc, washed with cold water, brine, dried on Na$_2$SO$_4$, purified by column chromatography to afford compound 30 as pale yellow solid (1.1 g, 50%).

$^1$H NMR (300 MHz, CDCl$_3$) δ7.16 (s, 1H), 5.16 (m, 1H), 4.49 (m, 2H), 4.26 (m, 1H), 1.92 (m, 3H), 2.98-2.86 (m, 2H), 1.65 (m, 2H), 1.47 (s, 9H), 1.46 (s, 9H).

5) Step e: Synthesis of tert-butyl (R)-5-(2-amino-1H-imidazol-1-yl)-2-((tert-butoxycarbonyl)amino)pentanoate (31)

Compound 30 (1.0 g, 2.6 mmol) was dissolved in EtOH (15 mL), Pd/C (200 mg) was added, stirred in H$_2$ atmosphere for 5 h, the solution was filtered through a pad of celite, concentrated and purified by column chromatography to afford compound 31 as a thick oil (900 mg, 98%).

$^1$H NMR (300 MHz, DMSO-d$_6$) δ7.14 (m, 1H), 6.51 (s, 1H), 6.35 (s, 1H), 5.32 (br, 2H), 3.80 (m, 1H), 3.63 (m, 2H), 1.52 (m, 4H), 1.61 (s, 9H), 1.59 (s, 9H).

6) Step f: Synthesis of (R)-2-amino-5-(2-amino-1H-imidazol-1-yl)pentanoic acid (32) Compound 31 (1.7 g, 4.8 mmol) was dioxane (20 mL), 4N HCl solution in dioxane (24 mL) was added dropwise, the result solution was stirred for 18 h, the Precipitate was collected by filteration, dried in vacuum to give pure target as off-white solid as HCl salt (32, 800 mg, 61%).

$^1$H NMR (300 MHz, D$_2$O) δ6.71 (s, 2H), 3.87 (m, 1H), 3.80 (m, 2H), 1.84 (m, 4H). MS (M+1): 199.0.

7) Step g: Synthesis of (R)-5-(2-amino-1H-imidazol-1-yl)-2-((tert-butoxycarbonyl)amino)pentanoic acid (1b)

A solution of Boc$_2$O (3.018 g, 13.83 mmol) in 15 mL of THF was added to a solution of 32 (1.5 g, 5.532 mmol) and sodium carbonate (2.345 g, 22.128 mmol) in 20 mL of water and 3 mL of THF. After overnight stirring, the reaction mixture was diluted with water and extracted with DCM. Aqueous layer was acidified with 5% citric acid and evaporated. Purification of crude material on reverse-phase flash chromatography gave 0.95 g of desired product acetate salt as white solid 1b.

$^1$H NMR (400 MHz, Methanol-d$_4$) δ6.87 (d, J=2.5 Hz, 1H), 6.80 (d, J=2.5 Hz, 1H), 4.02-4.00 (m, 1H), 3.88 (h, J=6.8 Hz, 2H), 1.84-1.66 (m, 4H), 1.44 (s, 9H).

8) Step h: Synthesis of (9H-fluoren-9-yl)methyl ((S)-1-(((S)-1-(3-benzyl-1,2,4-oxadiazol-5-yl)-3-((tort-butoxycarbonyl)amino)propyl)amino)-3-(4-hydroxy-2,6-dimethylphenyl)-1-oxopropan-2-yl)carbamate (34)

To a Fmoc-DMT-OH (33, 1.29 g, 3 mmol, 1 eq), 5h (1.0 g, 3 mmol, 1 eq), HOBt (689 mg, 4.5 mmol, 1.5 eq) in dry DMF (15 mL) EDC·HCl (1.43 g, 7.5 mmol, 2.5 eg) was added, then NMM (0.82 mL, 7.5 mmol, 2.5 eq) was added dropwise at 0° C. The reaction mixture was allowed to stir at r.t for 20 hrs. Then DMF was evaporated and crude product was washed with Et$_2$O (3×5 mL). Product was purified by reverse phase flash chromatography (eluent: H$_2$O (0.2% AcOH)/MeOH from 5% to 85% of methanol) to yield 34 as a white foam (1.24 g, 56%).

$^1$H-NMR (300 MHz, Methanol-d$_4$) δ7.79 (d, J=7.6 Hz, 2H), 7.63 (t, J=7.4 Hz, 2H), 7.38 (t, J=7.6 Hz, 2H), 7.29-7.27 (m, 5H), 7.24-7.18 (m, 2H), 6.36 (s, 2H), 5.25 dd, J=9.6, 5.4 Hz, 1H), 4.30 (d, J=6.5 Hz, 2H), 4.24 (t, J=7.7 Hz, 1H), 4.17

(t, J=7.1 Hz, 1H), 4.05 (s, 2H), 3.20-2.98 (m, 3H), 2.93-2.76 (m, 2H), 2.17 (s, 6H), 2.08-2.00 (m, 1H), 1.95-1.87 (m, 1H), 1.36 (s, 9H).

9) Step is Synthesis of tert-butyl ((S)-3-((S)-2-amino-3-(4-hydroxy-2,6-dimethylphenyl)propanamido)-3-(3-benzyl-1,2,4-oxadiazol-5-yl)propyl)carbamate (35)

Compound 34 (1.04 g, 1.2 mmol) was dissolved in the mixture (10 mL) of DMF and piperidine (8:2 by volume) and the mixture was stirred at rt for 1 h. The solvents were removed under vacuum at rt. Then $KHSO_4$ aq. solution (5%) was added to pH 4 and was extracted with EtOAc (4×30 mL). The extract was dried over $Na_2SO_4$ and evaporated to dryness. The residue was purified by reverse phase flash chromatography (eluent: $H_2O$ (0.2% AcOH)/MeOH from 5% to 85% of methanol) to yield 35 as a white foam (339 mg, 54%).

$^1$H-NMR (300 MHz, Methanol-$d_4$) δ7.31-7.22 (m, 5H), 6.38 (s, 2H), 5.26 (dd, J=9.2, 5.6 Hz, 1H), 4.07 (s, 2H), 3.89-3.76 (m, 1H), 3.19-2.91 (m, 4H), 2.14 (s, 6H), 1.94-1.84 (m, 2H), 1.42 (s, 9H).

10) Step j: Synthesis of tert-butyl ((8S,11S,14R)-17-(2-amino-1H-imidazol-1-yl)-8-(3-benzyl-1,2,4-oxadiazol-5-yl)-11-(4-hydroxy-2,6-dimethylbenzyl)-2,2-dimethyl-4,10,13-trioxo-3-oxa-5,9,12-triazaheptadecan-14-yl)carbamate (6h)

To 35 (343 mg, 0.553 mmol), compound 5h (165 mg, 0.553 mmol), HOBT (120 mg, 0.754 mmol), EDC.HCl (290 mg, 1.51 mmol) in 6 mL of DMF NMM (166 μL, 1.51 mmol) was added dropwise at 0° C. and the mixture was stirred at rt for 7 h. The solvent was removed under reduced pressure and the residue was purified by reverse phase flash chromatography (eluent: $H_2O$ (0.2% AcOH)/MeOH from 5% to 85% of methanol) to yield 6h as an oil (297 mg, 67%).

$^1$H-NMR (400 MHz, Methanol-$d_4$) δ7.30-7.28 (m, 4H), 7.25-7.20 (m, 1H), 6.77 (d, J=16.2 Hz, 2H), 6.64 (s, 1H), 6.37 (s, 1H), 5.24 (dt, J=9.6, 4.7 Hz, 1H), 4.78-4.70 (m, 1H), 4.04 (s, 2H), 3.99-3.95 (m, 2H), 3.80-3.70 (m, 2H), 3.27-3.13 (m, 2H), 3.02-2.83 (m, 2H), 2.29-2.22 (m, 8H), 1.65-1.51 (m, 4H), 1.42-1.36 (m, 18H).

11) Step k: Synthesis of (R)-2-amino-N-((S)-1-(((S)-3-amino-1-(3-benzyl-1,2,4-oxadiazol-5-yl)propyl)amino)-3-(4-hydroxy-2,6-dimethylphenyl)-1-oxopropan-2-yl)-5-(2-amino-1H-imidazol-1-yl)pentanamide (7j)

Compound 6h (290 mg, 0.361 mmol) was dissolved in DCM (4 mL) and cooled to 0° C., TFA (2.6 mL) was added dropwise and the solution was allowed to stir at 0° C. for 10 min, and then at rt for 2 h (LC/MS shows no starting material). Then reaction mixture was evaporated (at 0° C.) and additionally re-evaporated from DCM (20 mL, at 0-5° C.). The purification by preparative HPLC provided the target 7j as 3 TFA salt (220 mg, 74%).

$^1$H-NMR (400 MHz, Methanol-$d_4$) δ7.29 (d, J=4.4 Hz, 4H), 7.24-7.20 (m, 1H), 6.84 (dd, J=18.8, 2.5 Hz, 2H), 6.39 (s, 2H), 5.34 (dd, J=9.6, 5.1 Hz, 1H), 4.57 (dd, J=9.1, 6.9 Hz, 1H), 4.07 (s, 2H), 3.96 (t, J=6.0 Hz, 1H), 3.86-3.80 (m, 2H), 3.13-2.99 (m, 3H), 2.92-2.87 (m, 8H), 1.84-1.64 (m, 4H). MS: EI-MS: m/z 604.5 [M+1].

Example 41: Synthesis of (R)-2-amino-N-((S)-1-(((S)-4-amino-1-(3-benzyl-1,2,4-oxadiazol-5-yl)butyl)amino)-3-(4-hydroxy-2,6-dimethylphenyl)-1-oxopropan-2-yl)-4-guanidinobutanamide (D-Agb-DMT-NH(-((S)-4-amino-1-(3-benzyl-1,2,4-oxadiazol-5-yl)but-1-yl), 7k)

Compound 7k

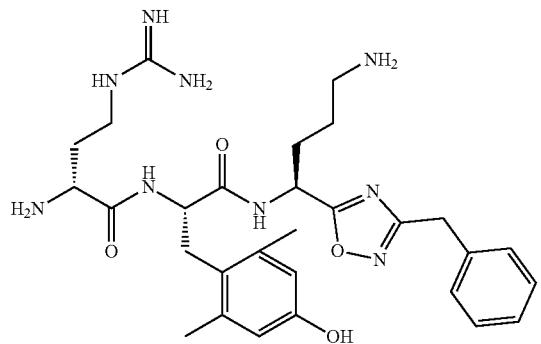

Scheme 44

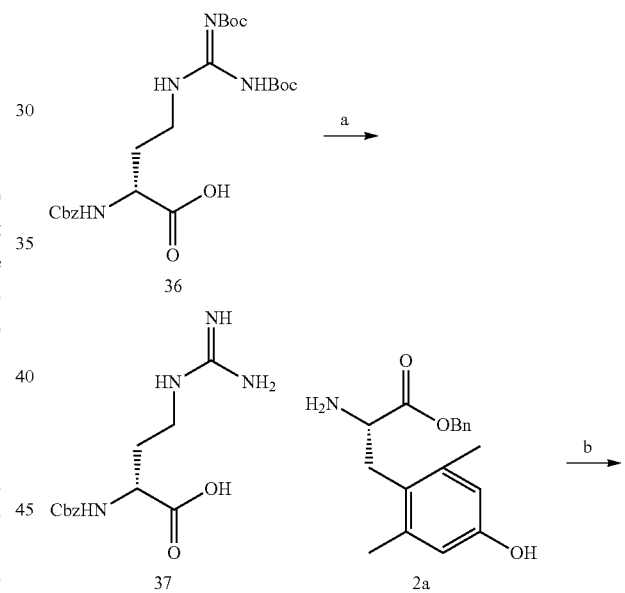

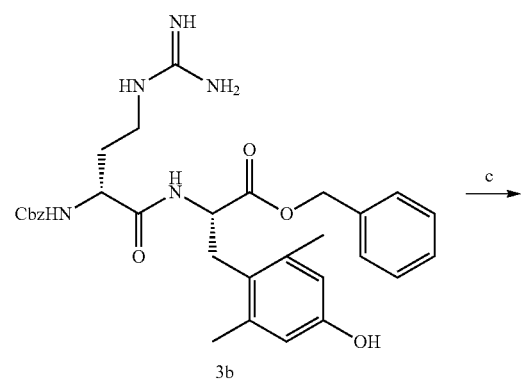

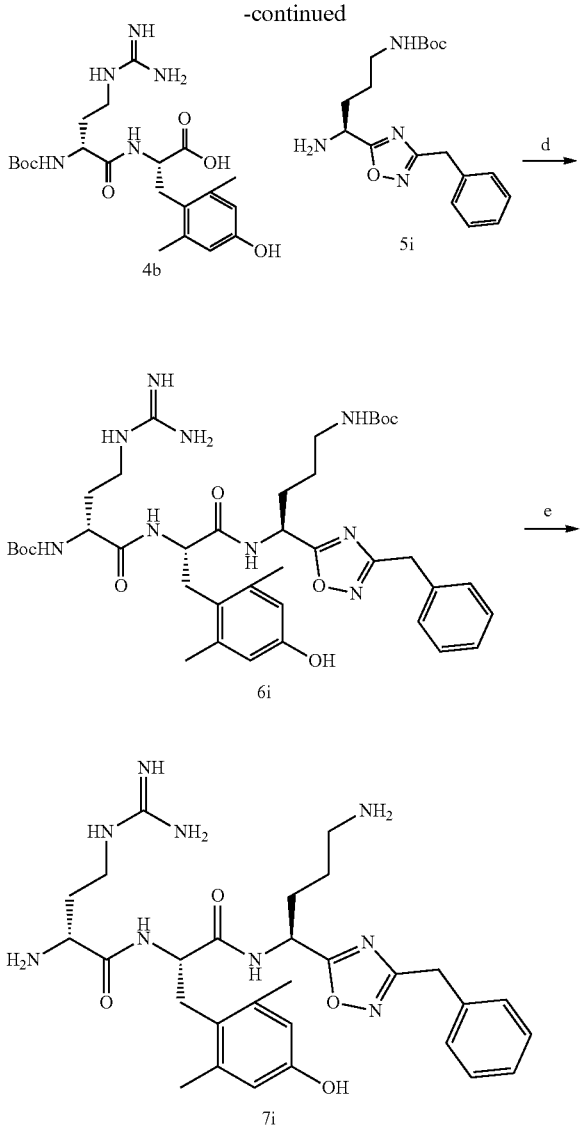

1) Step a: Synthesis of (R)-2-(((benzyloxy)carbonyl)amino)-4-guanidinobutanoic acid (37)

To the solution of N^α-((benzyloxy)carbonyl)-N^ω,N^ω'-bis(tert-butoxycarbonyl)-nor-D-arginine (36, 4.00 g; 8.1 mmol) in cold (0° C.) DCM (25 mL) was added trifluoroacetic acid (12 mL) dropwise. Solution was slowly warmed to ambient temperature over the course of 8 hours. Volatiles were removed under reduced pressure; residue was suspended in benzene and evaporated again. 3.26 g (99%) of a glassy solid 37 was obtained. Crude material was used directly in the next step.

$^1$H NMR (300 MHz, Methanol-$d_4$) δ7.45-7.31 (multiple peaks, 4H), 7.21 (m, 1H), 5.16 (s, 2H), 4.30 (dd, J=9.8, 4.7 Hz, 1H), 3.33 (multiple peaks overlapping with CD$_3$OH, 2H), 2.23 (m, 1H), 1.94 (m, 1H).

2) Step b: Synthesis of benzyl (S)-2-((R)-2-(((benzyloxy)carbonyl)amino)-4-guanidinobutanamido)-3-(4-hydroxy-2,6-dimethylphenyl)propanoate (3b) Compound 37 (2.86 g; 7.0 mmol), DMT-OBn (2a, 1.80 g; 6.0 mmol) and HOBT hydrate (766 mg; 5.0 mmol) were dissolved in dry DMF (35 mL). Solution was cooled to 0° C. and EDCI (3.07 g; 16.0 mmol) was added in one portion. Reaction mixture was stirred 15 minutes and then N-methylmorpholine (1.65 mL; 15.0 mmol) was added dropwise. Reaction was warmed to ambient temperature over the course of 8 hours. At this point, LC-MS analysis showed complete consumption of the starting materials and formation of the desired product. Volatiles were removed under reduced pressure and residue was purified by reverse-phase flash chromatography (120 g C18 Biotage column; mobile phase 0.1% aq TFA/MeOH with gradient 5% MeOH→80% MeOH v/v). 3.18 g (77%) of a white foam 3b was obtained.

$^1$H NMR (300 MHz, Methanol-$d_4$) δ7.44-7.14 (m, 10H), 6.45 (s, 2H), 5.12 (s, 2H), 5.07 (s, 2H), 4.73 (t, J=8.1 Hz, 1H), 4.21 (dd, J=8.4, 5.4 Hz, 1H), 3.23-3.05 (multiple peaks, 3H), 2.99 (dd, J=14.3, 8.6 Hz, 1H), 2.23 (s, 6H), 1.96 (m, 1H), 1.77 (m, 1H).

3) Step c: Synthesis of (S)-2-((R)-2-((tert-butoxycarbonyl)amino)-4-guanidinobutanamido)-3-(4-hydroxy-2,6-dimethylphenyl)propanoic acid (4b)

Compound 3b (3.16 g; 4.6 mmol), Boc$_2$O (3.27 g; 15.0 mmol) and Pd/C (10%; 300 mg) were suspended in EtOH (120 mL). Reaction mixture was stirred under a flow of hydrogen ~4 h. Reaction progress was monitored with LC-MS. Upon full conversion, reaction mixture was filtered through a pad of celite. Volatiles were removed under reduced pressure. Residue was re-suspended in EtOH (~20 mL). Product crystallized from the solution. Mother liquor was removed via a needle. Precipitate was dried under reduced pressure. 1.79 g (86%) of a white solid 4b was obtained. NMR showed that product contains some residual EtOH.

$^1$H NMR (300 MHz, Methanol-$d_4$) δ6.48 (s, 2H), 4.72 (dd, J=9.0, 5.8 Hz, 1H), 4.16 (dd, J=8.1, 5.7 Hz, 1H), 3.23 (dd, J=14.4, 6.0 Hz, 1H), 3.12 (t, J=6.4 Hz, 2H), 3.02 (dd, J=14.4, 10.0 Hz, 1H), 2.36 (s, 6H), 1.86 (m, 1H), 1.72 (m, 1H), 1.49 (s, 9H).

4) Step d: Synthesis of tert-butyl ((5R,8S,11R)-1-amino-11-(3-benzyl-1,2,4-oxadiazol-5-yl)-8-(4-hydroxy-2,6-dimethylbenzyl)-1-imino-18,18-dimethyl-6,9,16-trioxo-17-oxa-2,7,15-triazanonadecan-5-yl)carbamate (6i)

The same procedure as described in Scheme 36 by using 4b (677 mg; 1.5 mmol) and 5i (500 mg; 1.44 mmol) to give 642 mg (53%) of a white foam 6i.

$^1$H NMR (400 MHz, Methanol-$d_4$) δ7.24 (multiple peaks, 5H), 6.35 (s, 2H), 5.16 (dd, J=9.0, 5.8 Hz, 1H), 4.53 (t, J=8.1 Hz, 1H), 4.02 (multiple peaks, 3H), 3.21-2.88 (multiple peaks, 5H), 2.83 (dd, J=14.3, 7.4 Hz, 1H), 2.16 (s, 6H), 1.97-1.62 (multiple peaks, 7H), 1.58-1.31 (multiple peaks, 20H).

5) Step e: Synthesis of (R)-2-amino-N-((2S,5R)-8-amino-5-(3-benzyl-1,2,4-oxadiazol-5-yl)-1-(4-hydroxy-2,6-dimethylphenyl)-3-oxooctan-2-yl)-4-guanidinobutanamide (7k)

The same procedure as described in Scheme 36 by using 6i (400 mg; 0.41 mmol) to give 108 mg (36%) of 7k as a white solid.

$^1$H NMR (400 MHz, Methanol-$d_4$) δ7.27 (multiple peaks, 4H), 7.20 (m, 1H), 6.36 (s, 2H), 5.21 (dd, J=9.5, 5.5 Hz, 1H), 4.62 (dd, J=8.9, 7.4 Hz, 1H), 4.08 (t, J=6.6 Hz, 1H), 4.05 (m, 2H), 3.23-3.06 (ms, 3H), 2.96-2.88 (m, 3H), 2.20 (s, 6H), 2.07-1.85 (m, 4H), 1.84-1.61 (m, 2H). ). Molecular formula: $C_{29}H_{41}N_9O_4$·3HCl; Molecular weight: 689.08; Free base molecular weight: 579.71. EI-MS: m/z 580.5 [M+1].

Example 42: Synthesis of (R)-2-amino-N-((S)-1-(((S)-4-amino-1-(3-(cyclohexylmethyl)-1,2,4-oxadiazol-5 yl)butyl)amino)-3-(4-hydroxy-2,6-dimethylphenyl)-1-oxopropan-2-yl)-5-(2-amino-1H-imidazol-1-yl)pentanamide (D-(δ(2-amino-1H-imidazol-1-yl)-Nva-DMT-NH((S)-4-amino-1-(3-cyclohexylmethyl-1,2,4-oxadiazol-5-yl)but-1-yl), 71)

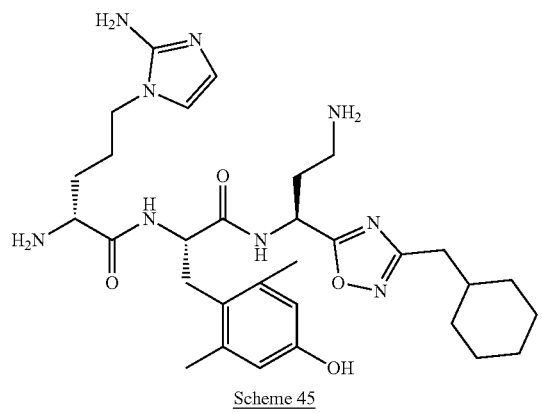 [SMILES: Cc1cc(O)cc(C)c1C[C@H](NC(=O)[C@H](N)CCCn1ccnc1N)C(=O)N[C@@H](CCN)c1nc(Cc2ccccc2)no1]

Scheme 45

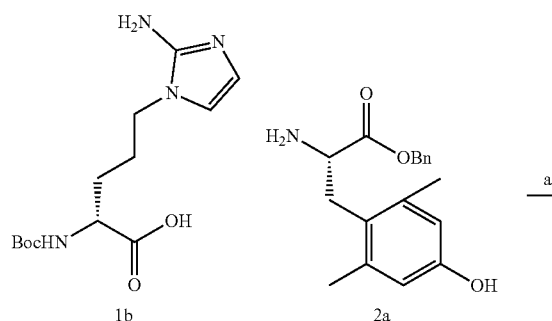

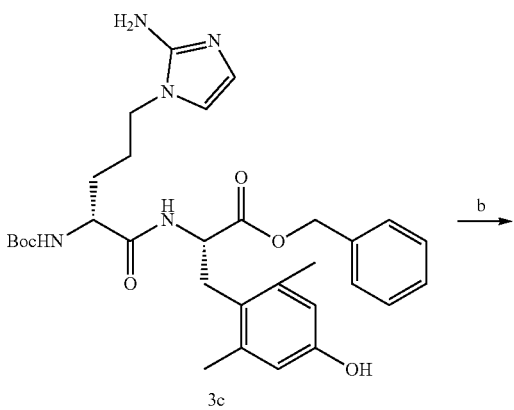

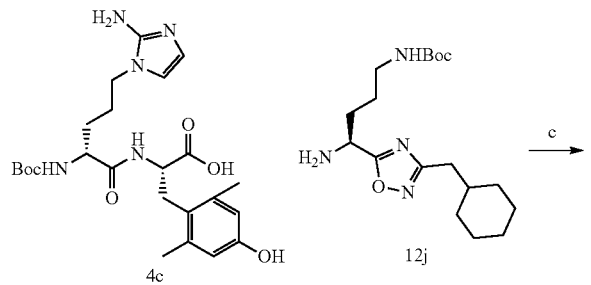

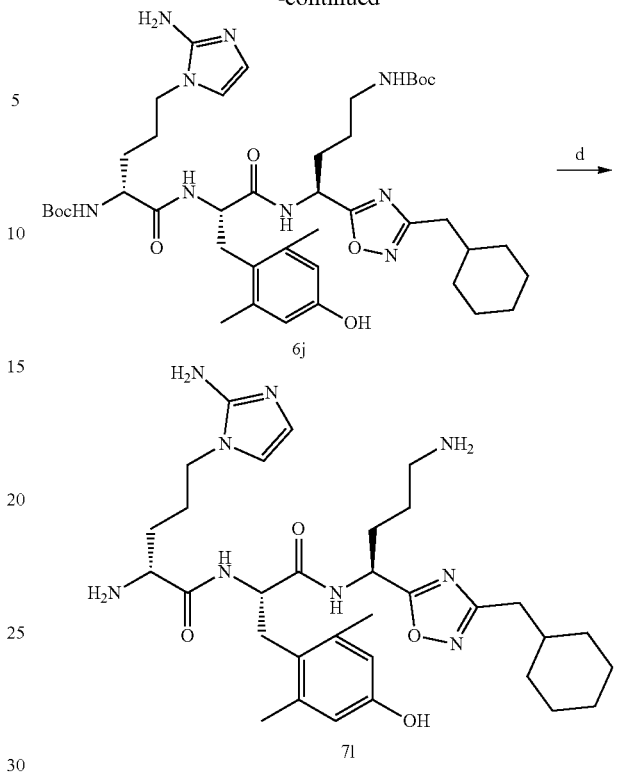

1) Step a: Synthesis of benzyl (S)-2-((R)-5-(2-amino-1H-imidazol-1-yl)-2-((tert-butoxycarbonyl)amino) pentanamido)-3-(4-hydroxy-2,6-dimethylphenyl)propanoate (3c)

To a mixture of (R)-5-(2-amino-1H-imidazol-1-yl)-2-((tert-butoxycarbonyl)amino)pentanoic acid (1b, 3.00 g, 10.1 mmol, made according to Scheme 43), benzyl (S)-2-amino-3-(4-hydroxy-2,6-dimethylphenyl)propanoate (2a, 3.63 g, 12.1 mmol), EDC (N-(3-dimethylaminopropyl)-N'-ethylcarbodiimide) hydrochloride (5.82 g, 30.3 mmol), and HOBt (1-hydroxybenzotriazole) (2.32 g, 15.2 mmol) was added dry DMF (60 mL) and the resulting mixture was stirred at r.t. for 15 min. Then, N-methyl morpholine (3.3 mL, 30.3 mmol) was added and the reaction mixture was stirred at r.t. for 20 h. The volatile matters were removed under reduced pressure and the residual mixture was diluted by EtOAc (800 mL) and sat. aq. NaHCO$_3$ (100 mL) and stirred at r.t. for 20 min. The aqueous phase was separated and the organic phase was washed with water (3×100 mL) and brine (100 mL) and concentrated under reduced pressure. The crude product was dissolved in EtOH (200 mL) and to the resulting solution was added 1% AcOH solution in EtOH (50 mL) and after removal of volatile matters the crude product was purified by reversed phase flash chromatography using a mixture of MeOH and 0.1% solution of AcOH in water as an eluent. The product came out of the column at 30-65% of MeOH to give 3c (3.8 g) in 59% yield.

$^1$H NMR (300 MHz, Methanol-d$_4$): δ=7.37-7.14 (m, 5H), 6.79-6.72 (m, 2H), 6.42 (s, 2H), 5.07 (s, 2H), 4.77-4.66 (m, 1H), 4.14-4.03 (m, 1H), 3.83-3.65 (m, 2H), 3.20-3.08 (m, 1H), 3.04-2.90 (m, 1H), 2.23 (s, 6H), 1.72-1.32 ppm (m, 13H).

2) Step b: Synthesis of (S)-2-((R)-5-(2-amino-1H-imidazol-1-yl)-2-((tert-butoxycarbonyl)amino)pentanamido)-3-(4-hydroxy-2,6-dimethylphenyl)propanoic acid (4c)

To a solution of 3c (3.8 g, 5.94 mmol) in MeOH (150 mL) was added palladium on activated carbon (10% wt, 190 mg).

Hydrogen was bubbled through the stirred suspension at r.t. for 1 h. The reaction mixture was filtered to remove palladium and activated carbon and the resulting clear solution was evaporated. The crude product was purified by reversed phase flash chromatography using a mixture of MeOH and 0.1% solution of AcOH in water as an eluent. The product came out of the column at 34% of MeOH to give 4c (2.60 g) in 80% yield.

$^1$H NMR (300 MHz, Methanol-$d_4$): δ=6.83-6.75 (m, 2H), 6.40 (s, 2H), 4.65-4.55 (m, 1H), 4.07-3.98 (m, 1H), 3.81-3.69 (m, 2H), 3.19-3.08 (m, 1H), 2.97-2.85 (m, 1H), 2.29 (s, 6H), 1.72-1.36 ppm (m, 13H).

3) Step c: Synthesis of tert-butyl ((9S,12S,15R)-18-(2-amino-1H-imidazol-1-yl)-9-(3-(cyclohexylmethyl)-1,2,4-oxadiazol-5-yl)-12-(4-hydroxy-2,6-dimethylbenzyl)-2,2-dimethyl-4,11,14-trioxo-3-oxa-5,10,13-triazaoctadecan-15-yl)carbamate (6j)

The same procedure as described in Scheme 36 by using 4c (422 mg, 0.77 mmol) and 12j (380 mg, 0.92 mmol) to give 6j (0.342 g, 53%).

$^1$H NMR (400 MHz, Methanol-$d_4$) δ6.83-6.76 (m, 2H), 6.36 (s, 2H), 5.18 (dd, J=9.1, 5.8 Hz, 1H), 4.71-4.61 (m, 1H), 4.01-3.95 (m, 1H), 3.84-3.69 (m, 2H), 3.19-3.10 (m, 1H), 3.09-3.01 (m, 2H), 2.92-2.82 (m, 1H), 2.58 (d, J=6.9 Hz, 2H), 2.30 (s, 1H), 2.23 (s, 6H), 2.05-1.85 (m, 2H), 1.95 (s, 4H), 1.79-1.61 (m, 9H), 1.60-1.48 (m, 4H), 1.42 (s, 19H), 1.32-1.15 (m, 4H), 1.08-0.95 (m, 21-1).

4) Step d: Synthesis of (R)-2-amino-N-((S)-1-(((S)-4-amino-1-(3-(cyclohexylmethyl)-1,2,4-oxadiazol-5-yl)butyl)amino)-3-(4-hydroxy-2,6-dimethylphenyl)-1-oxopropan-2-yl)-5-(2-amino-1H-imidazol-1-yl)pentanamide (7l)

The same procedure as described in Scheme 36 by using 6j (400 mg, 0.49 mmol) to give 7l (220 mg, 72%) as pale yellow foam.

$^1$H NMR (400 MHz, Methanol-$d_4$) δ6.88 (d, J=2.5 Hz, 1H), 6.83 (d, J=2.5 Hz, 1H), 6.38 (s, 2H), 5.21 (dd, J=9.2, 6.0 Hz, 1H), 4.71 (t, J=8.2 Hz, 1H), 3.97 (t, J=6.1 Hz, 1H), 3.82 (dt, J=14.1, 7.1 Hz, 2H), 3.17-3.08 (m, 1H), 3.00-2.86 (m, 3H), 2.60 (d, J=6.9 Hz, 2H), 2.24 (s, 6H), 2.12-2.01 (m, 1H), 2.00-1.90 (m, 1H), 1.83-1.56 (m, 12H), 1.33-1.15 (m, 3H), 1.10-0.96 (m, 2H). MS: EI-MS: m/z 624.6 [M+1].

Example 43: Synthesis of (R)-2-amino-N-((S)-1-(((S)-4-amino-1-(3-(bicyclo[2.2.2]octan-1-ylmethyl)-1,2,4-oxadiazol-5 yl)butyl)amino)-3-(4-hydroxy-2,6-dimethylphenyl)-1-oxopropan-2-yl)-5-(2-amino-1H-imidazol-1-yl)pentanamide (D-(δ(2-amino-1H-imidazol-1-yl)-Nva-DMT-NH((S)-4-amino-1-(3-(bicyclo[2.2.2]octan-1-yl)methyl-1,2,4-oxadiazol-5-yl)but-1-yl), 7m)

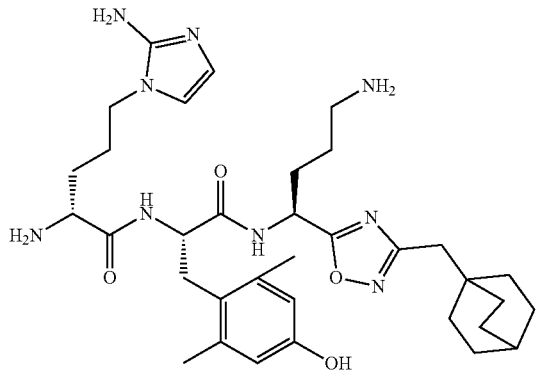

Compound 7m

Scheme 46

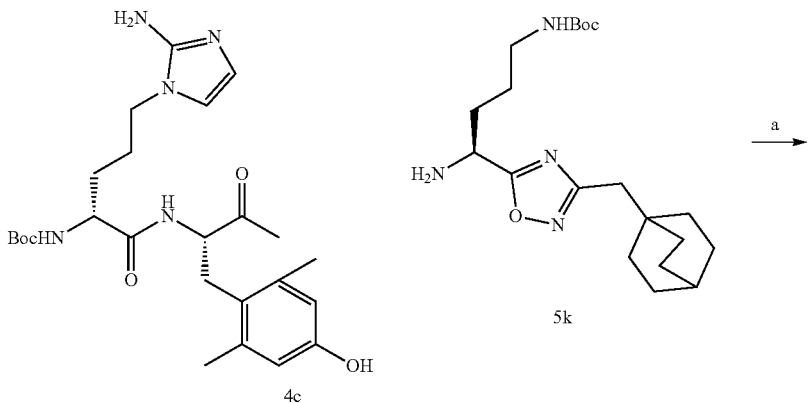

123

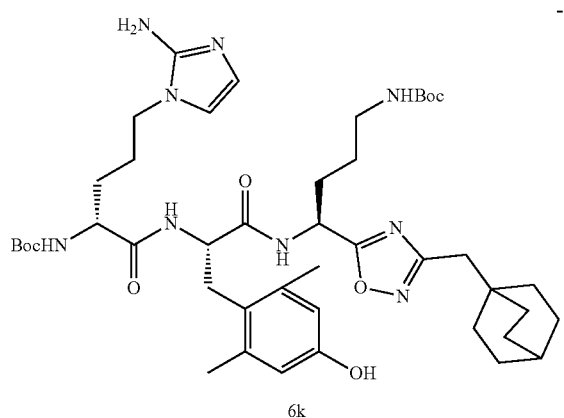

6k b →

124

-continued

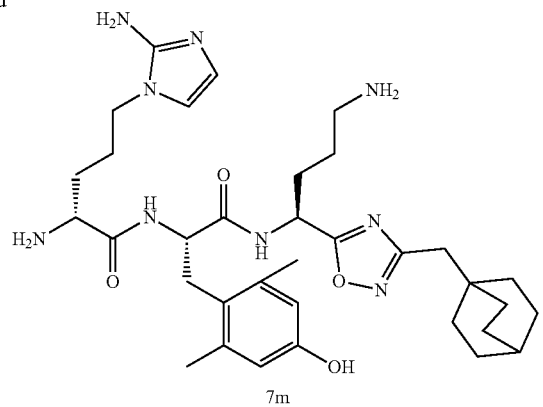

7m

1) Step a: Synthesis of tert-butyl ((9S,12S,15R)-18-(2-amino-1H-imidazol-1-yl)-9-(3-(bicyclo[2.2.2]octan-1-ylmethyl)-1,2,4-oxadiazol-5-yl)-12-(4-hydroxy-2,6-dimethylbenzyl)-2,2-dimethyl-4,11,14-trioxo-3-oxa-5,10,13-triazaoctadecan-15-yl)carbamate (6k)

The same procedure as described in Scheme 36 by using 4c (783 mg; 1.60 mmol) and 5k (490 mg; 1.3 mmol) to give 6k 106 mg (10%) of white foam. LC-MS analysis showed single peak with [M+H]+=850.5 Da. Product was used in the next step without further characterization.

2) Step b: Synthesis of (R)-2-amino-N-((S)-1-(((S)-4-amino-1-(3-(bicyclo[2.2.2]octan-1-ylmethyl)-1,2,4-oxadiazol-5-yl)butyl)amino)-3-(4-hydroxy-2,6-dimethylphenyl)-1-oxopropan-2-yl)-5-(2-amino-1H-imidazol-1-yl)pentanamide (7m)

The same procedure as described in Scheme 36 by using 6k (100 mg; 0.12 mmol) to give 7m (28 mg, 31%) as a white solid.

$^1$H NMR (400 MHz, Methanol-$d_4$) δ 6.86 (d, J=2.5 Hz, 1H), 6.84 (d, J=2.5 Hz, 1H), 6.36 (s, 2H), 5.19 (dd, J=9.3, 5.7 Hz, 1H), 4.72 (t, J=8.1 Hz, 1H), 4.00 (t, J=5.8 Hz, 1H), 3.92-3.74 (m, 2H), 3.12 (dd, J=14.2, 8.2 Hz, 1H), 3.02-2.84 (m, 3H), 2.45 (s, 2H), 2.23 (s, 6H), 2.11-1.88 m, 2H), 1.88-1.47 (m, 13H), 1.47-1.37 (m, 6H). Molecular formula: $C_{43}H_{55}N_9O_4$ 2HCl; Molecular weight: 834.89; Free base molecular weight: 761.97. EI-MS: m/z 762.7 [M+1].

Example 44: Synthesis of (R)-N-((S)-1-(((S)-1-(3-(adamantan-1 ylmethyl)-1,2,4-oxadiazol-5-yl)-4-aminobutyl)amino)-3-(4-hydroxy-2,6-dimethylphenyl)-1-oxopropan-2-yl)-2-amino-5-(2-amino-1H-imidazol-1-yl)pentanamide (D-(b (2-amino-1H-imidazol-1-yl)-Nva-DMT-NH((S)-1-(3-(adamantan-1-yl)methyl-1,2,4-oxadiazol-5-yl)-4-aminobut-1-yl), 7n)

Compound 7n

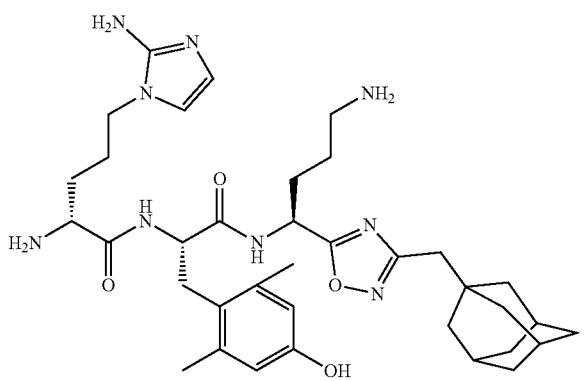

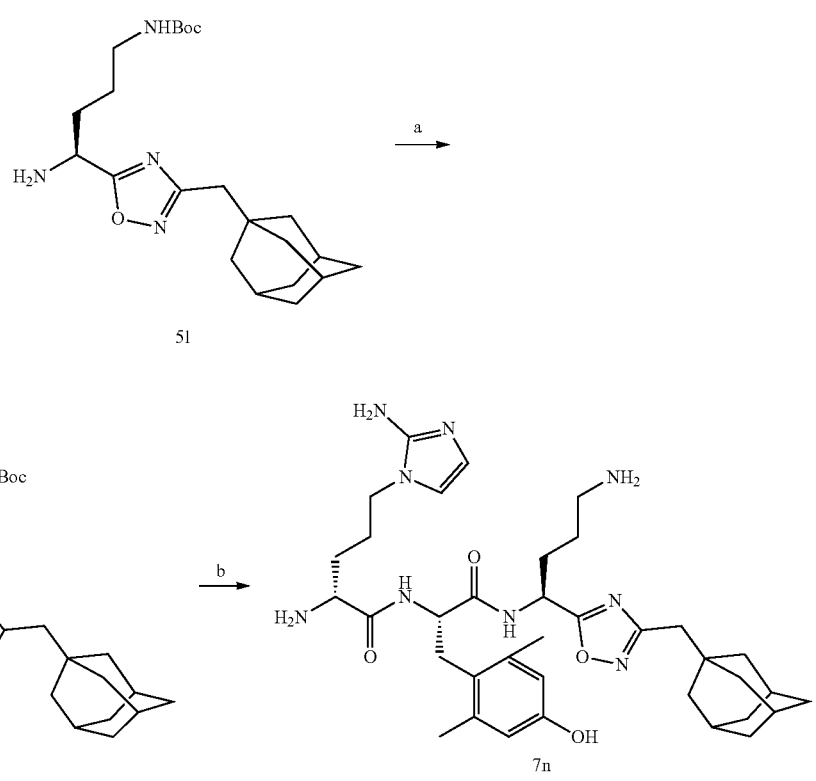

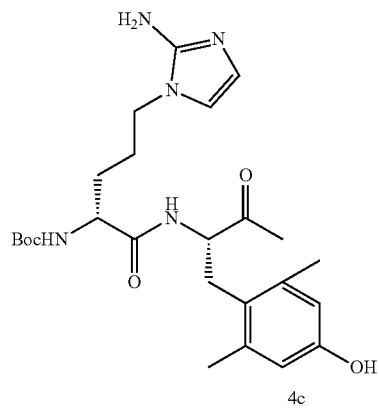

1) Step a: Synthesis of tert-butyl ((9S,12S,15R)-9-(3-(adamantan-1-ylmethyl)-1,2,4-oxadiazol-5-yl)-18-(2-amino-1H-imidazol-1-yl)-12-(4-hydroxy-2,6-dimethylbenzyl)-2,2-dimethyl-4,11,14-trioxo-3-oxa-5,10,13-triazaoctadecan-15-yl)carbamate (6l)

The same procedure as described in Scheme 36 by using 4c (5.0 g, 9.097 mmol) and 5l (4.05 g, 10.0 mmol) to give 6l (4.0 G) as acetate which was used in next step without further purification.

2) Step b: Synthesis of (R)-N-((S)-1-(((S)-1-(3-(adamantan-1-ylmethyl)-1,2,4-oxadiazol-5-yl)-4-aminobutyl)amino)-3-(4-hydroxy-2,6-dimethylphenyl)-1-oxopropan-2-yl)-2-amino-5-(2-amino-1H-imidazol-1-yl)pentanamide (7n)

The same procedure as described in Scheme 37 by using 6l (4.0 g, 4.273 mmol) to give 7n (2.3 g).

$^1$H NMR (400 MHz, Methanol-d$_4$) δ6.88 (d, J=2.5 Hz, 1H), 6.86 (d, J=2.5 Hz, 1H), 6.39 (s, 2H), 5.22 (dd, J=9.2, 5.6 Hz, 1H), 4.79-4.75 (m, 1H), 4.04-3.98 (m, 1H), 3.90-3.77 (m, 2H), 3.14 (dd, J=14.2, 8.2 Hz, 1H), 3.01-2.90 (m, 3H), 2.49 (s, 2H), 2.26 (s, 6H), 2.12-1.98 (m, 2H), 1.94 (s, 3H), 1.88-1.78 (m, 2H), 1.78-1.69 (m, 5H), 1.67-1.62 (m, 4H), 1.62-1.56 (m, 7H).). MS: EI-MS: m/z 676.7 [M+1].

Example 45: Synthesis of (R)-N-((S)-1-(((R)-1-(3-(adamantan-1-yl)methyl-1,2,4-oxadiazol-yl)-4-aminobutyl)amino)-3-(4-hydroxy-2,6-dimethylphenyl)-1-oxopropan-2-yl)-2-amino-5-(2-amino-1H-imidazol-1-yl)pentanamide (D-(δ(2-amino-1H-imidazol-1-yl)-Nva-DMT-NH((R)-1-(3-(adamantan-1-yl)methyl-1,2,4-oxadiazol-5-yl)-4-aminobut-1-yl), 7o)

Compound 7o

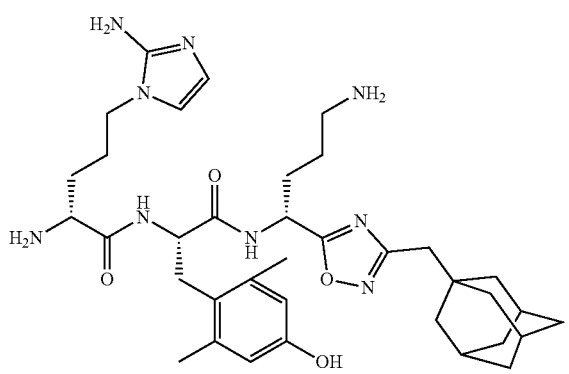

Compound 7o was isolated according to Scheme 47:

$^1$H NMR (400 MHz, Methanol-d$_4$) δ6.89 (m, 1H), 6.82 (m, 1H), 6.52 (s, 2H), 5.02 (m, 1H), 4.66 (m, 1H), 3.97 (m, 1H), 3.85 (m, 2H), 3.24 (m, 1H), 3.80 (m, 3H), 2.30 (m, 2H), 2.26 (s, 6H), 1.10-1.90 (m, 23H). MS: EI-MS: m/z 676.6 [M+1].

Example 46: Synthesis of (2R)-N-((2S)-1-(((1S)-1-(3-(adamantan-1-yl)-1,2,4-oxadiazol-5-yl)-4-aminobutyl)amino)-3-(4-hydroxy-2,6-dimethylphenyl)-1-oxopropan-2-yl)-2-amino-5-(2-amino-1H-imidazol-1-yl)pentanamide (D-(δ(2-amino-1H-imidazol-1-yl)-Nva-DMT-NH((S)-1-(3-(adamantan-1-yl)-1,2,4-oxadiazol-5-yl)-4-aminobut-1-yl), 7p)

The same procedure as described in Scheme 36 by using 4c (1.24 g, 2.304 mmol) and 5m (1.0 g, 2.56 mmol) to give 6m as a white foam (910 mg, 44%).

$^1$H-NMR (300 MHz, Methanol-$d_4$) δ6.80-6.78 (m, 2H), 6.37 (s, 2H), 5.22-5.16 (m, 1H), 4.68-4.61 (m, 1H), 4.01-3.96 (m, 1H), 3.82-3.71 (m, 2H), 3.09-3.02 (m, 2H), 2.90-2.83 (m, 1H), 2.23 (s, 6H), 2.07-2.03 (m, 14H), 1.86-1.79 (m, 6H), 1.67-1.50 (m, 4H), 1.42 (s, 18H).

2) Step b: Synthesis of (R)-N-((S)-1-(((S)-1-(3-(adamantan-1-ylmethyl)-1,2,4-oxadiazol-5-yl)-4-aminobutyl)amino)-3-(4-hydroxy-2,6-dimethylphenyl)-1-oxopropan-2-yl)-2-amino-5-(2-amino-1H-imidazol-1-yl)pentanamide (7p)

Compound 7p

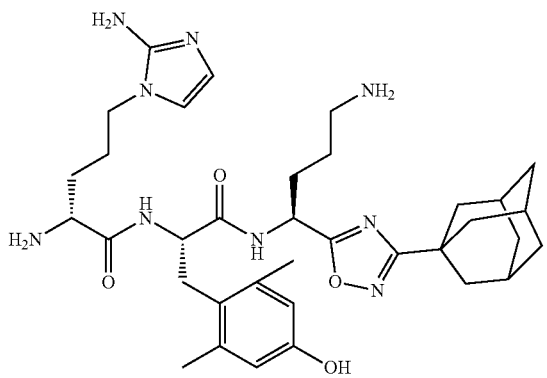

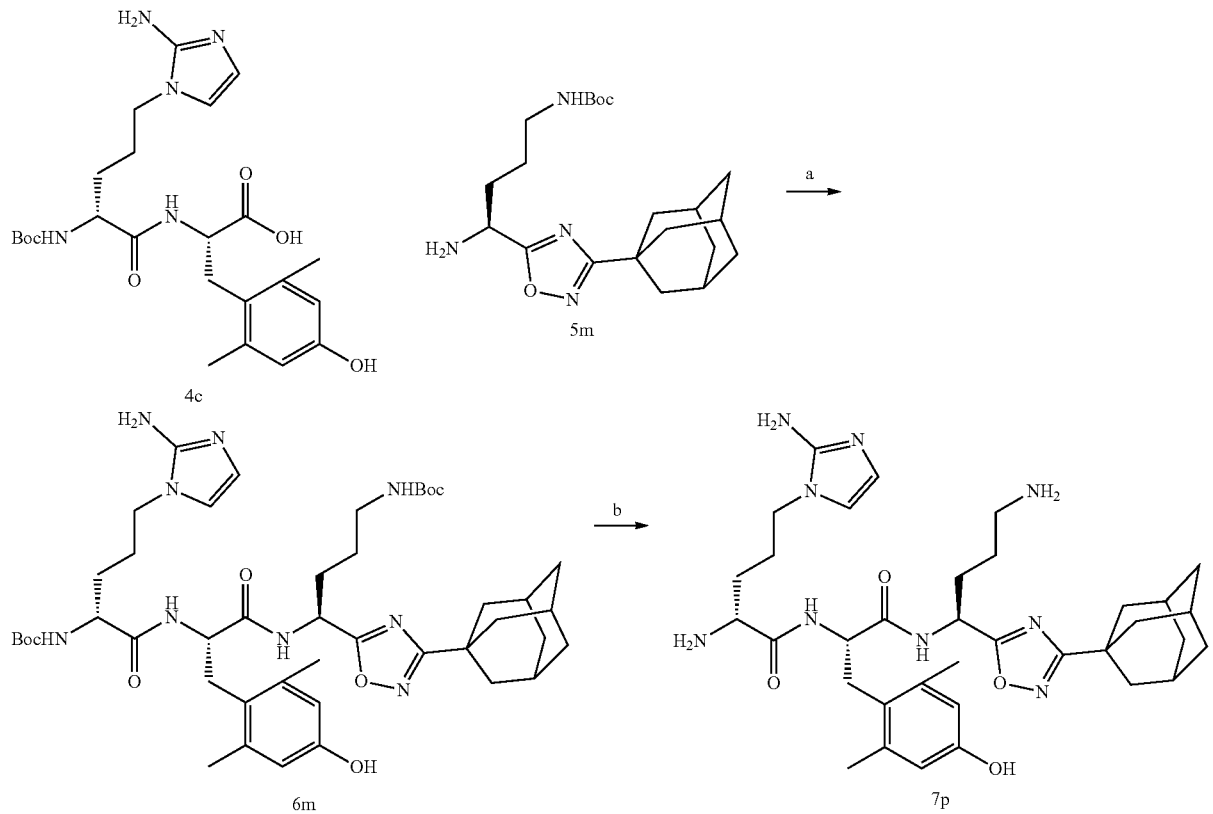

Scheme 48

1) Step a: Synthesis of tert-butyl ((9S,12S,15R)-9-(3-(adamantan-1-yl)-1,2,4-oxadiazol-5-yl)-18-(2-amino-1H-imidazol-1-yl)-12-(4-hydroxy-2,6-dimethylbenzyl)-2,2-dimethyl-4,11,14-trioxo-3-oxa-5,10,13-triazaoctadecan-15-yl) carbamate (6m)

The same procedure as described in Scheme 36 by using 6m (910 mg, 1.02 mmol) to give 7p (370 mg, 98%) as a white powder.

$^1$H-NMR (400 MHz, Methanol-$d_4$) δ6.88 (q, J=2.3 Hz, 2H), 6.38 (s, 2H), 5.24 (dd, J=9.1, 5.8 Hz, 1H), 4.70 (t, J=8.2

Hz, 1H), 4.06-3.97 (m, 1H), 3.14 (dd, J=14.2, 8.5 Hz, 1H), 3.00-2.87 (m, 3H), 2.25 (s, 6H), 2.09-1.98 (m, 11H), 1.88-1.59 (m, 12H). MS: 661.85. EI-MS: m/z 662.6 [M+1].

Example 47: Synthesis of (2R)-N-((2S)-1-(((1S)-1-(3-(adamantan-1-yl)-1,2,4-oxadiazol-5-yl)-5-(dimethylamino)pentyl)amino)-3-(4-hydroxy-2,6-dimethylphenyl)-1-oxopropan-2-yl)-2-amino-5-(2-amino-1H-imidazol-1-yl)pentanamide (D-(&(2-amino-1H-imidazol-1-yl)-Nva-DMT-NH((S)-1-(3-(adamantan-1-yl)methyl-1,2,4-oxadiazol-5-yl)-5-dimethylaminopent-1-yl), 7q)

1) Step a: Synthesis of tert-butyl ((2R)-1-(((2S)-1-(((1S)-1-(3-(adamantan-1-yl)-1,2,4-oxadiazol-5-yl)-5-(dimethylamino)pentyl)amino)-3-(4-hydroxy-2,6-dimethylphenyl)-1-oxopropan-2-yl)amino)-5-(2-amino-1H-imidazol-1-yl)-1-oxopentan-2-yl)carbamate (6n)

The same procedure as described in Scheme 36 by using 4c (100 g, 0.182 mmol) and 5n (102 mg, 0.182 mmol) to give 6n (121 mg, 72%, contains 11% of epimer) as a transparent amorphous solid.

$^1$H NMR (300 MHz, CD$_3$OD) δ: 6.84 (d, J=2.3 Hz, 1H), 6.81 (d, J=1.6 Hz, 1H), 6.37 (s, 2H), 5.18 (dd, J=8.5, 6.3 Hz, 1H), 4.60 (t, J=7.9 Hz, 1H), 4.03 (t, J=6.0 Hz, 1H), 3.91-3.68

Compound 7p

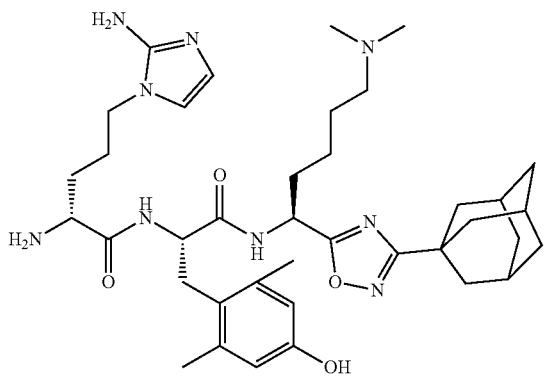

Scheme 49

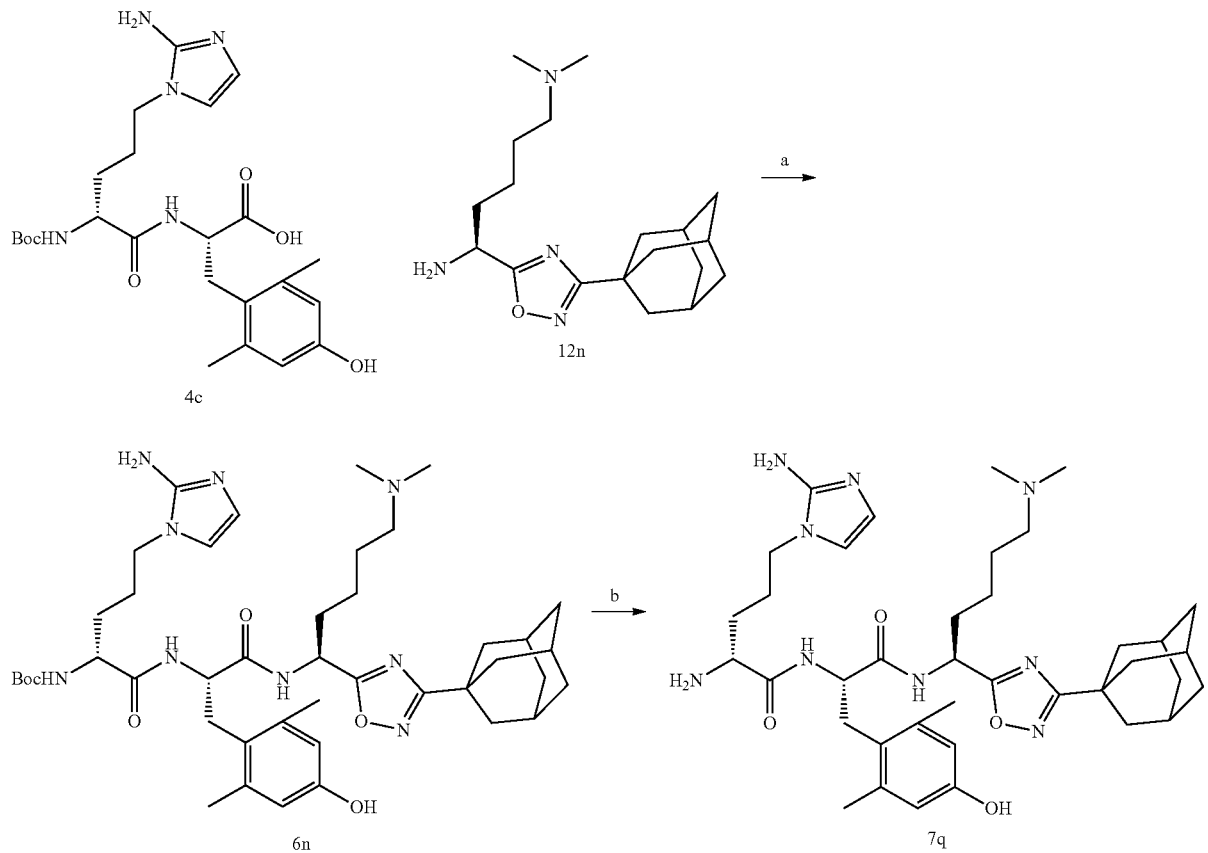

(m, 2H), 3.20-2.96 (m, 3H), 2.84 (s, 6H), 2.22 (s, 6H), 2.07 (br s, 3H), 2.03-1.90 (m, 11H), 1.89-1.46 (m, 14H), 1.42 (s, 9H).

2) Step b: Synthesis of (2R)-N-((2S)-1-(((1S)-1-(3-(adamantan-1-yl)-1,2,4-oxadiazol-5-yl)-5-(dimethylamino)pentyl) amino)-3-(4-hydroxy-2,6-dimethylphenyl)-1-oxopropan-2-yl)-2-amino-5-(2-amino-1H-imidazol-1-yl)pentanamide (7q)

The same procedure as described in Scheme 36 by using 6n (160 mg, 0.173 mmol) to give 7q (105 mg, 58%, HPLC purity-99.2% (210 nm)).

$^1$H NMR (400 MHz, CD$_3$OD) δ: 6.86 (d, J=2.4 Hz, 1H), 6.81 (d, J=2.5 Hz, 1H), 6.39 (s, 2H), 5.16 (dd, J=9.0, 6.0 Hz, 1H), 4.69 (t, J=8.1 Hz, 1H), 3.96 (t, J=6.0 Hz, 1H), 3.89-3.75 (m, 2H), 3.17-3.04 (m, 3H), 2.90 (dd, J=8.9, 5.4 Hz, 1H), 2.87 (s, 6H), 2.23 (s, 6H), 2.10-1.26 (m, 25H). MS: EI-MS: m/z 704.7 [M+1].

Example 48: Synthesis of (R)-2-amino-N-((S)-1-(((R)-5-amino-1-(3-benzyl-1,2,4-oxadiazol-yl)pentyl)amino)-3-(4-hydroxy-2,6-dimethylphenyl)-1-oxopropan-2-yl)-5-guanidinopentanamide (D-Arg-DMT-NH((R)-5-amino-1-(3-benzyl-1,2,4-oxadiazol-5-yl)pent-1-yl), 7r)

Compound 7r

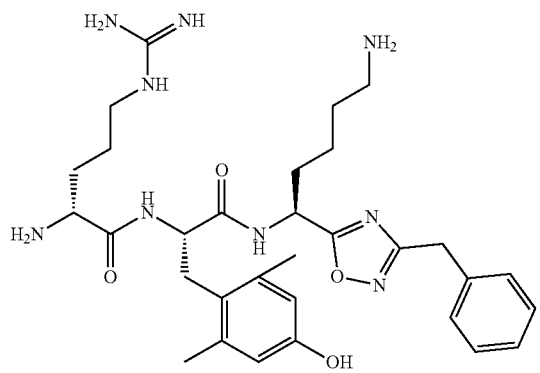

Scheme 50

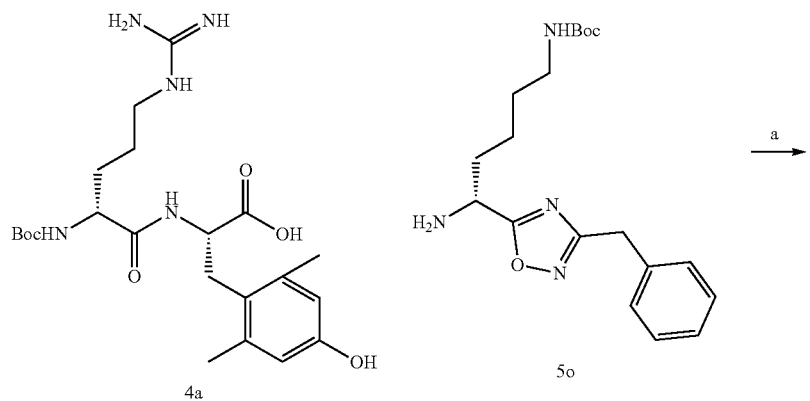

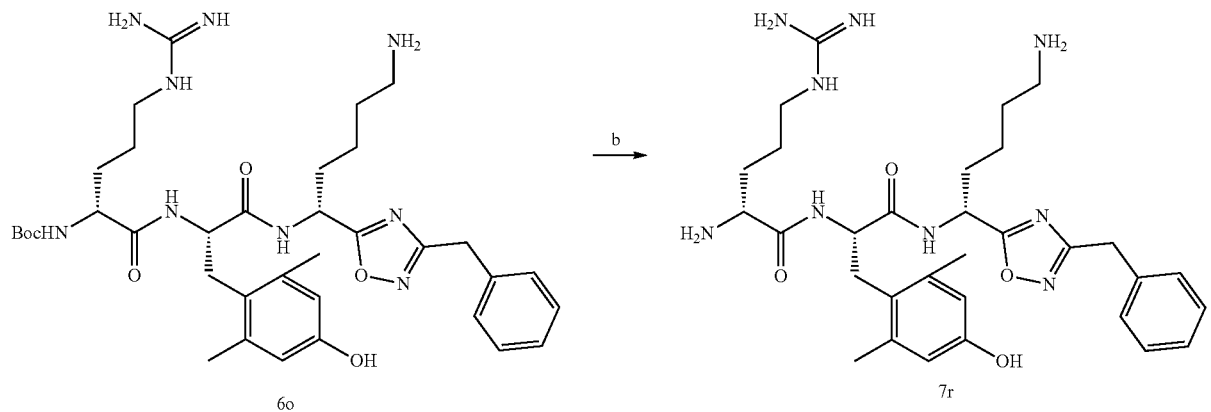

1) Step a: Synthesis of tert-butyl ((R)-1-(((S)-1-(((R)-5-amino-1-(3-benzyl-1,2,4-oxadiazol-5-yl)pentyl)amino)-3-(4-hydroxy-2,6-dimethylphenyl)-1-oxopropan-2-yl)amino)-5-guanidino-1-oxopentan-2-yl)carbamate (6o)

The same procedure as described in Scheme 36 by using 4a (3.63 g; 7.80 mmol) and 5o (2.30 g; 6.38 mmol) to give 6o (4.18 g, 78%) of white foam was obtained. HPLC and LC-MS showed sufficiently pure material. Reaction product was used in the next step without further purification and without characterization.

2) Step b: Synthesis of (R)-2-amino-N-((S)-1-(((R)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (7r)

The same procedure as described in Scheme 36 by using 6o (4.10 g; 4.86 mmol) to give 7r (1.56 g, 45%) as a white solid.

$^1$H NMR (400 MHz, Methanol-$d_4$) δ 7.34-7.12 (m, 5H), 6.47 (s, 2H), 5.02 (dd, J=8.9, 5.6 Hz, 1H), 4.74 (dd, J=9.9, 6.9 Hz, 1H), 4.01 (apparent singlet, 2H), 3.92 (t, J=6.4 Hz, 1H), 3.18 (t, J=7.0 Hz, 2H), 3.13 (dd, J=14.0, 9.8 Hz, 1H), 2.91 (dd, J=14.0, 6.9 Hz, 1H), 2.87-2.81 (m, 2H), 2.29 (s, 6H), 1.91-1.61 (m, 4H), 1.62-1.44 (m, 4H), 1.08 (p, J=8.0 Hz, 2H). MS: EI-MS: m/z 608.3 [M+1].

Example 49: Synthesis of (R)-2-amino-N-((S)-1-(((S)-5-amino-1-(3-benzyl-1,2,4-oxadiazol-5-yl)pentyl-2,2,3,3,4,4,5,5-d8)amino)-3-(4-hydroxy-2,6-dimethylphenyl)-1-oxopropan-2-yl)-5-guanidinopentanamide (D-Arg-DMT-NH((S)-5-amino-1-(3-benzyl-1,2,4-oxadiazol-5-yl)-2,2,3,3,4,4,5,5-d8-pent-1-yl), 7s)

Compound 7s

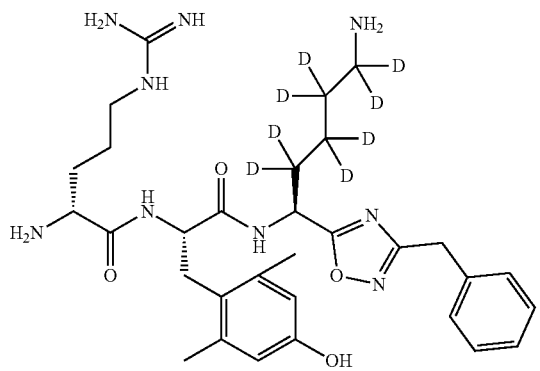

Example 50: Synthesis of (R)-2-amino-N-((S)-1-(((R)-5-amino-1-(3-benzyl-1,2,4-oxadiazol-5-yl)pentyl-2,2,3,3,4,4,5,5-d8)amino)-3-(4-hydroxy-2,6-dimethylphenyl)-1-oxopropan-2-yl)-5-guanidinopentanamide (D-Arg-DMT-NH((R)-5-amino-1-(3-benzyl-1,2,4-oxadiazol-5-yl)-2,2,3,3,4,4,5,5-d8 pent-1-yl), 7t)

Compound 7t

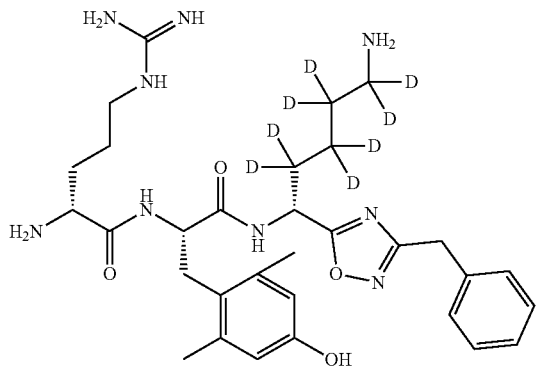

-continued
Scheme 51

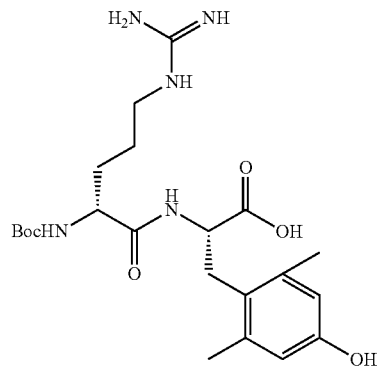
4a

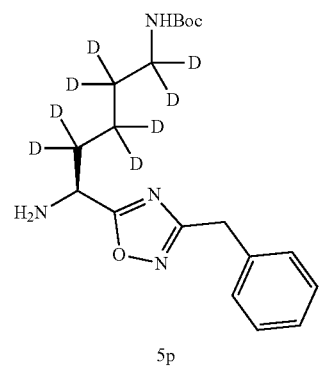
5p a →

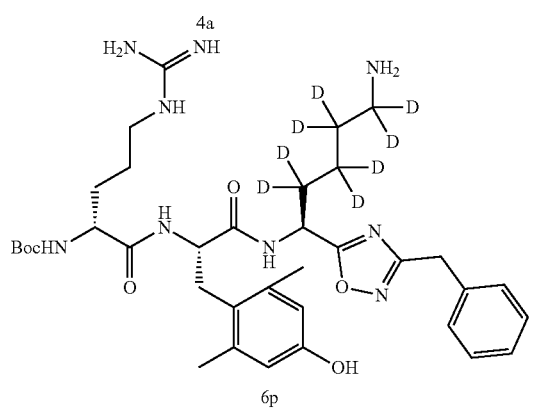
6p

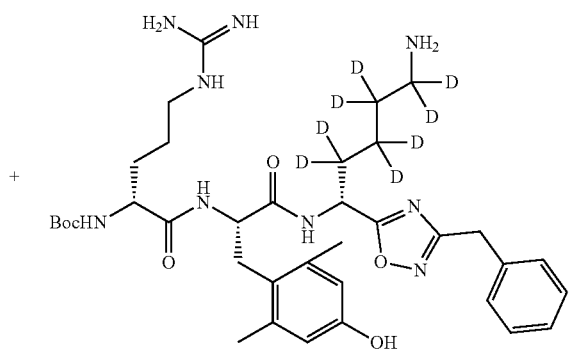
6q b →

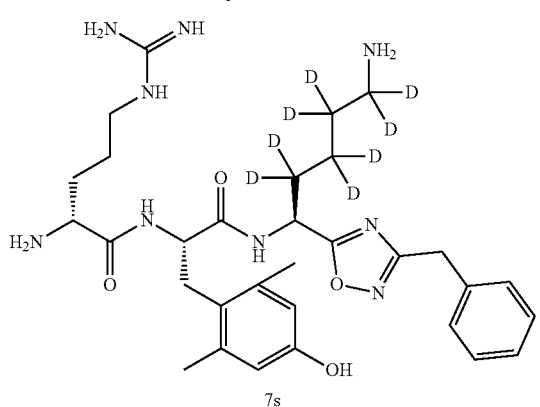
7s

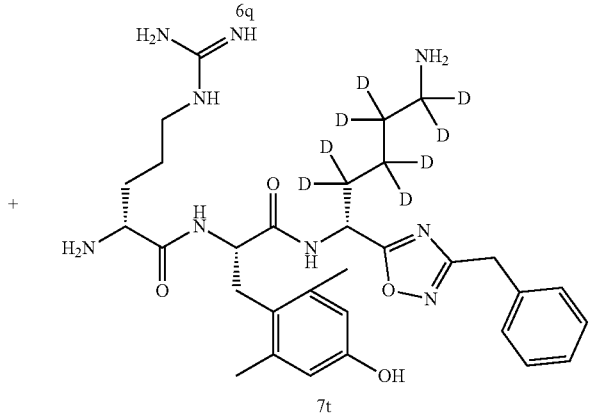
7t

1) Step a: Synthesis of tert-butyl ((R)-1-(((S)-1-(((S)-5-amino-1-(3-benzyl-1,2,4-oxadiazol-5-yl)pentyl-2,2,3,3,4,4,5,5-d8)amino)-3-(4-hydroxy-2,6-dimethylphenyl)-1-oxopropan-2-yl)amino)-5-guanidino-1-oxopentan-2-yl) carbamate (6p) and tert-butyl ((R)-1-(((S)-1-(((R)-5-amino-1-(3-benzyl-1,2,4-oxadiazol-5-yl)pentyl-2,2,3,3,4,4,5,5-d8) amino)-3-(4-hydroxy-2,6-dimethylphenyl)-1-oxopropan-2-yl)amino)-5-guanidino-1-oxopentan-2-yl)carbamate (6q)

The same procedure as described in Scheme 36 by using 4a (1213 mg, 2.61 mmol) and 5p (835 mg, 2.27 mmol) to give 6p and 6q as a white foam (1.68 g, 87%, 32% epimer by $^1$H NMR, HPLC purity 92%).

$^1$H NMR (300 MHz, CD$_3$OD) δ: 7.37-7.17 (m, 5H), 6.38 (s, 2H), 5.12 (s, 1H), 4.60 (t, J=7.5 Hz, 1H), 4.05 (s, 2H), 4.01-3.90 (m, 1H), 3.19-3.05 (m, 3H), 2.95-2.77 (m, 1H), 2.20 (s, 6H), 1.76-1.24 (m, 4H), 1.42 (s, 9H), 1.41 (s, 9H).

2) Step b: Synthesis of (R)-2-amino-N-((S)-1-(((R)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (7s) and (R)-2-amino-N-((S)-1-(((R)-5-amino-1-(3-benzyl-1,2,4-oxadiazol-5-yl)pentyl-2,2,3,3,4,4,5,5-d8)amino)-3-(4-hydroxy-2,6-dimethylphenyl)-1-oxopropan-2-yl)-5-guanidinopentanamide (7t)

The same procedure as described in Scheme 36 by using a mixture of 6p and 6q (1.68 g, 1.97 mmol) to give 7s (500 mg):

$^1$H NMR (400 MHz, CD$_3$OD) δ: 7.36-7.13 (m, 5H), 6.39 (s, 2H), 5.13 (s, 1H), 4.68 (dd, J=8.9, 7.4 Hz, 1H), 4.07 (d, J=2.0 Hz, 2H), 3.94 (t, J=6.3 Hz, 1H), 3.16 (t, J=7.0 Hz, 2H), 3.09 (dd, J=14.1, 9.0 Hz, 1H), 2.87 (dd, J=14.1, 7.4 Hz, 1H), 2.21 (s, 6H), 1.86-1.66 (m, 2H), 1.56-1.36 (m, 2H). MS: EI-MS: m/z 616.4 [M+1]; and 7t (150 mg): $^1$H NMR (400 MHz, CD$_3$OD) δ: 7.35-7.19 (m, 5H), 6.49 (s, 2H), 5.05-5.00 (m, 1H), 4.76 (dd, J=9.8, 6.8 Hz, 1H), 4.03 (s, 2H), 3.93 (t, J=6.4 Hz, 1H), 3.24-3.11 (m, 3H), 2.93 (dd, J=14.0, 7.0 Hz, 1H), 2.31 (s, 6H), 1.91-1.72 (m, 2H), 1.61-1.47 (m, 2H). MS: EI-MS: m/z 616.4 [M+1].

Example 51: Synthesis of (R)-N-((S)-1-(((S)-2-(1H-imidazol-4-yl)-1-(3 phenyl-1,2,4-oxadiazol-5 yl)ethyl)amino)-3-(4-hydroxy-2,6-dimethylphenyl)-1-oxopropan-2-yl)-2-amino-5-guanidinopentanamide (D-Arg-DMT-NH((S)-2-(1H-imidazol-4 yl)-1-(3 phenyl-1,2,4-oxadiazol-5 yl)eth-1-yl), 7u)

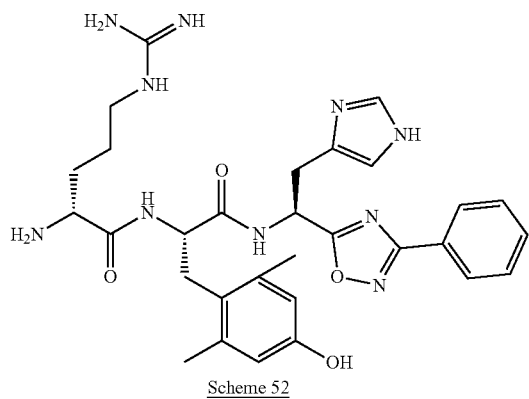

Compound 7u

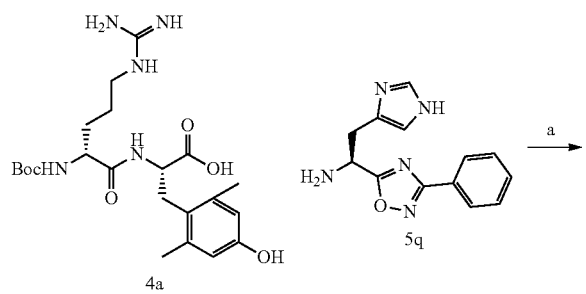

Scheme 52

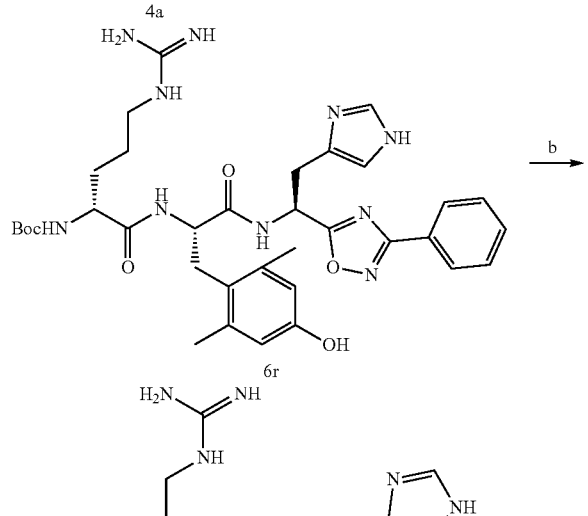

1) Step a: Synthesis of tert-butyl ((R)-1-(((5)-1-(((S)-2-(1H-imidazol-4-yl)-1-(3-phenyl-1,2,4-oxadiazol-5-yl)ethyl)amino)-3-(4-hydroxy-2,6-dimethylphenyl)-1-oxopropan-2-yl)amino)-5-guanidino-1-oxopentan-2-yl)carbamate (6r)

The same procedure as described in Scheme 36 by using 4a (112 mg, 0.241 mmol) and 5q (174 mg, 0.362 mmol) to give 6r (80 mg) as a white solid. $^1$H NMR (400 MHz, Methanol-$d_4$) δ: 8.81 (s, 1H), 8.05 (d, J=12 Hz, 2H), 7.60-7.49 (m, 3H), 7.39 (s, 1H), 6.37 (s, 2H), 5.65-5.61 (m, 1H), 4.58-4.53 (m, 1H), 4.05-3.98 (m, 1H), 3.59-3.33 (m, 2H), 3.26-3.10 (m, 3H), 2.93-2.86 (m, 1H), 2.23 (s, 6H), 1.72-1.37 (m, 4H), 1.42 (s, 9H).

2) Step b: Synthesis of (R)-N-((S)-1-(((S)-2-(1H-imidazol-4-yl)-1-(3-phenyl-1,2,4-oxadiazol-5-yl)ethyl)amino)-3-(4-hydroxy-2,6-dimethylphenyl)-1-oxopropan-2-yl)-2-amino-5-guanidinopentanamide (7u)

The same procedure as described in Scheme 36 by using a mixture of 6q (80 mg, 0.086 mmol) to give 7u (57 mg) as a white solid (HPLC purity>99%).

$^1$H NMR (400 MHz, Methanol-$d_4$) δ: 8.81 (s, 1H), 8.05 (d, J=11.6 Hz, 2H), 7.59-7.51 (m, 3H), 7.40 (s, 1H), 6.35 (s, 2H), 5.64-5.61 (m, 1H), 4.64-4.60 (m, 1H), 3.96-3.93 (m, 1H), 3.54-3.31 (m, 2H), 3.19-3.10 (m, 3H), 2.92-2.86 (m, 1H), 2.22 (s, 6H), 1.86-1.75 (m, 2H), 1.70-1.51 (m, 2H). ). MS: EI-MS: m/z 603.6 [M+1].

Example 52: Synthesis of (R)-2-amino-N-((S)-1-(((S)-1-(3-benzyl-1,2,4-oxadiazol-5-yl)-2-(1H-imidazol-4 yl)ethyl)amino)-3-(4-hydroxy-2,6-dimethylphenyl)-1-oxopropan-2-yl)-5-guanidinopentanamide (D-Arg-DMT-NH((S)-1-(3-benzyl-1,2,4-oxadiazol-5-yl)-2-(1H-imidazol-4 yl)eth-1-yl), 7v)

Compound 7v

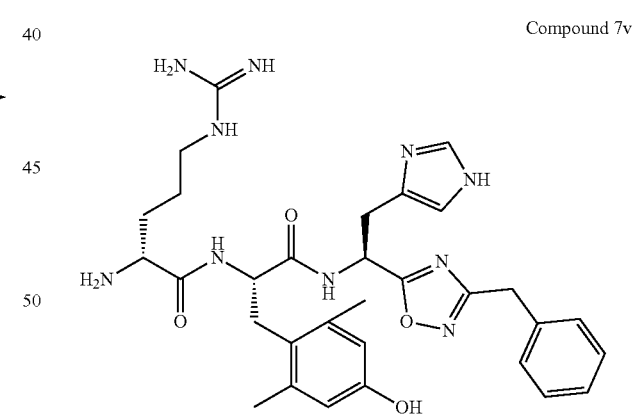

Scheme 53

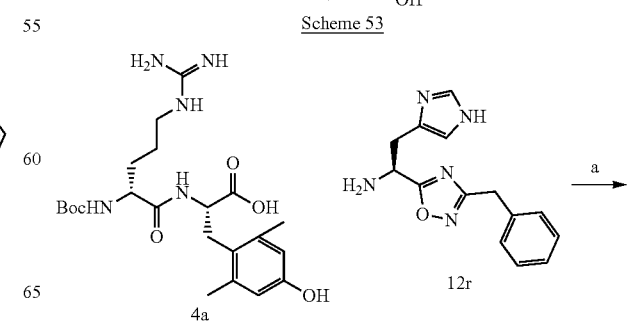

-continued

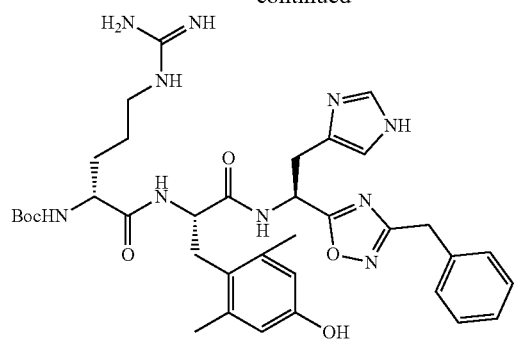

6s

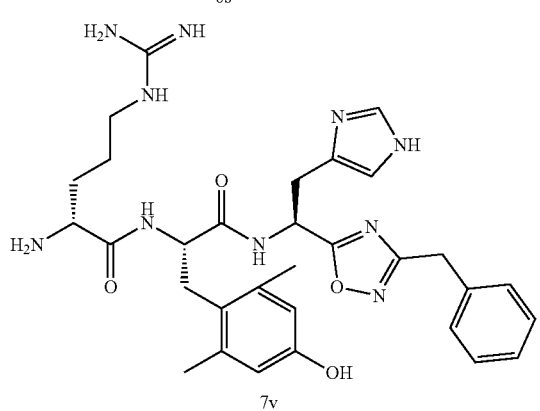

7v

1) Step a: Synthesis of tert-butyl ((R)-1-(((S)-1-(((S)-1-(3-benzyl-1,2,4-oxadiazol-5-yl)-2-(1H-imidazol-4-yl)ethyl)amino)-3-(4-hydroxy-2,6-dimethylphenyl)-1-oxopropan-2-yl)amino)-5-guanidino-1-oxopentan-2-yl)carbamate (6s)

The same procedure as described in Scheme 36 by using 4a (50 mg, 0.107 mmol) and 12r (80 mg, 0.160 mmol) to give 6s (30 mg) as a white solid.

$^1$H NMR (400 MHz, Methanol-$d_4$) δ: 8.74 (s, 1H), 7.34-7.21 (m, 6H), 6.38 (s, 2H), 5.54-5.48 (m, 1H), 4.51-4.46 (m, 1H), 4.07 (s, 2H), 4.08-3.98 (m, 2H), 3.41-3.26 (m, 1H), 3.24-3.11 (m, 3H), 2.88-2.81 (m, 1H), 2.19 (s, 6H), 1.73-1.30 (m, 4H), 1.42 (s, 9H).

2) Step b: Synthesis of (R)-2-amino-N-((S)-1-(((S)-1-(3-benzyl-1,2,4-oxadiazol-5-yl)-2-(1H-imidazol-4-yl)ethyl)amino)-3-(4-hydroxy-2,6-dimethylphenyl)-1-oxopropan-2-yl)-5-guanidinopentanamide (7v)

The same procedure as described in Scheme 36 by using a mixture of 6r (30 mg, 0.032 mmol) to give 7v (17 mg) as a white solid (HPLC purity>99%).

$^1$H NMR (400 MHz, Methanol-$d_4$) δ: 8.74 (s, 1H), 7.33-7.21 (m, 6H), 6.38 (s, 2H), 5.54-5.49 (m, 1H), 4.56-4.50 (m, 1H), 4.12 (s, 2H), 4.02-3.90 (m, 2H), 3.40-3.26 (m, 1H), 3.24-3.08 (m, 3H), 2.88-2.83 (m, 1H), 2.19 (s, 6H), 1.87-1.70 (m, 2H) 1.56-1.36 (m, 2H). MS: EI-MS: m/z 617.8 [M+1].

Example 53: Synthesis of (R)-N-((S)-1-(((S)-2-(1H-imidazol-4-yl)-1-(3 phenethyl-1,2,4-oxadiazol-5 yl)ethyl)amino)-3-(4-hydroxy-2,6-dimethylphenyl)-1-oxopropan-2-yl)-2-amino-5-guanidinopentanamide (D-Arg-DMT-NH((S)-2-(1H-imidazol-4 yl)-1-(3-phenethyl-1,2,4-oxadiazol-5-yl)eth-1-yl), 7w)

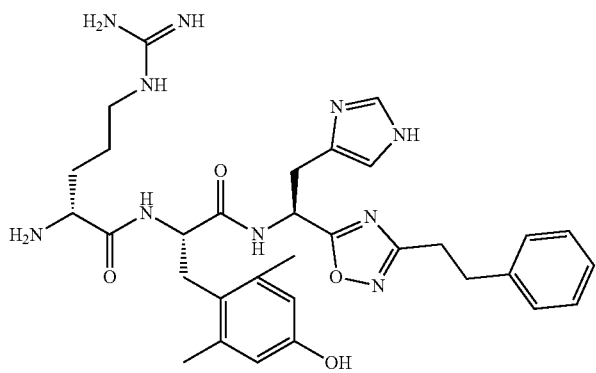

Compound 7w

Scheme 54

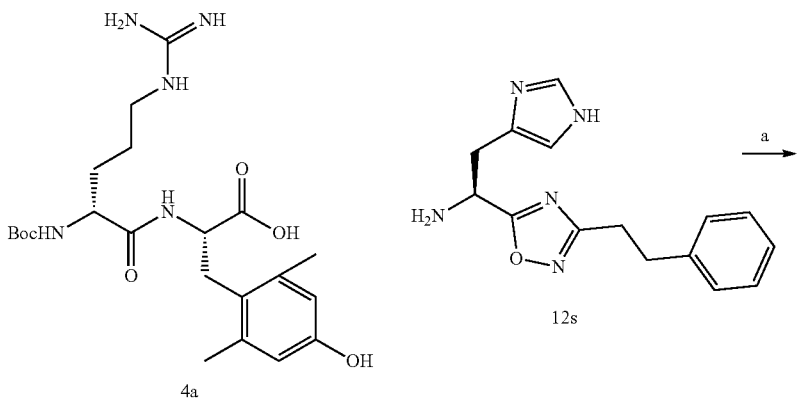

4a 12s

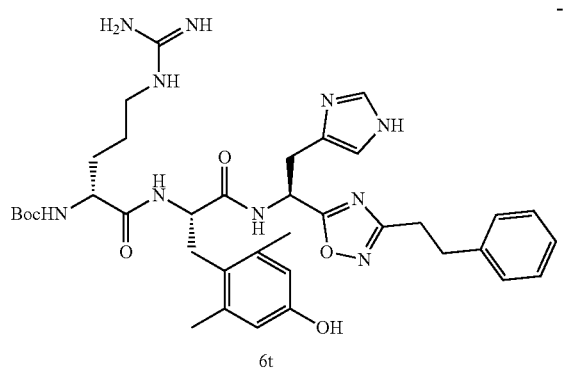

6t

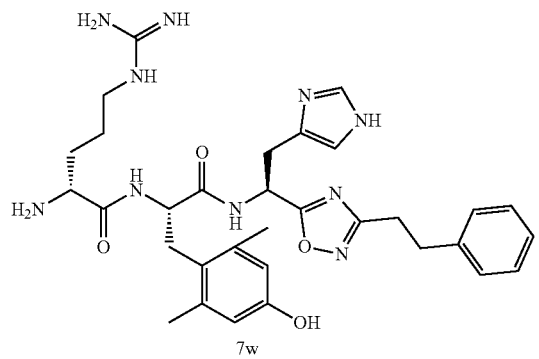

7w

1) Step a: Synthesis of tert-butyl ((R)-1-(((S)-1-(((S)-2-(1H-imidazol-4-yl)-1-(3-phenethyl-1,2,4-oxadiazol-5-yl)ethyl)amino)-3-(4-hydroxy-2,6-dimethylphenyl)-1-oxopropan-2-yl)amino)-5-guanidino-1-oxopentan-2-yl)carbamate (6t)

The same procedure as described in Scheme 36 by using 4a (122 mg, 0.262 mmol) and 12s (200 mg, 0.393 mmol) to give 6t (120 mg) as a white solid.

¹H NMR (400 MHz, Methanol-d₄) δ: 8.79 (s, 1H), 7.30-7.14 (m, 6H), 6.37 (s, 2H), 5.55-5.50 (m, 1H), 4.57-4.47 (m, 1H), 4.04-3.98 (m, 1H), 3.46-3.30 (m, 1H), 3.21-3.04 (m, 8H), 2.92-2.83 (m, 1H), 2.21 (s, 6H), 1.80-1.41 (m, 4H), 1.53 (s, 9H).

2) Step b: Synthesis of (R)-N-((S)-1-(((S)-2-(1H-imidazol-4-yl)-1-(3-phenethyl-1,2,4-oxadiazol-5-yl)ethyl)amino)-3-(4-hydroxy-2,6-dimethylphenyl)-1-oxopropan-2-yl)-2-amino-5-guanidinopentanamide (7w)

The same procedure as described in Scheme 36 by using a mixture of 6s (110 mg, 0.115 mmol) to give 7w (70 mg) as a white solid (HPLC purity>98%).

¹H NMR (400 MHz, Methanol-d₄) δ: 8.75 (s, 1H), 7.30-7.16 (m, 6H), 6.36 (s, 2H), 5.55-5.51 (m, 1H), 4.58-4.54 (m, 1H), 3.94-3.91 (m, 1H), 3.41-3.35 (m, 1H), 3.26-3.2.99 (m, 4H), 3.04 (s, 2H) 3.21-3.04 (m, 8H), 2.90-2.84 (m, 1H), 2.21 (s, 6H), 1.85-1.71 (m, 2H), 1.59-1.38 (m, 2H). ). MS: EI-MS: m/z 631.7 [M+1].

Example 54: Synthesis of (R)-N-((S)-1-(((S)-1-(3-([1,1'-biphenyl]-4-ylmethyl)-1,2,4-oxadiazol-5-yl)-2-(1H-imidazol-4 yl)ethyl)amino)-3-(4-hydroxy-2,6-dimethylphenyl)-1-oxopropan-2-yl)-2-amino-5-(2-amino-1H-imidazol-1-yl)pentanamide (D-(6 (2-amino-1H-imidazol-1-yl)-Nva-DMT-NH((S)-1-(3-([1,1'-biphenyl]-4-yl)methyl-1,2,4-oxadiazol-5-yl)-2-(1H-imidazol-4 yl)eth-1-yl), 7x)

Compound 7x

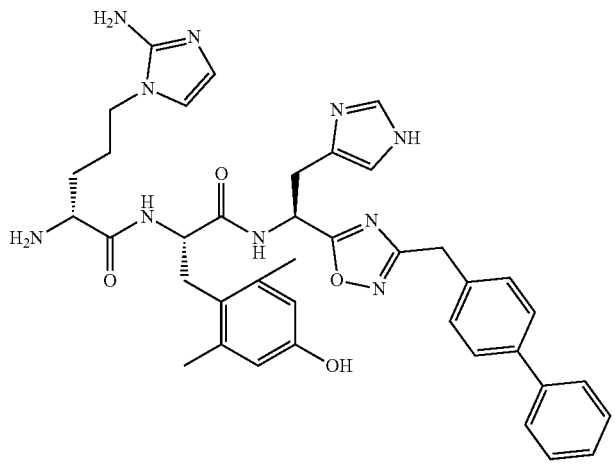

-continued
Scheme 55
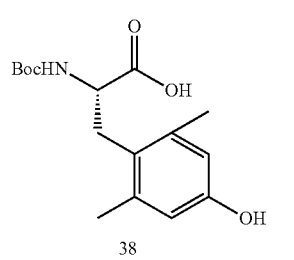 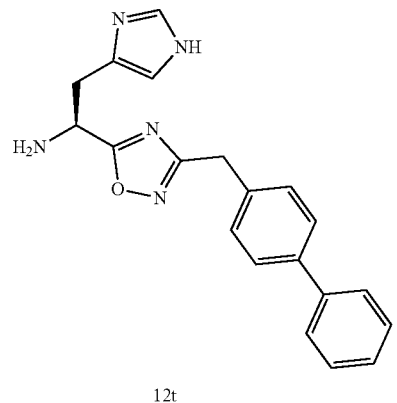
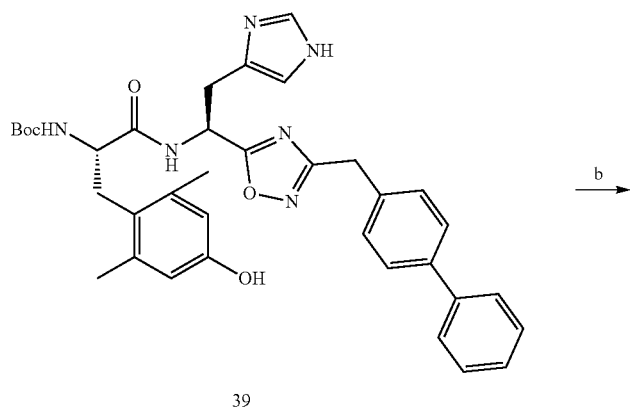
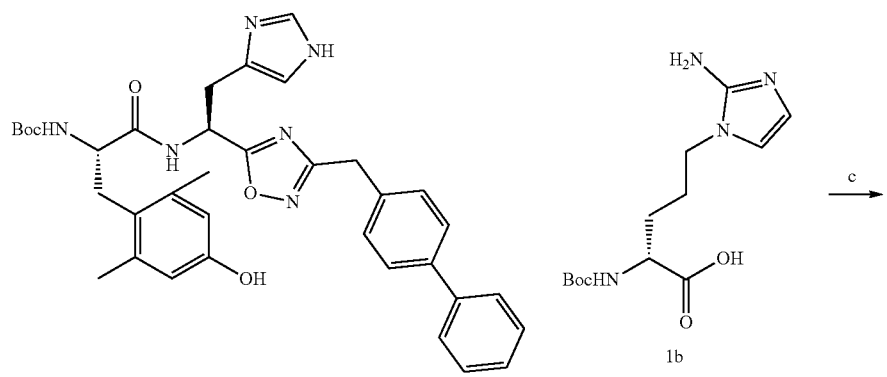

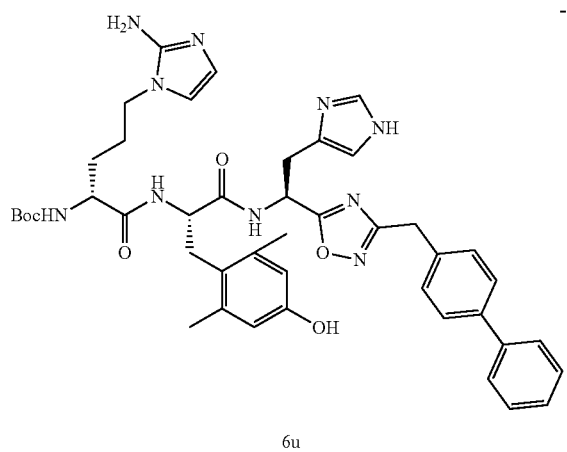

6u

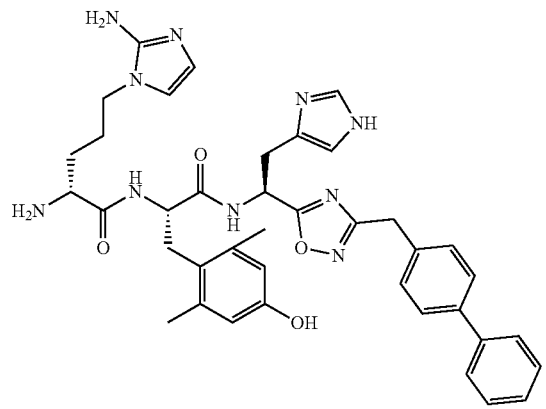

7x

1) Step a: Synthesis of tert-butyl ((S)-1-(((S)-1-(3-([1,1'-biphenyl]-4-ylmethyl)-1,2,4-oxadiazol-5-yl)-2-(1H-imidazol-4-yl)ethyl)amino)-3-(4-hydroxy-2,6-dimethylphenyl)-1-oxopropan-2-yl)carbamate (39)

To a mixture of 12t (0.15 g, 0.393 mmol) and Boc-DMT-OH (38, 0.134 g, 0.432 mmol) in 10 mL of DMF EDCI·HCl (0.188 G, 0.982 mmol) was added followed by addition of HOBt·H₂O (0.108 g, 0.707 mmol). After 10-15 min NMM (0.119 g, 1.179 mmol) was added and the mixture was stirred at ambient temperature overnight. Then volatiles were removed under reduced pressure and the residue was evaporated with 5% of citric acid aqueous solution. Obtained residue was purified by reverse-phase flash chromatography to afford desired product (39, 0.165 g).

2) Step b: Synthesis of (S)-N-((S)-1-(3-([1,1'-biphenyl]-4-ylmethyl)-1,2,4-oxadiazol-5-yl)-2-(1H-imidazol-4-yl)ethyl)-2-amino-3-(4-hydroxy-2,6-dimethylphenyl)propanamide (40)

To a cooled solution of 39 (0.165 g, 0.26 mmol) in DCM (20 mL) TFA (8 mL) was added. Then ice/water bath was removed and the mixture was stirred at ambient temperature for 2 h. Volatiles were removed under reduced pressure and the residue was concentrated from toluene (2×). Obtained residue (40) was used in next step without further purification.

¹H NMR (400 MHz, Methanol-d₄) δ8.71 (d, J=1.3 Hz, 1H), 7.59-7.56 (m, 4H), 7.44-7.40 (m, 2H), 7.36-7.31 (m, 3H), 7.18 (s, 1H), 6.38 (s, 2H), 5.59 (t, J=7.1 Hz, 1H), 4.12 (d, J=4.2 Hz, 2H), 3.91 (dd, J=11.2, 5.0 Hz, 1H), 3.29-3.13 (m, 3H), 2.97 (dd, J=14.0, 5.1 Hz, 1H), 2.16 (s, 6H).

3) Step c: Synthesis of tert-butyl ((R)-1-(((S)-1-(((S)-1-(3-([1,1'-biphenyl]-4-ylmethyl)-1,2,4-oxadiazol-5-yl)-2-(1H-imidazol-4-yl)ethyl)amino)-3-(4-hydroxy-2,6-dimethylphenyl)-1-oxopropan-2-yl)amino)-5-(2-amino-1H-imidazol-1-yl)-1-oxopentan-2-yl)carbamate (6u)

To a mixture of 1b (0.091 g, 0.254 mmol) and 40 (0.165 g, 0.254 mmol) in 15 mL of DMF EDCI·HCl (0.122 g, 0.635 mmol) was added followed by the addition of HOBt·H₂O (0.078 g, 0.508 mmol). After 10-15 min NMM (0.098 g, 0.965 mmol) was added and the mixture was stirred at ambient temperature overnight. Next, volatiles were removed under reduced pressure and the residue was evaporated with 5% of citric acid aqueous solution. Obtained residue was flushed thoroughly reverse-phase flash column and used in next step without further purification.

4) Step d: Synthesis of (R)-N-((S)-1-(((S)-1-(3-([1,1'-biphenyl]-4-ylmethyl)-1,2,4-oxadiazol-5-yl)-2-(1H-imidazol-4-yl)ethyl)amino)-3-(4-hydroxy-2,6-dimethylphenyl)-1-oxopropan-2-yl)-2-amino-5-(2-amino-1H-imidazol-1-yl)pentanamide (7x)

The same procedure as described in Scheme 36 by using a mixture of 6t (0.11 g, 0.125 mmol) to give 7x (52 mg) as white solid. (HPLC purity is 97.2% at 210 nm).

¹H NMR (400 MHz, Methanol-d₄) δ8.72 (d, J=1.3 Hz, 1H), 7.54-7.52 (m, 4H), 7.40-7.26 (m, 6H), 6.84 (d, J=2.5 Hz, 1H), 6.79 (d, J=2.5 Hz, 1H), 6.35 (s, 2H), 5.50 (dd, J=8.9, 5.8 Hz, 1H), 4.52 (dd, J=9.2, 7.1 Hz, 1H), 4.10 (s, 2H), 3.90 (t, J=6.1 Hz, 1H), 3.79 (p, J=7.3 Hz, 2H), 3.35 (dd, J=15.4, 5.6 Hz, 1H), 3.25-3.22 (m, 1H), 3.02 (dd, J=14.2, 9.2 Hz, 1H), 2.80 (dd, J=14.1, 7.1 Hz, 1H), 2.16 (s, 6H), 1.79-1.56 (m, 4H). MS: EI-MS: m/z 717.5 [M+1].

Example 55: Synthesis of (R)-N-((S)-1-(((S)-1-(3-(adamantan-1-ylmethyl)-1,2,4-oxadiazol-5-yl)-2-(1H-imidazol-4 yl)ethyl)amino)-3-(4-hydroxy-2,6-dim ethylphenyl)-1-oxopropan-2-yl)-2-amino-5-(2-amino-1H-imidazol-1-yl)pentanamide (D-(δ(2-amino-1H-imidazol-1-yl)-Nva-DMT-NH((S)-1-(3-(adamantan-1-yl)methyl-1,2,4-oxadiazol-5-yl)-2-(1H-imidazol-4-yl)eth-1-yl), 7y)

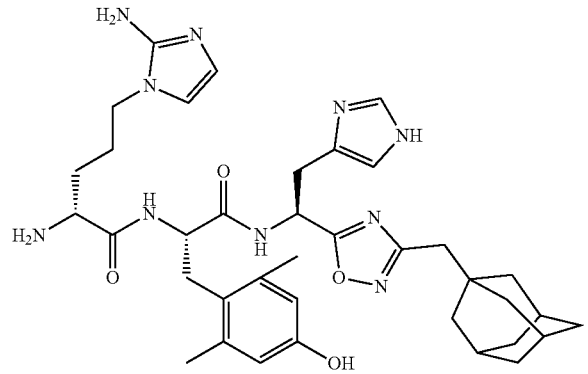

Compound 7y

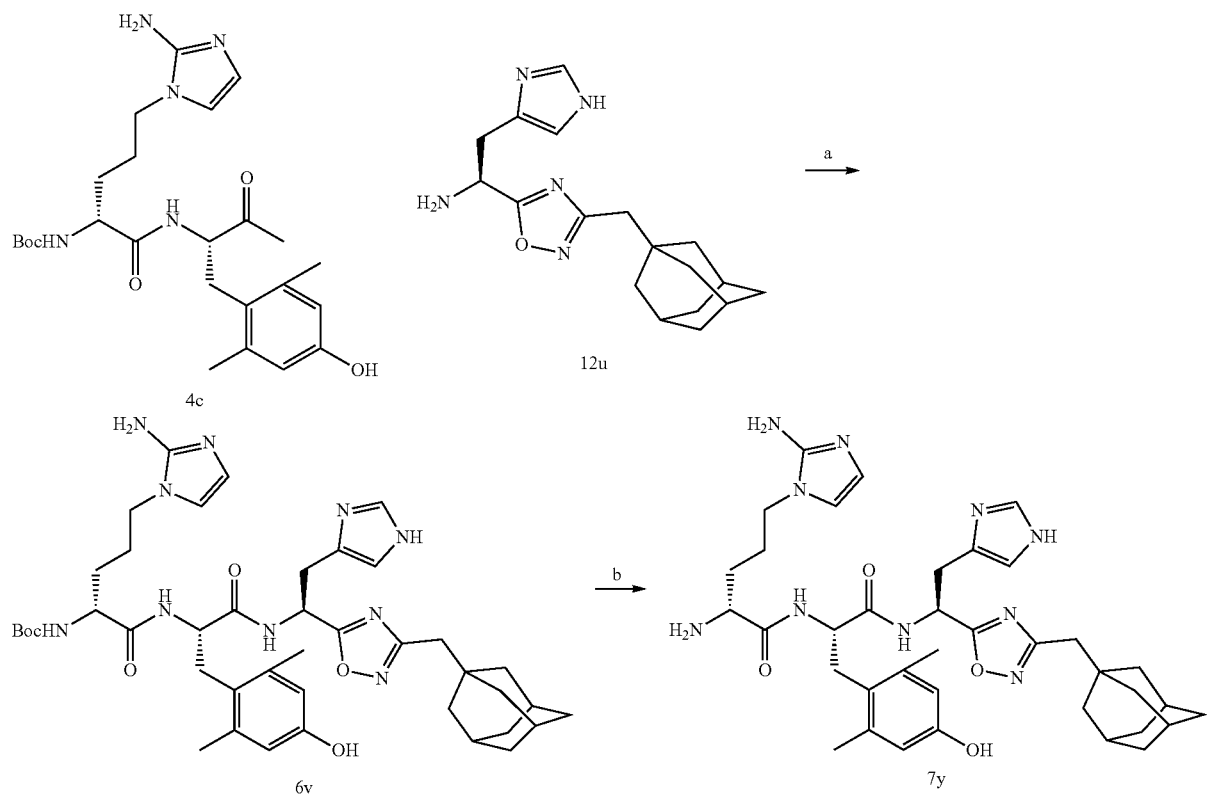

Scheme 56

1) Step a: Synthesis of tert-butyl ((R)-1-(((S)-1-(((S)-1-(3-(adamantan-1-ylmethyl)-1,2,4-oxadiazol-5-yl)-2-(1H-imidazol-4-yl)ethyl)amino)-3-(4-hydroxy-2,6-dimethylphenyl)-1-oxopropan-2-yl)amino)-5-(2-amino-1H-imidazol-1-yl)-1-oxopentan-2-yl)carbamate (6v)

The same procedure as described in Scheme 36 by using 12u (795 mg, 2.18 mmol) and 4c (1.0 g, 1.82 mmol) to give 6v (1.1 g, 71%) as a white foam.

¹H NMR (300 MHz, CD₃OD) δ: 7.88 (s, 1H), 6.92 (s, 1H), 6.84 (s, 1H), 6.81 (s, 1H), 6.36 (s, 2H), 5.48 (t, J=7.4 Hz, 1H), 4.65 (t, J=7.6 Hz, 1H), 4.01 (t, J=7.3 Hz, 1H), 3.88-3.66 (m, 2H), 3.10 (dd, J=14.2, 7.0 Hz, 1H), 2.85 (dd, J=14.3, 8.2 Hz, 1H), 2.45 (s, 2H), 2.22 (s, 6H), 1.94 (s, 3H), 1.79-1.48 (m, 15H), 1.43 (s, 9H).

2) Step b: Synthesis of (R)-N-((S)-1-(((S)-1-(3-(adamantan-1-ylmethyl)-1,2,4-oxadiazol-5-yl)-2-(1H-imidazol-4-yl)

ethyl)amino)-3-(4-hydroxy-2,6-dimethylphenyl)-1-oxopropan-2-yl)-2-amino-5-(2-amino-1H-imidazol-1-yl)pentanamide (7y)

The same procedure as described in Scheme 36 by using 6u (1.1 g, 1.28 mmol) to give 7y (305 mg, 31%, HPLC 98.4% (210 nm)).

$^1$H NMR (400 MHz, CD$_3$OD) δ: 8.86 (d, J=1.3 Hz, 1H), 7.42 (s, 1H), 6.88 (dd, J=5.4, 2.5 Hz, 2H), 6.38 (s, 2H), 5.55 (dd, J=8.7, 5.9 Hz, 1H), 4.62 (t, J=8.1 Hz, 1H), 4.03 (t, J=6.0 Hz, 1H), 3.97-3.79 (m, 2H), 3.43 (qd, J=15.4, 7.2 Hz, 2H), 3.11 (dd, J=14.2, 8.7 Hz, 1H), 2.88 (dd, J=14.2, 7.5 Hz, 1H), 2.49 (s, 2H), 2.23 (s, 6H), 1.95 (s, 3H), 1.87-1.53 (m, 16H).
MS: EI-MS: m/z 699.6 [M+1].

Example 56: Synthesis of (R)-N-((S)-1-(((S)-1-(3-(adamantan-1-ylmethyl)-1,2,4-oxadiazol-5-yl)-2-(1-methyl-1H-imidazol-4-yl)ethyl)amino)-3-(4-hydroxy-2,6-dimethylphenyl)-1-oxopropan-2-yl)-2-amino-5-(2-amino-1H-imidazol-1-yl)pentanamide (D-(δ(2-amino-1H-imidazol-1-yl)-Nva-DMT-NH((S)-1-(3-(adamantan-1-yl)methyl-1,2,4-oxadiazol-5-yl)-2-(l-methyl-1H-imidazol-4-yl)eth-1-yl), 7z)

Compound 7z

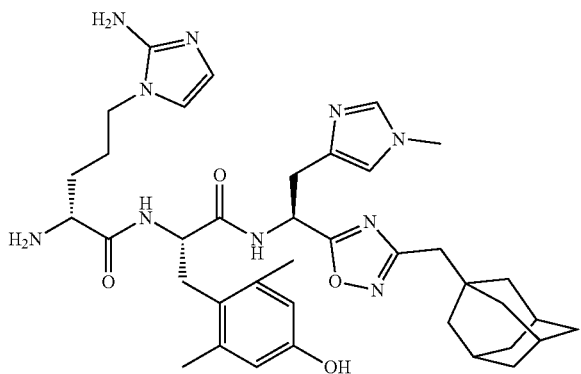

Scheme 57

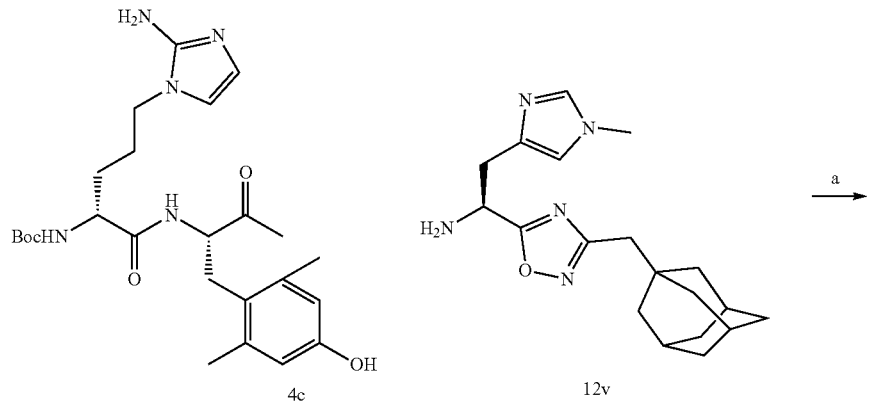

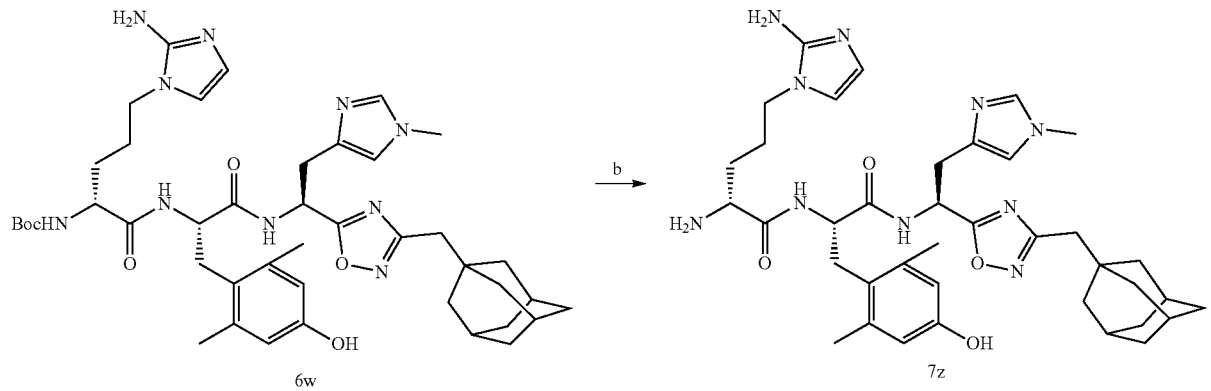

1) Step a: Synthesis of tert-butyl ((R)-1-(((S)-1-(((S)-1-(3-(adamantan-1-ylmethyl)-1,2,4-oxadiazol-5-yl)-2-(1-methyl-1H-imidazol-4-yl)ethyl)amino)-3-(4-hydroxy-2,6-dimethylphenyl)-1-oxopropan-2-yl)amino)-5-(2-amino-1H-imidazol-1-yl)-1-oxopentan-2-yl)carbamate (6w)
The same procedure as described in Scheme 36 by using 12v (446 mg, 1.18 mmol) and 4c (649 mg, 1.18 mmol) to give 6w (0.4 g) in 39% yield.

$^1$H NMR (300 MHz, Methanol-d$_4$): δ=7.49 (s, 1H), 6.86-6.75 (m, 3H), 6.36 (s, 2H), 5.45-5.36 (m, 1H), 4.73-4.62 (m, 1H), 4.64-4.52 (m, 2H), 4.04-3.96 (m, 1H), 3.83-3.71 (m, 2H), 3.66-3.55 (m, 3H), 2.90-2.77 (m, 2H), 2.45 (s, 2H), 2.22 (s, 6H), 1.98-1.89 (m, 3H), 1.79-1.28 ppm (m, 25H).

2) Step b: Synthesis of (R)-N-((S)-1-(((S)-1-(3-(adamantan-1-ylmethyl)-1,2,4-oxadiazol-5-yl)-2-(1-methyl-1H-imidazol-4-yl)ethyl)amino)-3-(4-hydroxy-2,6-dimethylphenyl)-1-oxopropan-2-yl)-2-amino-5-(2-amino-1H-imidazol-1-yl)pentanamide (7z)

The same procedure as described in Scheme 36 by using 6v (400 mg, 0.458 mmol) to give 7z (75 mg) in 22% yield.

$^1$H NMR (400 MHz, Methanol-d$_4$) δ8.82-8.81 (m, 1H), 7.38-7.36 (m, 1H), 6.90-6.86 (m, 2H), 6.37 (s, 2H), 5.52-5.46 (m, 1H), 4.63-4.57 (m, 1H), 4.03-3.95 (m, 1H), 3.93-3.80 (m, 5H), 3.45-3.33 (m, 2H), 3.16-3.08 (m, 1H), 2.91-2.83 (m, 1H), 2.55-2.46 (m, 2H), 2.23 (s, 6H), 1.98-1.91 (m, 3H), 1.86-1.54 ppm (m, 16H). MS: EI-MS: m/z 713.5 [M+1].

Example 57: Synthesis of (R)-2-amino-N-((S)-1-(((S)-1-(3-benzyl-1,2,4-oxadiazol-5-yl)-2-(1H-indol-3-yl)ethyl)amino)-3-(4-hydroxy-2,6-dimethylphenyl)-1-oxopropan-2-yl)-5-guanidinopentanamide (D-Arg-DMT-NH((S)-1-(3-benzyl-1,2,4-oxadiazol-5-yl)-2-(1H-indol-3 yl)eth-1-yl), 7aa)

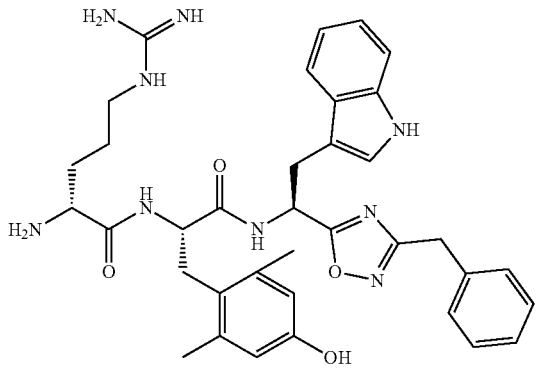

Compound 7aa

Scheme 58

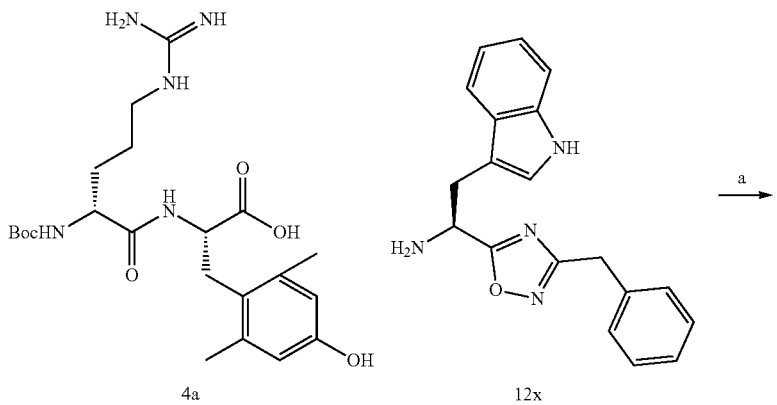

4a      12x 153 154

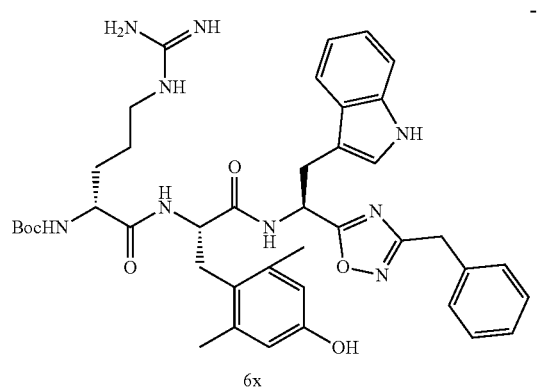

6x

→ b

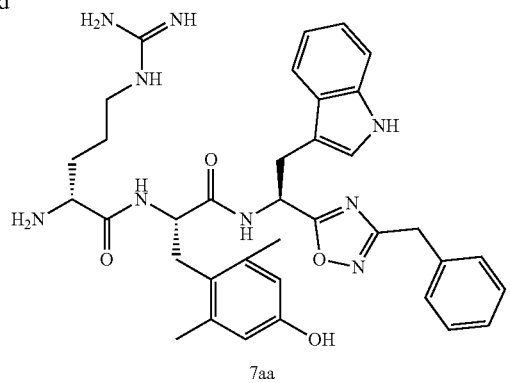

7aa

-continued

1) Step a: Synthesis of tert-butyl ((R)-1-(((S)-1-(((S)-1-(3-benzyl-1,2,4-oxadiazol-5-yl)-2-(1H-indol-3-yl)ethyl)amino)-3-(4-hydroxy-2,6-dimethylphenyl)-1-oxopropan-2-yl)amino)-5-guanidino-1-oxopentan-2-yl)carbamate (6x)

The same procedure as described in Scheme 36 by using 12x (64 mg, 0.20 mmol) and 4c (100 mg, 0.20 mmol) to give 6x (144 mg, 87%) as a yellowish foam.

$^1$H NMR (300 MHz, CD$_3$OD) δ: 7.40 (d, J=7.9 Hz, 1H), 7.32-7.13 (m, 7H), 7.06 (t, J=7.6 Hz, 1H), 6.94 (t, J=7.5 Hz, 1H), 6.36 (s, 2H), 5.44 (t, J=7.5 Hz, 1H), 4.64 (t, J=7.9 Hz, 1H), 4.06-3.90 (m, 3H), 3.13-2.93 (m, 3H), 2.80 (dd, J=14.2, 7.7 Hz, 1H), 2.15 (s, 6H), 1.71-1.31 (m, 4H), 1.42 (s, 9H).

2) Step b: Synthesis of (R)-2-amino-N-((S)-1-(((S)-1-(3-benzyl-1,2,4-oxadiazol-5-yl)-2-(1H-indol-3-yl)ethyl)amino)-3-(4-hydroxy-2,6-dimethylphenyl)-1-oxopropan-2-yl)-5-guanidinopentanamide (7aa)

The same procedure as described in Scheme 36 by using 6x (144 mg, 0.174 mmol) to give 7aa (82 mg, 53%) with HPLC purity—99.3%.

$^1$H NMR (300 MHz, CD$_3$OD) δ: 7.40 (d, J=7.9 Hz, 1H), 7.33-7.13 (m, 6H), 7.07 (t, J=7.1 Hz, 1H), 6.95 (t, J=7.1 Hz, 1H), 6.99-6.91 (m, 1H), 6.87 (s, 1H), 6.36 (s, 2H), 5.45 (dd, J=8.2, 6.8 Hz, 1H), 4.71 (dd, J=8.7, 7.6 Hz, 1H), 4.08-3.95 (m, 2H), 3.90 (t, J=6.2 Hz, 1H), 3.40-3.33 (m, 1H), 3.29-3.22 (m, 1H), 3.15 (t, J=6.9 Hz, 2H), 2.92 (ddd, J=21.5, 14.1, 8.2 Hz, 2H), 2.17 (s, 6H), 1.88-1.62 (m, 2H), 1.58-1.31 (m, 2H). MS: EI-MS: m/z 666.50 [M+1].

Example 58: Synthesis of (R)-N-((S)-1-(((S)-1-(3-([1,1'-biphenyl]-4 ylmethyl)-1,2,4-oxadiazol-5-yl)-2-(1H-indol-3-yl)ethyl)amino)-3-(4-hydroxy-2,6-dimethylphenyl)-1-oxopropan-2-yl)-2-amino-5-(2-amino-1H-imidazol-1-yl)pentanamide (D-(δ(2-amino-1H-imidazol-1-yl)-Nva-DMT-NH((S)-1-(3-([1,1'-biphenyl]-4-yl)methyl-1,2,4-oxadiazol-5-yl)-2-(1H-indol-3-yl)eth-1-yl), 7ab)

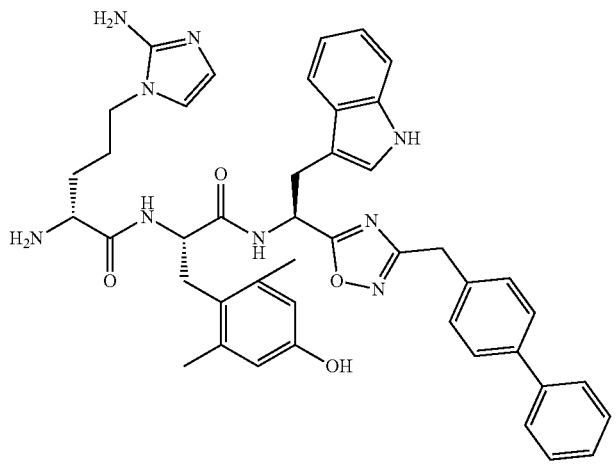

Compound 7ab

-continued
Scheme 59

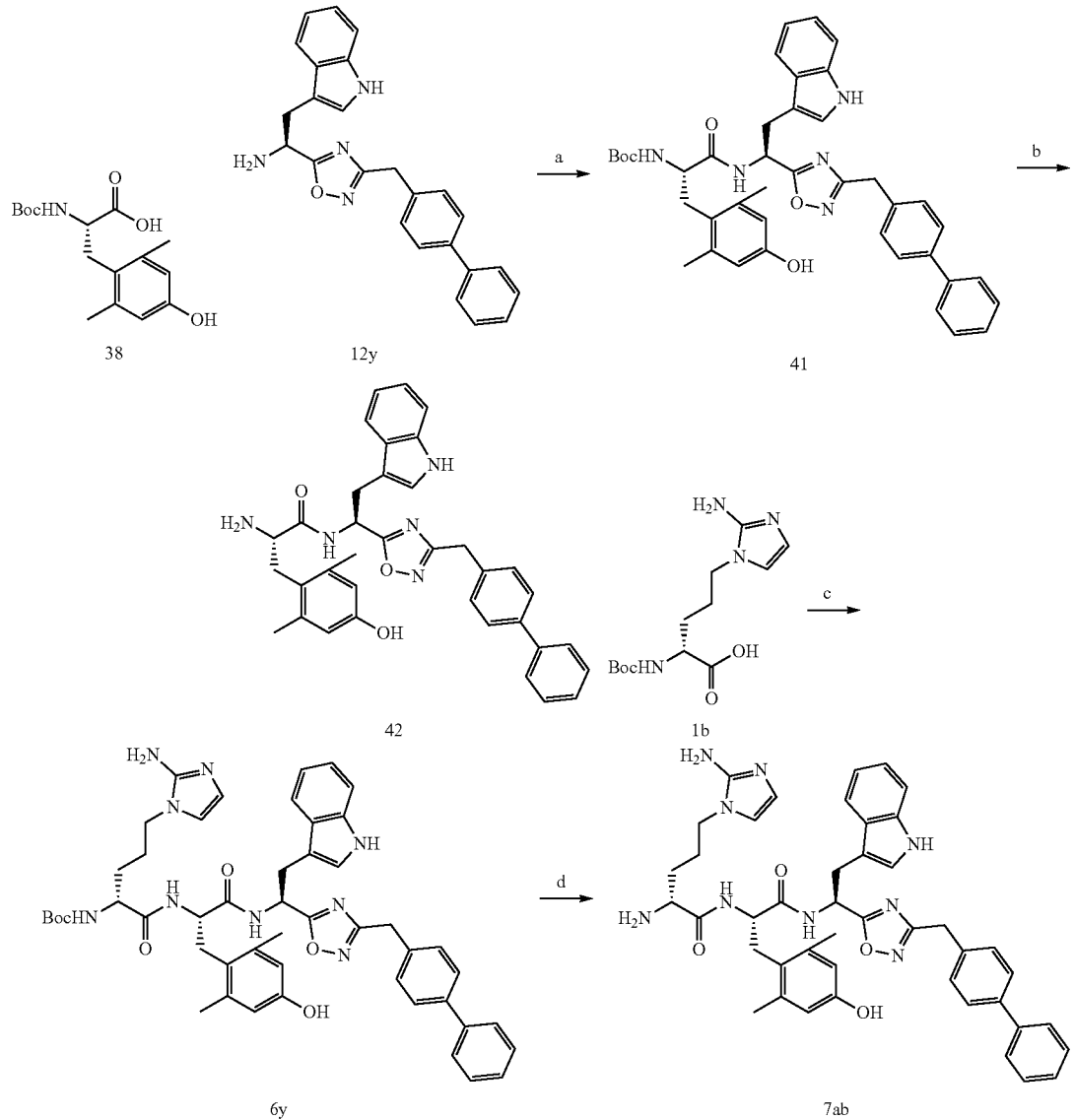

1) Step a: Synthesis of tert-butyl ((S)-1-(((S)-1-(3-([1,1'-biphenyl]-4-ylmethyl)-1,2,4-oxadiazol-5-yl)-2-(1H-indol-3-yl)ethyl)amino)-3-(4-hydroxy-2,6-dimethylphenyl)-1-oxopropan-2-yl)carbamate (41)

The same procedure as described in Scheme 55 by using 12y (0.5 g, 1.16 mmol) and 38 (0.395 g, 1.276 mmol) to give 41 (0.584 g) as brown solid.

$^1$H NMR (400 MHz, Methanol-$d_4$) δ7.56 (m, 2H), 7.53-7.50 (m, 2H), 7.40 (q, J=7.7 Hz, 3H), 7.34-7.28 (m, 2H), 7.22 (m, 2H), 7.05 (t, J=7.6 Hz, 1H), 6.96-6.92 (m, 2H), 6.34 (s, 2H), 5.47 (t, J=7.3 Hz, 1H), 4.22 (t, J=7.7 Hz, 1H), 4.04 (s, 2H), 3.35 (s, 2H), 2.94 (dd, J=14.1, 8.6 Hz, 1H), 2.74 (dd, J=14.2, 7.2 Hz, 1H), 2.14 (s, 6H), 1.38 (s, 9H).

2) Step b: Synthesis of (S)-N-((S)-1-(3-([1,1'-biphenyl]-4-ylmethyl)-1,2,4-oxadiazol-5-yl)-2-(1H-indol-3-yl)ethyl)-2-amino-3-(4-hydroxy-2,6-dimethylphenyl)propanamide (42)

The same procedure as described in Scheme 55 by using 41 (0.2 g, 0.292 mmol) to give 42 which was used in next step without futher purification.

$^1$H NMR (400 MHz, Methanol-$d_4$) δ7.59-7.51 (m, 4H), 7.45-7.28 (m, 5H), 7.22-7.19 (m, 2H), 7.06 (ddd, J=8.2, 7.1, 1.1 Hz, 1H), 6.94 (ddd, J=7.9, 7.2, 0.9 Hz, 1H), 6.83 (s, 1H), 6.34 (s, 2H), 5.56-5.50 (m, 1H), 4.05 (d, J=3.4 Hz, 2H), 3.88 (dd, J=11.1, 5.1 Hz, 1H), 3.28-3.23 (m, 2H), 3.14 (dd, J=13.9, 11.1 Hz, 1H), 2.96 (dd, J=14.0, 5.2 Hz, 1H), 2.10 (s, 6H).

3) Step c: Synthesis of tert-butyl ((R)-1-(((S)-1-(((S)-1-(3-([1,1'-biphenyl]-4-ylmethyl)-1,2,4-oxadiazol-5-yl)-2-(1H-indol-3-yl)ethyl)amino)-3-(4-hydroxy-2,6-dimethylphenyl)-1-oxopropan-2-yl)amino)-5-(2-amino-1H-imidazol-1-yl)-1-oxopentan-2-yl)carbamate (6y)

The same procedure as described in Scheme 55 by using 42 (0.32 g, 0.368 mmol) and 1b (0.145 g, 0.405 mmol) to give 6y, which was flushed thoroughly reverse-phase flash column and used in next step without futher purification 4) Step d: Synthesis of (S)-N-((S)-1-(3-([1,1'-biphenyl]-4-ylmethyl)-1,2,4-oxadiazol-5-yl)-2-(1H-indol-3-yl)ethyl)-2-amino-3-(4-hydroxy-2,6-dimethylphenyl)propanamide (7ab)

The same procedure as described in Scheme 36 by using 6y (0.1 g, 0.108 mmol) to give 7ab (35 mg) as white solid. (HPLC purity is 99.0% at 210 nm)

$^1$H NMR (400 MHz, Methanol-$d_4$) δ7.54-7.49 (m, 4H), 7.43-7.38 (m, 3H), 7.34-7.29 (m, 2H), 7.26-7.22 (m, 2H), 7.09-7.05 (m, 1H), 6.98-6.94 (m, 1H), 6.91 (s, 1H), 6.87 (d, J=2.4 Hz, 1H), 6.80 (d, J=2.4 Hz, 1H), 6.35 (s, 2H), 5.46 (dd, J=8.4, 6.7 Hz, 1H), 4.72 (t, J=8.2 Hz, 1H), 4.06 (s, 2H), 3.92-3.77 (m, 3H), 3.37 (dd, J=14.4, 8.5 Hz, 1H), 3.30-3.26 (m, 1H), 2.99 (dd, J=14.2, 8.8 Hz, 1H), 2.81 (dd, J=14.1, 7.7 Hz, 1H), 2.16 (s, 6H), 1.78-1.54 (m, 4H). MS: EI-MS: m/z 766.5 [M+1].

Example 59: Synthesis of (R)-N-((S)-1-(((S)-1-(3-(adamantan-1-ylmethyl)-1,2,4-oxadiazol-5-yl)-2-(1H-indol-3 yl)ethyl)amino)-3-(4-hydroxy-2,6-dimethylphenyl)-1-oxopropan-2-yl)-2-amino-5-(2-amino-1H-imidazol-1-yl)pentanamide (D-(δ(2-amino-1H-imidazol-1-yl)-Nva-DMT-NH((S)-1-(3-(adamantan-1-yl)methyl-1,2,4-oxadiazol-5-yl)-2-(1H-indol-3-yl)eth-1-yl), 7ac)

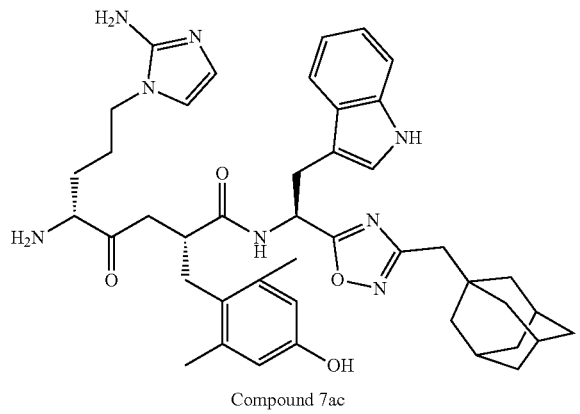

Compound 7ac

Scheme 60

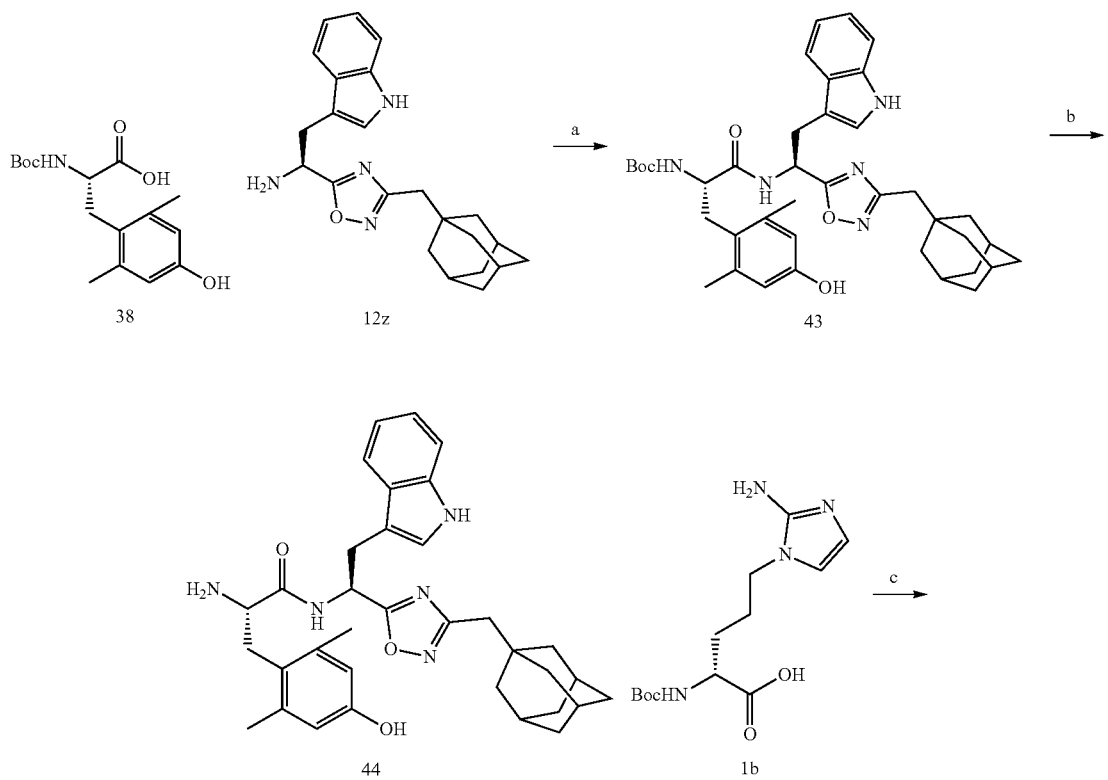

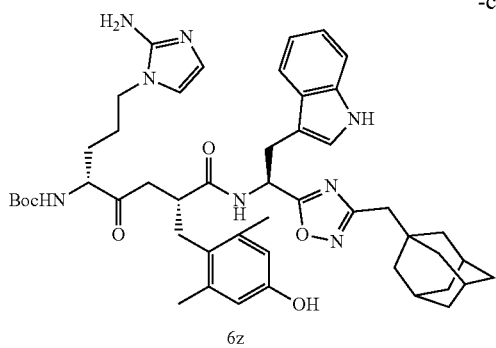

6z

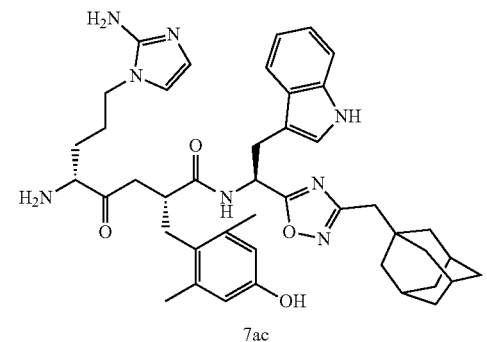

7ac

1) Step a: Synthesis of tert-butyl ((S)-1-(((S)-1-(3-(adamantan-1-ylmethyl)-1,2,4-oxadiazol-5-yl)-2-(1H-indol-3-yl)ethyl)amino)-3-(4-hydroxy-2,6-dimethylphenyl)-1-oxopropan-2-yl)carbamate (43)
The same procedure as described in Scheme 55 by using 12z (0.376 g, 1.0 mmol) and 38 (0.39 g, 1 mmol) to give 43 (0.51 g) and used for next step.

2) Step b: Synthesis of (S)-N-((S)-1-(3-(adamantan-1-ylmethyl)-1,2,4-oxadiazol-5-yl)-2-(1H-indol-3-yl)ethyl)-2-amino-3-(4-hydroxy-2,6-dimethylphenyl)propanamide (44)
The same procedure as described in Scheme 55 by using 43 (0.51 g, 0.76 mmol) to give 44 (0.75 g) which was used for next step without further purification.

3) Step c: Synthesis of tert-butyl ((R)-1-(((S)-1-(((S)-1-(3-(adamantan-1-ylmethyl)-1,2,4-oxadiazol-5-yl)-2-(1H-indol-3-yl)ethyl)amino)-3-(4-hydroxy-2,6-dimethylphenyl)-1-oxopropan-2-yl)amino)-5-(2-amino-1H-imidazol-1-yl)-1-oxopentan-2-yl)carbamate (6z)
The same procedure as described in Scheme 55 by using 44 (0.27 g, 0.4 mmol) and 1b (0.18 g, 0.5 mmol) to give 6z (128 mg) which was flushed thorough reverse-phase flash column and used in next step without futher purification 4) Step d: Synthesis of (R)-N-((S)-1-(((S)-1-(3-(adamantan-1-ylmethyl)-1,2,4-oxadiazol-5-yl)-2-(1H-indol-3-yl)ethyl) amino)-3-(4-hydroxy-2,6-dimethylphenyl)-1-oxopropan-2-yl)-2-amino-5-(2-amino-1H-imidazol-1-yl)pentanamide (7ac)
The same procedure as described in Scheme 36 by using 6z (0.120 g, 0.14 mmol) to give 7ac (24 mg) as white solid. (HPLC purity is 97.0% at 210 nm).
$^1$H NMR (400 MHz, Methanol-$d_4$) δ7.47 (d, J=8.0 Hz, 1H), 7.28 (d, J=8.0 Hz, 1H), 7.05 (dd, J=14.4, 7.2 Hz, 1H), 6.99 (dd, J=16.4, 7.2 Hz, 1H), 6.87 (m, 1H), 6.81 (d, J=2.4 Hz, 1H), 6.33 (s, 2H), 5.51 (dd, J=8.8, 6.4 Hz, 1H), 4.76 (dd, J=16.4, 8.8 Hz, 1H), 3.93-3.90 (m, 1H), 3.85-3.79 (m, 1H), 3.42-3.33 (m, 1H), 3.06-3.01 (m, 1H), 2.4 (s, 2H), 1.95 (s, 2H), 1.88-1.28 (multiple preaks, 22H). MS: EI-MS: m/z 748.6 [M+1].

Example 60: Synthesis of (R)-N-((S)-1-(((S)-1-(3-(adamantan-1-ylmethyl)-1,2,4-oxadiazol-5-yl)-2-(1-methyl-1H-indol-3 yl)ethyl)amino)-3-(4-hydroxy-2,6-dimethylphenyl)-1-oxopropan-2-yl)-2-amino-5-(2-amino-1H-imidazol-1-yl)pentanamide (D-(δ(2-amino-1H-imidazol-1-yl)-Nva-DMT-NH((S)-1-(3-(adamantan-1-yl)methyl-1,2,4-oxadiazol-5-yl)-2-(1-methyl-1H-indol-3-yl)eth-1-yl), 7ad)

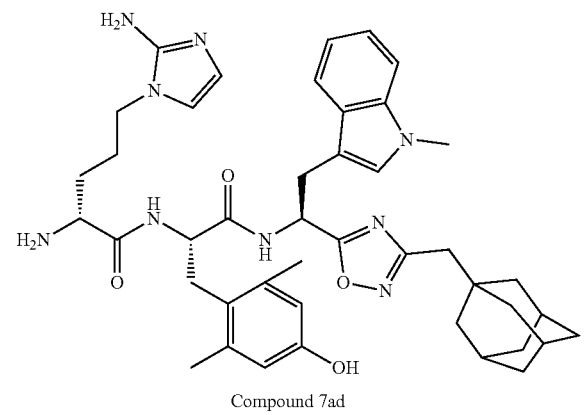

Compound 7ad

-continued
Scheme 61

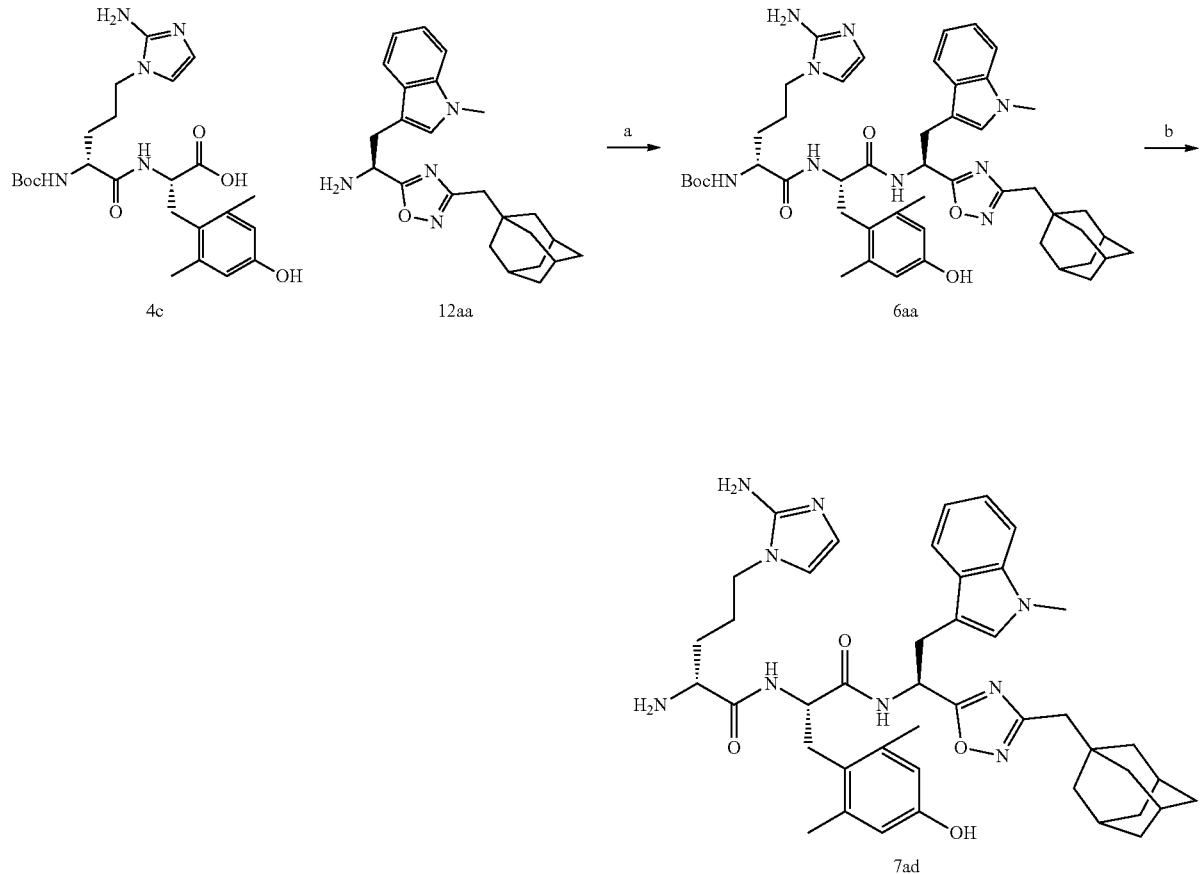

1) Step a: Synthesis of tert-butyl ((R)-1-(((S)-1-(((S)-1-(3-(adamantan-1-ylmethyl)-1,2,4-oxadiazol-5-yl)-2-(1-methyl-1H-indol-3-yl)ethyl)amino)-3-(4-hydroxy-2,6-dimethylphenyl)-1-oxopropan-2-yl)amino)-5-(2-amino-1H-imidazol-1-yl)-1-oxopentan-2-yl)carbamate (6aa)

The same procedure as described in Scheme 36 by using 12aa (188 mg; 0.44 mmol) and 4c (181 mg; 0.37 mmol) to give 6aa (115 mg, 36%) of white foam.

$^1$H NMR (300 MHz, Methanol-$d_4$) δ7.36 (d, J=7.9 Hz, 1H), 7.17 (d, J=8.2 Hz, 1H), 7.02 (t, J=7.5 Hz, 1H), 6.90 (t, J=7.2 Hz, 1H), 6.82 (bs, 1H), 6.54 (m, 2H), 6.24 (s, 2H), 5.37 (t, J=7.5 Hz, 1H), 4.56 (t, J=7.7 Hz, 1H), 3.90 (bs, 1H), 3.68-3.51 (m, 5H), 3.40-3.21 (m, 2H), 2.96 (dd, J=13.5, 8.2 Hz, 1H), 2.73 (dd, J=14.2, 7.8 Hz, 1H), 2.29 (s, 2H), 2.08 (s, 6H), 1.78 (bs, 3H), 1.67-1.39 (m, 10H), 1.40-1.24 (m, 15H).

2) Step b: Synthesis of (R)-N-((S)-1-(((S)-1-(3-(adamantan-1-ylmethyl)-1,2,4-oxadiazol-5-yl)-2-(1-methyl-1H-indol-3-yl)ethyl)amino)-3-(4-hydroxy-2,6-dimethylphenyl)-1-oxopropan-2-yl)-2-amino-5-(2-amino-1H-imidazol-1-yl)pentanamide (7ad)

The same procedure as described in Scheme 36 by using 6aa (115 mg; 0.13 mmol) to give 7ad (35 mg, 31%) as a white solid.

$^1$H NMR (400 MHz, Methanol-$d_4$) δ7.45 (d, J=7.9 Hz, 1H), 7.26 (d, J=8.2 Hz, 1H), 7.11 (t, J=7.6 Hz, 1H), 6.99 (t, J=7.5 Hz, 1H), 6.90 (s, 1H), 6.87-6.79 (m, 2H), 6.32 (s, 2H), 5.46 (dd, J=8.7, 6.4 Hz, 1H), 4.76 (t, J=8.0 Hz, 1H), 3.94 (t, J=6.1 Hz, 1H), 3.84 (m, 2H), 3.67 (s, 3H), 3.37 (dd, J=14.4, 8.7 Hz, 1H), 3.31 (dd, 1H), 3.03 (dd, J=14.0, 8.7 Hz, 1H), 2.85 (dd, J=14.0, 7.6 Hz, 1H), 2.38 (m, 2H), 2.17 (s, 6H), 1.86 (bs, 3H), 1.81-1.49 (m, 10H), 1.42 (bs, 6H). MS: EI-MS: m/z 762.7 [M+1].

Example 61: Synthesis of (R)-N-((S)-1-(((S)-1-(3-(adamantan-1 ylmethyl)-1,2,4-oxadiazol-5-yl)-2-(5 fluoro-1H-indol-3 yl)ethyl)amino)-3-(4-hydroxy-2, 6-dimethylphenyl)-1-oxopropan-2-yl)-2-amino-5-(2-amino-1H-imidazol-1-yl)pentanamide (D-(δ(2-amino-1H-imidazol-1-yl)-Nva-DMT-NH((S)-1-(3-(adamantan-1-yl)methyl-1,2,4-oxadiazol-5-yl)-2-(5-fluoro-1H-indol-3-yl)eth-1-yl), 7ae)

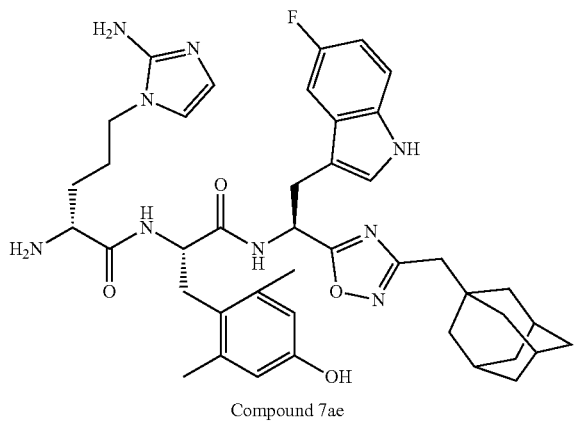
Compound 7ae

Scheme 62

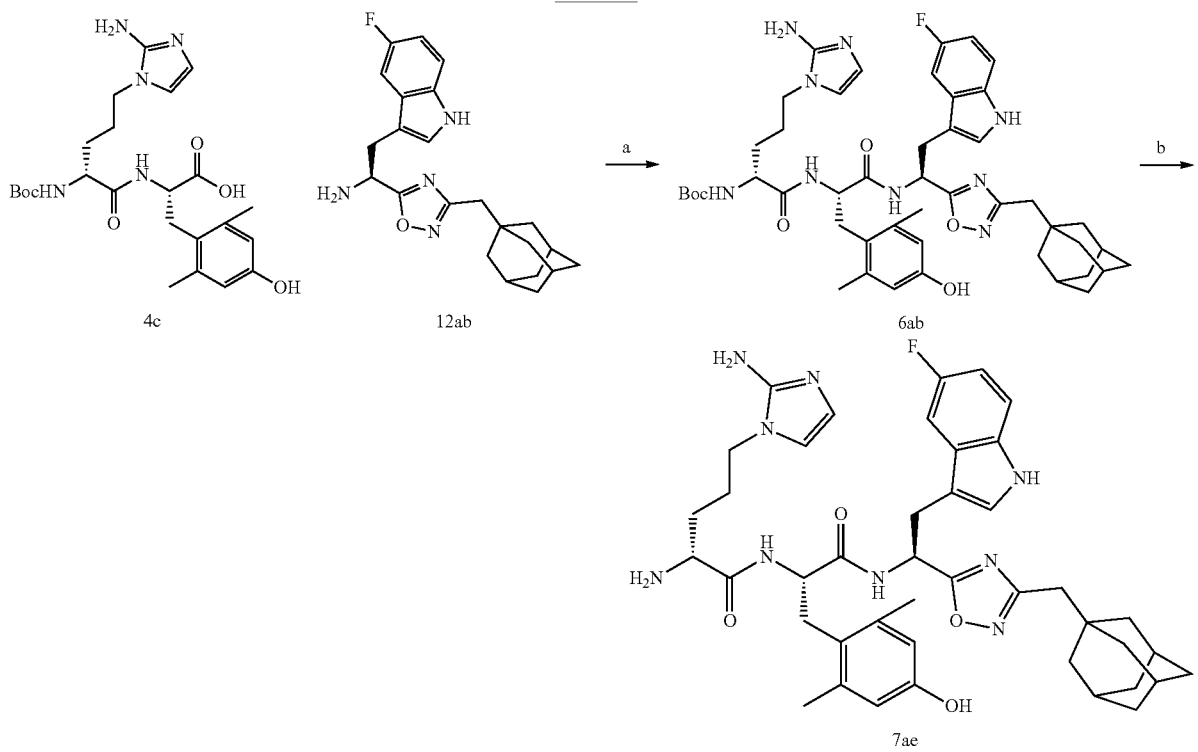

1) Step a: Synthesis of tert-butyl ((R)-1-(((S)-1-(((S)-1-(3-(adamantan-1-ylmethyl)-1,2,4-oxadiazol-5-yl)-2-(5-fluoro-1H-indol-3-yl)ethyl)amino)-3-(4-hydroxy-2,6-dimethylphenyl)-1-oxopropan-2-yl)amino)-5-(2-amino-1H-imidazol-1-yl)-1-oxopentan-2-yl)carbamate (6ab)

The same procedure as described in Scheme 36 by using 12ab (203 mg; 0.40 mmol) and 4c (188 mg; 0.32 mmol) to give 6ab (164 mg, 53%) of a yellowish foam.

$^1$H NMR (300 MHz, Methanol-$d_4$) δ7.26 (dd, J=8.9, 4.4 Hz, 1H), 7.17 (dt, J=9.9, 2.9 Hz, 1H), 7.07 (s, 1H), 6.91-6.76 (m, 3H), 6.69 (s, 2H), 5.49 (dd, J=8.9, 6.6 Hz, 1H), 4.71 (t, J=7.8 Hz, 1H), 4.04 (m, 1H), 3.94-3.70 (m, 2H), 3.44-3.26 (m, 2H), 3.18 (dd, J=13.8, 8.4 Hz, 1H), 2.96 (dd, J=14.0, 7.2 Hz, 1H), 2.45-2.36 (m, 2H), 2.29 (s, 6H), 1.91 (bs, 3H), 1.78-1.36 (m, 34H).

2) Step b: Synthesis of (R)-N-((S)-1-(((S)-1-(3-(adamantan-1-ylmethyl)-1,2,4-oxadiazol-5-yl)-2-(5-fluoro-1H-indol-3-yl)ethyl)amino)-3-(4-hydroxy-2,6-dimethylphenyl)-1-oxopropan-2-yl)-2-amino-5-(2-amino-1H-imidazol-1-yl)pentanamide (7ae)

The same procedure as described in Scheme 36 by using 6ab (164 mg; 0.17 mmol) to give 7ae (37 mg, 26%) as a yellowish solid.

¹H NMR (400 MHz, Methanol-d₄) δ7.23 (dd, J=8.8, 4.3 Hz, 1H), 7.12 (dd, J=9.8, 2.4 Hz, 1H), 7.04 (s, 1H), 6.88-6.84 (m, 2H), 6.81 (td, J=9.2, 2.4 Hz, 1H), 6.31 (s, 2H), 5.45 (dd, J=9.0, 6.4 Hz, 1H), 4.71 (t, J=8.1 Hz, 1H), 3.95 (t, J=5.9 Hz, 1H), 3.85 (m, 2H), 3.34 (dd, J=14.4, 9.1 Hz, 1H), 3.26 (dd, J=14.4, 6.3 Hz, 1H), 3.02 (dd, J=14.1, 8.7 Hz, 1H), 2.85 (dd, J=14.1, 7.6 Hz, 1H), 2.38 (m, 2H), 2.18 (s, 6H), 1.85 (bs, 3H), 1.81-1.57 (m, 7H), 1.53 (bd, J=11.7 Hz, 3H), 1.40 (bs, 6H). MS: EI-MS: m/z 766.7 [M+1].

Example 62: Synthesis of (R)-N-((S)-1-(((S)-1-(3-([1,1'-biphenyl]-4-ylmethyl)-1,2,4-oxadiazol-5-yl)-2-(1-methyl-1H-indol-3 yl)ethyl)amino)-3-(4-hydroxy-2,6-dimethylphenyl)-1-oxopropan-2-yl)-2-amino-5-(2-amino-1H-imidazol-1-yl)pentanamide (D-(δ(2-amino-1H-imidazol-1-yl)-Nva-DMT-NH((S)-1-(3-([1,1'-biphenyl]-4 yl)methyl-1,2,4-oxadiazol-5-yl)-2-(1-methyl-1H-indol-3-yl)eth-1-yl), 7af)

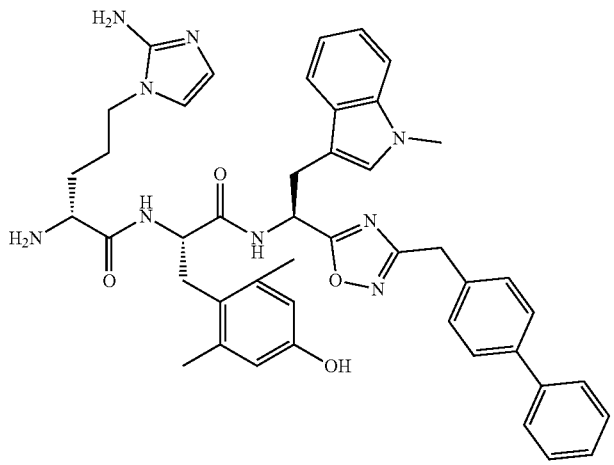

Compound 7af

Scheme 63

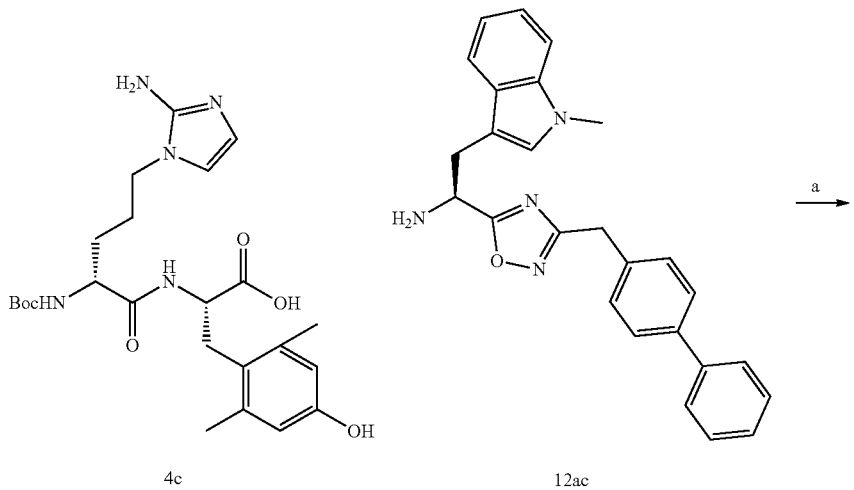

4c      12ac

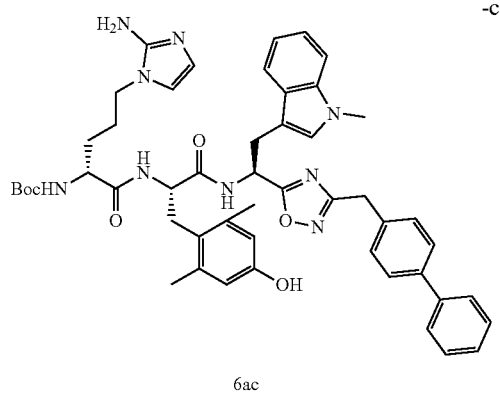

6ac

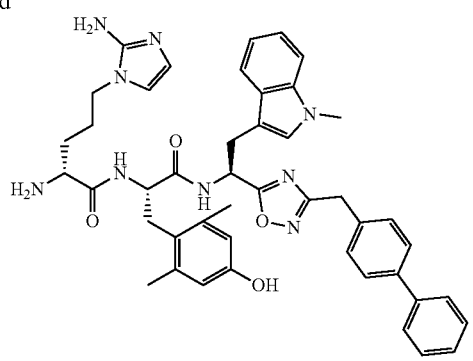

7af

1) Step a: Synthesis of tert-butyl ((R)-1-(((S)-1-(((S)-1-(3-([1,1'-biphenyl]-4-ylmethyl)-1,2,4-oxadiazol-5-yl)-2-(1-methyl-1H-indol-3-yl)ethyl)amino)-3-(4-hydroxy-2,6-dimethylphenyl)-1-oxopropan-2-yl)amino)-5-(2-amino-1H-imidazol-1-yl)-1-oxopentan-2-yl)carbamate (6ac)

The same procedure as described in Scheme 36 by using 12ac (311 mg; 0.60 mmol) and 4c (250 mg; 0.51 mmol) to give 6ac (130 mg, 39%) of white foam.

$^1$H NMR (300 MHz, Methanol-d$_4$) δ7.50-7.38 (multiple peaks, 4H), 7.36-7.08 (multiple peaks, 7H), 7.01 (t, J=7.5 Hz, 1H), 6.86 (t, J=7.4 Hz, 1H), 6.69 (bs, 1H), 6.43 (m, 2H), 6.24 (s, 2H), 5.31 (t, J=7.3 Hz, 1H), 4.52 (t, J=7.7 Hz, 1H), 3.97-3.82 (m, 3H), 3.59 (bs, 2H), 3.50 (s, 3H), 3.33-3.13 (m, 2H), 2.93 (dd, J=14.0, 7.6 Hz, 1H), 2.68 (dd, J=14.0, 7.9 Hz, 1H), 2.04 (s, 6H), 1.65-1.37 (m, 4H), 1.31 (s, 9H).

2) Step b: Synthesis of (R)-N-((S)-1-(((S)-1-(3-([1,1'-biphenyl]-4-ylmethyl)-1,2,4-oxadiazol-5-yl)-2-(1-methyl-1H-indol-3-yl)ethyl)amino)-3-(4-hydroxy-2,6-dimethylphenyl)-1-oxopropan-2-yl)-2-amino-5-(2-amino-1H-imidazol-1-yl)pentanamide (7af)

The same procedure as described in Scheme 36 by using 6ac (130 mg; 0.15 mmol) to give 7af (47 mg, 37%) as a white solid.

$^1$H NMR (400 MHz, Methanol-d$_4$) δ7.53-7.45 (m, 4H), 7.39 (m, 3H), 7.29 (t, J=7.3 Hz, 1H), 7.23 (m, 3H), 7.10 (t, J=7.6 Hz, 1H), 6.95 (t, J=7.5 Hz, 1H), 6.84 (m, 2H), 6.77 (s, 1H), 6.33 (s, 2H), 5.40 (dd, J=8.2, 6.6 Hz, 1H), 4.68 (t, J=8.2 Hz, 1H), 4.03 (m, 2H), 3.94 (t, J=5.9 Hz, 1H), 3.90-3.74 (m, 2H), 3.58 (s, 3H), 3.33 (dd, J=14.4, 8.2 Hz, 1H), 3.25 (dd, 1H), 2.98 (dd, J=14.2, 8.7 Hz, 1H), 2.80 (dd, J=14.2, 7.7 Hz, 1H), 2.14 (s, 6H), 1.83-1.53 (m, 4H). MS: EI-MS: m/z 780.6 [M+1].

Example 63: Synthesis of (R)-N-((S)-1-(((S)-1-(3-(adamantan-1-ylmethyl)-1,2,4-oxadiazol-5-yl)-2-(pyridin-4-yl)ethyl)amino)-3-(4-hydroxy-2,6-dimethylphenyl)-1-oxopropan-2-yl)-2-amino-5-guanidinopentanamide (D-Arg-DMT-NH((S)-1-(3-(adamantan-1-yl)methyl-1,2,4-oxadiazol-5-yl)-2-(pyridin-4 yl)eth-1-yl), 7ag)

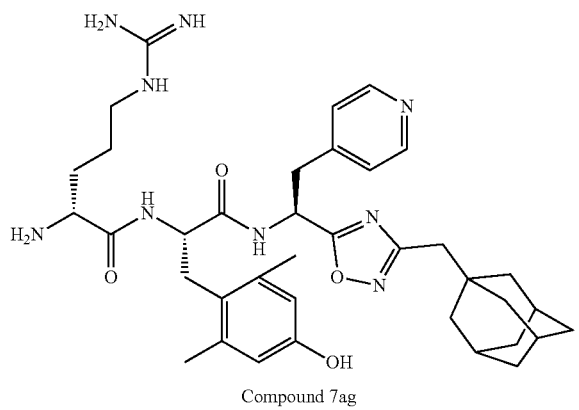

Compound 7ag

-continued

Scheme 64

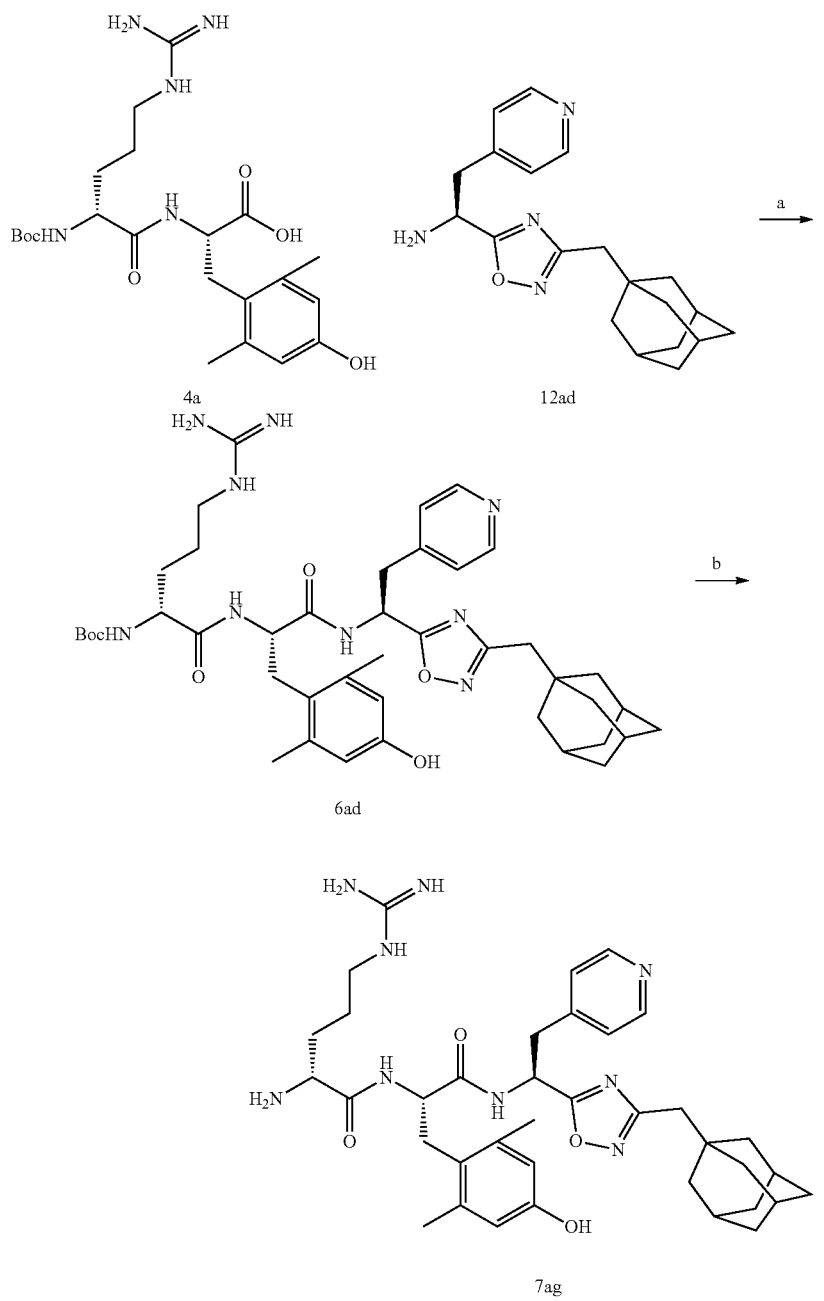

1) Step a: Synthesis of tert-butyl ((R)-1-(((S)-1-(((S)-1-(3-(adamantan-1-ylmethyl)-1,2,4-oxadiazol-5-yl)-2-(pyridin-4-yl)ethyl)amino)-3-(4-hydroxy-2,6-dimethylphenyl)-1-oxopropan-2-yl)amino)-5-guanidino-1-oxopentan-2-yl)carbamate (6ad)

The same procedure as described in Scheme 36 by using 12ad (0.482 g, 0.85 mmol) and 4a (0.356 g, 0.71 mmol) to give 6ad (250 mg, 37%).

$^1$H-NMR (300 MHz, Methanol-d$_4$) δ8.40 (d, J=5.5 Hz, 2H), 7.29 (d, J=5.5 Hz, 2H), 6.35 (s, 2H), 5.53 (t, 1H), 4.58 (t, 1H), 4.02-3.92 (m, 1H), 3.20-3.11 (m, 4H), 2.89-2.79 (m, 1H), 2.46 (s, 2H), 2.20 (s, 4H), 1.95 (s, 8H), 1.78-1.57 (m, 7H), 1.55-1.49 (m, 7H), 1.45 (s, 9H).

2) Step b: Synthesis of (R)-N-((S)-1-(((S)-1-(3-(adamantan-1-ylmethyl)-1,2,4-oxadiazol-5-yl)-2-(pyridin-4-yl)ethyl)amino)-3-(4-hydroxy-2,6-dimethylphenyl)-1-oxopropan-2-yl)-2-amino-5-guanidinopentanamide (7ag)

The same procedure as described in Scheme 36 by using 6ad (120 mg) to give 7ag (55 mg).

$^1$H-NMR (400 MHz, Methanol-d$_4$) δ8.64 (s, 2H), 7.77 (s, 2H), 6.36 (s, 2H), 5.63 (t, J=8.1 Hz, 1H), 4.57 (m, 1H), 3.88 (t, J=6.2 Hz, 1H), 3.58-3.48 (m, 1H), 3.44-3.38 (m, 1H), 3.16 (t, J=7.0 Hz, 2H), 3.11-3.03 (m, 1H), 2.89-2.80 (m, 1H), 2.49 (s, 2H), 2.20 (s, 6H), 1.94 (s, 3H), 1.84-1.67 (m, 5H), 1.66-1.57 (m, 3H), 1.56-1.52 (m, 6H), 1.51-1.38 (m, 2H).
MS: EI-MS: m/z 686.6 [M+1].

Example 64: Synthesis of (R)-2-amino-N-((S)-1-(((S)-5-amino-1-(3-benzyl-1,2,4-oxadiazol-5 yl)pentyl)amino)-3-(4-hydroxy-2,6-dimethylphenyl)-1-oxopropan-2-yl)-4-guanidinobutanamide (D-Agb-DMT-NH((S)-5-amino-1-(3-benzyl-1,2,4-oxadiazol-5-yl)pent-1-yl), 7ah)

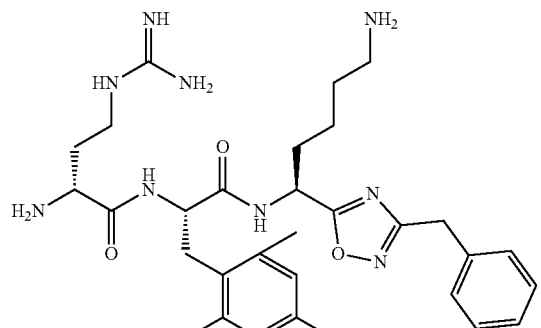

Compound 7ah

Scheme 65

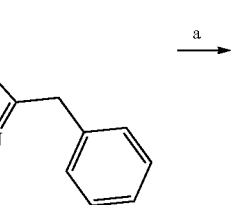

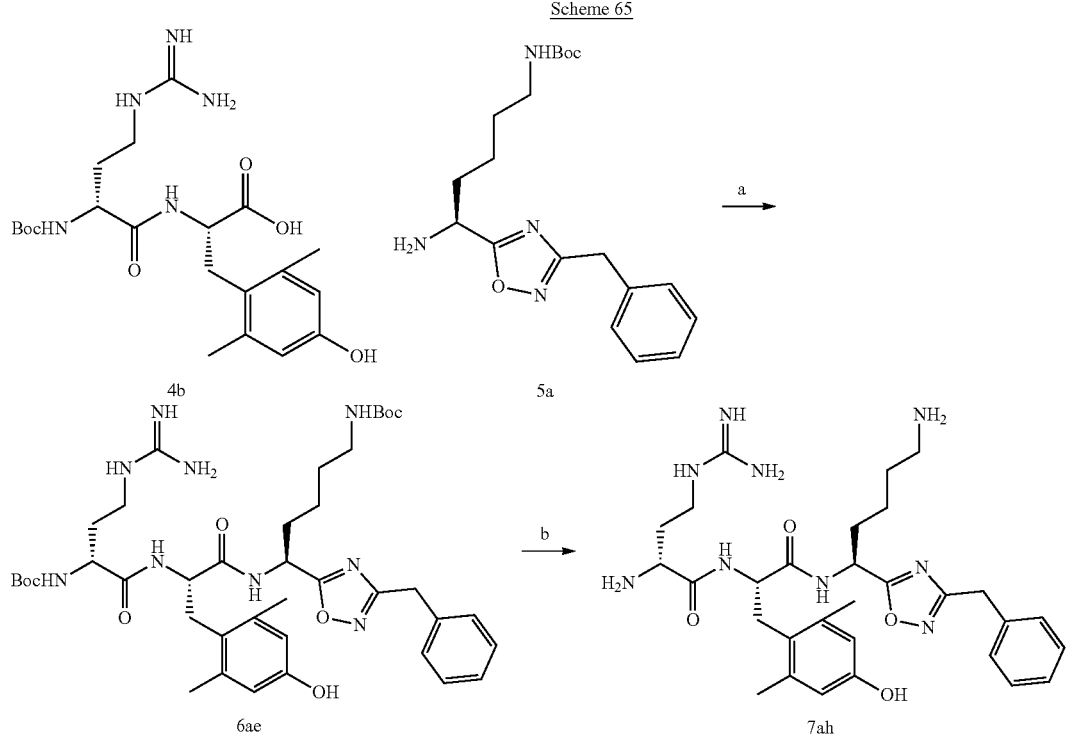

1) Step a: Synthesis of tert-butyl ((5R,8S,11S)-1-amino-11-(3-benzyl-1,2,4-oxadiazol-5-yl)-8-(4-hydroxy-2,6-dimethylbenzyl)-1-imino-19,19-dimethyl-6,9,17-trioxo-18-oxa-2,7,10,16-tetraazaicosan-5-yl)carbamate (6ae)

The same procedure as described in Scheme 36 by using 12ae (360 mg; 1.0 mmol) and 4b (420 mg; 0.93 mmol) to give 6ae (360 mg, 45%) of a white foam.

$^1$H NMR (300 MHz, Methanol-$d_4$) δ 7.39-7.18 (m, 5H), 6.42 (s, 2H), 5.19 (t, J=7.5 Hz, 1H), 4.60 (t, J=7.8 Hz, 1H), 4.09 (multiple peaks, 3H), 3.31-2.97 (multiple peaks, 5H), 2.88 (m, 1H), 2.24 (s, 6H), 2.03-1.85 (multiple peaks, 6H), 1.75 (m, 1H), 3.31-2.97 (multiple peaks, 22H).

2) Step b: Synthesis of (R)-2-amino-N-((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-4-guanidinobutanamide (7ah)

The same procedure as described in Scheme 36 by using 6ae (350 mg; 0.41 mmol) to give 7ah (165 mg, 57%) as a white solid.

$^1$H NMR (400 MHz, Methanol-$d_4$) δ 7.27 (m, 4H), 7.20 (m, 1H), 6.36 (s, 2H), 5.14 (t, J=6.4 Hz, 1H), 4.64 (t, J=8.0 Hz, 1H), 4.10 (m, 1H), 4.04 (m, 2H), 3.25-3.05 (m, 3H), 2.96-2.80 (m, 3H), 2.19 (s, 6H), 2.07-1.80 (m, 4H), 1.71-1.58 (m, 2H), 1.54-1.26 (m, 2H). MS: EI-MS: m/z 594.5 [M+1].

Example 65: Synthesis of (R)-2-amino-N-((S)-1-(((S)-5-amino-1-(3-(cyclohexylmethyl)-1,2,4-oxadiazol-5 yl)pentyl)amino)-3-(4-hydroxy-2,6-dimethylphenyl)-1-oxopropan-2-yl)-5-(2-amino-1H-imidazol-1-yl)pentanamide (D-(&(2-amino-1H-imidazol-1-yl)-Nva-DMT-NH((S)-5-amino-1-(3-(cyclohexylmethyl-1,2,4-oxadiazol-5-yl)pent-1-yl), 7ai)

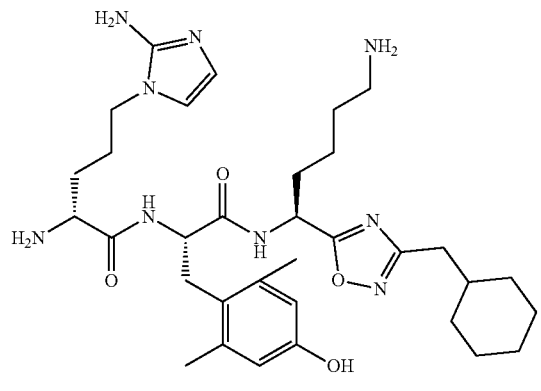
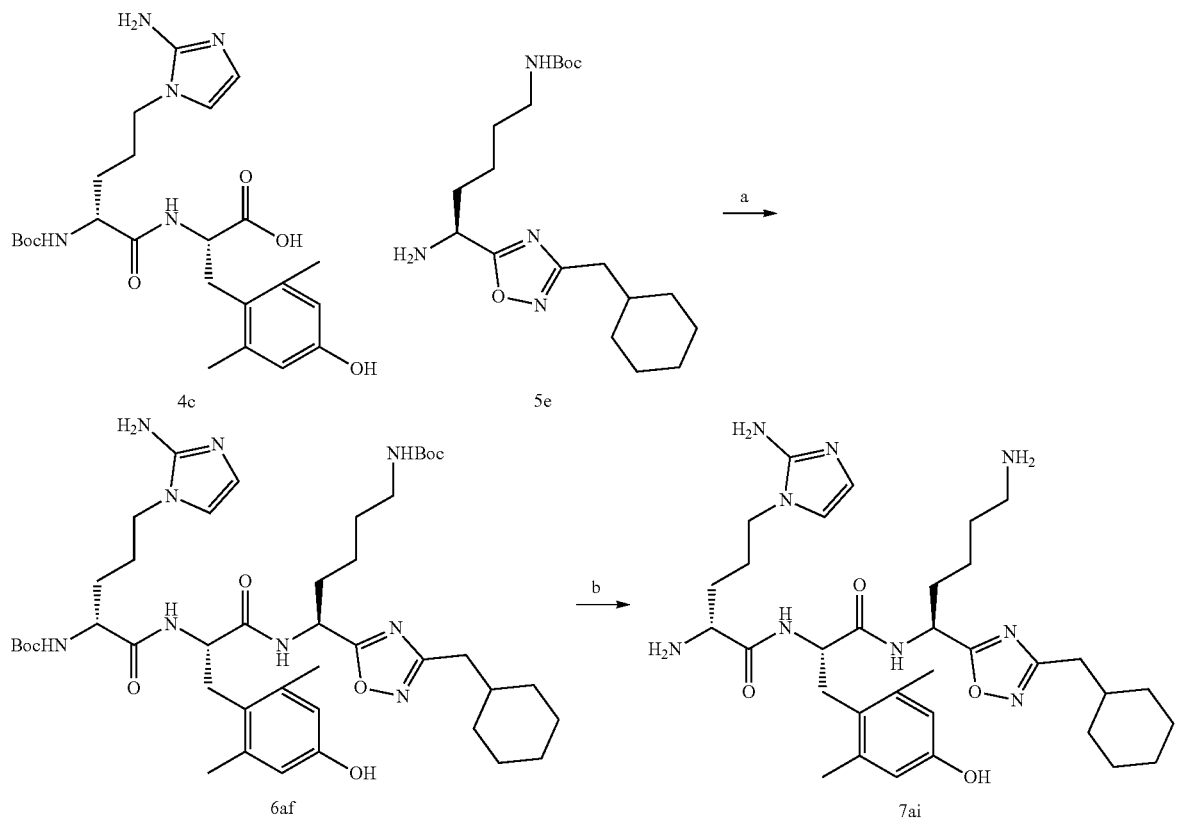

1) Step a: Synthesis of tert-butyl ((10S,13S,16R)-19-(2-amino-1H-imidazol-1-yl)-10-(3-(cyclohexylmethyl)-1,2,4-oxadiazol-5-yl)-13-(4-hydroxy-2,6-dimethylbenzyl)-2,2-dimethyl-4,12,15-trioxo-3-oxa-5,11,14-triazanonadecan-16-yl)carbamate (6af)

The same procedure as described in Scheme 36 by using 5e (799 mg, 2.18 mmol) and 4c (1.00 g, 1.82 mmol) to give 6af (0.63 g) in 39% yield.

$^1$H NMR (300 MHz, Methanol-$d_4$): δ=6.84-6.71 (m, 2H), 6.36 (s, 2H), 5.20-5.08 (m, 1H), 4.71-4.58 (m, 1H), 4.05-3.94 (m, 1H), 3.86-3.68 (m, 2H), 3.66-3.56 (m, 1H), 3.20-3.07 (m, 1H), 3.06-2.93 (m, 2H), 2.93-2.79 (m, 1H), 2.63-2.53 (m, 2H), 2.22 (s, 6H), 1.83-0.88 ppm (m, 38H).

2) Step b: Synthesis of (R)-2-amino-N-((S)-1-(((S)-5-amino-1-(3-(cyclohexylmethyl)-1,2,4-oxadiazol-5-yl)pentyl)amino)-3-(4-hydroxy-2,6-dimethylphenyl)-1-oxopropan-2-yl)-5-(2-amino-1H-imidazol-1-yl)pentanamide (7ai)
The same procedure as described in Scheme 36 by using 6af (0.63 g, 0.702 mmol) to give 7ai (258 mg) in 49% yield.
$^1$H NMR (400 MHz, Methanol-$d_4$): δ=6.90-6.84 (m, 2H), 6.38 (s, 2H), 5.19-5.11 (m, 1H), 4.78-4.71 (m, 1H), 4.03-3.96 (m, 1H), 3.92-3.77 (m, 2H), 3.17-3.08 (m, 1H), 2.97-2.86 (m, 3H), 2.62-2.57 (m, 2H), 2.25 (s, 6H), 2.05-1.88 (m, 2H), 1.84-0.95 ppm (m, 20H). MS: EI-MS: m/z 638.7 [M+1].

Example 66: Synthesis of (S)-N-((S)-1-(3-([1,1'-biphenyl]-4 ylmethyl)-1,2,4-oxadiazol-5-yl)-2-(1H-imidazol-4 yl)ethyl)-2-((R)-2-amino-2-(1-carbamimidoylpiperidin-4-yl)acetamido)-3-(4-hydroxy-2,6-dimethylphenyl)propanamide (D-(α-(1-carbamimidoylpiperidin-4 yl))-Gly-DMT-NH((S)-1-(3-([1,1'-biphenyl]-4-yl)methyl-1,2,4-oxadiazol-5-yl)-2-(1H-imidazol-4 yl)eth-1-yl), 7aj)

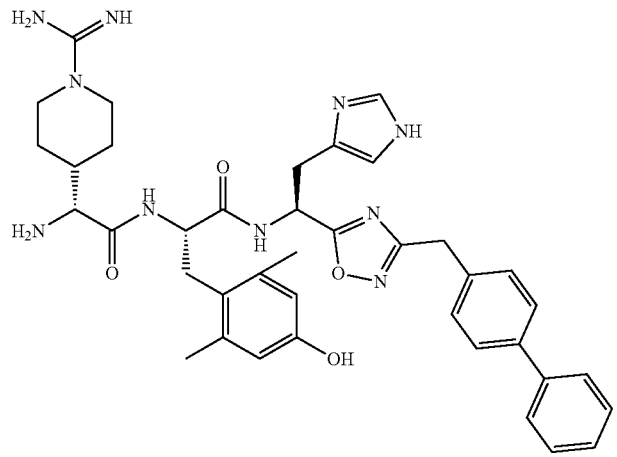

Compound 7aj

Scheme 67

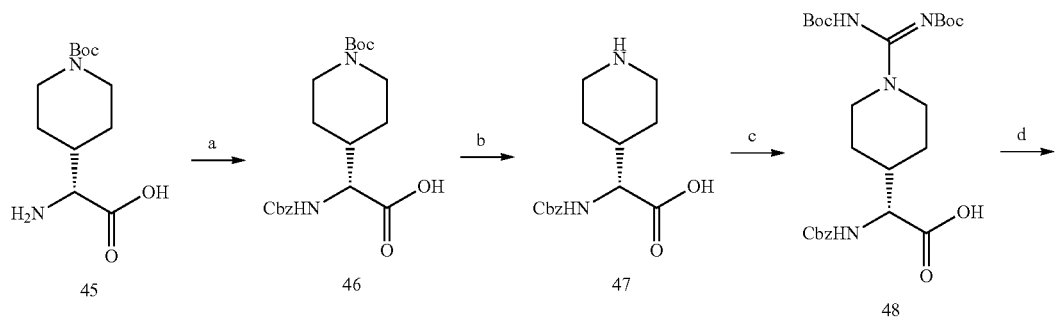

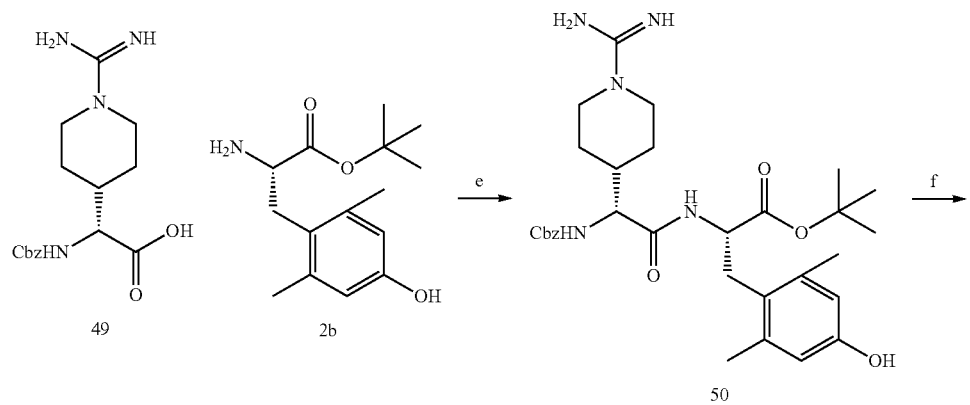

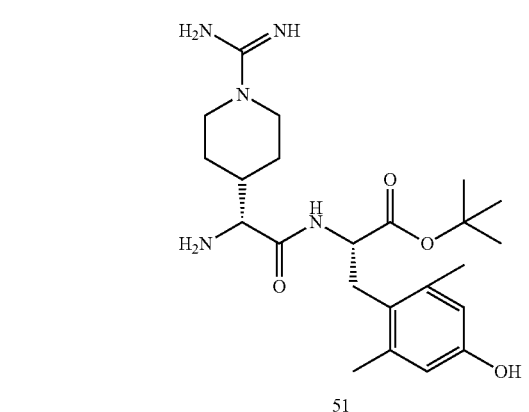

51

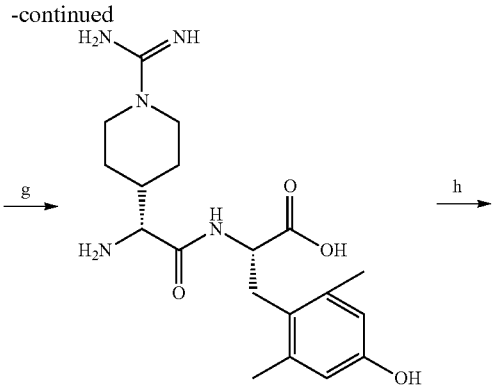

52

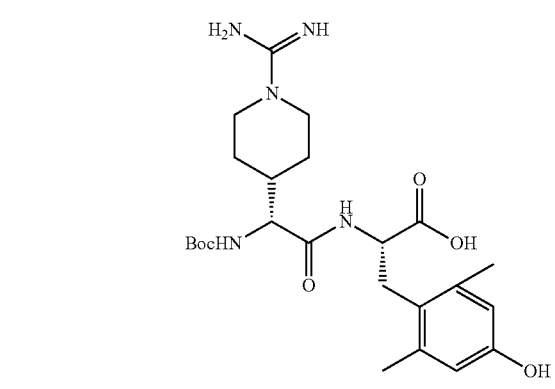

4d

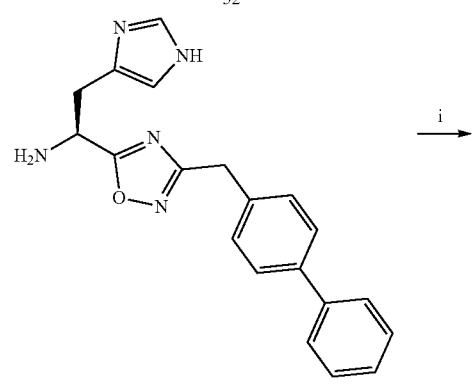

12t

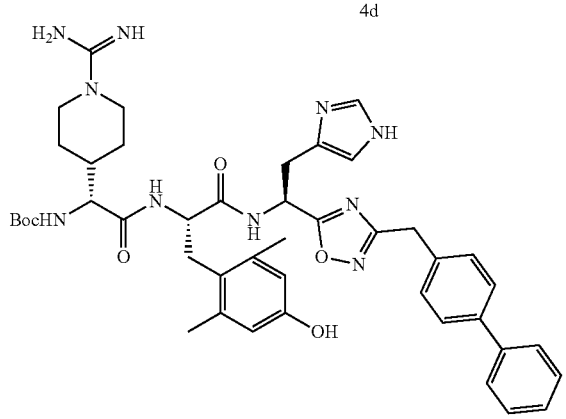

6ag

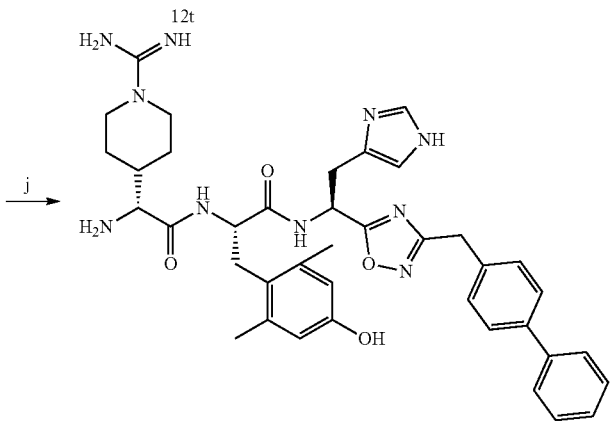

7aj

1) Step a: Synthesis of (R)-2-(((benzyloxy)carbonyl)amino)-2-(1-(tert-butoxycarbonyl)piperidin-4-yl)acetic acid (46)

Sodium bicarbonate (3.252 g, 38.71 mmol) was suspended in water (31 mL), then 45 (1 g, 3.871 mmol), THF (31 mL) and N-(benzyloxycarbonyloxy)succinimide (1.350, 5.419 mmol) was added. Biphasic mixture was allowed to vigorously stirring at RT overnight. Then additional water (31 mL) was added and reaction mixture was washed with $Et_2O$ (3×57 mL). To aqueous layer 5% solution of citric acid (85 mL) was added and product was extracted with DCM (4×85 mL). Organic layers was combined and dried over $Na_2SO_4$, filtered and evaporated. Residue was purified by reverse-phase flash column chromatography to gave desired product (46, 0.866 g) as white solid.

$^1$H NMR (400 MHz, Methanol-$d_4$) δ7.38-7.27 (m, 5H), 5.10 (d, J=2.4 Hz, 2H), 4.15 (d, J=5.9 Hz, 1H), 4.09 (d, J=13.3 Hz, 2H), 2.80-2.63 (m, 2H), 2.05-1.94 (m, 1H), 1.68-1.60 (m, 2H), 1.44 (s, 9H), 1.28 (pd, J=12.8, 4.4 Hz, 2H).

2) Step b: Synthesis of (R)-2-(((benzyloxy)carbonyl)amino)-2-(piperidin-4-yl)acetic acid (47)

To a cooled solution of 46 (0.866 g, 2.21 mmol) in DCM (50 mL) TFA (15 mL) was added. Then ice/water bath was removed and the mixture was stirred at ambient temperature for 2 h. Volatiles were removed under reduced pressure and the residue was concentrated from toluene (2×). Obtained crude material (47) was used in next step without futher purification.

$^1$H NMR (400 MHz, Methanol-$d_4$) δ7.38-7.28 (m, 5H), 5.14-5.07 (m, 2H), 4.22 (d, J=5.9 Hz, 1H), 3.40 (d, J=14.5 Hz, 2H), 2.98 (qd, J=13.2, 2.7 Hz, 2H), 2.21-2.12 (m, 1H), 1.93 (dd, J=32.9, 14.5 Hz, 2H), 1.65-1.52 (m, 2H).

3) Step c: Synthesis of (R,E)-2-(((benzyloxy)carbonyl)amino)-2-(1-(N,N'-bis(tert-butoxycarbonyl)carbamimidoyl)piperidin-4-yl)acetic acid (48)

To a solution of 47 (1.0 g, 2.46 mmol) in DMF (25 mL) N,N'-Di-Boc-1H-pyrazole-1-carboxamidine (0.840 g, 2.71 mmol) and DIPEA (3.817 g, 29.53 mmol) were added. The mixture was stirred overnight. Then MeOH was added till full dissolution of precipitates and left stir for 2 h. Concentration under reduced pressure gave residue which was diluted with EtOAc and washed with saturated NaHCO$_3$ and brine. The organic layer was concentrated and purified by reverse-phase flash chromatography. 1.0 g of desired product 48 was obtained as white solid.

$^1$H NMR (400 MHz, Methanol-d$_4$) δ7.38-7.26 (m, 5H), 5.09 (s, 2H), 4.16-4.09 (m, 3H), 3.01-2.91 (m, 2H), 2.15-2.06 (m, 1H), 1.72 (dd, J=25.7, 14.0 Hz, 2H), 1.51-1.45 (m, 2H), 1.48 (s, 18H).

4) Step d: Synthesis of (R)-2-(((benzyloxy)carbonyl)amino)-2-(1-carbamimidoylpiperidin-4-yl)acetic acid (49)

To a cooled solution of 48 (1.0 g, 1.87 mmol) in DCM (50 mL) TFA (15 mL) was added. Then ice/water bath was removed and the mixture was stirred at ambient temperature for 4 h. Volatiles were removed under reduced pressure and the residue was concentrated and purified by reverse-phase flash chromatography to give desired product (49, 0.5 g) as white solid.

$^1$H NMR (400 MHz, Methanol-d$_4$) δ7.39-7.27 (m, 5H), 5.10 (d, J=1.7 Hz, 2H), 4.19 (d, J=6.1 Hz, 1H), 3.91 (d, J=13.8 Hz, 2H), 3.12-3.02 (m, 2H), 2.21-2.11 (m, 1H), 1.79 (dd, J=25.0, 13.6 Hz, 2H), 1.50-1.37 (m, 2H).

5) Step e: Synthesis of tert-butyl (S)-2-((R)-2-(((benzyloxy)carbonyl)amino)-2-(1-carbamimidoylpiperidin-4-yl)acetamido)-3-(4-hydroxy-2,6-dimethylphenyl)propanoate (50)

To a mixture of 49 (0.2 g, 0.539 mmol) and H-DMT-OtBu (2b, 0.157 g, 0.593 mmol) in 20 mL of DMF EDCI·HCl (0.258 g, 1.347 mmol) was added followed by addition of HOBt·H$_2$O (0.165 g, 1.078 mmol). After 10-15 min NMM (0.153 g, 1.509 mmol) was added and the mixture was stirred at ambient temperature overnight. Then volatiles were removed under reduced pressure and the residue was evaporated with 5% of citric acid aqueous solution. Obtained residue was purified by reverse-phase flash chromatography to afford desired product (50, 0.17 g).

$^1$H NMR (400 MHz, Methanol-d$_4$) δ8.23 (d, J=8.4 Hz, 1H), 7.37-7.27 (m, 5H), 6.45 (s, 2H), 5.09 (s, 2H), 4.73-4.67 (m, 1H), 4.08 (d, J=6.8 Hz, 1H), 3.83 (d, J=13.5 Hz, 2H), 3.09 (dd, J=14.3, 6.8 Hz, 1H), 3.00-2.91 (m, 3H), 2.28 (s, 6H), 1.92-1.82 (m, 1H), 1.55-1.44 (m, 2H), 1.37 (s, 9H), 1.27-1.17 (m, 2H).

6) Step f: Synthesis of tert-butyl (S)-2-((R)-2-amino-2-(1-carbamimidoylpiperidin-4-yl)acetamido)-3-(4-hydroxy-2,6-dimethylphenyl)propanoate (51)

To a solution of 50 (0.170 G, 0.275 mmol) in MeOH (20 mL) Pd/C 10% w/w (0.044 G, 0.041 mmol) was added. The flask was flushed out with H$_2$ and the mixture was stirred for 2 h at RT. Then the mixture was filtered and volatiles were removed under reduced pressure. Obtained residue of desired product 51 was used in next step without futher purification.

$^1$H NMR (400 MHz, Methanol-d$_4$) δ6.46 (s, 2H), 4.77 (dd, J=9.8, 7.0 Hz, 1H), 3.86 (d, J=15.1 Hz, 2H), 3.11 (dd, J. 14.3, 7.1 Hz, 1H), 3.01-2.92 (m, 3H), 2.34-2.26 (m, 1H), 2.30 (s, 6H), 1.85-1.73 (m, 1H), 1.55-1.50 (m, 2H), 1.37 (s, 9H), 1.32-1.19 (m, 2H).

7) Step g: Synthesis of (S)-2-((R)-2-amino-2-(1-carbamimidoylpiperidin-4-yl)acetamido)-3-(4-hydroxy-2,6-dimethylphenyl)propanoic acid (52)

To a cooled solution of 51 (0.12 g, 0.268 mmol) in DCM (15 mL) TFA (6 mL) was added. Then ice/water bath was removed and the mixture was stirred at ambient temperature for 2 h. Volatiles were removed under reduced pressure and the residue was concentrated from toluene (2x). Obtained residue of desired product 52 was used in next step without futher purification.

$^1$H NMR (400 MHz, Methanol-d$_4$) δ7.23-7.09 (m, 2H), 6.47 (s, 2H), 5.02 (dd, J=11.2, 5.5 Hz, 1H), 3.90-3.81 (m, 2H), 3.23 (dd, J=14.7, 5.5 Hz, 1H), 3.05-2.90 (m, 3H), 2.33-2.30 (m, 1H), 2.32 (s, 6H), 1.91-1.80 (m, 1H), 1.50 (d, J=13.9 Hz, 1H), 1.30-1.11 (m, 4H).

8) Step h: Synthesis of (S)-2-((R)-2-((tert-butoxycarbonyl)amino)-2-(1-carbamimidoylpiperidin-4-yl)acetamido)-3-(4-hydroxy-2,6-dimethylphenyl)propanoic acid (4d)

To a cooled solution with ice/water bath of 52 (0.174 G, 0.344 mmol) in 10 mL of buffer solution (pH=8.5) Boc$_2$O (0.113 G, 0.516 mmol) dissolved in 15 mL of THF was added dropwise. Then reaction mixture was stirred in ice/water bath for 1 h, and overnight at rt. LCMS shows some amount of SM, and another 10 mL of buffer solution (pH=8.5) was added and stirring continued till full conversion. After that pH was adjusted to pH=4 with 5% acetic acid solution and evaporated. Purification by reverse-phase flash chromatography gave 0.120 G of desired product (4d).

$^1$H NMR (400 MHz, Methanol-d$_4$) δ6.41 (s, 2H), 4.71 (dd, J=10.3, 5.7 Hz, 1H), 4.03 (d, J=5.2 Hz, 1H), 3.84-3.77 (m, 2H), 3.15 (dd, J=14.4, 5.7 Hz, 1H), 3.00-2.87 (m, 3H), 2.32 (s, 6H), 1.93-1.84 (m, 1H), 1.55 (d, J=13.1 Hz, 1H), 1.44 (s, 9H), 1.34-1.12 (m, 3H).

9) Step is Synthesis of tert-butyl ((R)-2-(((S)-1-(((S)-1-(3-([1,1'-biphenyl]-4-ylmethyl)-1,2,4-oxadiazol-5-yl)-2-(1H-imidazol-4-yl)ethyl)amino)-3-(4-hydroxy-2,6-dimethylphenyl)-1-oxopropan-2-yl)amino)-1-(1-carbamimidoylpiperidin-4-yl)-2-oxoethyl)carbamate (6ag)

The same procedure as described in Scheme 36 by using 12t (0.047 g, 0.122 mmol) and 4d (0.061 g, 0.111 mmol) to give 6ag which was flushed thoroughly reverse-phase flash column and used in next step without futher purification.

10) Step j: Synthesis of (S)-N-((S)-1-(3-([1,1'-biphenyl]-4-ylmethyl)-1,2,4-oxadiazol-5-yl)-2-(1H-imidazol-4-yl)ethyl)-2-((R)-2-amino-2-(1-carbamimidoylpiperidin-4-yl)acetamido)-3-(4-hydroxy-2,6-dimethylphenyl)propanamide (7aj)

The same procedure as described in Scheme 36 by using 6ag (0.065 g, 0.074 mmol) to give 7aj (41 mg) as white solid. (HPLC purity is 97.5% at 210 nm)

$^1$H NMR (400 MHz, Methanol-d$_4$) δ8.77 (d, J=1.3 Hz, 1H), 7.57-7.53 (m, 4H), 7.43-7.30 (m, 6H), 6.40 (s, 2H), 5.55 (dd, J=9.0, 5.8 Hz, 1H), 4.66 (t, J=8.3 Hz, 1H), 4.13 (s, 2H), 3.94-3.87 (m, 2H), 3.79 (d, J=5.9 Hz, 1H), 3.41 (dd, J=15.5, 5.7 Hz, 1H), 3.09-2.95 (m, 3H), 2.86 (dd, J=14.2, 8.0 Hz, 1H), 2.21 (s, 6H), 2.02-1.92 (m, 1H), 1.57 (dd, J=41.4, 13.1 Hz, 2H), 1.37-1.22 (m, 3H). MS: EI-MS: m/z 719.5 [M+1].

Example 67: Synthesis of (R)-N-((S)-1-(((S)-1-(3-([1,1'-biphenyl]-4 ylmethyl)-1,2,4-oxadiazol-5-yl)-2-(1H-imidazol-4 yl)ethyl)amino)-3-(4-methoxy-2,6-dimethylphenyl)-1-oxopropan-2-yl)-2-amino-5-(2-amino-1H-imidazol-1-yl)pentanamide (D-(δ(2-amino-1H-imidazol-1-yl)-Nva-(O-methyl)-DMT-NH((S)-1-(3-([1,1'-biphenyl]-4-yl)methyl-1,2,4-oxadiazol-5-yl)-2-(1H-imidazol-4 yl)eth-1-yl), 7ak)
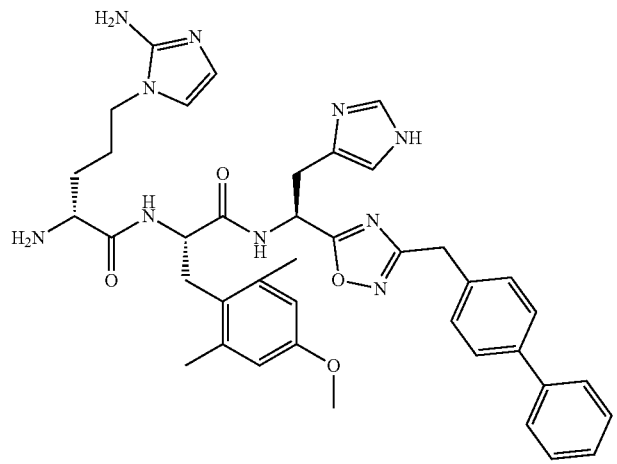
Compound 7ak
Scheme 68
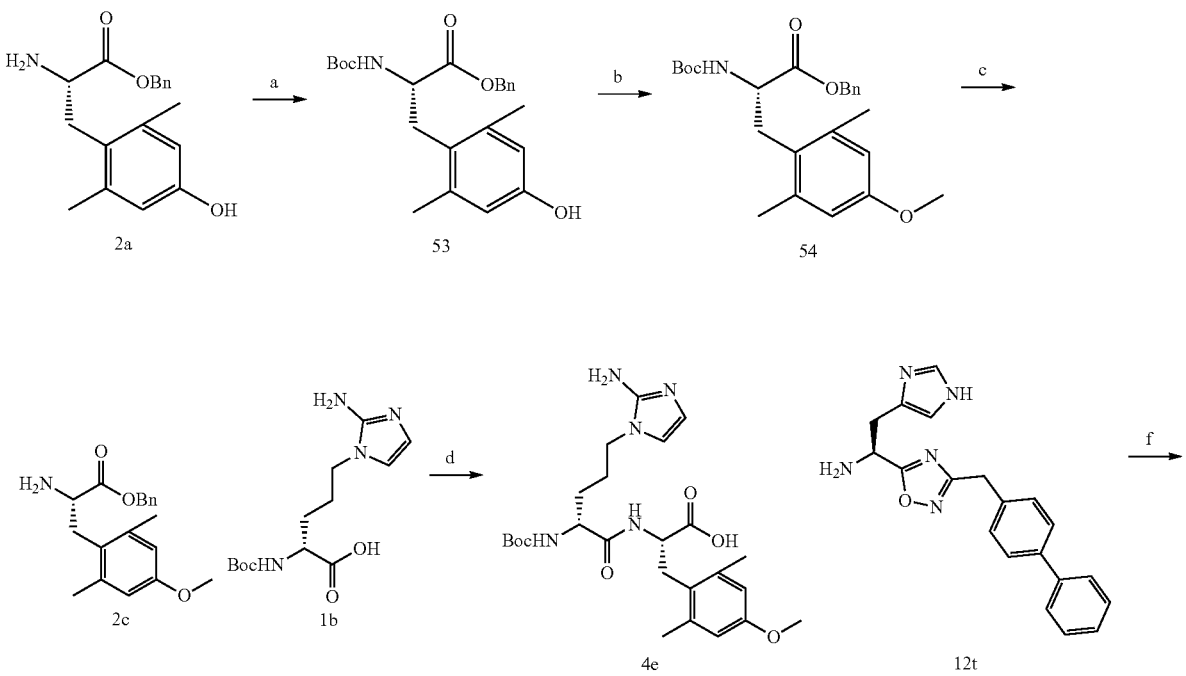

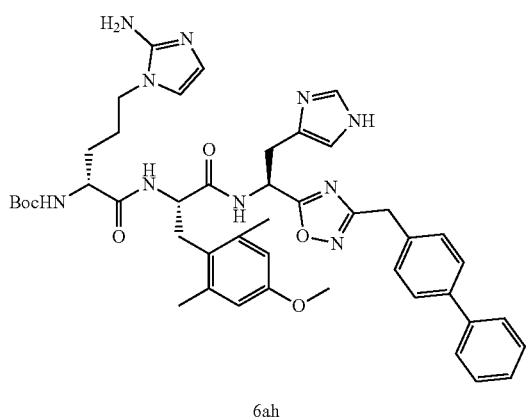

6ah

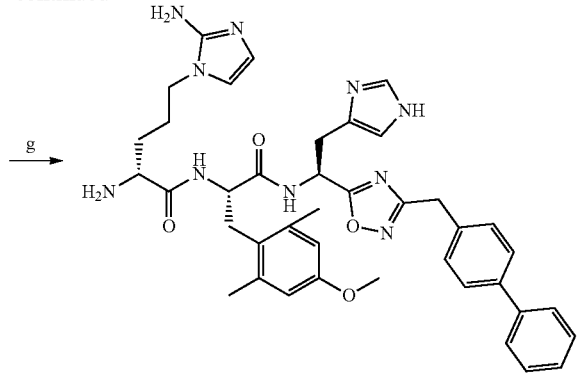

7ak

1) Step a: Synthesis of benzyl (S)-2-((tert-butoxycarbonyl) amino)-3-(4-hydroxy-2,6-dimethylphenyl)propanoate (53)
NaHCO$_3$ (5.61 g, 66.8 mmol) was suspended in water (53 mL) and added to the benzyl (S)-2-amino-3-(4-hydroxy-2, 6-dimethylphenyl)propanoate (2a) (2.00 g, 6.68 mmol). To the resulting suspension dropwise was added solution of Boc$_2$O (2.18 g, 10.0 mmol) in THF (50 mL) and the reaction mixture was stirred at r.t. for 24 h. Then, additional water (50 mL) was added and the resulting mixture was extracted with EtOAc (3×150 mL). Combined organic phases were washed with brine (80 mL), dried over anhydrous Na$_2$SO$_4$, and concentrated under reduced pressure. The crude product was purified by silica gel column chromatography using a mixture of PE and EtOAc (1:0-(2:1) as an eluent to give 53 (2.18 g) in 82% yield as a colorless glass-like solid.
$^1$H NMR (400 MHz, CDCl$_3$): δ=δ7.38-7.28 (m, 3H), 7.20-7.13 (m, 2H), 6.45 (s, 2H), 5.11-5.01 (m, 2H), 4.58-4.48 (m, 1H), 3.07-2.89 (m, 2H), 2.25 (s, 6H), 1.38 ppm (s, 9H).

2) Step b: Synthesis of benzyl (S)-2-((tert-butoxycarbonyl) amino)-3-(4-methoxy-2,6-dimethylphenyl)propanoate (54)
To a mixture of 53 (2.18 g, 5.46 mmol) and K$_2$CO$_3$ (3.47 g, 32.8 mmol) in dry DMF was added methyl iodide (6.1 mL, 98.3 mmol) and the resulting suspension was stirred at r.t. for 24 h. To the reaction mixture was added EtOAc (600 mL) and water (100 mL) and the resulting mixture was stirred at r.t. for 15 min. Then, the aqueous phase was separated and the organic phase was washed with water (3×80 mL) and brine (80 mL). After drying over anhydrous Na$_2$SO$_4$, the volatile matters were removed under reduced pressure and the crude product was purified by silica gel column chromatography (PE/EtOAc 1:0≥ 20:3) to give 54 (1.8 g) in 80% yield as a white amorphous solid.
$^1$H NMR (300 MHz, CDCl$_3$): δ=7.34-7.27 (m, 3H), 7.19-7.11 (m, 2H), 6.53 (s, 2H), 5.09-4.99 (m, 2H), 4.59-4.47 (m, 1H), 3.74 (s, 3H), 3.06-2.97 (m, 2H), 2.29 (s, 6H), 1.43-1.20 ppm (m, 9H).

3) Step c: Synthesis of benzyl (S)-2-amino-3-(4-methoxy-2,6-dimethylphenyl)propanoate (2c)
To a cooled (ice bath) solution of 54 (1.65 g, 0.318 mmol) in dry DCM (18 mL) dropwise was added TFA (6.0 mL) and the reaction mixture was stirred for 4 h while gradually reaching r.t. Then, volatile matters were removed under reduced pressure and the crude product was purified by reversed phase flash chromatography using mixture of EtOH/MeCN (4:1) and 0.01% aq. HCl as an eluent. The product came out of the coulmn at 28-36% of EtOH/MeCN (4:1) to give 2c (1.28 g) in 92% yield as white amorphous solid.
$^1$H NMR (300 MHz, Methanol-d$_4$) δ7.34-7.23 (m, 3H), 7.10-7.04 (m, 2H), 6.57 (s, 2H), 5.11-4.98 (m, 2H), 4.19-4.11 (m, 1H), 3.74 (s, 3H), 3.30-3.21 (m, 1H), 3.18-3.09 (m, 1H), 2.25 ppm (s, 2H).

4) Step d: Synthesis of benzyl (S)-2-((R)-5-(2-amino-1H-imidazol-1-yl)-2-((tert-butoxycarbonyl)amino)pentanamido)-3-(4-methoxy-2,6-dimethylphenyl)propanoate (3e)
The same procedure as described in Scheme 36 by using 2c (647 mg, 1.85 mmol) and 1b (0.500 g, 1.68 mmol) to give 3e (0.57 g) in 52% yield.
$^1$H NMR (300 MHz, Methanol-d$_4$) δ7.36-7.13 (m, 5H), 6.82-6.74 (m, 2H), 6.53 (s, 2H), 5.06 (s, 2H), 4.77-4.67 (m, 1H), 4.15-4.04 (m, 1H), 3.83-3.64 (m, 5H), 3.23-2.94 (m, 2H), 2.28 (s, 614), 1.75-1.06 (m, 13H).

5) Step e: Synthesis of (S)-2-((R)-5-(2-amino-1H-imidazol-1-yl)-2-((tert-butoxycarbonyl)amino)pentanamido)-3-(4-methoxy-2,6-dimethylphenyl)propanoic acid (4e)
The same procedure as described in Scheme 36 by using 3e (0.57 g, 0.872 mmol) to give 4e (0.42 g) in 74% yield.
$^1$H NMR (300 MHz, Methanol-d$_4$): δ=6.83-6.77 (m, 2H), 6.51 (s, 2H), 4.64-4.55 (m, 1H), 4.06-3.97 (m, 5H), 3.81-3.63 (m, 5H), 3.21-3.11 (m, 1H), 2.99-2.87 (m, 1H), 2.34 (s, 6H), 1.76-1.12 ppm (m, 13H).

6) Step f: Synthesis of tert-butyl ((R)-1-(((S)-1-(((S)-1-(3-([1,1'-biphenyl]-4-ylmethyl)-1,2,4-oxadiazol-5-yl)-2-(1H-imidazol-4-yl)ethyl)amino)-3-(4-methoxy-2,6-dimethylphenyl)-1-oxopropan-2-yl)amino)-5-(2-amino-1H-imidazol-1-yl)-1-oxopentan-2-yl)carbamate (6ah)
The same procedure as described in Scheme 36 by using 4d (100 mg, 0.199 mmol) and 12t (109 mg, 0.238 mmol) to give 6ah (87 mg).
$^1$H NMR (400 MHz, Methanol-d$_4$) δ8.44 (s, 1H), 7.53 (dd, J. 8.1, 2.0 Hz, 3H), 7.42-7.30 (m, 5H), 7.19 (s, 1H), 6.75 (dd, J. 11.2, 2.3 Hz, 2H), 6.43 (s, 2H), 5.56-5.47 (m, 1H), 4.52 (t, J=7.6 Hz, 1H), 4.05-4.00 (m, 2H), 3.81 (s, 1H), 3.67 (s, 3H), 3.40-3.35 (m, 1H), 3.12-3.00 (m, 1H), 2.90-2.82 (m, 1H), 2.20 (s, 6H), 1.78-1.53 (m, 4H), 1.36 (s, 9H).

7) Step g: Synthesis of (R)-N-((S)-1-(((S)-1-(3-([1,1'-biphenyl]-4-ylmethyl)-1,2,4-oxadiazol-5-yl)-2-(1H-imidazol-4-yl)ethyl)amino)-3-(4-methoxy-2,6-dimethylphenyl)-1-oxopropan-2-yl)-2-amino-5-(2-amino-1H-imidazol-1-yl) pentanamide (7ak)
The same procedure as described in Scheme 36 by using 6ah (87 mg, 0.105 mmol) to give 7ak (40 mg).

¹H NMR (400 MHz, Methanol-d₄) δ8.75 (s, 114), 7.56 (d, J=8.0 Hz, 3H), 7.45-7.28 (m, 5H), 6.84 (dd, J=22.3, 2.4 Hz, 2H), 6.46 (s, 2H), 5.54 (dd, J=8.9, 5.7 Hz, 1H), 4.51 (dd, J=9.4, 6.7 Hz, 1H), 4.11 (s, 2H), 3.94 (t, J=5.9 Hz, 1H), 3.84 (q, J=6.6 Hz, 2H), 3.71 (s, 3H), 3.36 (dd, J=15.6, 5.3 Hz, 1H), 3.28-3.22 (m, 1H), 3.08 (dd, J=14.0, 9.6 Hz, 1H), 2.85 (dd, J=14.1, 6.6 Hz, 1H), 2.22 (s, 6H), 1.89-1.59 (m, 4H). MS: EI-MS: m/z 731.6 [M+1].

Example 68: Synthesis of (R)-N-((S)-1-(((S)-1-(3-(adamantan-1-yl)methyl-1,2,4-oxadiazol-5-yl)-2-(1H-imidazol-4 yl)ethyl)amino)-3-(4-hydroxy-2,6-dimethylphenyl)-1-oxopropan-2-yl)-2-amino-4-guanidinobutanamide (D-Agb-DMT-NH((S)-1-(3-(adamantan-1-yl)methyl-1,2,4-oxadiazol-5-yl)-2-(1H-imidazol-4 yl)eth-1-yl), 7al)

nyl)-1-oxopropan-2-yl)amino)-4-guanidino-1-oxobutan-2-yl)carbamate (6ai)

The same procedure as described in Scheme 36 by using 4b (300 mg; 0.66 mmol) and 12u (666 mg; 1.2 mmol) to give 6ai (340 mg, 57%) of a white foam.

¹H NMR (300 MHz, Methanol-d₄) δ7.85 (s, 1H), 6.92 (s, 1H), 6.39 (s, 2H), 5.51 (t, J=7.4 Hz, 1H), 4.62 (t, J=7.9 Hz, 1H), 4.08 (dd, J=8.2, 5.8 Hz, 1H), 3.36-3.02 (multiple peaks, 5H), 2.89 (dd, J=14.2, 7.7 Hz, 1H), 2.48 (s, 2H), 2.23 (s, 6H), 2.03-1.87 (multiple peaks, 7H), 1.81-1.69 (multiple peaks, 4H), 1.69-1.59 (multiple peaks, 3H), 1.56 (bs, 6H), 1.47 (s, 9H).

2) Step b: Synthesis of (R)-N-((S)-1-(((S)-1-(3-(adamantan-1-yl)methyl-1,2,4-oxadiazol-5-yl)-2-(1H-imidazol-4-yl)ethyl)amino)-3-(4-hydroxy-2,6-dimethylphenyl)-1-oxopropan-2-yl)-2-amino-4-guanidinobutanamide (7al)

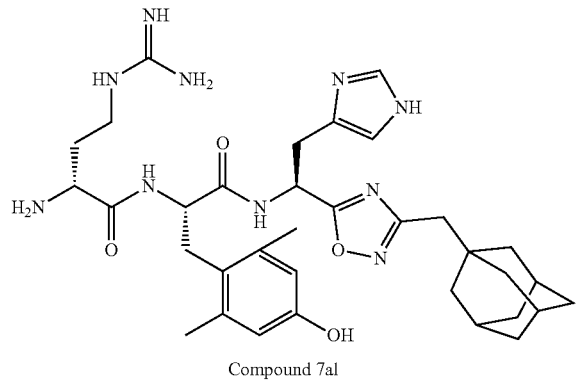

Compound 7al

Scheme 69

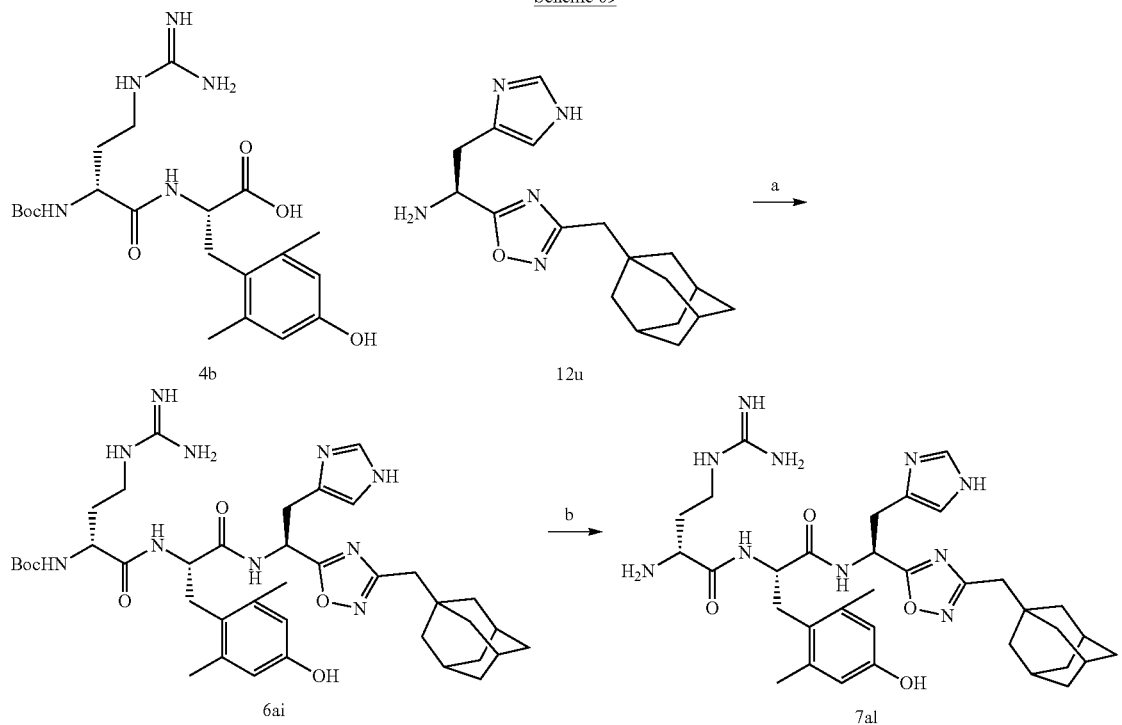

1) Step a: Synthesis of tert-butyl ((R)-1-(((S)-1-(((S)-1-(3-(adamantan-1-yl)methyl-1,2,4-oxadiazol-5-yl)-2-(1H-imidazol-4-yl)ethyl)amino)-3-(4-hydroxy-2,6-dimethylphenyl)

The same procedure as described in Scheme 36 by using 6ai (340 mg; 0.38 mmol) to give 7al (126 mg, 42%) as a white solid.

$^1$H NMR (400 MHz, Methanol-d$_4$) δ 8.83 (s, 1H), 7.40 (s, 1H), 6.34 (s, 2H), 5.54 (dd, J=8.7, 5.9 Hz, 1H), 4.58 (dd, J=9.1, 7.3 Hz, 1H), 4.08 (t, J=6.6 Hz, 1H), 3.42 (dd, J=15.5, 5.7 Hz, 1H), 3.34 (dd, J=15.3, 8.6 Hz, 1H), 3.25-3.05 (multiple peaks, 3H), 2.88 (dd, J=14.1, 7.2 Hz, 1H), 2.47 (multiple peaks, 2H), 2.21 (s, 6H), 2.08-1.87 (multiple peaks, 5H), 1.72 (bd, J=12.2 Hz, 3H), 1.61 (bd, J=11.4 Hz, 3H), 1.54 (bs, 6H). MS: EI-MS: m/z 661.6 [M+1].

Example 69: Synthesis of (R)-N-((S)-1-(((S)-1-(3-(adamantan-1-ylmethyl)-1,2,4-oxadiazol-5-yl)-2-(1H-imidazol-4 yl)ethyl)amino)-3-(4-hydroxy-2,6-dimethylphenyl)-1-oxopropan-2-yl)-2-(dimethylamino)-4-guanidinobutanamide (D-(N2,N2-dimethyl)-Agb-DMT-NH((S)-1-(3-(adamantan-1-yl)methyl-1,2,4-oxadiazol-5-yl)-2-(1H-imidazol-4 yl)eth-1-yl), 7am)

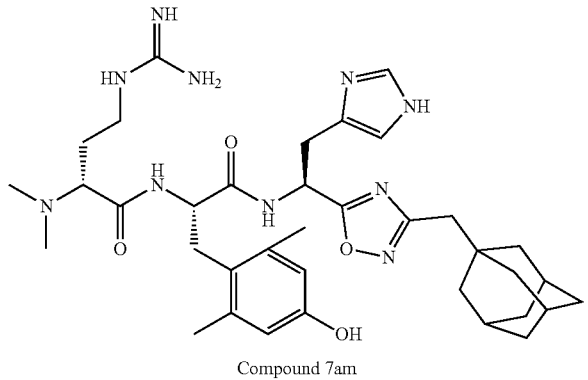

Compound 7am

Scheme 70

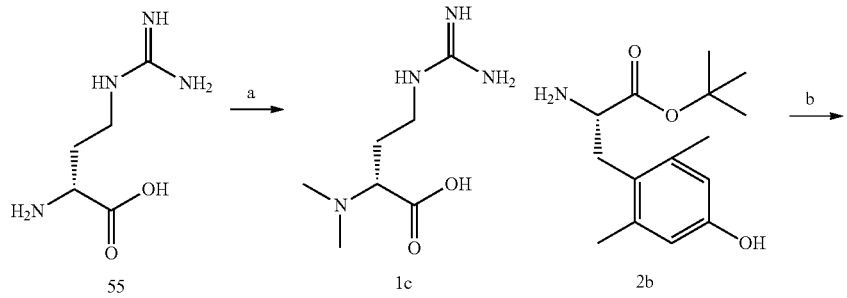

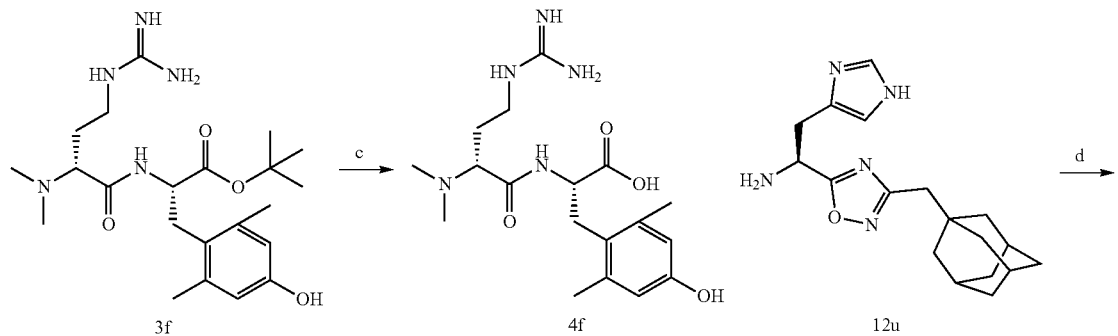

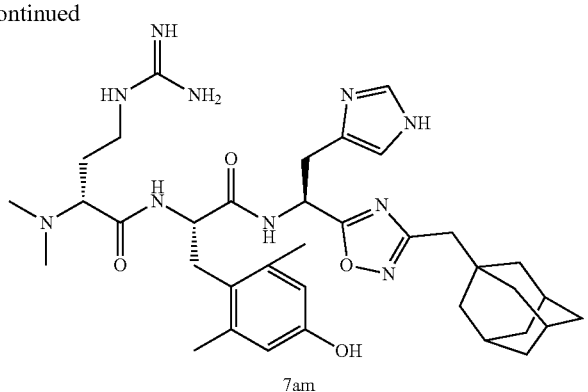

7am

1) Step a: Synthesis of (R)-2-(dimethylamino)-4-guanidinobutanoic acid (1c)
Nor-(D-)Arginine triflate (55, 2.32 g, 6.00 mmol) was added to a stirred solution of 8.2 g sodium acetate in 2 L of water at rt and then 4.46 mL (59.8 mmol) of 37% aqueous solution of formaldehyde (37%) and 3.78 g (60.2 mmol) of sodium cyanoborohydride were quickly added to the reaction mixture. The resulting mixture was stirred overnight and then concentrated to dryness at 40° C. under pressure. The resulting residue was dried overnight under vacuum to remove residual formaldehyde, and then was dissolved in 40 mL of water and purified by column chromatography using ion-exchange resin. Amberlite IR-120 (28-35 mesh, H$^+$ form) was emploed and the product was eluted using H$_2$O (700 mL), diluted NH$_3$ (0.5 N, 400 mL), and 3 N aqueous NH$_3$ (400 mL). The fractions were collected were monitored by TLC on silica gel plates using a 1:3 mixture of CH$_3$OH and conc. NH$_3$. The aqueous solutions containing the product were combined and the water was removed at 40° C. The residue was dried at rt under vacuo, to afford 0.77 g (68%) of product 1c.

$^1$H-NMR (300 MHz, Methanol-d$_4$) δ3.27 (dd, J=10.2, 3.4 Hz, 2H), 3.01 (dd, J=8.1, 6.4 Hz, 1H), 2.44 (s, 6H), 1.99-1.80 (m, 2H).

2) Step b: Synthesis of tert-butyl (S)-2-((R)-2-(dimethylamino)-4-guanidinobutanamido)-3-(4-hydroxy-2,6-dimethylphenyl)propanoate (3f)
The same procedure as described in Scheme 36 by using 1c (0.68 g, 3.6 mmol) and 2b (0.79 g, 3 mmol) to give 3f (980 mg, 62%) a white foam.

$^1$H-NMR (300 MHz, Methanol-d$_4$) δ6.46 (s, 2H), 4.71-4.62 (m, 1H), 4.05-4.00 (m, 1H), 3.22-2.95 (m, 10H, overlapping signals), 2.29 (s, 6H), 1.35-1.26 (m, 11H, overlapping signals).

3) Step c: Synthesis of (S)-2-((R)-2-(dimethylamino)-4-guanidinobutanamido)-3-(4-hydroxy-2,6-dimethylphenyl)propanoic acid (4e)

3f (900 mg, 2.07 mmol) was dissolved in DCM (8 mL) and cooled to 0° C. TFA (8 mL) was added dropwise and the solution was allowed to stir at 0° C. for 10 min, and then at rt for 2 h (LC/MS shows no starting material). Then reaction mixture was evaporated (at 0-5° C.) and additionally re-evaporated from DCM (20 mL, at 0-5° C.) yielding 4f (1.0 g, 90%) as an amorphous powder.

4) Step d: Synthesis of (R)-N-((S)-1-(((S)-1-(3-(adamantan-1-ylmethyl)-1,2,4-oxadiazol-5-yl)-2-(1H-imidazol-4-yl)ethyl)amino)-3-(4-hydroxy-2,6-dimethylphenyl)-1-oxopropan-2-yl)-2-(dimethylamino)-4-guanidinobutanamide (7am)

The same procedure as described in Scheme 36 by using 4f (170 mg; 0.37 mmol) and 12u (388 mg; 0.70 mmol) to give 7am (24 mg, 8%) as a white solid.

$^1$H NMR (400 MHz, Methanol-d$_4$) δ8.87 (s, 1H), 7.38 (s, 1H), 6.33 (s, 2H), 5.51 (dd, J=8.8, 5.8 Hz, 1H), 4.46 (dd, J=10.0, 6.4 Hz, 1H), 4.07 (dd, J=10.0, 4.0 Hz, 1H), 3.43-3.30 (multiple peaks, 21-1), 3.18-2.95 (multiple peaks, 3H), 2.91 (multiple peaks, 7H), 2.48 (multiple peaks, 2H), 2.29-2.05 (multiple peaks, 8H), 1.93 (bs, 3H), 1.72 (d, J=12.3 Hz, 3H), 1.61 (d, J=11.6 Hz, 3H), 1.55 (bs, 6H). ). MS: EI-MS: m/z 689.7 [M+1].

Example 70: Synthesis of (R)-N-((S)-1-(((S)-1-(3-([1,1'-biphenyl]-4-ylmethyl)-1,2,4-oxadiazol-5-yl)-2-(1-methyl-1H-imidazol-4-yl)ethyl)amino)-3-(4-methoxy-2,6-dimethylphenyl)-1-oxopropan-2-yl)-2-amino-5-(2-amino-1H-imidazol-1-yl)pentanamide (D-(δ(2-amino-1H-imidazol-1-yl)-Nva-(O-methyl)-DMT-NH((S)-1-(3-([1,1'-biphenyl]-4-yl)methyl-1,2,4-oxadiazol-5-yl)-2-(1-methyl-1H-imidazol-4 yl)eth-1-yl), 7an)

1) Step a: Synthesis of tert-butyl ((R)-1-(((S)-1-(((S)-1-(3-([1,1'-biphenyl]-4-ylmethyl)-1,2,4-oxadiazol-5-yl)-2-(1-methyl-1H-imidazol-4-yl)ethyl)amino)-3-(4-methoxy-2,6-dimethylphenyl)-1-oxopropan-2-yl)amino)-5-(2-amino-1H-imidazol-1-yl)-1-oxopentan-2-yl)carbamate (6aj)

The same procedure as described in Scheme 36 by using 4e (210 mg, 0.321 mmol) and 12w (160 mg, 0.404 mmol) to give 6aj (250 mg) in 86% yield.

$^1$H NMR (300 MHz, Methanol-$d_4$): =7.79 (s, 1H), 7.60-7.50 (m, 4H), 7.45-7.27 (m, 5H), 6.86-6.72 (m, 3H), 6.45 (s,

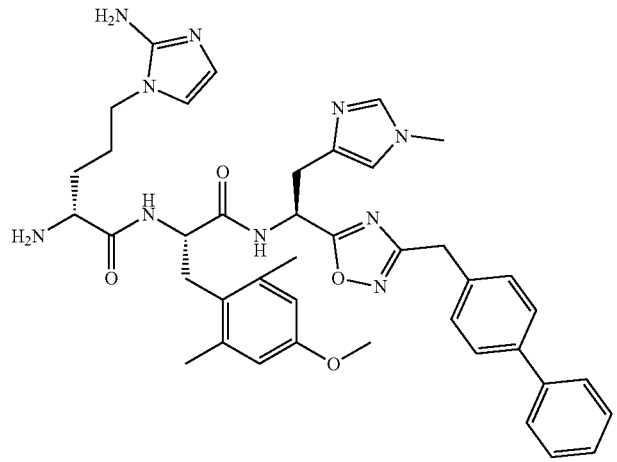

Compound 7an

Scheme 71

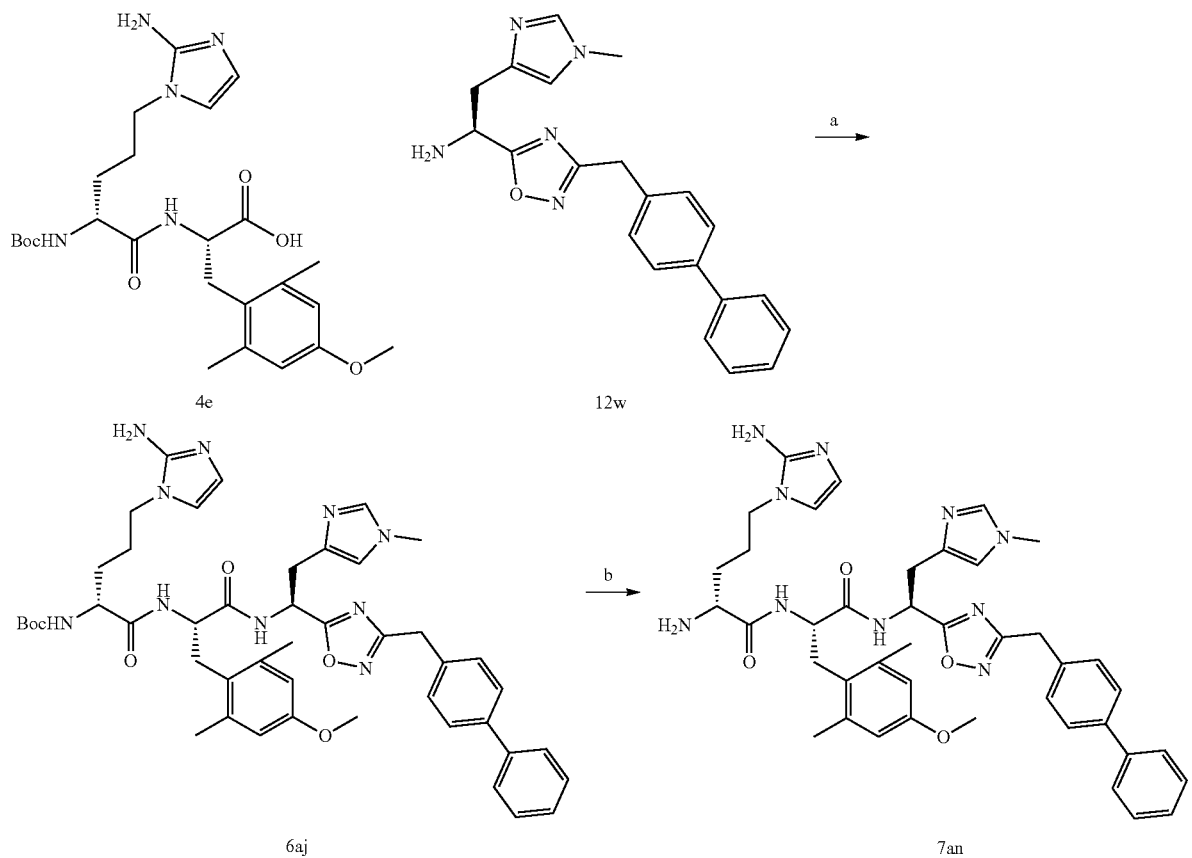

2H), 5.46-5.37 (m, 1H), 4.62-4.53 (m, 1H), 4.08 (s, 2H), 4.07-3.93 (m, 1H), 3.84-3.52 (m, 8H), 3.28-2.97 (m, 3H), 2.90-2.77 (m, 2H), 2.22 (s, 6H), 1.75-1.28 ppm (m, 13H).

2) Step b: Synthesis of (R)-N-((S)-1-(((S)-1-(3-([1,1'-biphenyl]-4-ylmethyl)-1,2,4-oxadiazol-5-yl)-2-(1-methyl-1H-imidazol-4-yl)ethyl)amino)-3-(4-methoxy-2,6-dimethylphenyl)-1-oxopropan-2-yl)-2-amino-5-(2-amino-1H-imidazol-1-yl)pentanamide (7an)

The same procedure as described in Scheme 36 by using 6aj (250 mg, 0.276 mmol) to give 7an.

$^1$H NMR (400 MHz, Methanol-$d_4$): δ=8.72 (s, 1H), 7.61-7.53 (m, 4H), 7.45-7.29 (m, 5H), 7.27-7.23 (m, 1H), 6.88 (d, J=2.5 Hz, 1H), 6.82 (d, J=2.5 Hz, 1H), 6.46 (s, 2H), 5.54-5.47 (m, 1H), 4.52-4.45 (m, 1H), 4.16-4.06 (m, 2H), 3.99-3.92 (m, 1H), 3.90-3.78 (m, 5H), 3.73-3.68 (m, 3H), 3.30-3.19 (m, 2H), 3.14-3.05 (m, 1H), 2.92-2.82 (m, 1H), 2.21 (s, 6H), 1.92-1.54 ppm (m, 4H). MS: EI-MS: m/z 745.6 [M+1].

Example 71: Synthesis of (R)-2-amino-N-((S)-1-(((S)-1-(3-benzyl-1,2,4-oxadiazol-5-yl)-2-(1H-indol-3-yl)ethyl)amino)-3-(4-hydroxy-2,6-dimethylphenyl)-1-oxopropan-2-yl)-4-guanidinobutanamide (D-Agb-DMT-NH((S)-1-(3-benzyl-1,2,4-oxadiazol-5-yl)-2-(1H-indol-3 yl)eth-1-yl), 7ao)

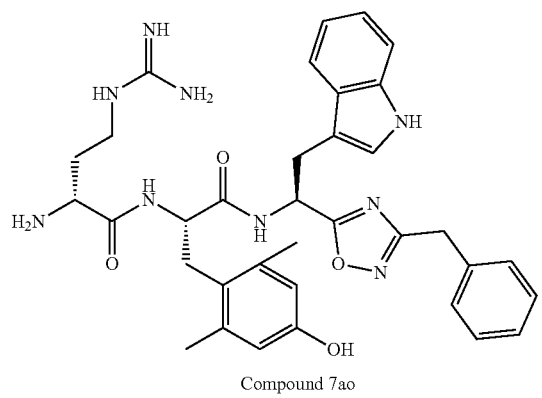

Compound 7ao

Scheme 72

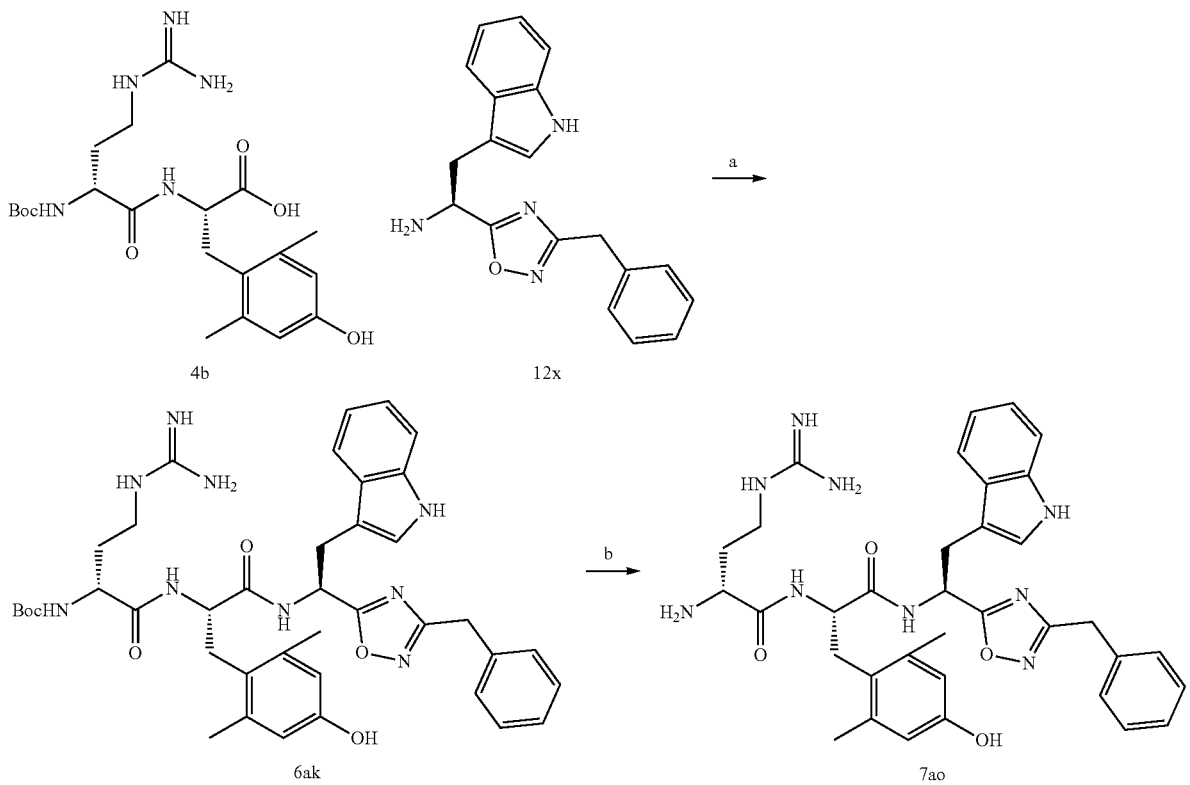

1) Step a: Synthesis of tert-butyl ((R)-1-(((S)-1-(((S)-1-(3-benzyl-1,2,4-oxadiazol-5-yl)-2-(1H-indol-3-yl)ethyl)amino)-3-(4-hydroxy-2,6-dimethylphenyl)-1-oxopropan-2-yl)amino)-4-guanidino-1-oxobutan-2-yl)carbamate (6ak)

The same procedure as described in Scheme 36 by using 4b (320 mg; 0.71 mmol) and 12x (287 mg; 0.9 mmol) to give 6ak (427 mg, 74%) of yellowish foam.

¹H NMR (300 MHz, Methanol-d₄) δ8.61 (d, J=8.1 Hz, 1H), 7.42 (d, J=7.9 Hz, 1H), 7.37-7.15 (multiple peaks, 6H), 7.09 (t, J=7.5 Hz, 1H), 6.97 (t, J=7.5 Hz, 1H), 6.87 (s, 1H), 6.36 (s, 2H), 5.47 (m, 1H), 4.69 (dd, J=9.1, 7.2 Hz, 1H), 4.04 (multiple peaks, 2H), 3.99 (t, J=6.5 Hz, 1H), 3.41-3.22 (multiple peaks overlapping with CHD₂OD, 2H), 3.14 (t, J=7.2 Hz, 2H), 3.05 (dd, 1H), 2.88 (dd, 1H), 2.18 (s, 6H), 2.10-1.89 (multiple peaks, 5H).

2) Step b: Synthesis of (R)-2-amino-N-((S)-1-(((S)-1-(3-benzyl-1,2,4-oxadiazol-5-yl)-2-(1H-indol-3-yl)ethyl)amino)-3-(4-hydroxy-2,6-dimethylphenyl)-1-oxopropan-2-yl)-4-guanidinobutanamide (7ao)

The same procedure as described in Scheme 36 by using 6ak (400 mg; 0.49 mmol) to give 7ao (111 mg, 31%) as yellowish solid.

¹H NMR (400 MHz, Methanol-d₄) δ7.37 (d, J=7.9 Hz, 1H), 7.30-7.22 (multiple peaks, 3H), 7.19 (m, 1H), 7.14 (d, J=6.9 Hz, 2H), 7.04 (t, J=7.6 Hz, 1H), 6.92 (t, J=7.5 Hz, 1H), 6.86 (s, 1H), 6.32 (s, 2H), 5.43 (dd, J=8.3, 6.9 Hz, 1H), 4.64 (dd, J=8.8, 7.2 Hz, 1H), 4.07-3.91 (multiple peaks, 3H), 3.36-3.22 (multiple peaks, 2H), 3.13 (t, J=7.2 Hz, 2H), 3.01 (dd, J=14.0, 9.1 Hz, 1H), 2.84 (dd, J=14.0, 7.2 Hz, 1H), 2.14 (s, 6H), 2.08-1.82 (multiple peaks, 2H). MS: EI-MS: m/z 652.5 [M+1].

Example 72: Synthesis of (S)-N-((S)-1-(3-([1,1'-biphenyl]-4-ylmethyl)-1,2,4-oxadiazol-5-yl)-2-(1H-indol-3 yl)ethyl)-2-((R)-2-amino-2-(1-carbamimidoylpiperidin-4-yl)acetamido)-3-(4-hydroxy-2,6-dimethylphenyl)propanamide (D-(α-(1-carbamimidoylpiperidin-4 yl))-Gly-DMT-NH((S)-1-(3-([1,1'-biphenyl]-4-yl)methyl-1,2,4-oxadiazol-5-yl)-2-(1H-indol-3-yl)eth-1-yl), 7ap)

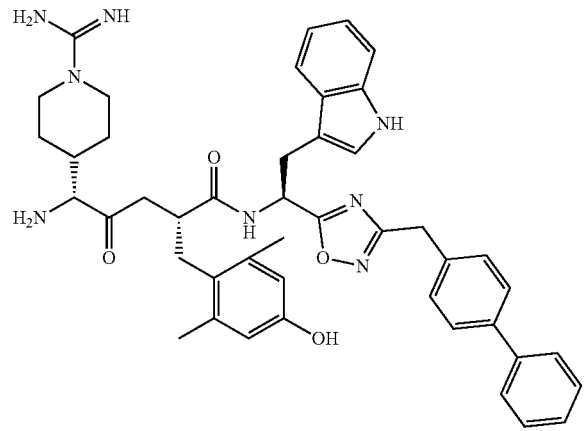

Compound 7ap

Scheme 73

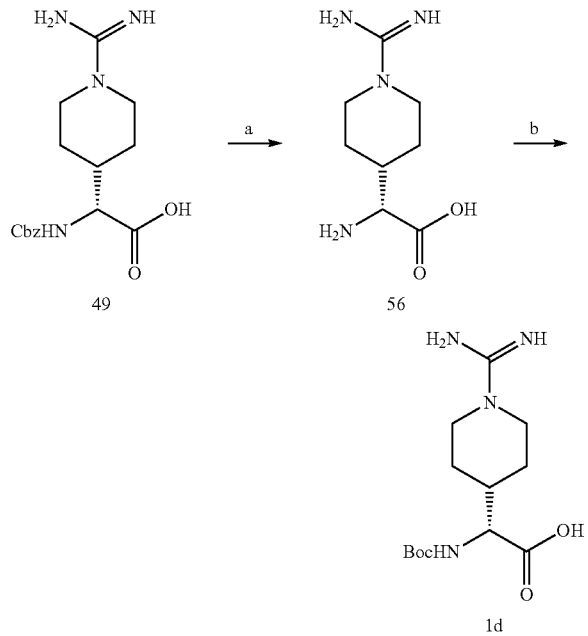

-continued
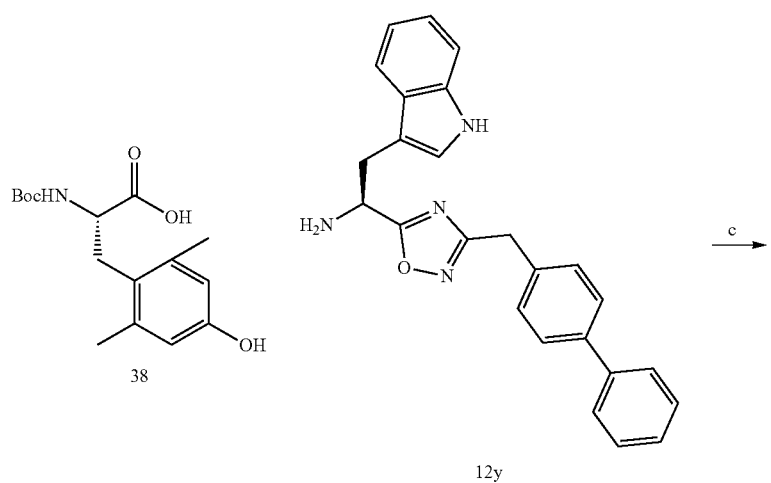
38, 12y
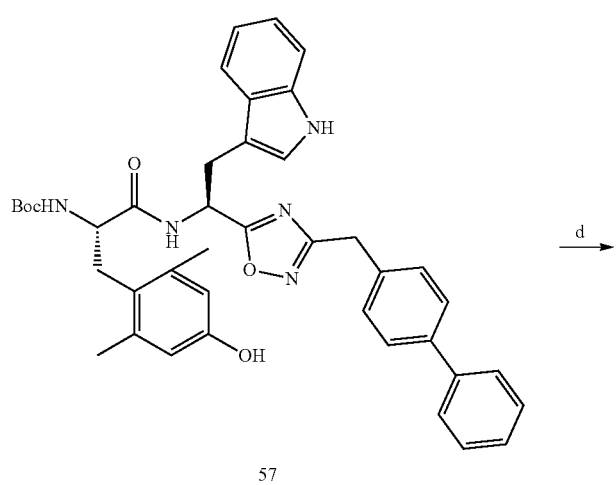
57
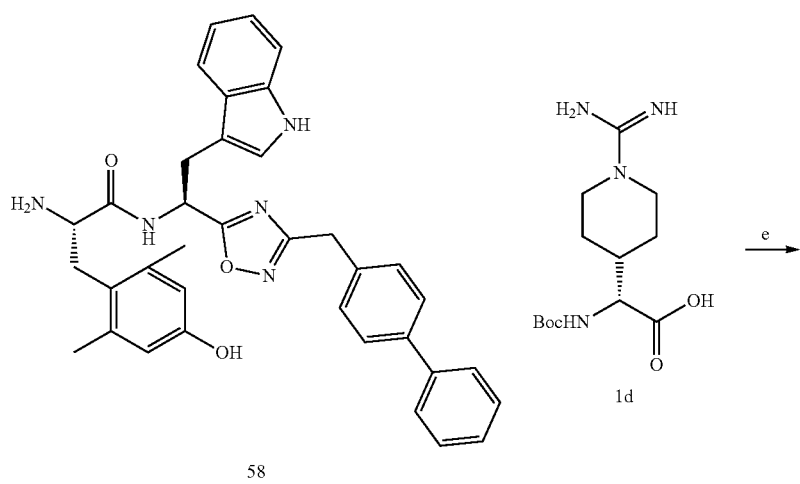
58, 1d

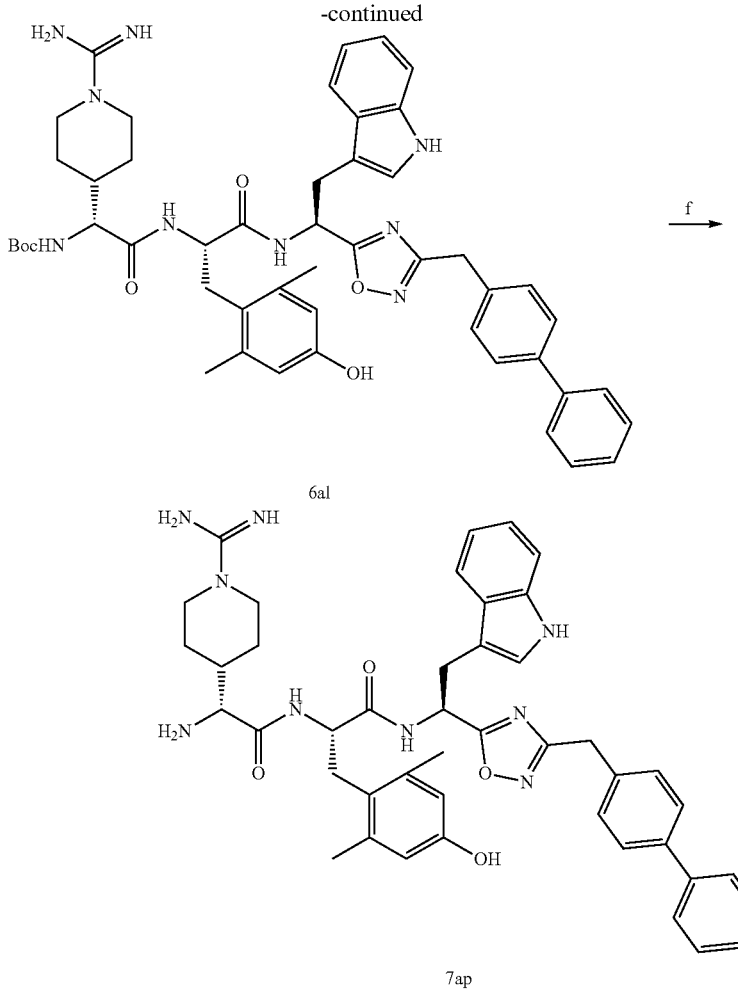

1) Step a: Synthesis of (R)-2-amino-2-(1-carbamimidoylpiperidin-4-yl)acetic acid (56)
To a solution of 49 (0.21 g, 0.566 mmol) in MeOH (20 mL) and Pd/C 10% w/w (0.090 G, 0.085 mmol). The flask was flushed out with H$_2$ and the mixture was stirred for 2 h at RT. A crude product 56 was filtered and volatiles were removed under reduced pressure.

2) Step b: Synthesis of (R)-2-((tert-butoxycarbonyl)amino)-2-(1-carbamimidoylpiperidin-4-yl)acetic acid (1d)
To a cooled solution in ice/water bath of obtained residue of desired product (56, 0.125 g, 0.528 mmol) in 10 mL of buffer solution (pH=8.5) was added dropwise Boc$_2$O (0.173 g, 0.792 mmol) dissolved in 15 mL of THF. After that reaction mixture was stirred in ice/water bath for 1 h, and then overnight at rt. LCMS shows some amount of SM, and another 10 mL of buffer solution (pH=8.5) was added and stirring continued to full conversion. Next, pH was adjusted to 4 by 5% acetic acid solution and evaporated. Purification by reverse-phase flash chromatography gave 0.1 g of desired product 1d.

$^1$H NMR (400 MHz, Methanol-d$_4$) δ3.96 (d, J=5.0 Hz, 1H), 3.88 (m, 2H), 3.02 (m, 2H), 2.09-1.99 (m, 1H), 1.75 (m, 2H), 1.44 (s, 9H), 1.42-1.29 (m, 2H).

3) Step c: Synthesis of tert-butyl ((S)-1-(((S)-1-(3-([1,1'-biphenyl]-4-ylmethyl)-1,2,4-oxadiazol-5-yl)-2-(1H-indol-3-yl)ethyl)amino)-3-(4-hydroxy-2,6-dimethylphenyl)-1-oxopropan-2-yl)carbamate (57)

The same procedure as described in Scheme 55 by using 12y (0.5 g, 1.16 mmol) and 38 (0.395 g, 1.276 mmol) to give 57 (0.584 g) as brown solid.

$^1$H NMR (400 MHz, Methanol-d$_4$) δ7.56 (m, 2H), 7.53-7.50 (m, 2H), 7.40 (q, J=7.7 Hz, 3H), 7.34-7.28 (m, 2H), 7.22 (m, 2H), 7.05 (t, J=7.6 Hz, 1H), 6.96-6.92 (m, 2H), 6.34 (s, 2H), 5.47 (t, J=7.3 Hz, 1H), 4.22 (t, J=7.7 Hz, 1H), 4.04 (s, 2H), 3.35 (s, 2H), 2.94 (dd, J=14.1, 8.6 Hz, 1H), 2.74 (dd, J=14.2, 7.2 Hz, 1H), 2.14 (s, 6H), 1.38 (s, 9H).

4) Step d: Synthesis of (S)-N-((S)-1-(3-([1,1'-biphenyl]-4-ylmethyl)-1,2,4-oxadiazol-5-yl)-2-(1H-imidazol-4-yl)ethyl)-2-amino-3-(4-hydroxy-2,6-dimethylphenyl)propanamide (58)
The same procedure as described in Scheme 55 by using 57 (0.2 g, 0.292 mmol) to give 58 (0.148 g). Obtained residue of desired product was used in next step without futher purification.

$^1$H NMR (400 MHz, Methanol-d$_4$) δ7.59-7.51 (m, 4H), 7.45-7.28 (m, 5H), 7.22-7.19 (m, 2H), 7.06 (ddd, J=8.2, 7.1, 1.1 Hz, 1H), 6.94 (ddd, J=7.9, 7.2, 0.9 Hz, 1H), 6.83 (s, 1H), 6.34 (s, 2H), 5.56-5.50 (m, 1H), 4.05 (d, J=3.4 Hz, 2H), 3.88 (dd, J=11.1, 5.1 Hz, 1H), 3.28-3.23 (m, 2H), 3.14 (dd, J=13.9, 11.1 Hz, 1H), 2.96 (dd, J=14.0, 5.2 Hz, 1H), 2.10 (s, 6H).

5) Step e: Synthesis of tert-butyl ((R)-2-(((S)-1-(((S)-1-(3-([1,1'-biphenyl]-4-ylmethyl)-1,2,4-oxadiazol-5-yl)-2-(1H-indol-3-yl)ethyl)amino)-3-(4-hydroxy-2,6-dimethylphenyl)-1-oxopropan-2-yl)amino)-1-(1-carbamimidoylpiperidin-4-yl)-2-oxoethyl)carbamate (6al)

The same procedure as described in Scheme 36 by using 58 (0.148 g, 0.201 mmol) and 1d (0.066 g, 0.183 mmol) to give 6al (0.115 g).

¹H NMR (400 MHz, Methanol-d₄) δ7.51 (m, 4H), 7.39 (m, 3H), 7.29 (m, 2H), 7.22 (m, 2H), 7.05 (t, J=7.2 Hz, 1H), 6.93 (m, 2H), 6.36 (s, 2H), 5.44 (t, J=7.5 Hz, 1H), 4.78-4.73 (m, 1H), 4.03 (s, 2H), 3.82-3.73 (m, 1H), 3.77 (d, J=36.3 Hz, 2H), 3.39 (dd, J=18.1, 7.3 Hz, 1H), 3.01 (dd, J=13.7, 7.1 Hz, 1H), 2.95-2.66 (m, 5H), 2.27-2.21 (m, 1H), 2.16 (s, 6H), 1.80-1.70 (s, 1H), 1.54-1.45 (m, 1H), 1.38 (s, 9H), 1.22-1.10 (m, 2H).

6) Step f: Synthesis of (S)-N-((S)-1-(3-([1,1'-biphenyl]-4-ylmethyl)-1,2,4-oxadiazol-5-yl)-2-(1H-indol-3-yl)ethyl)-2-((R)-2-amino-2-(1-carbamimidoylpiperidin-4-yl)acetamido)-3-(4-hydroxy-2,6-dimethylphenyl)propanamide (7ap)

The same procedure as described in Scheme 36 by using 6al (0.105 g, 0.113 mmol) to give 7ap (29 mg) as white solid. (HPLC purity is 97.7% at 210 nm).

¹H NMR (400 MHz, Methanol-d₄) δ7.51-7.46 (m, 4H), 7.42-7.36 (m, 3H), 7.31-7.27 (m, 2H), 7.23 (d, J=8.3 Hz, 2H), 7.06 (t, J=8.1 Hz, 1H), 6.98-6.90 (m, 2H), 6.35 (s, 2H), 5.47-5.43 (m, 1H), 4.04 (s, 2H), 3.86 (d, J=13.7 Hz, 2H), 3.72 (d, J=5.8 Hz, 1H), 3.38 (dd, J=14.4, 8.2 Hz, 1H), 3.00-2.91 (m, 3H), 2.81 (dd, J=14.4, 8.7 Hz, 1H), 2.17 (s, 6H), 1.93-1.83 (m, 1H), 1.54 (d, J=13.2 Hz, 1H), 1.44 (d, J=11.6 Hz, 1H), 1.30-1.18 (m, 3H). MS: EI-MS: m/z 768.6 [M+1].

Example 73: Synthesis of (R)-N-((S)-1-(((S)-1-(3-(adamantan-1-ylmethyl)-1,2,4-oxadiazol-5-yl)-2-(1H-indol-3-yl)ethyl)amino)-3-(4-hydroxy-2,6-dimethylphenyl)-1-oxopropan-2-yl)-2-amino-4-guanidinobutanamide (D-Agb-DMT-NH((S)-1-(3-(adamantan-1-yl)methyl-1,2,4-oxadiazol-5-yl)-2-(1H-indol-3 yl)eth-1-yl), 7aq)

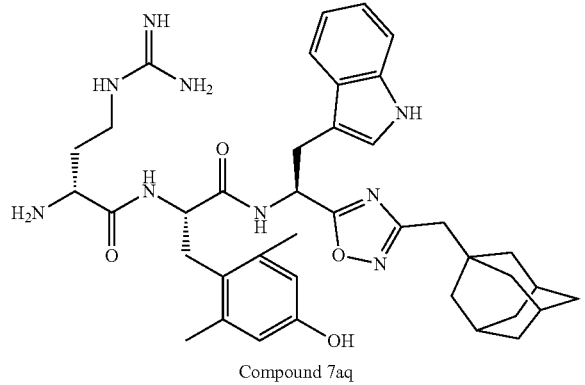

Compound 7aq

Scheme 74

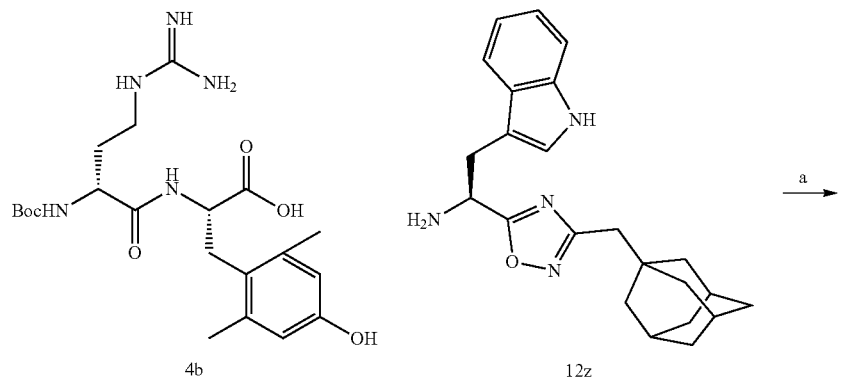

4b     12z

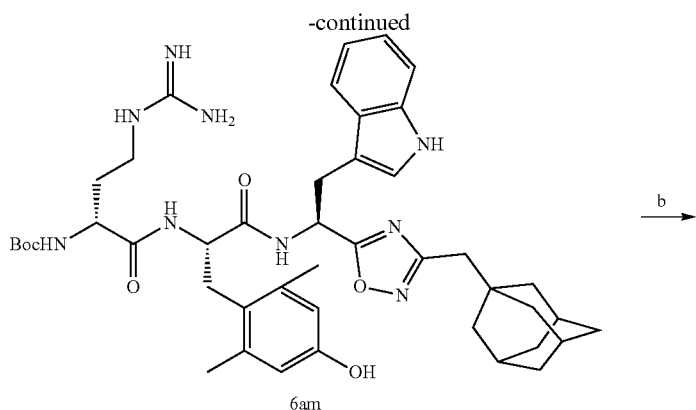

6am

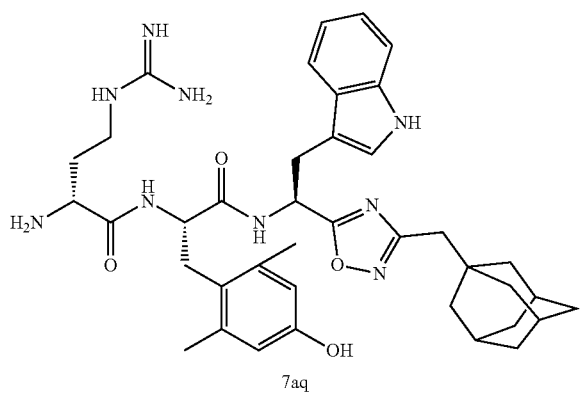

7aq

1) Step a: Synthesis of tert-butyl ((R)-1-(((S)-1-(((S)-1-(3-(adamantan-1-ylmethyl)-1,2,4-oxadiazol-5-yl)-2-(1H-indol-3-yl)ethyl)amino)-3-(4-hydroxy-2,6-dimethylphenyl)-1-oxopropan-2-yl)amino)-3-(4-hydroxy-2,6-dimethylphenyl)-1-oxopropan-2-yl)amino)-4-guanidino-1-oxobutan-2-yl) carbamate (6am)

The same procedure as described in Scheme 36 by using 4b (320 mg; 0.71 mmol) and 12z (339 mg; 0.9 mmol) to give 6am (148 mg, 26%) of white foam.

$^1$H NMR (300 MHz, Methanol-$d_4$) δ7.50 (d, J=7.8 Hz, 1H), 7.31 (d, J=7.9 Hz, 1H), 7.08 (t, J=7.5 Hz, 1H), 7.01 (multiple peaks, 2H), 6.36 (s, 2H), 5.53 (dd, J=8.6, 6.7 Hz, 1H), 4.64 (t, J=7.9 Hz, 1H), 4.09 (dd, J=7.5, 5.8 Hz, 1H), 3.49-3.28 (multiple peaks overlapping with CD$_2$HOD, 2H), 3.26-2.98 (multiple peaks, 3H), 2.88 (dd, J=14.1, 7.5 Hz, 1H), 2.42 (multiple peaks, 2H), 2.20 (s, 6H), 2.05 (s, 3H), 2.07-1.89 (multiple peaks, 4H), 1.84-1.65 (multiple peaks, 4H), 1.65-1.53 (multiple peaks, 3H), 1.53-1.33 (multiple peaks, 15H).

2) Step b: Synthesis of (R)-N-((S)-1-(((S)-1-(3-(adamantan-1-ylmethyl)-1,2,4-oxadiazol-5-yl)-2-(1H-indol-3-yl)ethyl)amino)-3-(4-hydroxy-2,6-dimethylphenyl)-1-oxopropan-2-yl)-2-amino-4-guanidinobutanamide (7aq)

The same procedure as described in Scheme 36 by using 6am (142 mg; 0.16 mmol) to give 7aq (30 mg, 23%) as a yellowish solid.

$^1$H NMR (400 MHz, Methanol-$d_4$) δ7.46 (d, J=7.8 Hz, 1H), 7.27 (d, J=8.0 Hz, 1H), 7.04 (t, J=7.2 Hz, 1H), 7.01-6.91 (multiple peaks, 2H), 6.31 (s, 2H), 5.49 (dd, J=8.9, 6.5 Hz, 1H), 4.70 (t, J=7.9 Hz, 1H), 4.01 (t, J=6.7 Hz, 1H), 3.37 (dd, J=14.4, 9.0 Hz, 1H), 3.29 (dd, 1H), 3.12 (t, J=7.4 Hz, 2H), 3.05 (dd, J=14.1, 9.0 Hz, 1H), 2.88 (dd, J=14.0, 7.4 Hz, 1H), 2.38 (multiple peaks, 2H), 2.18 (s, 6H), 2.07-1.89 (multiple peaks, 2H), 1.86 (bs, 3H), 1.66 (bd, J=11.7 Hz, 3H), 1.54 (bd, J=12.3 Hz, 3H), 1.41 (bs, 6H). MS: EI-MS: m/z 710.7 [M+1].

Example 74: Synthesis of (R)-2-amino-N-((R)-1-
(((S)-5-amino-1-(3-benzyl-1,2,4-oxadiazol-5-yl)
pentyl)amino)-3-(4-hydroxy-2,6-dimethylphenyl)-1-
oxopropan-2-yl)-5-guanidinopentanamide (D-Arg-
D-DMT-NH((S)-5-amino-1-(3-benzyl-1,2,4-
oxadiazol-5-yl)pent-1-yl), 7ar)
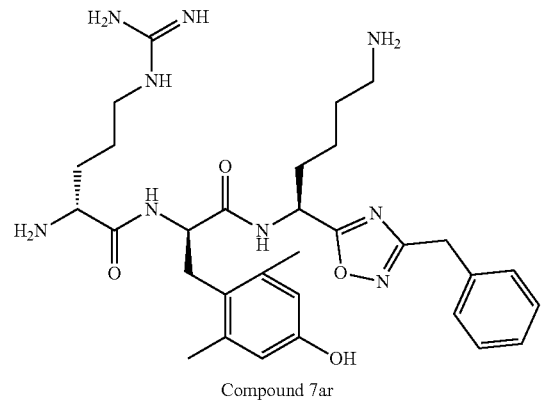
Compound 7ar
Scheme 75
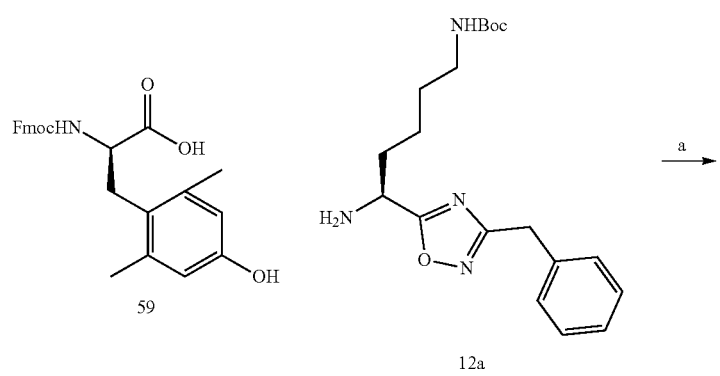
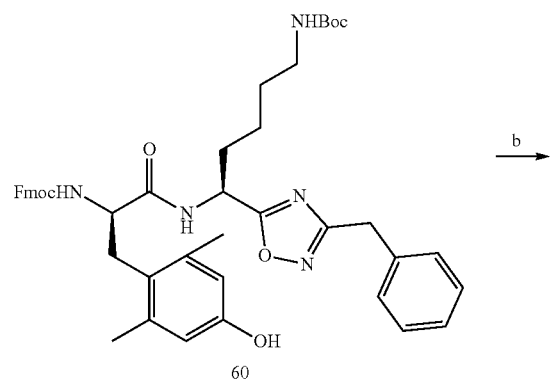

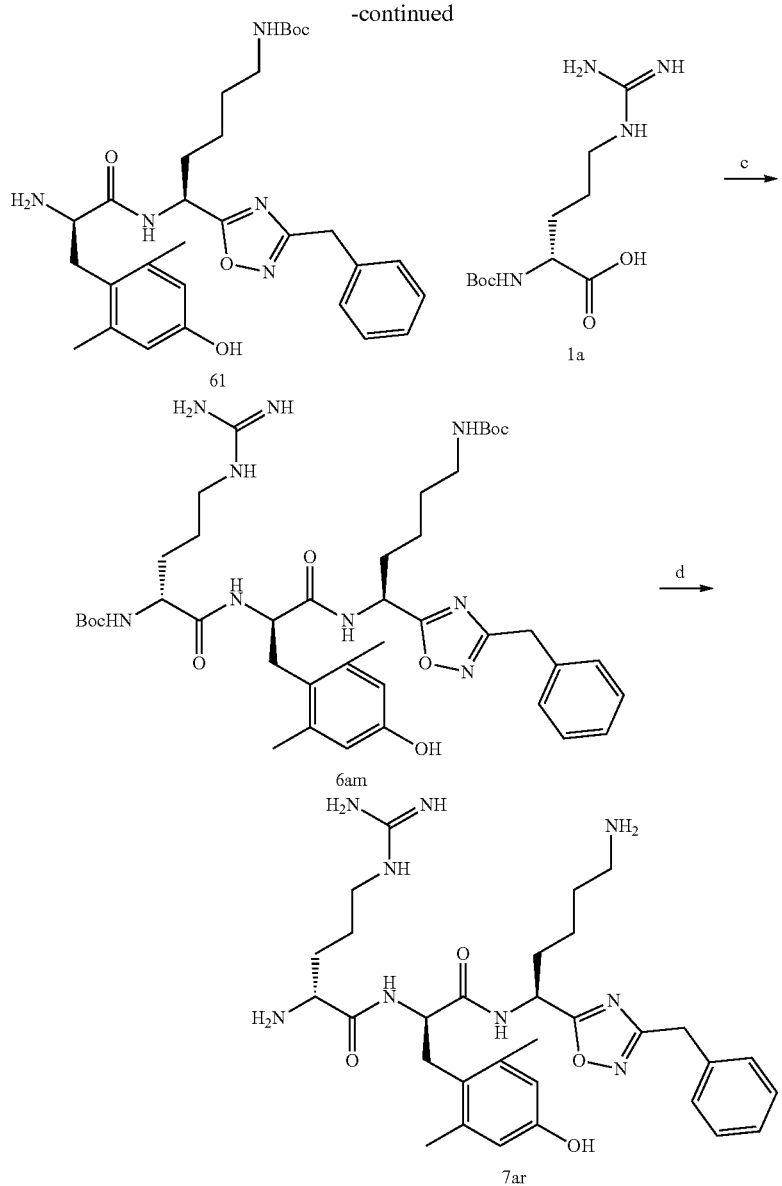

1) Step a: Synthesis of (9H-fluoren-9-yl)methyl ((R)-1-(((S)-1-(3-benzyl-1,2,4-oxadiazol-5-yl)-5-((tert-butoxycarbonyl)amino)pentyl)amino)-3-(4-hydroxy-2,6-dimethylphenyl)-1-oxopropan-2-yl)carbamate (60)

(R)-Fmoc-DMT (59, 2.35 g; 5.6 mmol), 12a (2.40 g; 4.5 mmol) and HOBT hydrate (0.92 g; 6.0 mmol) were dissolved in dry DMF (25 mL), and then N-methylmorpholine (300 µL; 2.3 mmol) was added dropwise. Solution was cooled to 0° C. and EDCI (2.68 g; 14.0 mmol) was added in one portion. Reaction was warmed to ambient temperature over the course of 4 hours. At this point LC-MS analysis showed complete consumption of the starting materials and formation of the desired product. Reaction was partitioned between EtOAc (250 mL) and water (100 mL). Organic phase was separated and washed with sat. aq NaHCO$_3$ (2×50 mL) and with brine (100 mL). Organic phase was dried over Na$_2$SO$_4$, filtered and evaporated under reduced pressure. 3.56 g (60, ~100%) of white foam was obtained. HPLC and LC-MS showed sufficiently pure material. Reaction product was used in the next step without further purification and characterization.

2) Step b: Synthesis of tert-butyl ((S)-5-((R)-2-amino-3-(4-hydroxy-2,6-dimethylphenyl)propanamido)-5-(3-benzyl-1,2,4-oxadiazol-5-yl)pentyl)carbamate (61)

60 (3.56 g; ~4.5 mmol) was dissolved in dry DCM (35 mL). Piperidine (20 mL) was added dropwise. After 30 min LC-MS showed complete conversion. Volatiles were removed under reduced pressure and residue was purified by silica gel column chromatography (mobile phase hexanes/EtOAc/MeOH with gradient 1/1/0→0/1/0→0/10/1). 1.70 g (66%) of white foam (61) was obtained. HPLC and LC-MS showed sufficiently pure material. Reaction product was used in the next step without further purification and characterization.

3) Step c: Synthesis of tert-butyl ((6R,9R,12S)-1-amino-12-(3-benzyl-1,2,4-oxadiazol-5-yl)-9-(4-hydroxy-2,6-dimethylbenzyl)-1-imino-20,20-dimethyl-7,10,18-trioxo-19-oxa-2,8,11,17-tetraazahenicosan-6-yl)carbamate (6an)

61 (1.00 g; 1.81 mmol), Boc-D-Arginine (1a, 777 mg; 2.5 mmol) and HOBT hydrate (276 mg; 1.8 mmol) were dissolved in dry DMF (10 mL). Solution was cooled to 0° C. and EDCI (959 mg; 5.0 mmol) was added in one portion. Reaction was warmed to ambient temperature over the course of 4 hours. At this point LC-MS analysis showed complete consumption of the starting materials and formation of the desired product. Reaction was partitioned between EtOAc (250 mL) and water (100 mL). Organic phase was separated and washed with sat. aq NaHCO$_3$ (4×50 mL) and with brine (100 mL). Organic phase was dried over Na$_2$SO$_4$, filtered and evaporated under reduced pressure. 1.40 g (6an, 91%) of white foam was obtained. HPLC and LC-MS showed sufficiently pure material. Reaction product was used in the next step without further purification and characterization.

4) Step d: Synthesis of (R)-2-amino-N-((R)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (7ar)

The same procedure as described in Scheme 36 by using 6an (1.40 g; 1.66 mmol) to give 7ar (675 mg, 57%) as a white solid.

$^1$H NMR (400 MHz, Methanol-d$_4$) δ7.34-7.19 (multiple peaks, 5H), 6.50 (s, 2H), 4.93 (dd, J=9.3, 5.0 Hz, 1H), 4.62 (dd, J=11.6, 4.8 Hz, 1H), 4.02 (apparent s, 2H), 3.99 (t, J=6.2 Hz, 1H), 3.26-3.09 (multiple peaks, 3H), 2.90 (dd, J=13.9, 4.8 Hz, 1H), 2.84 (m, 2H), 2.28 (s, 6H), 1.98-1.82 (multiple peaks, 2H), 1.81-1.45 (multiple peaks, 6H), 1.05-0.82 (multiple peaks, 2H). MS: EI-MS: m/z 608.5 [M+1].

Example 75: Synthesis of (S)-2-amino-N-((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (Arg-DMT-NH((S)-5-amino-1-(3-benzyl-1,2,4-oxadiazol-5 yl)pent-1-yl), 7as)

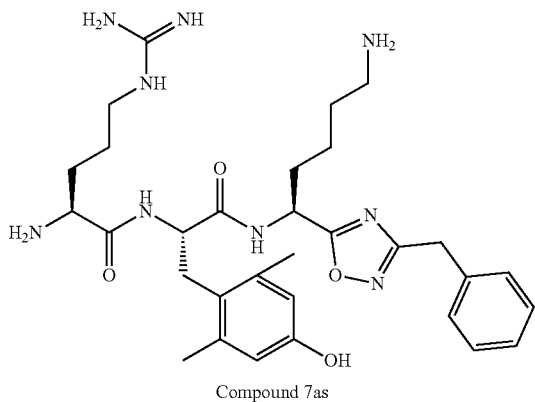

Compound 7as

Scheme 76

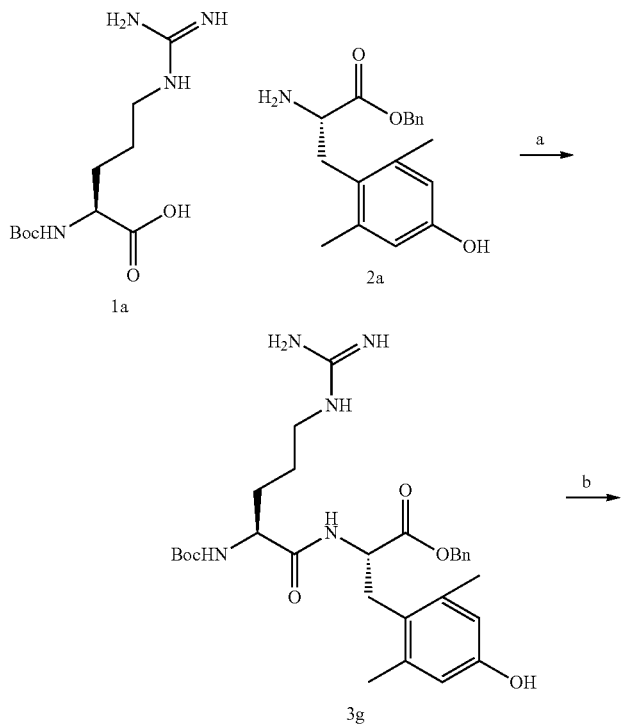

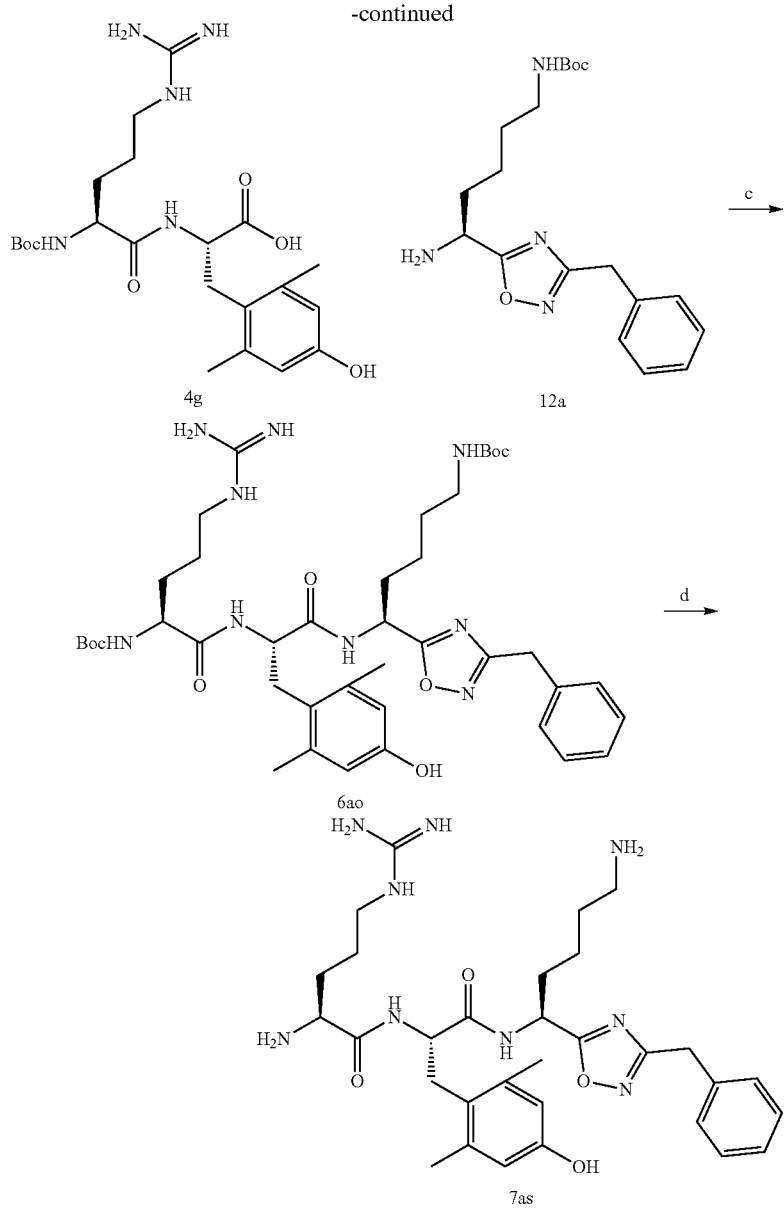

1) Step a: Synthesis of benzyl (S)-2-((S)-2-((tert-butoxycarbonyl)amino)-5-guanidinopentanamido)-3-(4-hydroxy-2,6-dimethylphenyl)propanoate (3g)

The same procedure as described in Scheme 36 by using 1e (4.00 g; 12.2 mmol) and 2a (3.0 g; 10.0 mmol) to give 3g (5.6 g, 95%) of white foam. LC-MS, HPLC and NMR showed sufficiently pure product. Reaction product was used in the next step without further purification.

$^1$H NMR (300 MHz, Methanol-$d_4$) δ7.31 (multiple peaks, 3H), 7.14 (m, 2H), 6.45 (s, 2H), 5.07-4.97 (multiple peaks, 2H), 4.70 (t, J=8.1 Hz, 1H), 4.09 (m, 1H), 3.23-3.11 (multiple peaks, 3H), 3.01 (dd, J=14.2, 7.7 Hz, 1H), 2.24 (s, 6H), 1.85-1.53 (multiple peaks, 4H), 1.47 (s, 9H).

2) Step b: Synthesis of (S)-2-((S)-2-((tert-butoxycarbonyl)amino)-5-guanidinopentanamido)-3-(4-hydroxy-2,6-dimethylphenyl)propanoic acid (4g)

The same procedure as described in Scheme 36 by using 3g (5.6 g; 9.5 mmol) to give 4g (4.6 g, 95%) of a white solid was obtained. LC-MS, NMR and HPLC showed sufficiently pure material. Reaction product was used in the next step without further purification.

$^1$H NMR (400 MHz, Methanol-$d_4$) δ6.41 (s, 2H), 4.61 (t, J=7.7 Hz, 1H), 4.00 (t, J=6.6 Hz, 1H), 3.19-3.06 (multiple peaks, 3H), 2.93 (dd, J=14.3, 8.8 Hz, 1H), 2.26 (s, 6H), 1.71-1.46 (multiple peaks, 4H), 1.42 (s, 9H).

3) Step c: Synthesis of tert-butyl ((6S,9S,12S)-1-amino-12-(3-benzyl-1,2,4-oxadiazol-5-yl)-9-(4-hydroxy-2,6-dimethylbenzyl)-1-imino-20,20-dimethyl-7,10,18-trioxo-19-oxa-2,8,11,17-tetraazahenicosan-6-yl)carbamate (6ao)

The same procedure as described in Scheme 36 by using 4g (700 mg; 1.39 mmol) and 12a (586 mg; 1.10 mmol) to give 6ao (750 mg, 81%) of white foam. HPLC and LC-MS showed pure material.

$^1$H NMR (400 MHz, Methanol-$d_4$) δ7.30-7.15 (m, 511), 6.33 (s, 2H), 5.07 (dd, J=8.4, 6.4 Hz, 1H), 4.44 (dd, J=9.6, 5.9 Hz, 1H), 4.08-3.99 (m, 3H), 3.14 (t, J=6.9 Hz, 2H), 3.03

(dd, J=14.0, 10.0 Hz, 1H), 2.95 (t, J=6.3 Hz, 2H), 2.80 (dd, J=14.0, 5.8 Hz, 1H), 2.13 (s, 6H), 1.79-1.49 (m, 10H), 1.43 (s, 9H), 1.39 (s, 9H).

4) Step d: Synthesis of (S)-2-amino-N-((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (7as)

The same procedure as described in Scheme 36 by using 6ao (740 mg; 0.87 mmol) to give 7as (300 mg, 45%) as a white solid.

$^1$H NMR (400 MHz, Methanol-$d_4$) δ7.35-7.12 (m, 5H), 6.34 (s, 2H), 5.04 (dd, J=8.6, 6.2 Hz, 1H), 4.39 (dd, J=11.2, 4.7 Hz, 1H), 4.07 (d, J=15.4 Hz, 1H), 4.02 (d, J=15.3 Hz, 1H), 3.97 (t, J=6.3 Hz, 1H), 3.23 (t, J=7.0 Hz, 2H), 3.11 (dd, J=13.8, 11.3 Hz, 1H), 2.86 (m, 3H), 2.13 (s, 6H), 1.98-1.89 (m, 2H), 1.88-1.53 (m, 6H), 1.41-1.19 (m, 2H). MS: EI-MS: m/z 608.3 [M+1].

Example 76: Synthesis of (S)-2-amino-N-((R)-1-(((S)-5-amino-1-(3-benzyl-1,2,4-oxadiazol-yl)pentyl)amino)-3-(4-hydroxy-2,6-dimethylphenyl)-1-oxopropan-2-yl)-5-guanidinopentanamide (Arg-D-DMT-NH((S)-5-amino-1-(3-benzyl-1,2,4-oxadiazol-5-yl)pent-1-yl), 7at)

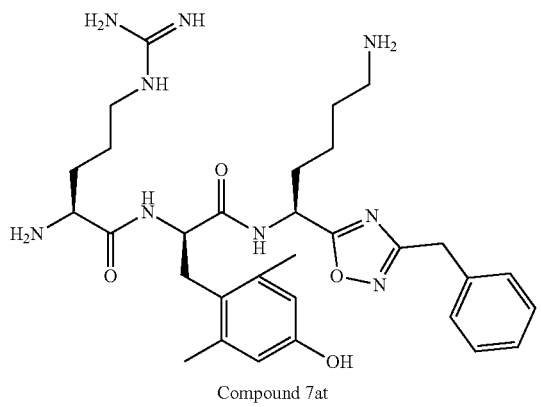

Compound 7at

Scheme 77

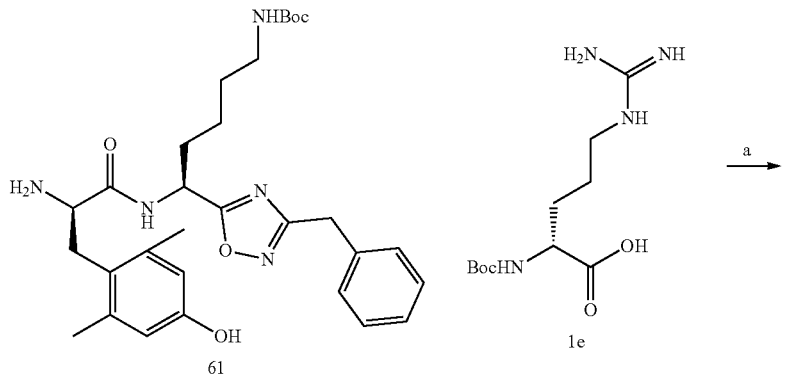

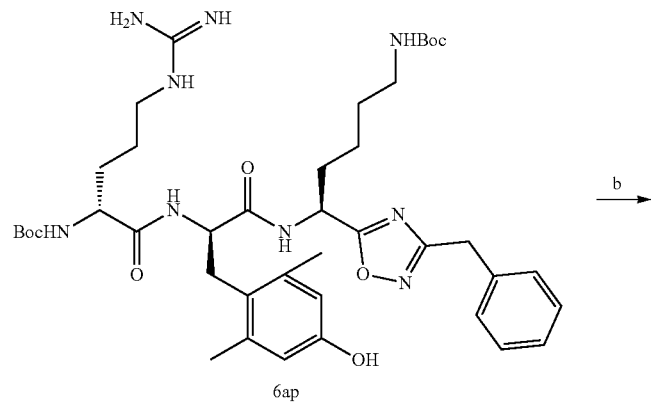

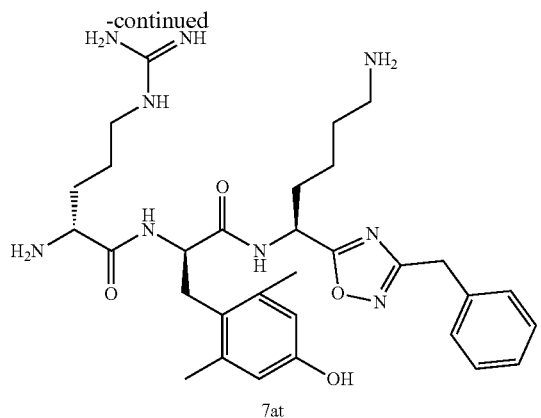

7at

1) Step a: Synthesis of (9H-fluoren-9-yl)methyl ((R)-1-(((S)-1-(3-benzyl-1,2,4-oxadiazol-5-yl)-5-((tert-butoxycarbonyl)amino)pentyl)amino)-3-(4-hydroxy-2,6-dimethylphenyl)-1-oxopropan-2-yl)carbamate (6ap)

The same procedure as described in Scheme 76 and Scheme 36 by using 61 (300 mg, 0.544 mmol) and 1e (197 mg, 0.599 mmol) to give 6ap (400 mg) in 85% yield.

$^1$H NMR (400 MHz, CD$_3$OD): δ=7.32-7.20 (m, 5H), 6.46 (s, 2H), 5.09-5.01 (m, 1H), 4.71-4.65 (m, 1H), 4.04 (s, 2H), 3.98-3.91 (m, 1H), 3.16-3.06 (m, 3H), 3.00-2.94 (m, 2H), 2.94-2.86 (m, 1H), 2.28 (s, 6H), 1.88-1.29 (m, 26H), 1.18-1.05 ppm (m, 2H).

2) Step b: Synthesis of (R)-2-amino-N-((R)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (7at)

The same procedure as described in Scheme 36 by using 6ap (400 mg, 0.461 mmol) to give 7at (80 mg) in 23% yield. HPLC purity of the product was 97.4%.

$^1$H NMR (400 MHz, CD$_3$OD): δ=7.33-7.20 (m, 5H), 6.49 (s, 2H), 5.07-5.01 (m, 1H), 4.80-4.74 (m, 1H), 4.08-3.99 (m, 2H), 3.96-3.91 (m, 1H), 3.23-3.11 (m, 3H), 2.97-2.83 (m, 3H), 2.31 (s, 6H), 1.90-1.44 (m, 8H), 1.16-1.05 ppm (m, 2H). MS: EI-MS: m/z 608.5 [M+1].

Example 77: Synthesis of (R)-2-amino-N-((R)-1-(((R)-5-amino-1-(3-benzyl-1,2,4-oxadiazol-5 yl)pentyl)amino)-3-(4-hydroxy-2,6-dimethylphenyl)-1-oxopropan-2-yl)-5-guanidinopentanamide (D-Arg-D-DMT-NH((R)-5-amino-1-(3-benzyl-1,2,4-oxadiazol-5-yl)pent-1-yl), 7au)

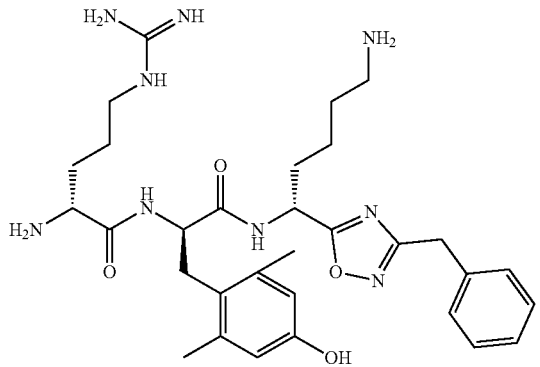

Compound 7au

-continued
Scheme 78
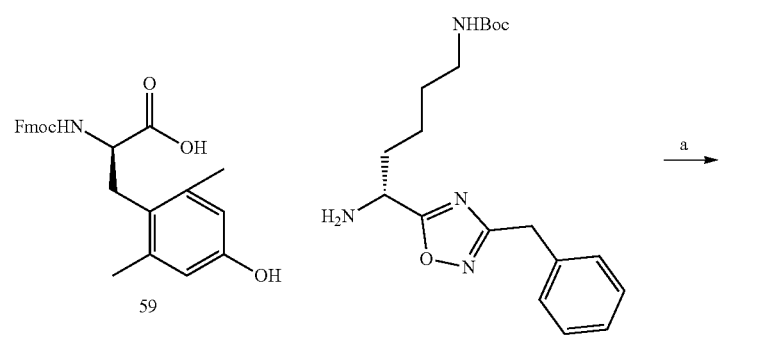
59    5o
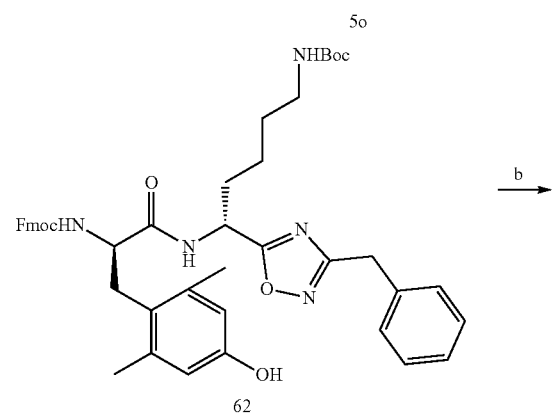
62
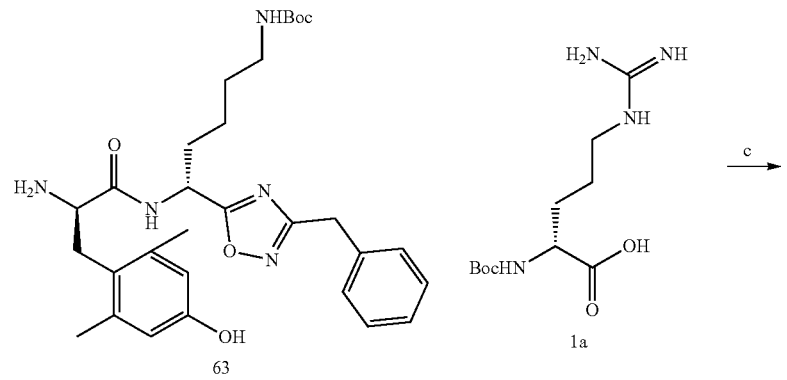
63    1a
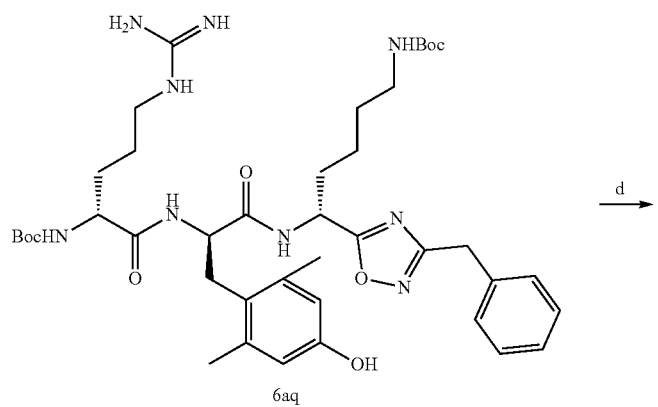
6aq

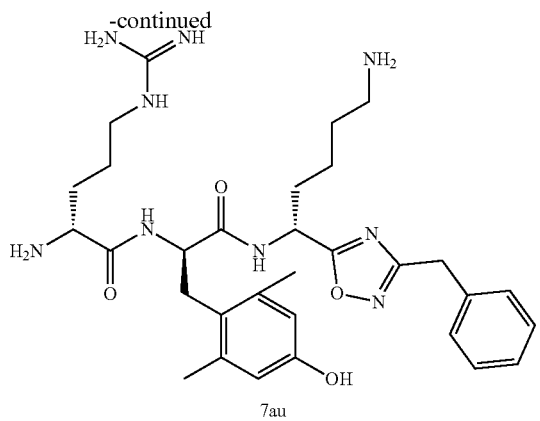

7au

1) Step a: Synthesis of (9H-fluoren-9-yl)methyl ((R)-1-(((R)-1-(3-benzyl-1,2,4-oxadiazol-5-yl)-5-((tert-butoxycarbonyl)amino)pentyl)amino)-3-(4-hydroxy-2,6-dimethylphenyl)-1-oxopropan-2-yl)carbamate (62)

The same procedure as described in Scheme 76 by using 59 (1.84 g; 4.4 mmol) and 5o (1.58 g; 4.4 mmol) to give 62 (3.20 g, ~96%) of white foam was obtained. HPLC and LC-MS showed sufficiently pure material. Reaction product was used in the next step without further purification and characterization.

2) Step b: Synthesis of tert-butyl ((R)-5-((R)-2-amino-3-(4-hydroxy-2,6-dimethylphenyl)propanamido)-5-(3-benzyl-1,2,4-oxadiazol-5-yl)pentyl)carbamate (63)

The same procedure as described in Scheme 77 by using 62 (3.20 g; 4.2 mmol) to give 63 (1.20 g, 52%) of white foam. HPLC and LC-MS showed sufficiently pure material. Reaction product was used in the next step without further purification and characterization.

3) Step c: Synthesis of tert-butyl ((6R,9R,12R)-1-amino-12-(3-benzyl-1,2,4-oxadiazol-5-yl)-9-(4-hydroxy-2,6-dimethylbenzyl)-1-imino-20,20-dimethyl-7,10,18-trioxo-19-oxa-2,8,11,17-tetraazahenicosan-6-yl)carbamate (6aq)

The same procedure as described in Scheme 77 by using 63 (1.20 g; 2.18 mmol) and 1a (777 mg; 2.5 mmol) to give 6aq (1.67 g, 91%) of white foam. HPLC and LC-MS showed sufficiently pure material. Reaction product was used in the next step without further purification and characterization.

4) Step d: Synthesis of (R)-2-amino-N-((R)-1-(((R)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (7au)

The same procedure as described in Scheme 36 by using 6aq (1.67 g; 1.98 mmol) to give 7au (793 mg, 56%) as white solid.

$^1$H NMR (400 MHz, Methanol-$d_4$) δ7.37-7.15 (multiple peaks, 5H), 6.36 (s, 2H), 5.04 (dd, J=8.8, 6.2 Hz, 1H), 4.40 (dd, J=11.2, 4.7 Hz, 1H), 4.09 (d, J=15.4 Hz, 1H), 4.04 (d, J=15.3 Hz, 1H), 3.99 (t, J=6.3 Hz, 1H), 3.24 (t, J=7.0 Hz, 2H), 3.12 (dd, J=13.8, 11.3 Hz, 1H), 2.93-2.80 (multiple peaks, 3H), 2.14 (s, 6H), 2.00-1.53 (multiple peaks, 8H), 1.43-1.17 (multiple peaks, 2H). MS: EI-MS: m/z 608.4 [M+1].

Example 78: Synthesis of (S)-2-amino-N-((S)-1-(((R)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (Arg-DMT-NH((R)-5-amino-1-(3-benzyl-1,2,4-oxadiazol-5-yl)pent-1-yl), 7av)

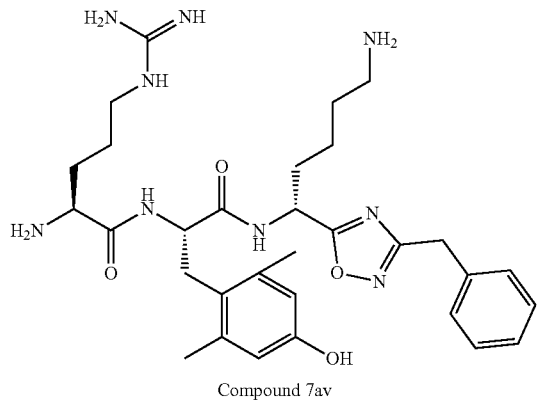

Compound 7av

-continued
Scheme 79

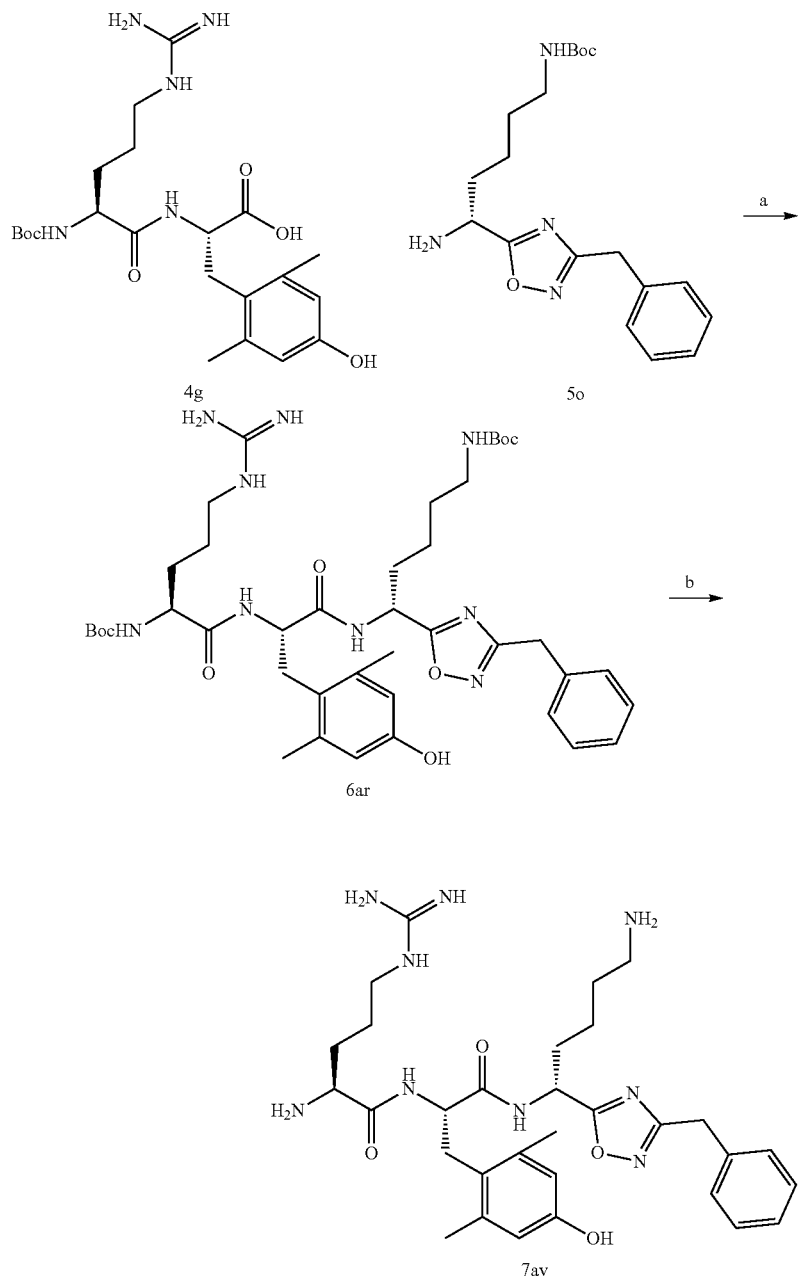

1) Step a: Synthesis of tert-butyl (((6S,9S,12R)-1-amino-12-(3-benzyl-1,2,4-oxadiazol-5-yl)-9-(4-hydroxy-2,6-dimethylbenzyl)-1-imino-20,20-dimethyl-7,10,18-trioxo-19-oxa-2,8,11,17-tetraazahenicosan-6-yl)carbamate (6ar)

The same procedure as described in Scheme 36 by using 4g (803 mg; 1.60 mmol) and 5o (477 mg; 1.32 mmol) to give 6ar (934 mg, 84%) of white foam. HPLC and LC-MS showed sufficiently pure material. Reaction product was used in the next step without further purification.

$^1$H NMR (400 MHz, Methanol-$d_4$) δ7.34-7.16 (m, 4H), 6.45 (s, 2H), 5.02-4.90 (m, 1H), 4.59 (dd, J=9.2, 6.5 Hz, 1H), 4.05-3.95 (m, 3H), 3.15-3.05 (m, 3H), 2.95 (t, J=7.0 Hz, 2H), 2.88 (dd, J=13.9, 6.4 Hz, 1H), 2.25 (s, 6H), 1.81-1.42 (m, 6H), 1.40 (s, 9H), 1.37 (s, 9H), 1.16-0.92 (m, 2H).

2) Step b: Synthesis of (S)-2-amino-N-((S)-1-(((R)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (7av)

The same procedure as described in Scheme 36 by using 6ar (930 mg; 1.10 mmol) to give 7av (310 mg, 39%) as a white solid.

$^1$H NMR (400 MHz, Methanol-$d_4$) δ7.34-7.14 (m, 5H), 6.48 (s, 2H), 4.92 (dd, J=9.6, 5.1 Hz, 1H), 4.61 (dd, J=11.7, 4.8 Hz, 1H), 4.00 (s, 2H), 3.96 (t, J=6.2 Hz, 1H), 3.20 (dd, J=13.7, 11.7 Hz, 1H), 3.13 (t, J=6.9 Hz, 2H), 2.88 (dd, J=13.9, 4.8 Hz, 1H), 2.85-2.77 (m, 2H), 2.27 (s, 6H), 1.96-1.80 (m, 2H), 1.80-1.43 (m, 6H), 1.02-0.82 (m, 2H). MS: EI-MS: m/z 608.3 [M+1].

Example 79: Synthesis of (S)-2-amino-N-((R)-1-(((R)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (Arg-D-DMT-NH((R)-5-amino-1-(3-benzyl-1,2,4-oxadiazol-5-yl)pent-1-yl), 7aw)
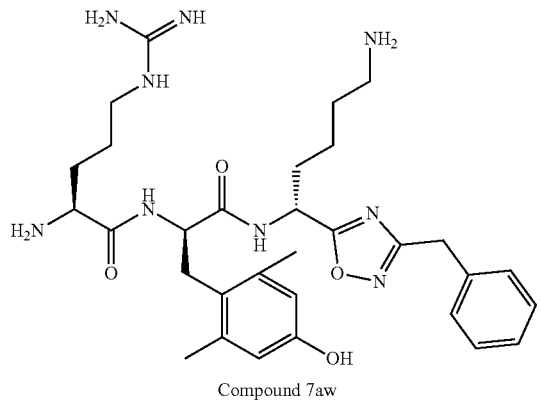
Compound 7aw
Scheme 80
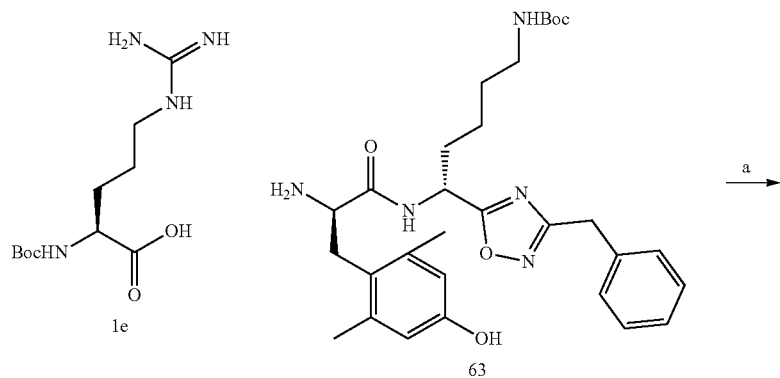
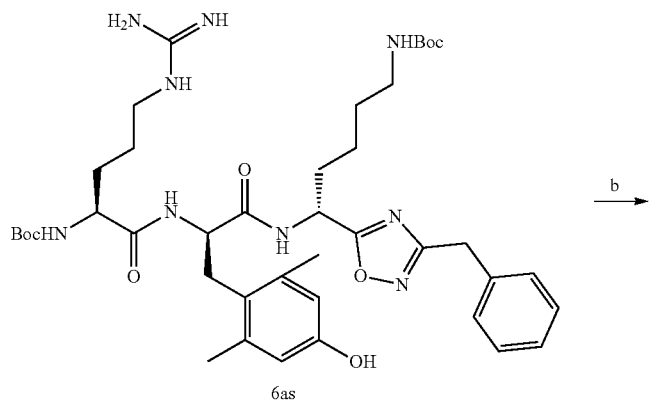

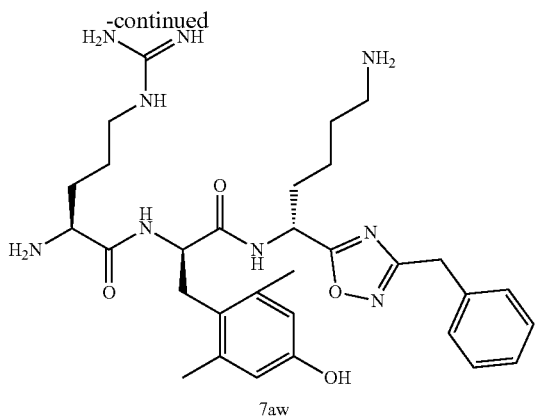
7aw

1) Step a: Synthesis of tert-butyl ((6S,9R,12R)-1-amino-12-(3-benzyl-1,2,4-oxadiazol-5-yl)-9-(4-hydroxy-2,6-dimethylbenzyl)-1-imino-20,20-dimethyl-7,10,18-trioxo-19-oxa-2,8,11,17-tetraazahenicosan-6-yl)carbamate (6as)

The same procedure as described in Scheme 77 by using 63 (200 mg, 0.363 mmol) and 1e (131 mg, 0.399 mmol) to give 6as (210 mg) in 67% yield. ¹H NMR (300 MHz, Methanol-d₄): =7.33-7.19 (m, 5H), 6.38 (s, 2H), 5.18-5.10 (m, 1H), 4.64-4.57 (m, 1H), 4.10-4.00 (m, 2H), 4.00-3.93 (m, 1H), 3.16-3.06 (m, 3H), 3.03-2.95 (m, 2H), 2.89-2.80 (m, 1H), 2.20 (s, 6H), 1.97-1.83 (m, 2H), 1.71-1.22 ppm (m, 26H).

2) Step b: Synthesis of (S)-2-amino-N-((R)-1-(((R)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (7aw)

The same procedure as described in Scheme 36 by using 6as (210 mg, 0.242 mmol) to give 7aw (154 mg) in 85% yield. HPLC purity of the product was 96.3%.
¹H NMR (300 MHz, Methanol-d₄): δ=7.35-7.19 (m, 5H), 6.39 (s, 2H), 5.17-5.10 (m, 1H), 4.71-4.65 (m, 1H), 4.12-4.02 (m, 2H), 3.96-3.90 (m, 1H), 3.19-3.05 (m, 3H), 2.91-2.83 (m, 3H), 2.21 (s, 6H), 1.99-1.28 ppm (m, 10H). MS: EI-MS: m/z 608.6 [M+1].

Example 80: Synthesis of (R)-2,5-diamino-N-((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)pentanamide (D-Org-DMT-NH ((S)-5-amino-1-(3-benzyl-1,2,4-oxadiazol-5-yl)pent-1-yl), 7ax)

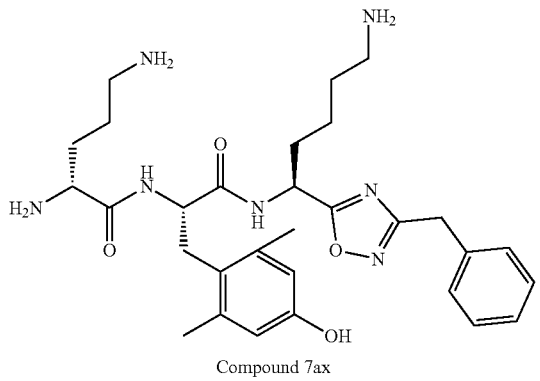
Compound 7ax

Scheme 81

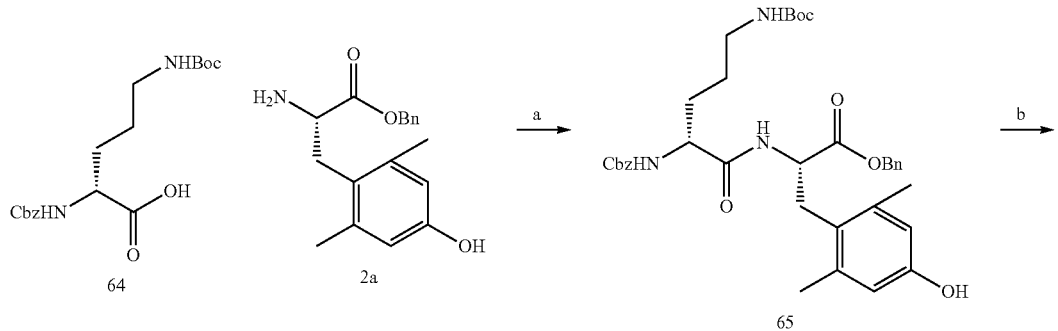

-continued
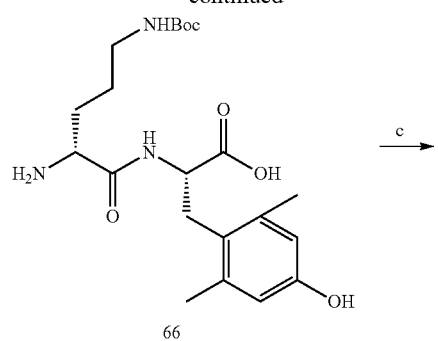
66
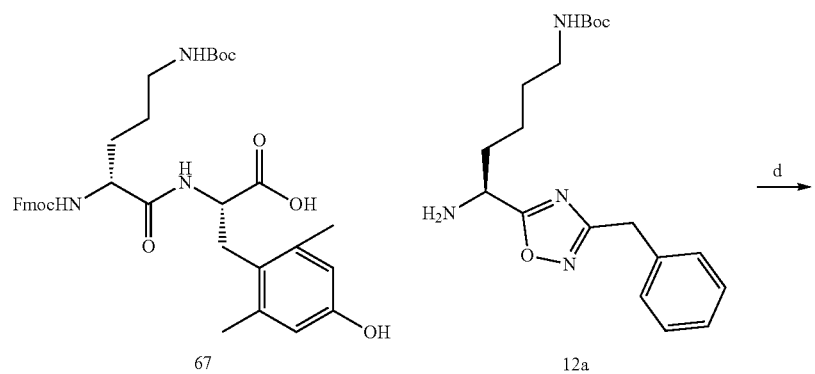
67  12a
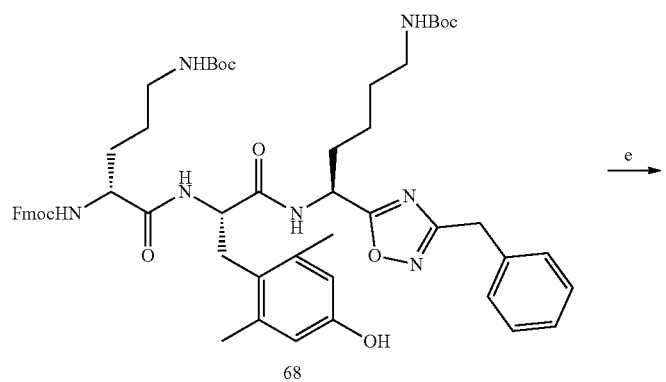
68
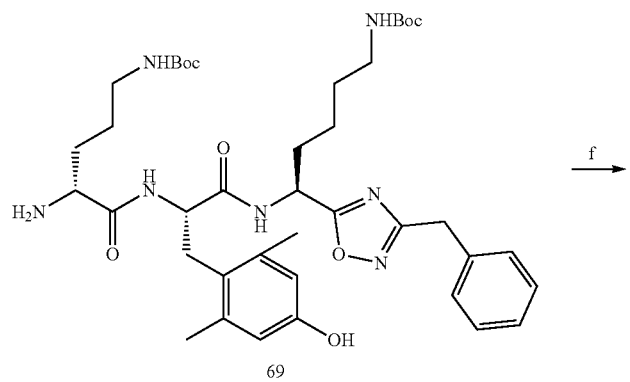
69

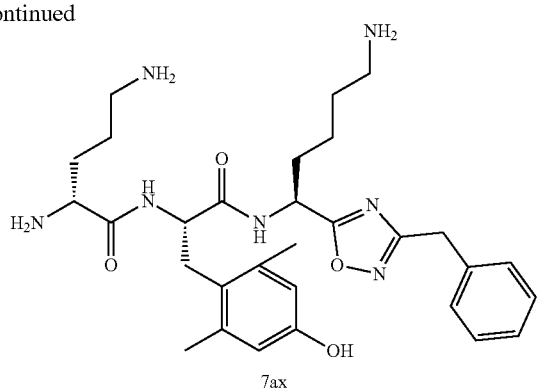

7ax

1) Step a: Synthesis of benzyl (S)-2-((R)-2-(((benzyloxy)carbonyl)amino)-5-((tert-butoxycarbonyl)amino)pentanamido)-3-(4-hydroxy-2,6-dimethylphenyl)propanoate (65)

(L)-DMT-OBn(HCl) (2a, 2.69 g; 8.0 mmol), N$^\alpha$-Z-N$^\delta$-Boc-D-ornithine (64, 602 mg; 1.2 mmol) and HOBT hydrate (1.23 g; 8.0 mmol) were dissolved in dry DMF (25 mL). N-methylmorpholine (880$\mu$L; 8.0 mmol) was added dropwise. Solution was cooled to 0° C. and EDCI (3.64 g; 19.0 mmol) was added in one portion. Reaction was warmed to ambient temperature over the course of 4 hours. At this point LC-MS analysis showed complete consumption of the starting materials and formation of the desired product. Reaction was partitioned between EtOAc (350 mL) and agHCl (1M; 100 mL). Organic phase was separated and washed with agHCl (1M; 100 mL) followed by sat. aq NaHCO$_3$ (2×150 mL) and brine (100 mL). Organic phase was dried over Na$_2$SO$_4$, filtered and evaporated under reduced pressure. 5.3 g (~100%) of 65 as white foam was obtained. HPLC and LC-MS showed sufficiently pure material. Reaction product was used in the next step without further purification and characterization.

2) Step b: Synthesis of (S)-2-((R)-2-amino-5-((tert-butoxycarbonyl)amino)pentanamido)-3-(4-hydroxy-2,6-dimethylphenyl)propanoic acid (66) 65 (5.3 g; 8.1 mmol) and Pd/C (10%; 800 mg) were suspended in EtOH (120 mL). Reaction mixture was stirred under 7 bars of hydrogen ~4 h. Reaction progress was monitored with LC-MS. Upon full conversion, reaction mixture was filtered through a pad of celite. Volatiles were removed under reduced pressure. 3.44 g (95%) of a white solid was obtained. LC-MS, NMR and HPLC showed sufficiently pure material. Reaction product 66 was used in the next step without further purification.

$^1$H NMR (300 MHz, Methanol-d$_4$) δ6.45 (s, 2H), 4.78 (dd, J=10.8, 5.5 Hz, 1H), 3.76 (t, J=6.4 Hz, 1H), 3.25 (dd, J=14.5, 5.6 Hz, 1H), 3.07-2.83 (m, 3H), 2.34 (s, 6H), 1.81-1.51 (multiple peaks, 2H), 1.47 (s, 9H), 1.14-0.91 (multiple peaks, 2H).

3) Step c: Synthesis of (S)-2-((R)-2-((((9H-fluoren-9-yl)methoxy)carbonyl)amino)-5-((tert-butoxycarbonyl)amino)pentanamido)-3-(4-hydroxy-2,6-dimethylphenyl)propanoic acid (67)

66 (3.40 g; 8.0 mmol) was suspended in THF (80 mL) and water (60 mL). NaHCO$_3$ (2.52 g; 30 mmol) and Fmoc-OSu (3.44 g; 10.2 mmol) were added. Reaction mixture was stirred at ambient temperature 16 h. At this point LC-MS showed complete conversion. Reaction was partitioned between EtOAc (350 mL) and agHCl (1M; 100 mL). Organic phase was separated and washed with aq HCl (1M; 100 mL) and brine (100 mL). Organic phase was dried over MgSO$_4$, filtered and evaporated under reduced pressure. 4.1 g (79%) of white solid (67) was obtained. HPLC and LC-MS showed sufficiently pure material. Reaction product was used in the next step without further purification and characterization.

4) Step d: Synthesis of (9H-fluoren-9-yl)methyl tert-butyl ((10S,13S,16R)-10-(3-benzyl-1,2,4-oxadiazol-5-yl)-13-(4-hydroxy-2,6-dimethylbenzyl)-2,2-dimethyl-4,12,15-trioxo-3-oxa-5,11,14-triazanonadecane-16,19-diyl)dicarbamate (68)

67 (4.10 g; 6.35 mmol), 12a (3.25 g; 6.1 mmol) and HOBT hydrate (1.23 g; 8.0 mmol) were dissolved in dry DMF (25 mL). N-methylmorpholine (880 μL; 8.0 mmol) was added dropwise. Solution was cooled to 0° C. and EDCI (3.64 g; 19.0 mmol) was added in one portion. Reaction was warmed to ambient temperature over the course of 4 hours. At this point LC-MS analysis showed complete consumption of the starting materials and formation of the desired product. Reaction was partitioned between EtOAc (350 mL) and agHCl (1M; 100 mL). Organic phase was separated and washed with agHCl (1M; 100 mL) followed by sat. aq NaHCO$_3$ (4×150 mL) and brine (100 mL). Organic phase was dried over MgSO$_4$, filtered and evaporated under reduced pressure. 5.90 g (94%) of white foam 68 was obtained. HPLC and LC-MS showed sufficiently pure material. Reaction product was used in the next step without further purification and characterization.

5) Step e: Synthesis of tert-butyl ((10S,13S,16R)-16-amino-10-(3-benzyl-1,2,4-oxadiazol-5-yl)-13-(4-hydroxy-2,6-dimethylbenzyl)-2,2-dimethyl-4,12,15-trioxo-3-oxa-5,11,14-triazanonadecan-19-yl)carbamate (69)

68 (5.90 g; 5.97 mmol) was dissolved in dry DCM (35 mL). Piperidine (20 mL) was added dropwise. After 30 min LC-MS showed complete conversion. Volatiles were removed under reduced pressure and residue was purified by silica gel column chromatography (mobile phase hexanes/EtOAc/MeOH with gradient 1/1/0→0/1/0→0/5/1). 2.90 g (63%) of amorphous solid 69 was obtained. HPLC and LC-MS showed sufficiently pure material. Reaction product was used in the next step without further purification and characterization.

6) Step f: Synthesis of (S)-2-amino-N-((S)-1-(((5)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (7ax)

TFA (15 mL) was added to a suspension of 69 (1.00 g; 1.31 mmol) in dry DCM (20 mL) at 0° C. Reaction mixture was stirred at 0° C. 6 h and then volatiles were removed under reduced pressure at 0° C. Purification was performed by reverse-phase flash chromatography (120 g C18 Biotage column; mobile phase 0.1% aq TFA/MeOH with gradient 5% MeOH→80% MeOH v/v). Fractions containing pure 7ax were concentrated and remaining glassy solid was dissolved in minimal amount of MeOH and treated with HCl/diethylether (2M; 5 mL). Volatiles were removed under reduced pressure and HCl/diethylether treatment was repeated two more times. Residue was crystallized from MeCN (~7 mL). Mother liquor was carefully removed by centrifugation. After drying in vacuum 534 mg (61%) of 7ax was isolated as a white solid.

$^1$H NMR (400 MHz, Methanol-$d_4$) δ7.31-7.27 (multiple peaks, 4H), 7.22 (m, 1H), 6.38 (s, 2H), 5.14 (dd, J=8.8, 6.2 Hz, 1H), 4.66 (dd, J=9.3, 7.1 Hz, 1H), 4.08 (d, J=15.3 Hz, 1H), 4.05 (d, J=15.3 Hz, 1H), 3.98 (t, J=6.3 Hz, 1H), 3.10 (dd, J=14.1, 9.4 Hz, 1H), 2.91 (m, 5H), 2.20 (s, 6H), 1.97-1.51 (m, 8H), 1.52-1.28 (m, 2H). MS: EI-MS: m/z 566.5 [M+1].

Example 81: Synthesis of (R)-4-amino-N-((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-2-guanidinobutanamide (D-(N-(2 formimidamido)-Dab-DMT-NH((S)-5-amino-1-(3-benzyl-1,2,4-oxadiazol-5 yl)pent-1-yl), 7ay)

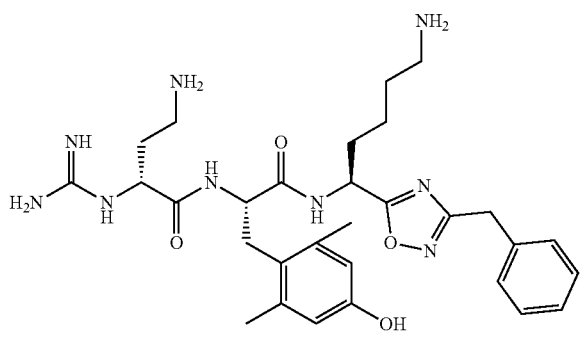

Compound 7ay

Scheme 82

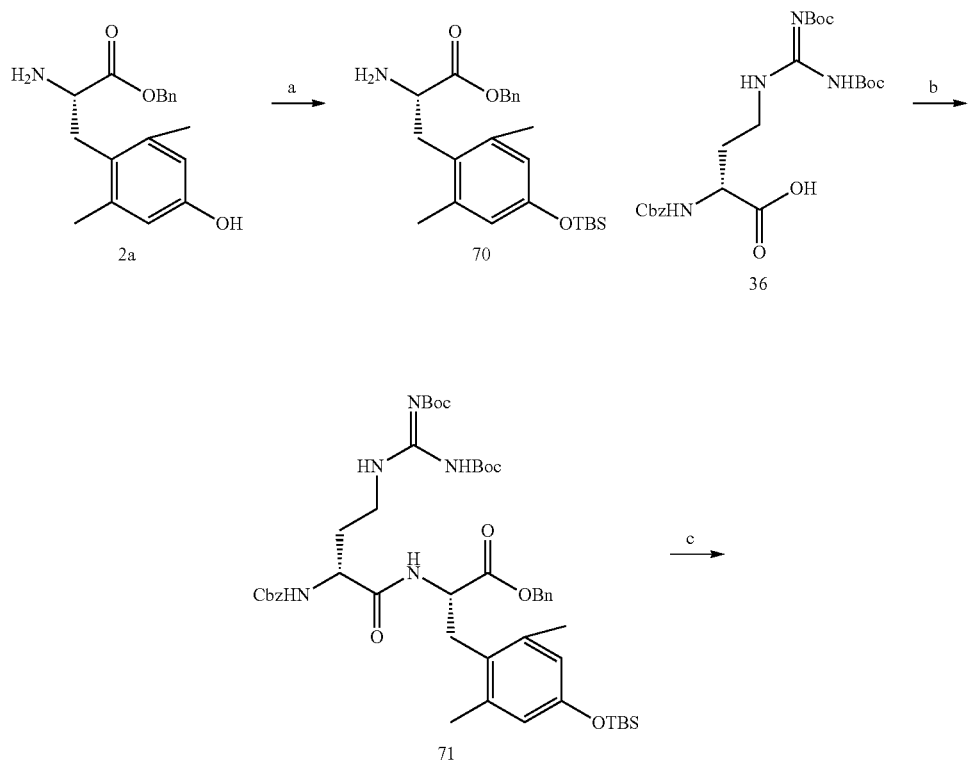

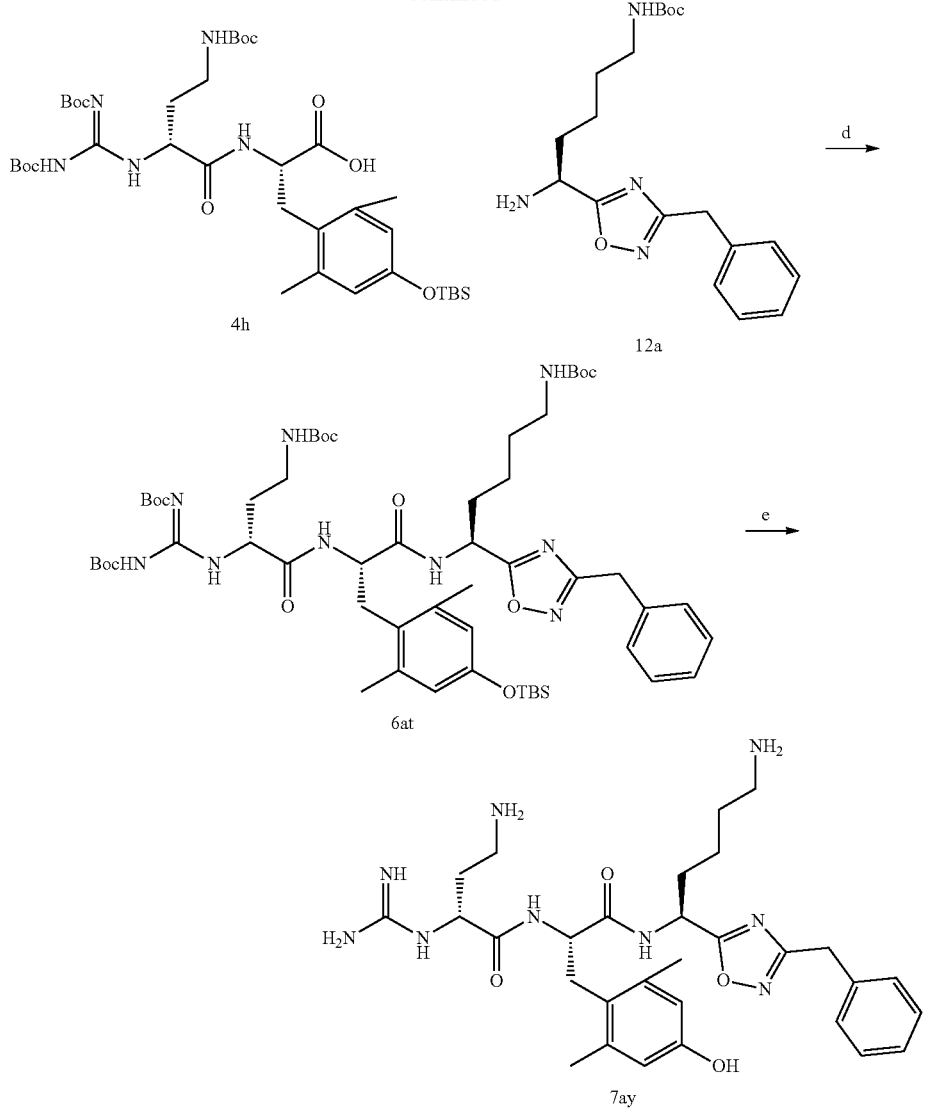

1) Step a: Synthesis of benzyl (S)-2-amino-3-(4-((tert-butyldimethylsilyl)oxy)-2,6-dimethylphenyl)propanoate (70)

To a cold (0° C.) solution of DMT-OBn (2a, 4.00 g; 13.4 mmol) and imidazole (1.91 g; 28.0 mmol) in dry DCM (150 mL) was added TBS-Cl (5.96 g; 39.5 mmol) portion-wise. Solution allowed to slowly warm to ambient temperature over a period of 6 hours. Then, reaction mixture was diluted with DCM (100 mL) and washed with water (3×200 mL) and brine (100 mL). Organic phase was dried over anhydrous $Na_2SO_4$ and evaporated under reduced pressure. Residue was dissolved in ~30 mL of DCM/hexanes (1/1) and filtered through a pad of silica (eluting first with hexanes and then with EtOAc). Fractions containing the product were concentrated under reduced pressure. 5.50 g (99%) of viscous oil 70 was obtained.

$^1$H NMR (300 MHz, Chloroform-d) δ7.23-7.11 (multiple peaks, 3H), 7.11-7.02 (m, 2H), 6.32 (s, 2H), 4.95 (d, J=12.3 Hz, 1H), 4.89 (d, J=12.3 Hz, 1H), 3.55 (dd, J=9.0, 5.9 Hz, 1H), 2.85 (dd, J=14.1, 5.9 Hz, 1H), 2.67 (dd, J=14.1, 9.0 Hz, 1H), 2.09 (s, 6H), 1.28 (bs, 2H), 0.80 (s, 9H), 0.00 (s, 6H).

2) Step b: Synthesis of benzyl (10R,13S,E)-10-(((benzyloxy)carbonyl)amino)-6-((tert-butoxycarbonyl)amino)-13-(4-((tort-butyldimethylsilyl)oxy)-2,6-dimethylbenzyl)-2,2-dimethyl-4,11-dioxo-3-oxa-5,7,12-triazatetradec-5-en-14-oate (71) 70 (5.50 g; 13.3 mmol), $N^α$-(benzyloxycarbonyl)-$N^ω,N^{ω'}$-bis(tert-butoxycarbonyl)-nor-D-arginine (36, 10.88 g; 22.0 mmol) and HOBT hydrate (1.53 g; 10.0 mmol) were dissolved in dry DMF (150 mL) at 0° C. EDCI (6.71 g; 35 mmol) was added in one portion. Then the reaction mixture was stirred at 0° C. 20 min N-methylmorpholine (3.85 mL, 35 mmol) was added portion-wise. Solution was allowed to slowly warm to ambient temperature over a period of 6 hours. Reaction mixture was then partitioned between EtOAc (350 mL) and aq $KHSO_4$ (5%, 350 mL). Organic phase was separated, washed with water (3×150 mL) and brine (200 mL), dried over anhydrous $MgSO_4$ and evaporated under reduced pressure. Residue was purified by column chromatography (hex/EtOAc with gradient 5/1→2/1). Desired product elutes as a first major fraction followed by a sideproduct (structure assigned based on Mas-spec and NMR). Fractions containing pure 71 were concentrated under reduced pressure. 7.4 g (62%) of white foam was obtained.

$^1$H NMR (300 MHz, Methanol-$d_4$) δ7.40-7.12 (multiple peaks, 10H), 6.42 (s, 2H), 5.05 (multiple peaks, 4H), 4.73 (dd, J=9.8, 7.4 Hz, 1H), 4.15 (dd, J=8.8, 4.4 Hz, 1H), 3.36-3.18 (multiple peaks, 2H), 3.11 (dd, J=14.3, 6.8 Hz, 1H), 2.97 (dd, J=14.1, 9.2 Hz, 1H), 2.21 (s, 6H), 1.87-1.72 (m, 1H), 1.62 (m, 1H), 1.45 (multiple peaks, 18H), 0.94 (s, 9H), 0.12 (s, 6H).

3) Step c: Synthesis of (8R,11S,Z)-6-((tort-butoxycarbonyl)amino)-8-(2-((tert-butoxycarbonyl)amino) ethyl)-11-(4-((tert-butyldimethylsilyl)oxy)-2,6-dimethylbenzyl)-2,2-dimethyl-4,9-dioxo-3-oxa-5,7,10-triazadodec-5-en-12-oic acid (4h)

71 (4.50 g; 5.1 mmol), NaHCO$_3$ (924 mg; 11 mmol), Pd on carbon (10%; 500 mg) and Boc$_2$O (2.20 g; 10 mmol) were suspended in EtOH (250 mL). Reaction flask was flushed with hydrogen and reaction mixture was stirred under a flow of hydrogen ~4 h. Reaction progress was monitored by LC-MS. After complete conversion reaction mixture was filtered through a pad of celite and evaporated under reduced pressure. Residue was partitioned between aq KHSO$_4$ (5%, 200 mL) and EtOAc (300 mL). Organic phase was washed with brine, dried over anhydrous MgSO$_4$, and evaporated under reduced pressure. Residue was purified by a silica-gel flash chromatography (hexanes/EtOAc with gradient 3/1 →1/1). 4h elutes first (mainly with hexanes/EtOAc=2/1). Fractions containing pure 4h were combined and evaporated under reduced pressure. 1.53 g (39%) of 4h was obtained in a form of white foam.

$^1$H NMR (300 MHz, Methanol-$d_4$) δ6.31 (s, 2H), 4.53 (dd, J=9.9, 5.8 Hz, 1H), 4.47 (dd, J=9.3, 4.2 Hz, 1H), 3.02 (dd, J=14.4, 5.9 Hz, 1H), 2.97-2.88 (m, 1H), 2.83 (dd, J=14.3, 10.0 Hz, 1H), 2.71 (m, 1H), 2.13 (s, 6H), 1.73-1.53 (m, 1H), 1.43-1.20 (multiple peaks, 28H), 0.81 (s, 9H), 0.00 (s, 6H).

4) Step d: Synthesis of N-(((S)-1-tert-butoxylcarbonylamino)-(3-benzyl-1,2,4-oxadiazol-5-yl)pent-5-yl) (8R,11S,Z)-6-((tert-butoxycarbonyl)amino)-8-(2-((tert-butoxycarbonyl)amino)ethyl)-11-(4-((tert-butyldimethylsilyl)oxy)-2,6-dimethylbenzyl)-2,2-dimethyl-4,9-dioxo-3-oxa-5,7,10-triazadodec-5-en-12-oic amide (6at)

The same procedure as described in Scheme 36 by using 4h (680 mg; 0.85 mmol) and 12a (460 mg; 1.28 mmol) to give 6at (520 mg, 55%) as an off-white foam.

$^1$H NMR (300 MHz, Methanol-$d_4$) δ7.18-6.96 (multiple peaks, 5H), 6.25 (s, 2H), 4.97 (dd, J=8.5, 6.5 Hz, 1H), 4.48 (dd, J=8.7, 4.5 Hz, 1H), 4.38 (t, J=7.7 Hz, 1H), 3.87 (multiple peaks, 2H), 3.07-2.63 (multiple peaks, 6H), 2.02 (s, 6H), 1.78-1.57 (multiple peaks, 3H), 1.46 (m, 1H), 1.40-1.09 (multiple peaks, 40H), 0.81 (s, 9H), 0.01 (s, 3H), 0.00 (s, 3H).

5) Step e: Synthesis of (R)-4-amino-N-((S)-1-(((5)-5-amino-1-(3-benzyl-1,2,4-oxadiazol-5-yl)pentyl)amino)-3-(4-hydroxy-2,6-dimethylphenyl)-1-oxopropan-2-yl)-2-guanidinobutanamide (7ay)

The same procedure as described in Scheme 36 by using 6at (400 mg; 0.36 mmol) to give 7ay (129 mg, 51%) as a white solid.

$^1$H NMR (CD$_3$OD): δ7.27 (multiple peaks, 4H), 7.21 (m, 1H), 6.36 (s, 2H), 5.15 (dd, J=8.6, 6.5 Hz, 1H), 4.49 (dd, J=9.5, 6.5 Hz, 1H), 4.36 (dd, J=7.4, 5.4 Hz, 1H), 4.05 (d, J=15.3 Hz, 1H), 4.04 (d, J=15.3 Hz, 1H), 3.10 (dd, J=14.1, 9.6 Hz, 1H), 2.99-2.81 (multiple peaks, 5H), 2.17 (multiple peaks, 7H), 2.04 (m, 1H), 1.86 (multiple peaks, 2H), 1.72-1.54 (multiple peaks, 2H), 1.51-1.25 (multiple paks, 2H). MS: EI-MS: m/z 594.5 [M+1].

Example 82: Synthesis of (R)-4-amino-N-((S)-1-(((5)-4-amino-1-(3-benzyl-1,2,4-oxadiazol-5-yl)butyl)amino)-3-(4-hydroxy-2,6-dimethylphenyl)-1-oxopropan-2-yl)-2-guanidinobutanamide (D-(N-(2 formimidamido)-Dab-DMT-NH((S)-4-amino-1-(3-benzyl-1,2,4-oxadiazol-5 yl)but-1-yl), 7az)

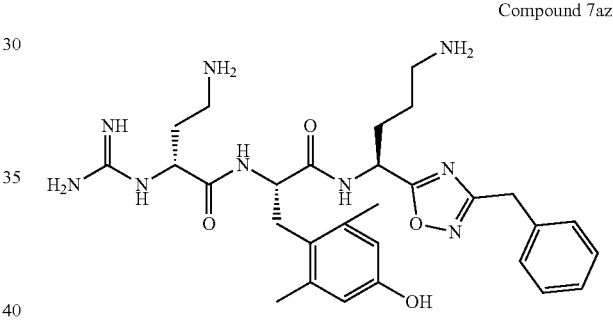

Compound 7az

Example 83: Synthesis of (R)-4-amino-N-((S)-1-(((R)-4-amino-1-(3-benzyl-1,2,4-oxadiazol-5-yl)butyl)amino)-3-(4-hydroxy-2,6-dimethylphenyl)-1-oxopropan-2-yl)-2-guanidinobutanamide (D-(N-(2 formimidamido)-Dab-DMT-NH((R)-4-amino-1-(3-benzyl-1,2,4-oxadiazol-5-yl)but-1-yl), 7ba)

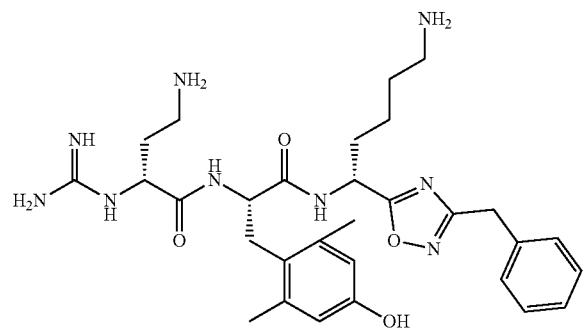

Compound 7ba

-continued
Scheme 83
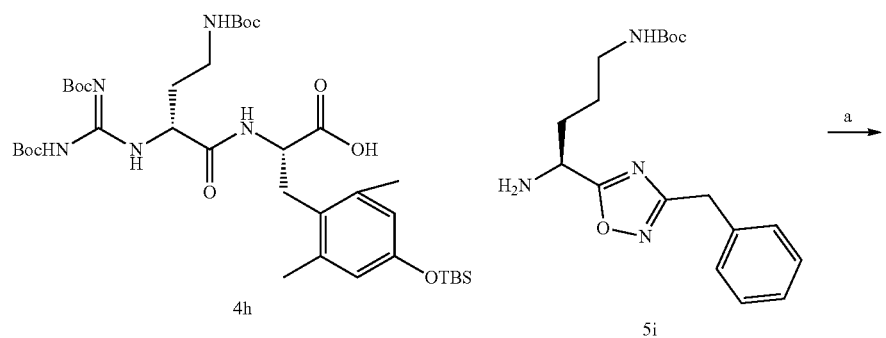
4h  5i
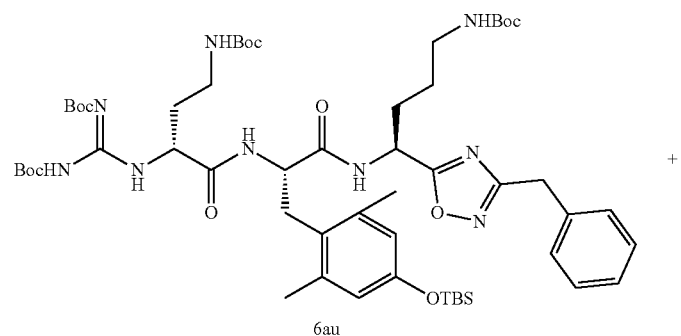
6au
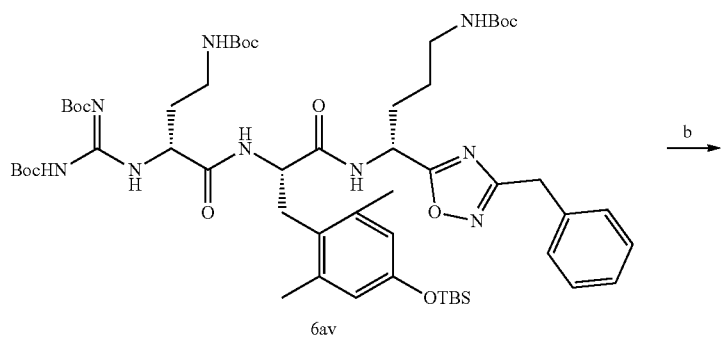
6av
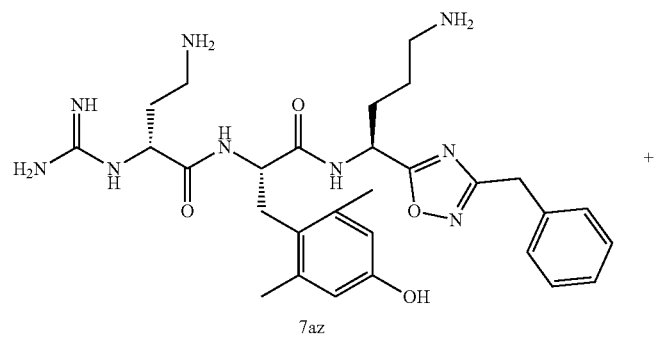
7az

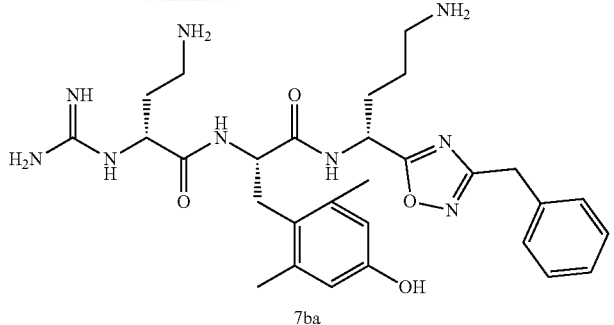

7ba

1) Step a: Synthesis of N-(((S)-1-tert-butoxylcarbonylamino)-(3-benzyl-1,2,4-oxadiazol-5-yl)but-4-yl) (8R,11S,Z)-6-((tert-butoxycarbonyl)amino)-8-(2-((tert-butoxycarbonyl)amino)ethyl)-11-(4-((tert-butyldimethylsilyl)oxy)-2,6-dimethylbenzyl)-2,2-dimethyl-4,9-dioxo-3-oxa-5,7,10-triazadodec-5-en-12-oic amide (6az) and N-(((R)-1-tert-butoxylcarbonylamino)-(3-benzyl-1,2,4-oxadiazol-5-yl)but-4-yl) (8R,11S,Z)-6-((tert-butoxycarbonyl)amino)-8-(2-((tert-butoxycarbonyl)amino)ethyl)-11-(4-((tert-butyldimethylsilyl)oxy)-2,6-dimethylbenzyl)-2,2-dimethyl-4,9-dioxo-3-oxa-5,7,10-triazadodec-5-en-12-oic amide (6ba)

The same procedure as described in Scheme 36 by using 4h (1.25 g; 1.63 mmol) and 5i (623 mg; 1.8 mmol) to give 6au and 6av (1.32 g, 74%) as an off-white foam.

$^1$H NMR (300 MHz, Methanol-$d_4$) δ7.18-6.97 (multiple peaks, 5H), 6.25 (s, 2H), 5.00 (dd, J=8.9, 5.9 Hz, 1H), 4.47 (dd, J=8.7, 4.5 Hz, 1H), 4.40 (t, J=7.7 Hz, 1H), 3.87 (s, 2H), 3.05-2.62 (multiple peaks, 6H), 2.03 (s, 6H), 1.79-1.56 (multiple peaks, 3H), 1.40-1.12 (multiple peaks, 39H), 0.81 (s, 9H), 0.01 (s, 3H), 0.00 (s, 3H).

2) Step b: Synthesis of (R)-4-amino-N-((S)-1-(((S)-4-amino-1-(3-benzyl-1,2,4-oxadiazol-5-yl)butyl)amino)-3-(4-hydroxy-2,6-dimethylphenyl)-1-oxopropan-2-yl)-2-guanidinobutanamide (7az) and (R)-4-amino-N-((S)-1-(((R)-4-amino-1-(3-benzyl-1,2,4-oxadiazol-5-yl)butyl)amino)-3-(4-hydroxy-2,6-dimethylphenyl)-1-oxopropan-2-yl)-2-guanidinobutanamide (7ba)

The same procedure as described in Scheme 36 by using a mixture of 6au and 6av (2.960 g; 2.70 mmol) to give 7az (990 mg, 53%) as a white solid.

$^1$H NMR (CD$_3$OD): δ7.26 (multiple peaks, 4H), 7.20 (m, 1H), 6.36 (s, 2H), 5.22 (dd, J=9.3, 5.5 Hz, 1H), 4.51-4.34 (multiple peaks, 2H), 4.06 (d, J=15.4 Hz, 1H), 4.01 (d, J=15.4 Hz, 1H), 3.11 (dd, J=14.0, 9.6 Hz, 1H), 2.91 (multiple peaks, 5H), 2.17 (s, 6H), 2.13-1.99 (multiple peaks, 2H), 1.98-1.81 (multiple peaks, 2H), 1.71 (multiple peaks, 2H). MS: EI-MS: m/z 580.6 [M+1]. And 7ba (13 mg) as a white solid. $^1$H NMR (CD$_3$OD): δ7.26 (multiple peaks, 5H), 6.49 (s, 2H), 5.07 (dd, J=8.8, 5.6 Hz, 1H), 4.69-4.65 (multiple peaks, 2H), 4.29-4.26 (m, 1H), 4.03 (2H, s), 3.19-3.13 (m, 1H), 2.98-2.80 (multiple peaks, 5H), 2.24 (s, 6H), 2.20-1.90 (multiple peaks, 2H), 1.93-1.64 (multiple peaks, 2H), 1.40-1.32 (multiple peaks, 2H). MS: EI-MS: m/z 580.5 [M+1].

Example 84: Synthesis of (R)-N-((S)-1-(((S)-1-(3-(adamantan-1-yl)methyl-1,2,4-oxadiazol-5-yl)-2-(1H-imidazol-4 yl)ethyl)amino)-3-(4-hydroxy-2,6-dimethylphenyl)-1-oxopropan-2-yl)-4-amino-2-guanidinobutanamide (D-(N-(2 formimidamido)-Dab-DMT-NH((S)-1-(3-(adamantan-1-yl)methyl-1,2,4-oxadiazol-5-yl)-2-(1H-imidazol-4-yl)eth-1-yl), 7bb)

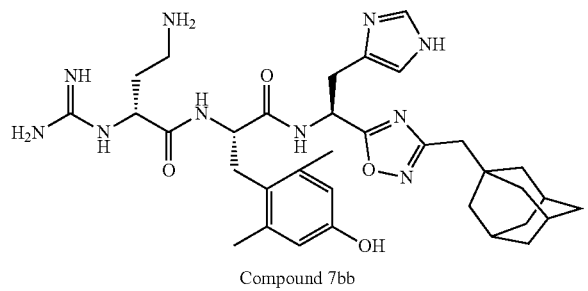

Compound 7bb

-continued
Scheme 84

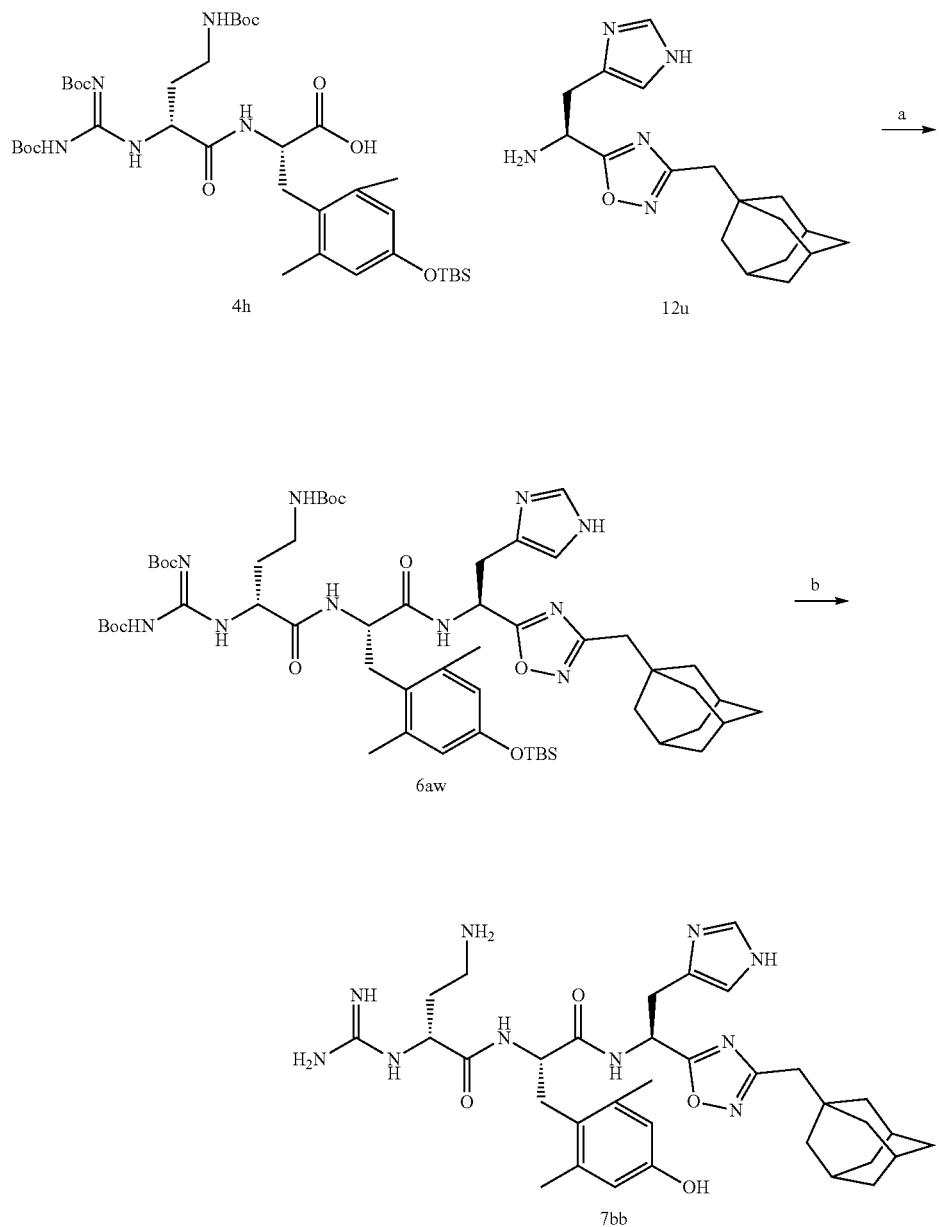

1) Step a: Synthesis of N-((S)-1-(3-(adamantan-1-ylmethyl)-1,2,4-oxadiazol-5-yl)-2-(1H-imidazol-4-yl)ethan-1-amine) (8R,11S,Z)-6-((tert-butoxycarbonyl)amino)-8-(2-((tert-butoxycarbonyl)amino)ethyl)-11-(4-((tert-butyldimethylsilyl)oxy)-2,6-dimethylbenzyl)-2,2-dimethyl-4,9-dioxo-3-oxa-5,7,10-triazadodec-5-en-12-oic amide (6aw)
The same procedure as described in Scheme 36 by using 4h (467 mg; 0.61 mmol) and 12u (427 mg; 0.77 mmol) to give 6aw (172 mg, 26%) as a white foam. LC-MS analysis showed a single peak with [M+H]+=1075.6 Da. 6aw was used in the next step without further characterization.
2) Step b: Synthesis of (R)-N-((S)-1-(((S)-1-(3-(adamantan-1-ylmethyl)-1,2,4-oxadiazol-5-yl)-2-(1H-imidazol-4-yl)ethyl)amino)-3-(4-hydroxy-2,6-dimethylphenyl)-1-oxopropan-2-yl)-4-amino-2-guanidinobutanamide (7bb)

The same procedure as described in Scheme 36 by using 6aw (2.960 g; 2.70 mmol) to give 7bb (36 mg, 39%) as a white solid.

$^1$H NMR (400 MHz, Methanol-$d_4$) δ 8.84 (s, 1H), 7.38 (s, 1H), 6.35 (s, 2H), 5.55 (dd, J=8.5, 6.1 Hz, 1H), 4.45 (t, J=7.5 Hz, 1H), 4.37 (t, J=6.0 Hz, 1H), 3.40 (dd, J=15.4, 6.0 Hz, 1H), 3.33 (dd, 1H), 3.10 (dd, J=14.1, 9.5 Hz, 1H), 3.01-2.81 (multiple peaks, 3H), 2.48 (multiple peaks, 2H), 2.19 (multiple peaks, 7H), 2.05 (m, 1H), 1.93 (bs, 3H), 1.72 (bd, J=12.2 Hz, 3H), 1.61 (bd, J=11.5 Hz, 3H), 1.54 (bs, 6H). MS: EI-MS: m/z 661.6 [M+1].

Example 85: Synthesis of (R)-2-amino-N-((S)-1-(((S)-1-(5-benzyl-1,3,4-oxadiazol-2-yl)-2-(1H-imidazol-4-yl)ethyl)amino)-3-(4-hydroxy-2,6-dimethylphenyl)-1-oxopropan-2-yl)-5-guanidinopentanamide (D-Arg-DMT-NH((S)-1-(5-benzyl-1,3,4-oxadiazol-2-yl)-2-(1H-imidazol-4-yl)eth-1-yl), 7bc)
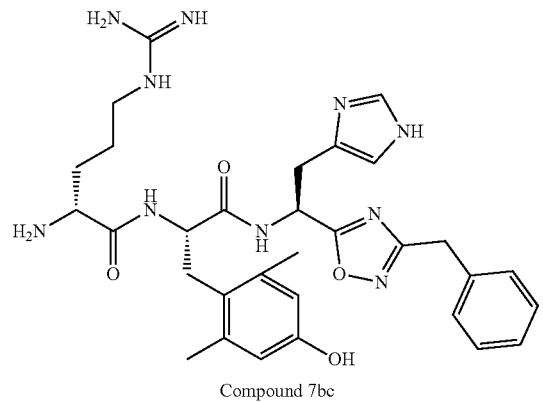
Compound 7bc
Scheme 85
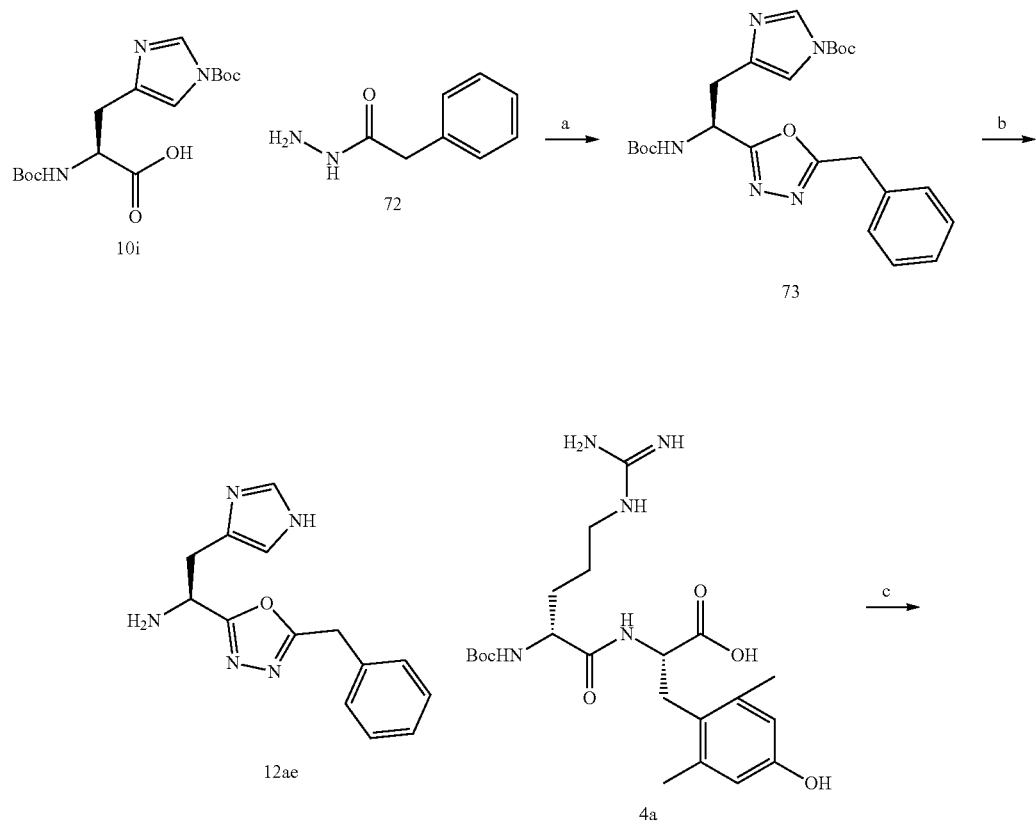

-continued

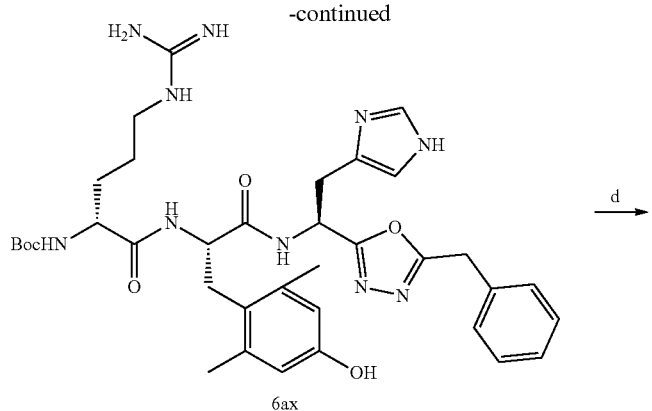

6ax

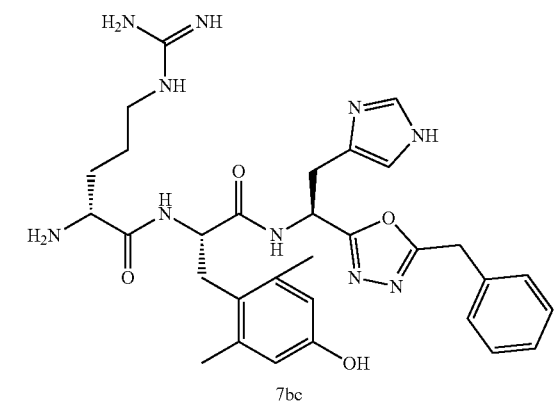 [SMILES: Cc1cc(O)cc(C)c1C[C@H](NC(=O)[C@H](N)CCCNC(=N)N)C(=O)N[C@@H](Cc1c[nH]cn1)c1nnc(Cc2ccccc2)o1]

7bc

1) Step a: Synthesis of tert-butyl (S)-4-(2-(5-benzyl-1,3,4-oxadiazol-2-yl)-2-((tert-butoxycarbonyl)amino)ethyl)-1H-imidazole-1-carboxylate (73)

To a solution of 10i (0.3 g, 0.957 mmol), 2-phentlacethyl-hydrazyde (72, 0.143 g, 0.957 mmol), and HATU (0.364 g, 0.957 mmol) in dry THF (10 mL) 0.21 mL of NMM (1.91 mmol) was added and reaction allowed to stir at room temperature for 3 h. Next, after initial compound consumption (check by LC-MS) 0.228 g of Burgess Reagent (2.39 mmol) was added in one portion. Then 2 mL of water was added and solvents were evaporated. Crude product was purified by reverse flash chromatography (eluent: water/MeCN) to give 73 (0.4 g, 89%) as amorphous solid.

$^1$H NMR (300 MHz, Chloroform-d) δ7.91 (d, J=1.1 Hz, 1H), 7.35-7.22 (m, 5H), 7.06 (s, 1H), 6.09-5.89 (m, 1H), 5.37-5.16 (m, 1H), 4.16 (s, 214), 3.14 (d, J=5.4 Hz, 2H), 2.00 (s, 2H), 1.60 (s, 9H), 1.42 (s, 9H).

2) Step b: Synthesis of (S)-1-(5-benzyl-1,3,4-oxadiazol-2-yl)-2-(1H-imidazol-4-yl)ethan-1-amine (12ae)

To a solution of 73 (0.4 g, 0.85 mmol) in DCM (5 mL) at ° C. was added TFA (1 mL) and reaction mixture allowed to warm to room temperature and stirred for 2 hours. After solvent removal crude 12ae was isolated 0.42 g as TFA salt.

3) Step c: Synthesis of tert-butyl ((R)-1-(((S)-1-(((S)-1-(5-benzyl-1,3,4-oxadiazol-2-yl)-2-(1H-imidazol-4-yl)ethyl)amino)-3-(4-hydroxy-2,6-dimethylphenyl)-1-oxopropan-2-yl)amino)-5-guanidino-1-oxopentan-2-yl)carbamate (6ax)

To mixture of 12ae (0.35 g, 0.7 mmol) and Boc-(D-)-Arg-DMT-OH (4a, 0.406 g, 0.7 mmol) in 10 mL of DMF HOBt*$H_2O$ (0.183 g, 1.2 mmol), EDC*HCl (0.384 g, 2.0 mmol) and NMM (0.55 mL, 5 mmol) were added in a period of 5 min. Reaction mixture was stirred at room temperature for 4 h. Then it was diluted with 200 mL of ethyl acetate, washed with water (7 times, 50 mL) and dried over sodium sulfate. Crude product was purified by reverse flash chromatography to afford 0.43 g (yield: 78%) of 6ax. It was immediately utilized in next step.

4) Step d: Synthesis of (R)-2-amino-N-((S)-1-(((S)-1-(5-benzyl-1,3,4-oxadiazol-2-yl)-2-(1H-imidazol-4-yl)ethyl)amino)-3-(4-hydroxy-2,6-dimethylphenyl)-1-oxopropan-2-yl)-5-guanidinopentanamide (7bc)

To a cooled solution of 6ax (0.43 g) in DCM (10 mL) was added TFA (4 mL). After that ice/water bath was removed and the mixture was stirred at ambient temperature for 2 h. Volatiles were removed under reduced pressure and the residue was concentrated from toluene (2×). Purification by preparative HPLC gave 45 mg of desired product 7bc. (HPLC purity is 95.1% at 210 nm).

$^1$H NMR (400 MHz, Methanol-$d_4$) δ8.74 (t, J=1.5 Hz, 1H), 7.39-7.16 (m, 6H), 6.39 (s, 2H), 5.55 (t, J=7.2 Hz, 1H), 4.48 (d, J=12.1 Hz, 1H), 4.30-4.19 (m, 2H), 3.93 (t, J=6.5 Hz, 1H), 3.22-3.15 (m, 2H), 3.03 (dd, J=14.0, 9.9 Hz, 1H), 2.84 (dd, J=13.9, 6.5 Hz, 1H), 2.19 (s, 6H), 1.91-1.73 (m, 2H), 1.61-1.44 (m, 2H). EI-MS: m/z 617.5 [M+1].

Example 86: Synthesis of (R)-2-amino-N-((S)-1-
(((S)-5-amino-1-(3-phenoxyphenyl)pentyl)amino)-3-
(4-hydroxy-2,6-dimethylphenyl)-1-oxopropan-2-yl)-
5-guanidinopentanamide (D-Arg-DMT-NH((S)-5-
amino-1-(3 phenoxyphenyl)pent-1-yl), 7bd)
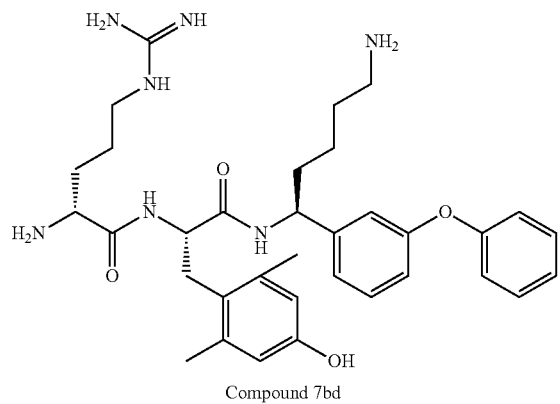
Compound 7bd
Scheme 86
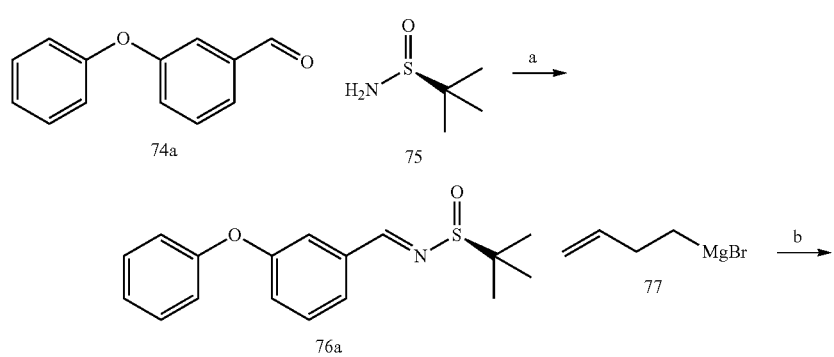
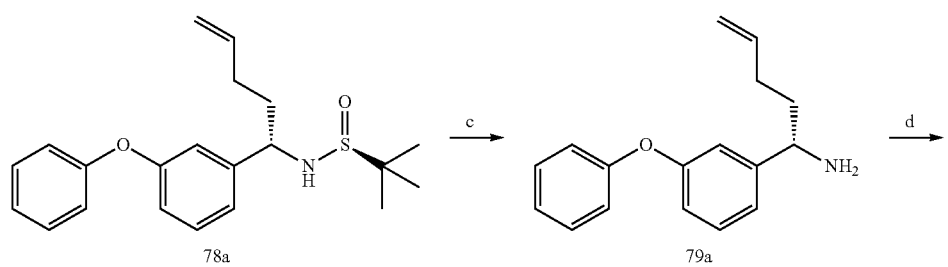
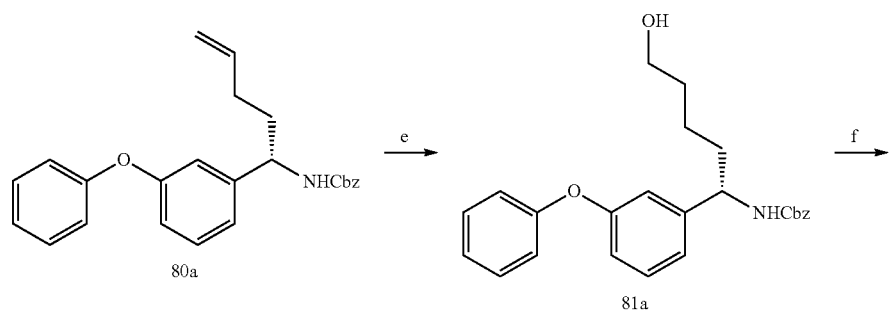

-continued
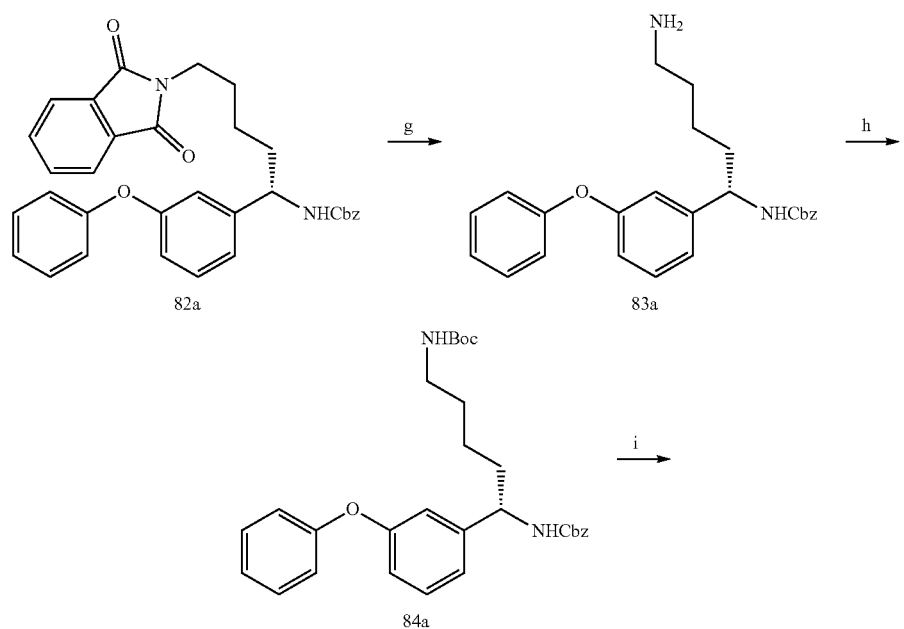
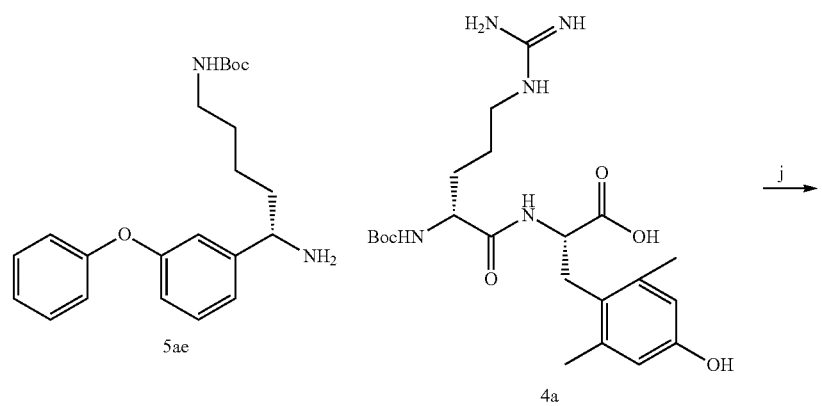
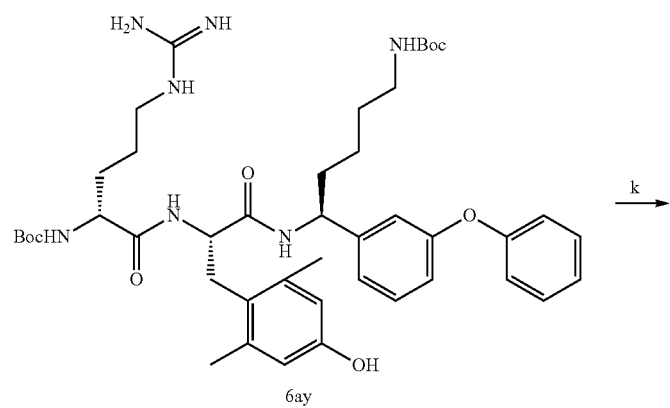

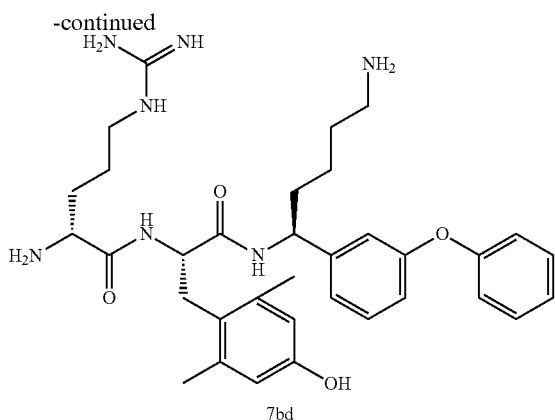

7bd

5) Step a: Synthesis of (S,E)-2-methyl-N-(3-phenoxybenzylidene)propane-2-sulfinamide (76a)

To a solution of compound 74a (19.8 g, 0.1 mol, 1.0 eq) in THF (200 mL), was added (S) tert-butanesulfinamide (75, 12.1 g, 0.1 mol, 1.0 eq), and isopropyl titanate (68.4 g, 0.3 mol, 3.0 eq) was added dropwise over 20 min to the mixture. Then the mixture was stirred overnight. The reaction mixture was quenched with saturated aqueous sodium chloride solution, the mixture was filtered and extracted with EA for 2 times. The organic layer washed with brine, dried over sodium sulfate, concentrated and purified by silica column to give the desired product as white solid (76a, 25 g, 83.3%).

6) Step b: Synthesis of (S)-2-methyl-N-((S)-1-(3-phenoxyphenyl)pent-4-en-1-yl)propane-2-sulfinamide (78a)

Compound 76a (15 g, 0.05 mol, 1.0 eq) was dissolved in THF (150 mL) and cooled to −75° C. The 0.5 M 3-butenylmagnesium bromide (77, 300 mL, 0.15 mol, 3.0 eq) was added dropwise over 20 min to the mixture under $N_2$ atmosphere. When the addition completed, the reaction was allowed to warm to the room temperature and stirred under $N_2$ atmosphere overnight. After LCMS indicated completion, the reaction mixture was quenched with saturated aqueous ammonium chloride, the mixture was filtered and extracted with EA for 2 times. The organic layer washed with brine, dried over sodium sulfate, concentrated and purified by silica column to give the desired product (78a, mixture of diastereoisomers with 56:44 ratio, inseparable by column, 14 g, 79%).

7) Step c: Synthesis of (S)-1-(3-phenoxyphenyl)pent-4-en-1-amine (79a) Compound 78a (10.7 g, 0.03 mol) was dissolved in 4 M hydrochloric acid isopropyl alcohol solution (100 mL), and the mixture was stirred at room temperature for 30 min. After LCMS indicated completion, the reaction mixture was concentrated. The residue was added DCM and adjust pH=7–8 with saturated aqueous sodium bicarbonate solution. The organic layer washed with brine, dried over sodium sulfate, and concentrated to give the desired crude product (79a, 7.8 g) which used to the next step directly.

8) Step d: Synthesis of benzyl (S)-(1-(3-phenoxyphenyl)pent-4-en-1-yl)carbamate (80a)

To a solution of compound 79a (7.6 g, 0.03 mol, 1.0 eq) in THF (80 mL) was added $NaHCO_3$ (7.56 g, 0.09 mol, 3.0 eq) and cooled to 0° C. Benzyl carbonchloridate (6.1 g, 0.036 mol, 1.2 eq) was added dropwise over 15 min to the mixture. After the addition completed, the reaction kept the temperature and stirred for 2 h. After LCMS indicated completion, the reaction mixture was quenched with $H_2O$ and extracted with DCM for 2 times. The organic layer washed with brine, dried over sodium sulfate, concentrated and purified by silica column to give the desired product (80a, 9.7 g, 82.8%).

9) Step e: Synthesis of benzyl (S)-(5-hydroxy-1-(3-phenoxyphenyl)pentyl)carbamate (81a)

To a solution of compound 80a (9.7 g, 0.025 mol, 1.0 eq) in THF (100 mL) was added 0.5 M 9-BBN (100 mL, 0.05 mol, 2.0 eq) and the mixture was stirred at room temperature overnight. LCMS indicated completion, the reaction mixture was quenched with $H_2O_2$ and extracted with DCM for 2 times. The organic layer washed with brine, dried over sodium sulfate, concentrated and purified by silica column to give the desired product (81a, 7.6 g, 74.2%).

10) Step f: Synthesis of benzyl (S)-(5-(1,3-dioxoisoindolin-2-yl)-1-(3-phenoxyphenyl)pentyl)carbamate (82a)

To a solution of compound 81a (7.3 g, 0.018 mol, 1.0 eq) in THF (80 mL) was added Triphenylphosphine (7.08 g, 0.027 mol, 1.5 eq) and isoindoline-1,3-dione (3.17 g, 0.0216 mol, 1.2 eq). The mixture was cooled to −0° C. and DIAD (5.45 g, 0.027 mol, 1.5 eq) was added dropwise over 15 min to the mixture. After the addition completed, the reaction was allowed to warm to the room temperature and stirred for 2 h. After LCMS indicated completion, the reaction mixture was quenched with $H_2O$ and extracted with DCM for 2 times. The organic layer washed with brine, dried over sodium sulfate, concentrated and purified by silica column to give the desired product (82a, 6.8 g, 65%).

11) Step g: Synthesis of benzyl (S)-(5-amino-1-(3-phenoxyphenyl)pentyl)carbamate (83a)

A solution of compound 82a (6.4 g, 0.012 mol, 1.0 eq) in MeOH (80 mL) was added Hydrazine hydrate (0.9 g, 0.018 mol, 1.5 eq). The reaction mixture was heated to reflux for 2 h. After LCMS indicated completion, the reaction mixture was concentrated. The residue was dissolved in DCM and filtered, the filtrate was concentrated to give the desired crude product (83a, 5.8 g) which used to the next step directly.

12) Step h: Synthesis of benzyl tert-butyl (1-(3-phenoxyphenyl)pentane-1,5-diyl)(S)-dicarbamate (84a)

A solution of compound 83a (5.6 g, 0.014 mol, 1.0 eq) in DCM (60 mL) was added triethyl amine (2.8 g, 0.028 mol, 2.0 eq) and cooled to 0° C. $(Boc)_2O$ (4.6 g, 0.021 mol, 1.5 eq) was added dropwise over 15 min to the mixture. After the addition completed, the reaction was allowed to warm to the room temperature and stirred for 2 h. After LCMS indicated completion, the reaction mixture was quenched with $H_2O$ and extracted with DCM for 2 times. The organic layer washed with brine, dried over sodium sulfate, concentrated and purified by silica column to give the desired product (84a, 4.8 g, 61.5%). 13) Step is Synthesis of tert-butyl (S)-(5-amino-5-(3-phenoxyphenyl)pentyl)carbamate (5ae)

To a solution of compound 84a (4.0 g, 8 mmol) in MeOH (40 mL) was added Pd/C (2 g). The mixture was stirred under $H_2$ atmosphere overnight. After LCMS indicated completion, the mixture was filtered, washed with MeOH, the filtrate was concentrated and purified by silica column (2.8 g, 94.6%) and chiral separation by Daicel to give the desired product 5ae (HPLC 98%, 98% ee).

$^1$H NMR (300 MHz, DMSO-$d_6$) δ7.40 (m, 2H), 7.30 (m, 1H), 7.12 (m, 2H), 7.00 (m, 3H), 6.85 (m, 1H), 6.75 (br, 1H), 3.74 (m, 1H), 2.86 (m, 2H), 1.50 (m, 2H), 1.31 (s, 9H), 1.25 (m, 4H). MS (M+1)=371.1.

14) Step j: Synthesis of tert-butyl ((6R,9S,12S)-1-amino-9-(4-hydroxy-2,6-dimethylbenzyl)-1-imino-20,20-dimethyl-7,10,18-trioxo-12-(3-phenoxyphenyl)-19-oxa-2,8,11,17-tetraazahenicosan-6-yl)carbamate (6ay) The same procedure as described in Scheme 36 by using Sac (0.200 g, 0.540 mmol) and 4a (0.271 g, 0.540 mmol) to give 6ay (0.200 g). Obtained residue was flushed thoroughly reverse-phase flash column and used in next step without further purification.

15) Step k: Synthesis of (R)-2-amino-N-((S)-1-(((S)-5-amino-1-(3-phenoxyphenyl)pentyl)amino)-3-(4-hydroxy-2,6-dimethylphenyl)-1-oxopropan-2-yl)-5-guanidinopentanamide (7bd)

The same procedure as described in Scheme 36 by using 6ay (0.200 G, 0.228 mmol) to give 7bd (83 mg) as white solid. (HPLC purity is 98.8% at 210 nm).

$^1$H NMR (400 MHz, Methanol-$d_4$) δ7.37-7.321 (m, 2H), 7.25 (t, J=7.9 Hz, 1H), 7.13-7.09 (m, 1H), 7.04-7.02 (m, 1H), 6.97-6.93 (m, 3H), 6.79 (ddd, J=8.2, 2.5, 1.0 Hz, 1H), 6.50 (s, 2H), 4.69 (dd, J=10.2, 5.9 Hz, 1H), 4.65-4.61 (m, 1H), 3.87 (t, J=6.4 Hz, 1H), 3.21-3.12 (m, 3H), 2.92-2.82 (m, 3H), 2.32 (s, 6H), 1.88-1.73 (m, 2H), 1.59-1.50 (m, 6H), 1.07-0.97 (m, 2H). MS: EI-MS: m/z 618.6 [M+1].

Example 87: Synthesis of (R)-2-amino-N-((S)-1-(((S)-5-amino-1-(4-phenoxyphenyl)pentyl)amino)-3-(4-hydroxy-2,6-dimethylphenyl)-1-oxopropan-2-yl)-5-guanidinopentanamide (D-Arg-DMT-NH((S)-5-amino-1-(4 phenoxyphenyl)pent-1-yl), 7be)

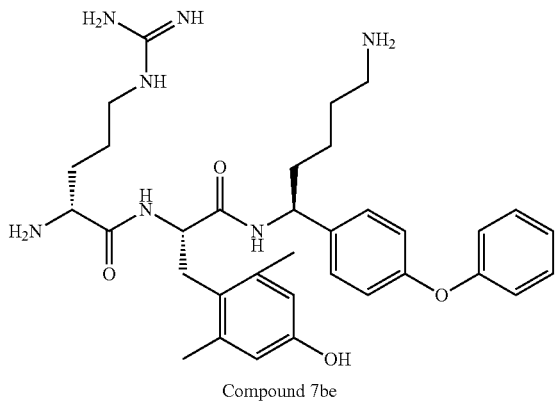

Compound 7be

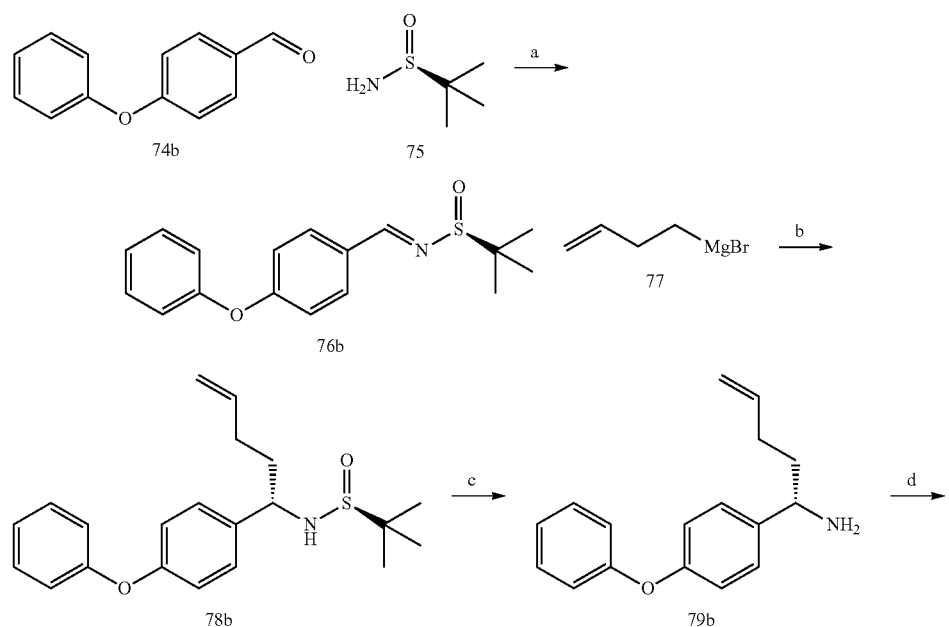

Scheme 87

-continued
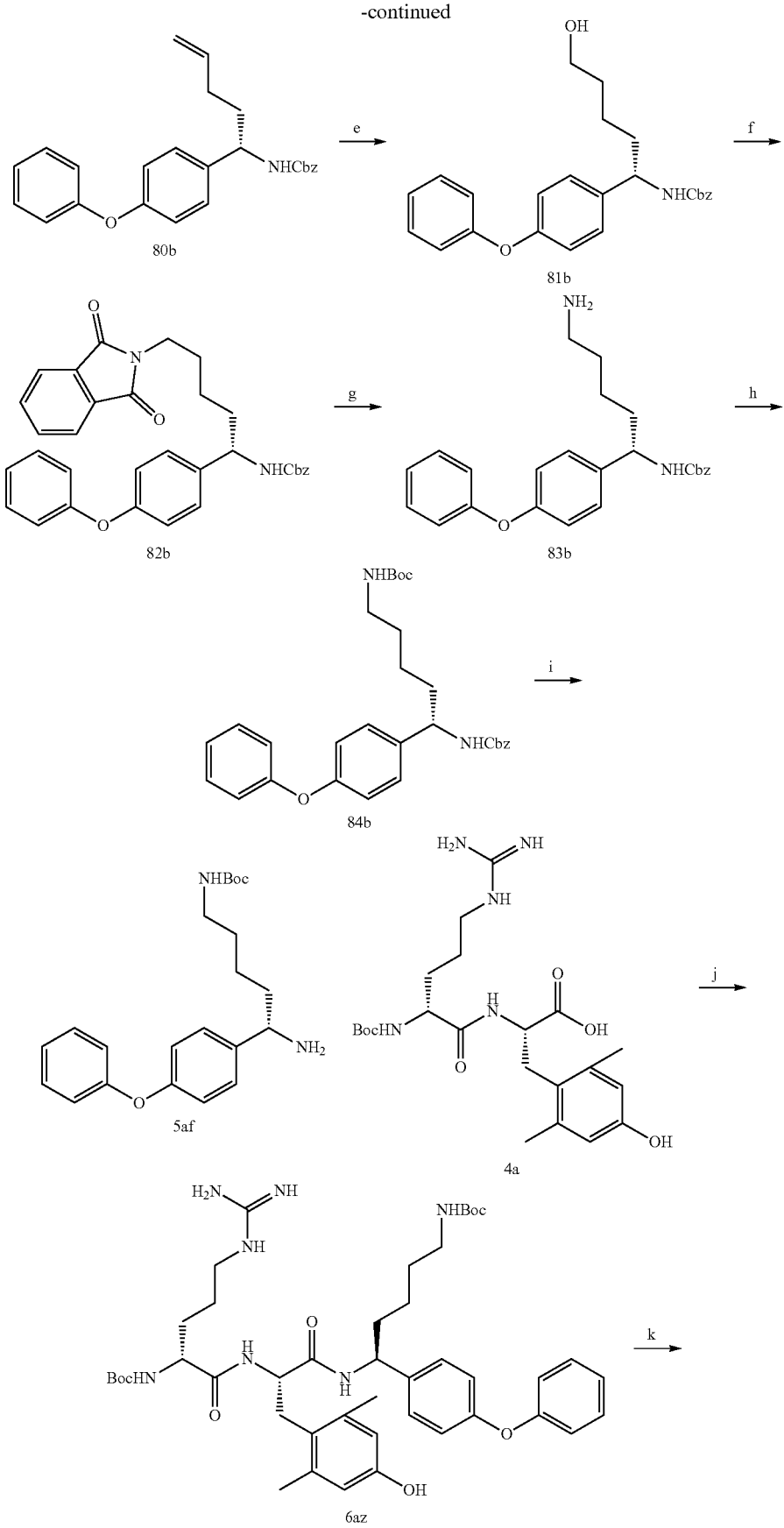

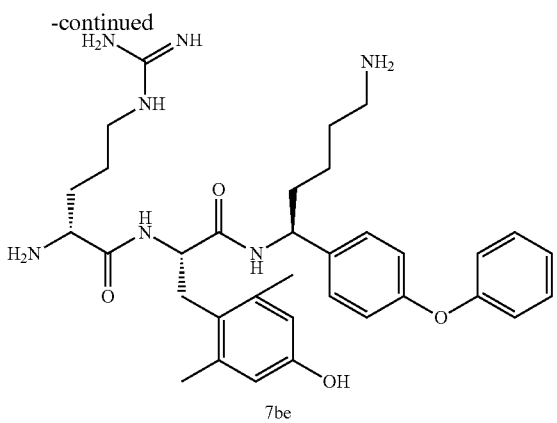

7be

1) Step a: Synthesis of (S,E)-2-methyl-N-(4-phenoxybenzylidene)propane-2-sulfinamide (76b)
The same procedure as described in Scheme 86 by using 74b (19.8 g, 0.1 mol, 1.0 eq) and (S) tert-butanesulfinamide (75, 12.1 g, 0.1 mol, 1.0 eq) to give the desired product as white solid (76b, 25 g, 83.3%).

2) Step b: Synthesis of (S)-2-methyl-N-((S)-1-(4-phenoxyphenyl)pent-4-en-1-yl)propane-2-sulfinamide (78b)
The same procedure as described in Scheme 86 by using 76b (15 g, 0.05 mol, 1.0 eq) and 0.5 M 3-butenylmagnesium bromide (77, 300 mL, 0.15 mol, 3.0 eq) to give the desired product (78b, 5 g, 28%, 96% de, the diastereoisomers were separable by column).

3) Step c: Synthesis of (S)-1-(4-phenoxyphenyl)pent-4-en-1-amine (79b)
The same procedure as described in Scheme 86 by using 78b (10.7 g, 0.03 mol) to give desired crude product (79b, 7.8 g) which used to the next step directly.

4) Step d: Synthesis of benzyl (S)-(1-(4-phenoxyphenyl)pent-4-en-1-yl)carbamate (80b)
The same procedure as described in Scheme 86 by using 79b (7.6 g, 0.03 mol, 1.0 eq) to give the desired product (80b, 9.7 g, 82.8%).

5) Step e: Synthesis of benzyl (S)-(5-hydroxy-1-(4-phenoxyphenyl)pentyl)carbamate (81b)
The same procedure as described in Scheme 86 by using 80b (9.7 g, 0.025 mol, 1.0 eq) to give the desired product (81b, 7.6 g, 74.2%).

6) Step f: Synthesis of benzyl (S)-(5-(1,3-dioxoisoindolin-2-yl)-1-(4-phenoxyphenyl)pentyl)carbamate (82b)
The same procedure as described in Scheme 86 by using 81b (7.3 g, 0.018 mol, 1.0 eq) to give the desired product (82b, 6.8 g, 65%).

7) Step g: Synthesis of benzyl (S)-(5-amino-1-(4-phenoxyphenyl)pentyl)carbamate (83b)
The same procedure as described in Scheme 86 by using 82b (6.4 g, 0.012 mol, 1.0 eq) to give the desired crude product (83b, 5.8 g) which used to the next step directly.

8) Step h: Synthesis of benzyl tert-butyl (1-(4-phenoxyphenyl)pentane-1,5-diyl)(S)-dicarbamate (84b)
The same procedure as described in Scheme 86 by using 83b (5.6 g, 0.014 mol, 1.0 eq) to give the desired product (84b, 4.8 g, 61.5%).

9) Step i is Synthesis of tert-butyl (S)-(5-amino-5-(4-phenoxyphenyl)pentyl)carbamate (5af)
The same procedure as described in Scheme 86 by using 84b (4.0 g, 8 mmol) to give the desired product 5af (HPLC 99.5%, 98% ee).

$^1$H NMR (300 MHz, DMSO-d$_6$) δ7.35 (m, 4H), 7.12 (m, 1H), 6.95 (m, 4H), 6.72 (br, 1H), 3.72 (m, 1H), 2.88 (m, 2H), 1.55 (m, 2H), 1.35 (s, 9H), 1.26 (m, 4H). MS (M+1)=371.1.

10) Step j: Synthesis of tert-butyl ((6R,9S,12S)-1-amino-9-(4-hydroxy-2,6-dimethylbenzyl)-1-imino-20,20-dimethyl-7,10,18-trioxo-12-(3-phenoxyphenyl)-19-oxa-2,8,11,17-tetraazahenicosan-6-yl)carbamate (6az)
The same procedure as described in Scheme 36 by using 5ae (0.200 G, 0.540 mmol) and 4a (0.271 G, 0.540 mmol) to give 6az (0.200 g). Obtained residue was flushed thoroughly reverse-phase flash column and used in next step without further purification.

11) Step k: Synthesis of (R)-2-amino-N-((S)-1-(((S)-5-amino-1-(3-phenoxyphenyl)pentyl)amino)-3-(4-hydroxy-2,6-dimethylphenyl)-1-oxopropan-2-yl)-5-guanidinopentanamide (7be)
The same procedure as described in Scheme 36 by using 6az (0.200 G, 0.228 mmol) to give 7be (90 mg) as white solid. (HPLC purity is 99.5% at 210 nm).

$^1$H NMR (400 MHz, Methanol-d$_4$) δ7.36-7.30 (m, 2H), 7.27-7.24 (m, 2H), 7.12-7.08 (m, 1H), 6.95-6.91 (m, 2H), 6.90-6.86 (m, 2H), 6.50 (s, 2H), 4.66 (td, J=9.3, 8.3, 6.4 Hz, 2H), 3.87 (t, J=6.4 Hz, 1H), 3.21-3.14 (m, 3H), 2.92-2.84 (m, 3H), 2.33 (s, 6H), 1.90-1.73 (m, 2H), 1.61-1.49 (m, 6H), 1.10-0.98 (m, 2H). MS: EI-MS: m/z 618.6 [M+1].

Example 88: Radioligand Displacement Methods and Procedures

1) Radioligand Displacement Methods and Procedures
1.1 Rat Heart Homogenate Preparation
Aptuit is committed to the highest standards of animal welfare and is subject to legislation under the Italian Legislative Decree no. 26/2014. All studies were conducted in accordance with national legislation and under authorization issued by the Italian Ministry of Health.
The rat heart homogenate aliquots were prepared according to the following procedure. Hearts from 20 Sprague Dawley male rats were dissected out and quickly frozen at −80° C. On the day of homogenate preparation, hearts were thawed at 4° C. Groups of 2 hearts in 2 volumes of ice cold 20 mM HEPES, 1 mM EDTA, pH 7.4 buffer were homogenized with the GentleMACS dissociator (Miltenyi Biotec) using the D02 protocol. The final suspension of 20 hearts was divided in 4 aliquots with additional ice cold buffer up to 200 mL for each tube, homogenized with a Polytron and centrifuged at 24,000g for 40 min at 4° C. (T21 Sorvall, Rotor SL0250T, 13,500 rpm). For each tube, the supernatant was discarded, and the pellet resuspended with 100 mL of ice cold buffer, homogenized and centrifuged. This step was repeated twice. The final pellets were collected together in one tube with 70 mL of buffer. After homogenization the suspension was aliquoted in 1.5 mL vials and stored at −80° C. The protein content, measured with the Bradford (Bio-Rad) method using BSA as standard was 6.15 mg/mL. All binding experiments were performed using the same rat heart homogenate preparation.

1.2 Compound Plate Preparation
- 3 fold serial dilutions were manually performed in DMSO to generate 11 point CRCs, at a concentration which was 300-fold the final concentration (final range of concentration for compounds was 30 μM to 0.51 nM, unless specified otherwise)
- from this compound plate, 1 μL of each well was stamped into 96-deep well plate (assay plate)
- Non Specific Binding (NSB) was defined by the addition of 1 μL of 9 mM SBT-031(30 μM final) and Total Binding (TB) was defined by the addition of 1 μL of DMSO.

| Assay plate layout | | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| A | SBT-031 | | | | | 30 μM -> 0.51 nM | | | | | | TB |
| C | | | | | | | | | | | | |
| D | CPD1 | | | | | 30 μM -> 0.51 nM | | | | | | |
| B | | | | | | | | | | | | |
| E | CPD2 | | | | | 30 μM -> 0.51 nM | | | | | | NSB |
| F | | | | | | | | | | | | |
| G | CPD3 | | | | | 30 μM -> 0.51 nM | | | | | | |
| H | | | | | | | | | | | | |

1.3 Reagents and Buffer Solutions $^3$H D-Arg-DMT-Lys-Phe-NH$_2$ was obtained from Moravek, cat.no MT-1002819, lots 745-110-0241-A-20160502-DJI and 750-006-0237-A-20160909-DJI. The composition of assay buffer was: 20 mM HEPES, pH7.1, 10 mM KCl, 0.01% Pluronic F127 and protease inhibitor cocktail (Abcam, ab65621) 1:500. The composition of the ice cold wash buffer was: 20 mM HEPES, 10 mM KCl, pH 7.1.

1.4 $^3$H D-Arg-DMT-Lys-Phe-NH$_2$ Filtration Binding Assay

Displacement binding experiments were performed in a 96-deep well plate at room temperature with a final assay volume of 300 μL/well, according to the following protocol:
- 150 μL of $^3$H D-Arg-DMT-Lys-Phe-NH$_2$ in assay buffer were added to the deep well plate containing 1 μL of compounds dissolved in DMSO to have a final radioligand concentration in the assay of 6-8 nM. The exact concentration was determined by Liquid Scintillation Counting (LSC)
- The displacement binding was started by the addition of 150 μL of rat heart homogenate in assay buffer to have final assay concentration of 16 μg/mL, corresponding to 5 μg/well
- The plate was incubated on a shaker at 23° C. for 60 min
- The reaction was terminated by rapid filtration through Unifilter-96 GF/C filter plate pre-soaked for one hour in Polyethylenimine (PEI) 1% (w/v) solution and briefly washed with about 0.5 mL of ice cold assay buffer using the Cell Harvester instrument (PerkinElmer)
- The filter plate was washed 3 times with about 0.5 mL ice-cold buffer and then left to dry for about one hour at 50° C.
- 50 μL of Microscint-20 were added to each well and the plate was sealed with a top-seal A (PerkinElmer)
- Bound radioactivity was measured using the microplate reader TopCount or Microbeta2
- Radioligand concentration was determined as follows: 50 μL of $^3$H SBT-031 solution plus 3 mL FilterCount (PerkinElmer) were mixed together in the total added vial and read in 13-Counter TriCarb 2900

2) Data Handling and Analysis

Radioligand binding raw data consisted of cpm values from TopCount reader. Compound curve data analysis was performed using the percent of TB, calculated according to the formula:

$$\text{Percent of TB} = (\text{sample}/\text{TB}) * 100$$

Sample cpm from test compound well
TB average cpm from TB control wells
Curve fitting and pIC$_{50}$ (the negative log of IC$_{50}$) estimations was carried out using GraphPad Prism. A statistical fit comparison between one site and two sites models was used to select which model was preferred (P<0.05). In both models the bottom of the curve was forced to be greater than 0. In case of a two site model the fraction of the high affinity site was also reported (fraction high). The automatic outlier elimination option in GraphPad was applied, integrated with manual data exclusion in case of evident sample outlier. For each compound an average fit including all experimental replicates was also performed.

The plate acceptance criteria based on Z' factor was applied (Zhang et al., 1999); only plates with Z'>0.5 were considered for data analysis. The pharmacological standard quality control was based on unlabeled SBT-031 curve; its high affinity value had to stay in the range of pIC$_{50}$ 7.6±0.5 (pIC$_{50}$ of 7.1÷8.1, corresponding to IC$_{50}$ of 80 nM+8 nM). If none of the $^3$H D-Arg-DMT-Lys-Phe-NH$_2$ displacement curve satisfied this requisite, the entire experiment was rejected.

3) Archiving

The original signed report, any amendments or deviations, raw data and associated documentation will be retained under the responsibility of the Central Archive Aptuit Verona for a period of 2 years after completion of the study. After this period the Sponsor will be contacted for further instruction.

Electronic data will be retained; duplicate PDF electronic copies of the final report will be retained on two separate and appropriately labelled CD/DVDs (one copy on each CD/DVD). These PDF files are considered to be outside the scope of FDA 21 CFR Part 11.

4) Results

Compounds were tested in $^3$H D-Arg-DMT-Lys-Phe-NH$_2$ displacement binding. Reference D-Arg-DMT-Lys-Phe-NH$_2$ displacement curve was present in each experiment. Compound binding affinity results obtained from the average of normalized percent of inhibition are reported in FIG. 1.

5) References

Zhang J H, Chung T D, Oldenburg K R: A simple statistical parameter for use in evaluation and validation of high throughput screening assays. *J Biomol Screen.* (1999), 4: 67-73

Example 89: Langendorff Study

Ischemia-reperfusion injury-Langendorff heart preparation Protocol (Latvian Institute of Organic Synthesis)

The infarction study is performed according to the Langendorff technique as described previously (Kuka J, Vilskersts R, Cirule H, Makrecka M, Pugovics O, Kalvinsh I, et al. The cardioprotective effect of mildronate is diminished after co-treatment with L-carnitine. J Cardiovasc Pharmacol Ther. 2012; 17:215-222), with some modifications. Rats are anaesthetized with sodium pentobarbital (60 mg/kg) and heparin is administered intraperitoneally. For the infarction studies, the hearts are perfused with oxygenated (95% 02-5% CO2) Krebs-Henseleit (KH) buffer solution (118 mmol/L NaCl, 4.7 mmol/L KCl, 1.24 mmol/L $CaCl_2$, 1.64 mmol/L MgCl2, 24.88 mmol/L NaHCO3, 1.18 mmol/L KH2PO4, and 0.05 mmol/L EDTA; pH 7.3-7.5; 36.8-37.0° C.) supplemented with 10 mM glucose at a constant perfusion pressure of 60 mmHg. A water-ethanol mixture (1:1)-filled balloon connected to a physiological pressure transducer (ADInstruments) is inserted into the left ventricle, and the baseline end-diastolic pressure set at 5-10 mmHg. The heart rate (HR), flow, left-ventricle developed pressure (LVDP), contractility (+dp/dt) are continuously recorded using a PowerLab 8/35 system from ADInstruments. The isolated rat hearts are adapted for 20 min and the left anterior descending coronary artery (LAD) is subsequently occluded for 30 min followed by 120 min of reperfusion. KH perfusion solution with or without added compound of interest (vehicle or 1 µM concentration) will be used for the whole time of isolated heart perfusion. Occlusion is confirmed by ~-40% drop in coronary flow. The infarct size is determined as described previously (Kuka J, Vilskersts R, Cirule H, Makrecka M, Pugovics O, Kalvinsh I, Dambrova M, Liepinsh E. The cardioprotective effect of mildronate is diminished after co-treatment with L-carnitine. J Cardiovasc Pharmacol Ther. 2012 Jun.;17(2):215-22. doi: 10.1177/1074248411419502.; Liepinsh E, Kuka J, Dambrova M. Troubleshooting digital macro photography for image acquisition and the analysis of biological samples. J Pharmacol Toxicol Methods. 2013 Mar.-Apr.;67(2):98-106. doi: 10.1016/j.vascn.2012.11.001.). Briefly, at the end of the reperfusion, the LAD is re-occluded, and the heart is perfused with 0.1% methylene blue dissolved in KH buffer solution. Afterwards, hearts are sectioned transversely from the apex to the base in 6 slices (5 if smaller heart) of 2 mm thickness and incubated in 1% triphenyl-tetrazolium chloride in phosphate buffer (pH 7.4, 37° C.) for 10 min to stain viable tissue red and necrotic tissue white. The planemetric analysis of cross-sectional images is performed using Image-Pro Plus v6.3 software to determine the area at risk (AR) and area of necrosis (AN), each expressed as a percentage of cross-sectional slice area. The obtained values are then used to calculate the infarct size (IS) as a percentage of the risk area according to the formula:

$$IS (\%) = AN/AR \times 100\%$$

Area of necrosios is determined by combining areas of white necrotic and pink tissue.

Study outline
    20 min. adaptation+30 min. ischemia (LAD ligation)+120 min. reperfusion. Vehicle or compound 1 µM
    The test article concentration(s) may be adjusted. Any changes will be recorded in the study file and the final report.
    Endpoints: HR, flow, LVDP, ±dP/dt, infarct size-area of necrosis
    CTRL (vehicle)+up to 4 compounds (n=8 per treatment) tested per set The protocol and the number of compounds to be tested may be modified based on the experimental results and discussions with the Sponsor. Any changes to the protocol will be documented in the study file and in the protocol amendment.

TABLE 1

Infarct Size, % of Area at Risk

| Treatment | Ctrl. | Ex. 31 | Ctrl. | Ex. 38 | Ctrl. | Ex. 82 | Ctrl. | Ex. 64 | Ctrl. | Ex. 65 | Ctrl. | Ex. 53 | Ctrl. | Ex. 68 |
|---|---|---|---|---|---|---|---|---|---|---|---|---|---|---|
| Infarct size, % of area at risk | 44 | 35 | 46 | 31 | 49 | 42 | 52 | 38 | 39 | 24 | 38 | 30 | 52 | 35 |

TABLE 2

White Necrotic Tissue Area, % of Area at Risk

| Treatment | Ctrl. | Ex. 31 | Ctrl. | Ex. 38 | Ctrl. | Ex. 82 | Ctrl. | Ex. 64 | Ctrl. | Ex. 65 | Ctrl. | Ex. 53 | Ctrl. | Ex. 68 |
|---|---|---|---|---|---|---|---|---|---|---|---|---|---|---|
| White Necrotic Area, % of area at risk | 31 | 22 | 25 | 15 | 29 | 24 | 31 | 20 | 25 | 17 | 25 | 21 | 31 | 18 |

Example 90: Rat Myocardial Infarction Model

The Rat Myocardial Infarction Model was performed by IPST Therapeutique Inc, Sherbrooke, Quebec, Canada. The animals were randomized in terms of even distribution between treatment groups based on their body weight by the Study Director with the aim of scheduling animal from each treatment group for each day of surgery (when possible).
    1) Sham group: size of the group: n=2. Route of administration: n/a;
    2) Vehicle group: size of the group: n=8. Route of administration: s.c.;
    3) Testing article group: size of the group: n=8. Route of administration: s.c.; Treatment dose: 2×2 mg/kg, 30 min before ischemia and 5 min before reperfusion.
Experimental Procedures
Study Design
    1) On the day of the surgery, the rat will be anaesthetized with a mixture of 2 to 2.5%. isoflurane USP (Abbot Laboratories, Montreal Canada) in oxygen, and placed on a heating pad to maintain body temperature.
    2) The animal will be intubated and immediately ventilated by means of a positive-pressure rodent respirator set at 10 mL/kg bodyweight at a frequency of 65-70 strokes/min.

3) A baseline blood sample (1 mL) will be taken from the jugular vein for baseline biomarkers quantification. The blood will be collected in lithium heparin microtainers and centrifuged at 3000 rpm, at 4±2° C. for 10 minutes. The plasma will be aliquoted in 2 samples of equal volume (approximately 250 μL). One aliquot will be stored at 4±2° C. and one at −20±2° C. until biomarkers analysis.

4) A thoracotomy will be performed through the left forth intercostal space to exposed the heart.

5) A 5-0 sofsilk suture will be placed around the left anterior descending (LAD) artery, 2-3 mm below the left atrium.

6) The suture will be briefly snared to verify the size and location of myocardial ischemia based on color change and will then be tied to produce a large anterolateral myocardial infarction (around 50%).

7) 30 minutes following LAD occlusion, the suture will be removed to allow a reperfusion of the muscle.

8) The thoracotomy will be closed with a 4-0 suture and a meloxicam (1 mg/kg) subcutaneous injection will be done for postoperative pain management.

9) Before to put the animal back in its cage, a second blood draw will be taken as was done before the ischemia for the 30 min post-reperfusion biomarkers analysis.

10) 24 hours post-reperfusion, the animal will be re-anesthetised (isoflurane 2%). A 1 mL blood sample will be taken from the jugular vein, for 24 hrs biomarkers quantification.

11) The heart will be excised and mounted into a Langendorff apparatus. Oxygenated Tyrode's solution heated at 35±2° C. will perfuse the heart in a retrograde manner at a pressure of approximately 70 mmHg and a flow rate on the order of 10 mL/min.

12) A cannula with a fluid-filled balloon connected to a pressure transducer will be inserted into the left ventricular through the pulmonary vein and mitral valve in order to measure the left ventricular pressure (LVP). A PV-loop will be performed to evaluate left ventricle contractility parameters.

13) The heart will then be perfused with Evans blue dye to evaluate the size of the myocardial infarction. Following Evans blue staining, the heart will be removed from the Langendorff apparatus and immersed in cold ethanol (−50° C.). The heart will be cut in transversal slices sections of approximately 2 mm. The slices will be scanned to evaluate the area at risk (AAR) before to be incubated in phosphate buffer containing 1% TTC for 30 minutes at 35±2° C. and then transfer in formalin 4% for 24 hours at 4±2° C. The slices will be re-scanned to measure the infracted area.

Calculations

Infarct Size (%)=(Infarcted Area/Area at Risk)*100

Computer Systems

A networked personal computer running either Microsoft Windows8, XP Professional or Microsoft Windows Vista Business will be used for data acquisition. The analysis software will be Microsoft Office Excel 2007 installed on networked personal computers running Microsoft Windows8, XP Professional or vista.

TABLE 3

| Infract Size (%)/ Compound | Infarct size (%) | | | | |
| --- | --- | --- | --- | --- | --- |
| | Sham | Vehicle | Example 37 | Example 38 | Example 31 |
| Mean | 1.20 | 47.3 | 29.2 | 30.6 | 16.4 |
| SEM | 1.2 | 2.6 | 4.8 | 5.6 | 2.1 |
| $T_{test}$ vs. vehicle | n/a | n/a | 0.005 | 0.016 | 0.000 |

Example 91: The Rat Acute Kidney Injury (AKI) Model

The Rat Acute Kidney Injury (AKI) Model was performed by IPST Therapeutique Inc, Sherbrooke, Quebec, Canada. The animals were randomized in terms of even distribution between treatment groups based on their body weight by the Study Director with the aim of scheduling animal from each group at each day of surgery. The rats will be given free access to food and water.

Experimental Procedures

Induction of Ischemia-Reperfusion

1. Rats will be anaesthetized with isoflurane USP (Abbot Laboratories, Montreal Canada) 2% in oxygen and placed on a heated pad to maintain body temperature. The ECG and oxygen saturation will be monitored for the entire surgical process. The body temperature will be monitored with a probe thermometer introduced into the abdomen, very close to the kidneys.

2. A 1 mL blood draw will be taken from the jugular vein. The blood will be collected into lithium heparin tubes and centrifuged at 3000 rpm for 10 min. to obtain the plasma. The plasma will be separated into 200 μL aliquot and stored at −20° C. until dosage of biomarkers.

3. The abdomen will be disinfected with providone iodine and alaparotomy will be performed.

4. The kidneys will be exposed and a temporary suture will be placed around renal artery of the two kidneys. Renal ischemia will be visually confirmed by a gradual changed of the kidneys colour going from red to dark purple within a couple of minutes following the start of the ischemia. During the ischemia, the kidneys will be kept moist and warm using a heat lamp and sterile gauze soaked in warm (37° C.) saline. The temperature will be monitored with a probe thermometer introduced into the abdomen, very close to the kidneys.

5. After 30 minutes of occlusion, the suture will be removed.

6. The abdominal wounds will be closed with 4-0 silk suture, and the animal will be return to its cage.

7. Twenty-four hours after reperfusion the rats will be re-anesthetized. A second blood draw will be taken as was done before the ischemia.

8. Sham will be treated under same conditions as vehicle, except, kidneys will not be subjected to ischemic conditions.

Detection of Biomarkers

A 200 μL aliquot of plasma sample will be taken before the ischemia and 24 hours following the ischemia; both will be sent to the clinical laboratory of the CHUS (Centre Hospitalier Universitaire de Sherbrooke, Quebec, Canada) for detection of plasma level of creatinine (p.Cr) and Blood Urea Nitrogen (BUN).

Computer Systems

The following are the validated computer systems to be used during the conduct of this study. The analysis software will be Microsoft Office Excel 2007 installed on networked personal computers running Microsoft Windows8, XP Professional or Vista.

Data Analysis

Values are presented as means±SEM (standard error of the means) and presented by the symbol+on the graph. Repeat un-paired Student's t-tests were performed in Microsoft Excel 2007 on all experimental data. Differences were considered significant when p≤ 0.05.

The vehicle group was compared to the sham group while the test article was compared to the vehicle group.

The plasma creatinine post-UR (% mean of vehicle) was calculated using the following formula:

$$\frac{((p.Cr24hpost\text{-}isch.) - (p.Crpre\text{-}isch.)) - \text{Mean } \Delta p.Cr \text{ in sham group}}{\text{Mean } \Delta p.Cr \text{ in vehicle group}} \times 100$$

Where:

p.Cr=Plasma creatinine

Mean Δ plasma creatinine in sham group=Mean (plasma creatinine 24 h post-isch.–plasma creatinine pre-isch.) in sham group Mean Δ plasma creatinine in vehicle group=Mean ((plasma creatinine 24 h post-inch.–plasma creatinine pre-isch.)–Mean Δ plasma creatinine in sham group) in vehicle group The BUN post-I/R (% mean of vehicle) was calculated using the following formula:

$$\frac{((BUN24hpost\text{-}isch.) - (BUNpre\text{-}isch.)) - \text{Mean } \Delta BUN \text{ in sham group}}{\text{Mean } \Delta BUN \text{ in vehicle group}} \times 100$$

Where:

BUN=Blood Urea Nitrogen

Mean Δ BUN in sham group=Mean (BUN 24 h post-isch.–BUN pre-isch.) in sham group

Mean Δ BUN in vehicle group=Mean ((BUN 24 h post-isch.–BUN pre-inch.)–Mean Δ BUN in sham group) in vehicle group % Protection was calculated using the following formulas:

% Protection (plasma creatinine)=100%−A plasma creatinine post-UR (% mean of vehicle)

% Protection (BUN)=100%−A BUN post-I/R (% mean of veh.)

TABLE 4

Plasma Crearinine, % Protection

| Plasma Creatinine, % Protection | Vehicle | Ex. 31 | Vehicle | Ex. 37 | Vehicle | Ex. 42 | Vehicle | Ex. 33 | Vehicle | Ex. 82 |
|---|---|---|---|---|---|---|---|---|---|---|
| Mean | 0 | 86.2 | 0 | 30.7 | 0.0 | 53.4 | 0 | 38.9 | 0 | 32.0 |
| SEM | 31.8 | 3.6 | 24.1 | 24.2 | 24.1 | 20.7 | 21.7 | 32.5 | 23.9 | 13.6 |

TABLE 5

BUN, % Protection

| BUN, % Protection | Vehicle | Ex. 31 | Vehicle | Ex. 37 | Vehicle | Ex. 42 | Vehicle | Ex. 33 | Vehicle | Ex. 82 |
|---|---|---|---|---|---|---|---|---|---|---|
| Mean | 0 | 81.4 | 0 | 44.3 | 0.0 | 50.4 | 0 | 35.9 | 0 | 25.5 |
| SEM | 21.4 | 4.2 | 23.7 | 14.0 | 23.7 | 27.2 | 27.3 | 15.9 | 18.6 | 12.7 |

Example 92: Rat Permeabilized Cardiac Fiber A/R Study

Mitochondrial Functionality In Vitro Anoxia-Reoxygenation (A/R) Model

1) Thf Preparation of Permeabilized Cardiac Fibers

The permeabilized cardiac fibers are prepared from normoxic heart as described previously (Kuka J, Vilskersts R, Cirule H, Makrecka M, Pugovics O , Kalvinsh I, Dambrova M, Liepinsh E. The cardioprotective effect of mildronate is diminished after co-treatment with L-carnitine. J Cardiovasc Pharmacol Ther. 2012 Jun.;17(2):215-22. doi: 10.1177/1074248411419502) with some modifications. The bundles of fibers are permeabilized using 50 µg/mL saponin and 0.5 mg/mL collagenase at 4° C. in 1 mL of buffer A (20 mM imidazole, 0.5 mM dithiothreitol, 20 mM taurine, 7.1 mM $MgCl_2$, 50 mM MES, 5 mM ATP, 15 mM phosphocreatine, 2.6 mM $CaK_2EGTA$, 7.4 mM $K_2EGTA$, pH 7.0 at 0° C.). After 15 min incubation, the fibers are washed for 15 min in 2 mL of buffer B (20 mM imidazole, 0.5 mM dithiothreitol, 20 mM taurine, 1.6 mM $MgCl_2$, 100 mM MES, 3 mM $KH_2PO_4$, 2.9 mM $CaK_2EGTA$, 7 mM $K_2EGTA$, pH 7.1 at 37° C.) supplemented with compound (e.g. 100 nM) or vehicle.

2) Respiration Measurements with Simultaneous $N_2O_2$ Flux Detection

Medium for respiration measurements: MiR05-110 mM sucrose, 60 mM K-lactobionate, 0.5 mM EGTA, 3 mM $MgCl_2$, 20 mM taurine, 10 mM $KH_2PO_4$, 20 mM HEPES, pH 7.1 at 30° C., and 0.1% BSA essentially fatty acid free.

Protocol

To induce anoxia maximal respiration rate of sample is stimulated by the addition of substrates, succinate (10 mM) with rotenone (0.5 µM) and ADP (5 mM), and preparation is left to consume all 02 in respiratory chamber (within 10-20 min), thereby entering into an anoxic state (Makrecka M, Svalbe B, Volska K, Sevostjanovs E, Liepins J, Grinberga S, Pugovics O , Liepinsh E, Dambrova M. Mildronate, the inhibitor of L-carnitine transport, induces brain mitochondrial uncoupling and protects against anoxia-reoxygenation. Eur J Pharmacol. 2014 Jan. 15; 723:55-61. doi: 10.1016/j.ejphar.2013.12.006.). After 30 min anoxia, 02 is reintroduced to the chamber by opening the chamber to achieve reoxygenation. After 02 concentration in chamber reaches initial concentration, the chamber is closed and 02 flux is monitored for 10 min. $H_2O_2$ flux (ROS flux) is measured simultaneously with respirometry in the O2k-Fluorometer using the $H_2O_2$-sensitive probe Ampliflu™ Red (AmR) (Makrecka-Kuka M, Krumschnabel G, Gnaiger E. High-Resolution Respirometry for Simultaneous Measurement of Oxygen and Hydrogen Peroxide Fluxes in Permeabilized Cells, Tissue Homogenate and Isolated Mitochondria. Biomolecules. 2015 Jun. 29; 5(3):1319-38. doi: 10.3390/biom5031319). 10 µM AmR, 1 U/mL horse radish peroxidase (HRP) and 5 U/mL superoxide dismutase (SOD) are added to the chamber. The reaction product between AmR and $H_2O_2$, catalyzed by HRP, is fluorescent, similar to resorufin. Calibrations are performed with $H_2O_2$ repeatedly added at 0.1 µM steps. Additional AmR can be added to ensure $H_2O_2$ flux measurements after reoxygenation.

The tested compound or vehicle is added at baseline (before addition of permeabilized fibers).

Study outline:
- Permeabilized cardiac fibers CII OXPHOS state+30 min. anoxia+10 min. reoxygenation, in the presence of the $H_2O_2$-sensitive probe Ampliflu™ Red
- Parameters: CII OXPHOS (normoxia, after reoxygenation), $H_2O_2$ (ROS) flux (normoxia, after reoxygenation), $H_2O_2/O_2$ ratio (normoxia, after reoxygenation)
- CTRL (vehicle)+3-4 SBT compounds at 100 nM concentrations (n=5–6) are tested in parallel per set. The number of compounds tested in parallel as well as compound concentration(s) may be adjusted and will be recorder in the study file and in the final report.

The protocol may be modified based on the experimental results and discussions with the Sponsor. Any changes to the protocol will be documented in the study file and in the protocol amendment.

Figure 7:
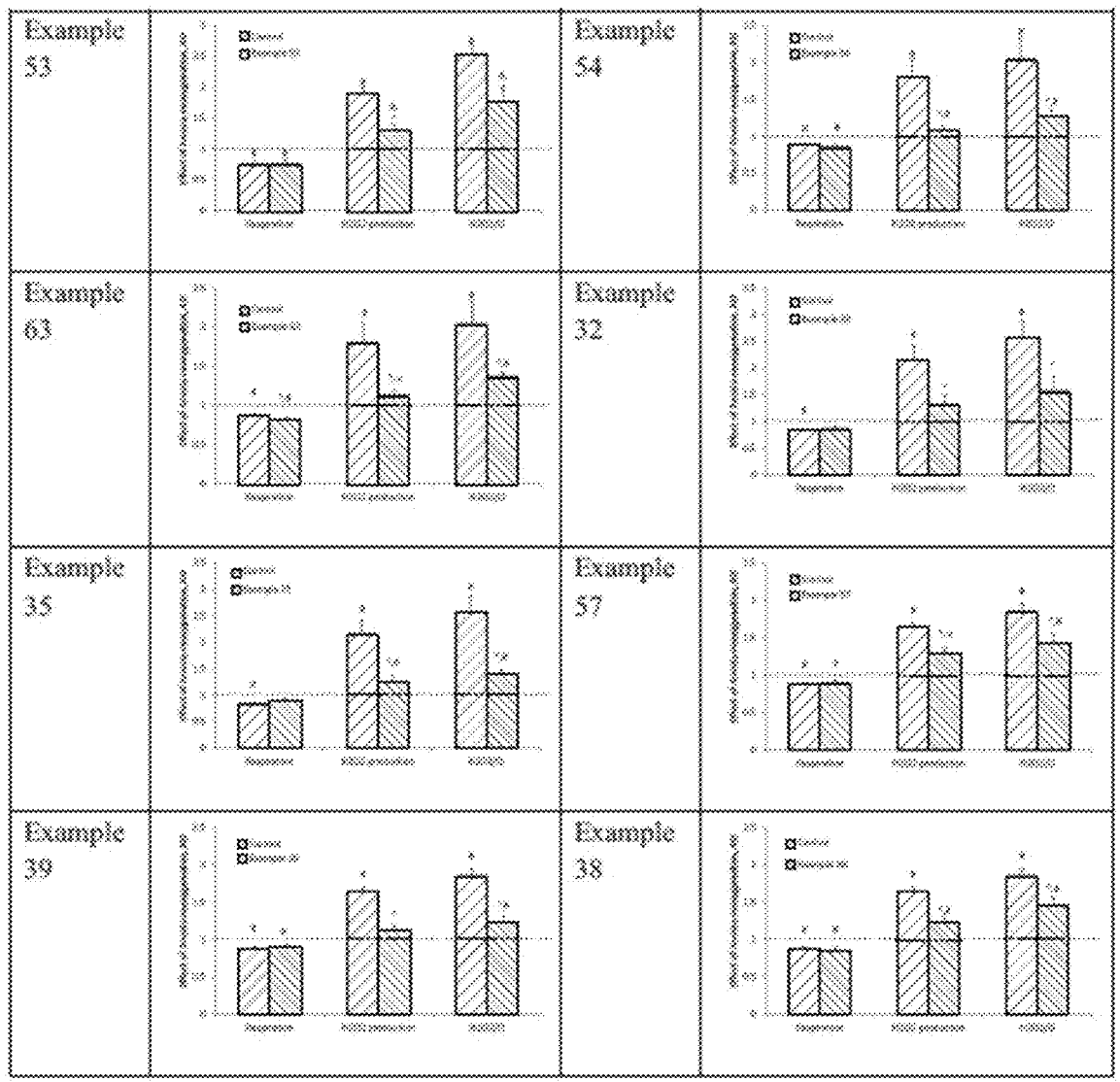
FIG. 7 is a series of bar graphs that show the effect of compounds on mitochondrial function after anoxia-reoxygenation in vitro; mitochondrial respiration rate, $H_2O_2$ (ROS) production rate, and $H_2O_2$/O flux ratio.

Results are shown in FIG. 7. Specifically, FIG. 7 shows the effect of compounds on mitochondrial function after anoxia-reoxygenation in vitro; mitochondrial respiration rate, $H_2O_2$ (ROS) production rate, and $H_2O_2/O$ flux ratio. Results represent mean value±SEM. * p<0.05 compared to control group (Student's t-test). #p<0.05 compared to respective group measurement in normoxia (paired Student's t-test).

EQUIVALENTS

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

INCORPORATION BY REFERENCE

All U.S. patents and U.S. and PCT published patent applications mentioned in the description above are incorporated by reference herein in their entirety.

We claim:

1. A compound of Formula (I), or a pharmaceutically acceptable salt thereof:

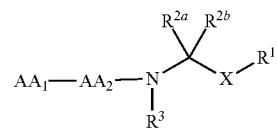

wherein $AA_1$ is selected from

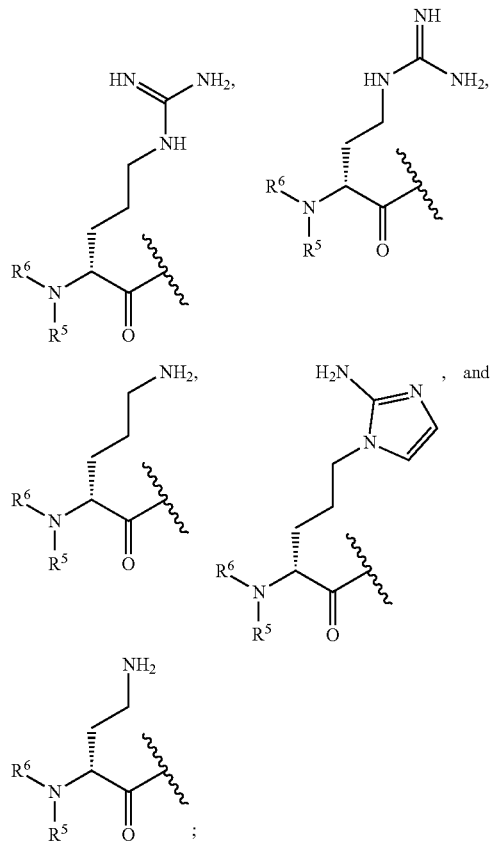

$AA_2$ is selected from

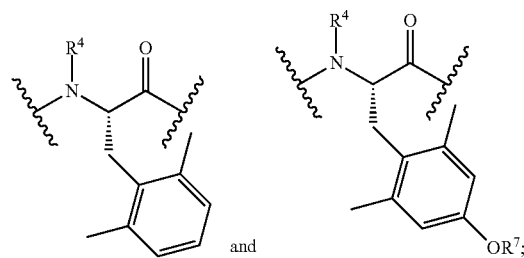

R[1] is selected from

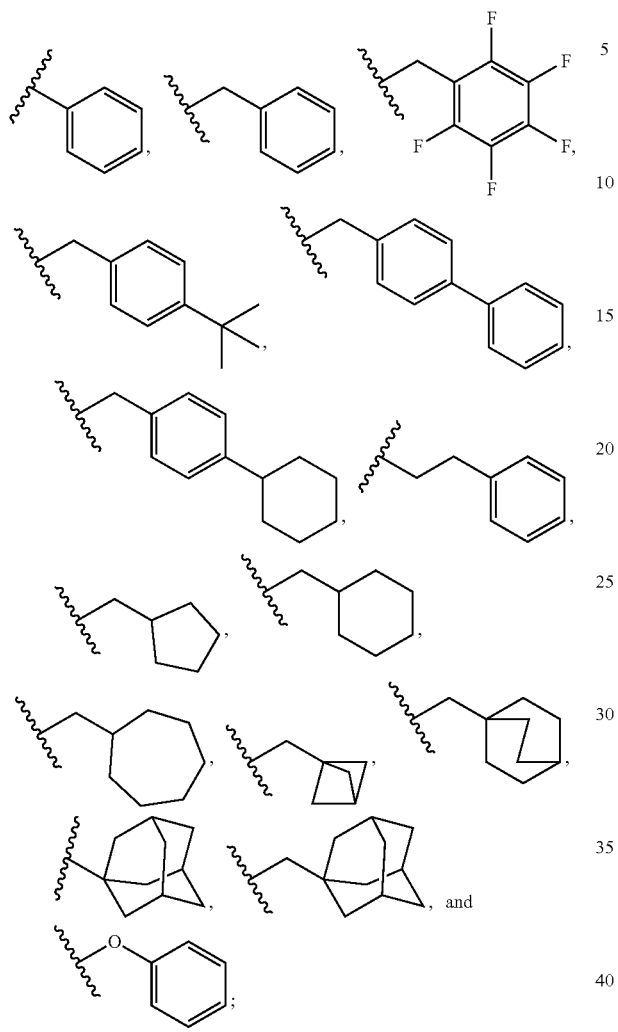

R[2a] is selected from

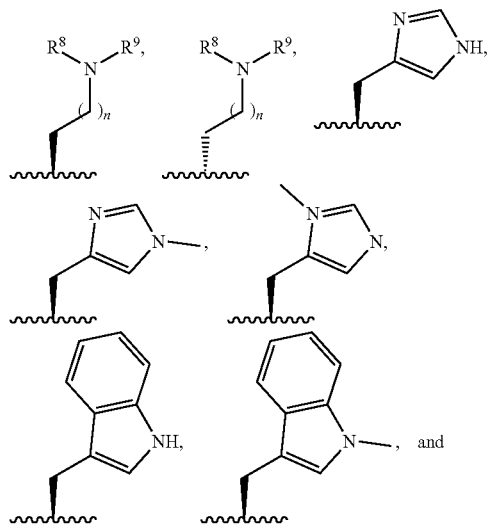

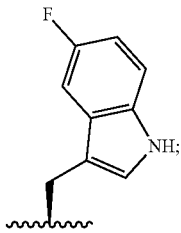

R[2b] is H or Me;

R[3] and R[4] are independently selected from H and (C1-C6)alkyl;

R[5] and R[6] are independently H, methyl, ethyl, propyl, cyclopropyl, or cyclobutyl; or R[5] and R[6] together with the N atom to which they are attached form a 4-6-membered heterocyclyl;

R[7] is selected from H, (C1-C6)alkyl, cycloalkyl, and aryl;

R[8] and R[9] are independently selected from H, (C1-C6) alkyl, cycloalkyl, and aryl; or R[8] and R[9] together with the N atom to which they are attached form a 4-6-membered heterocyclyl;

n is 1, 2, or 3;

X is selected from

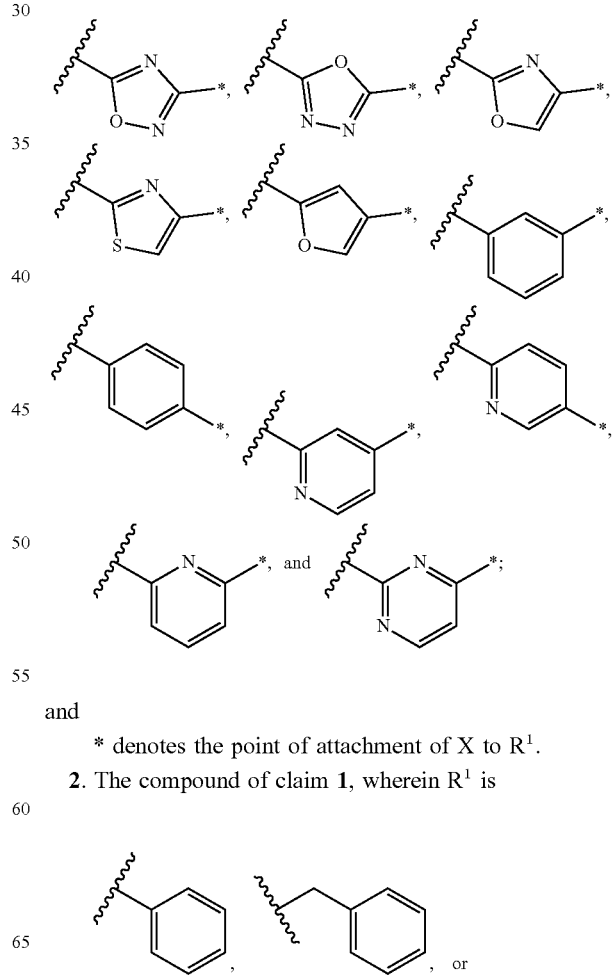

and

* denotes the point of attachment of X to R[1].

2. The compound of claim 1, wherein R[1] is

-continued

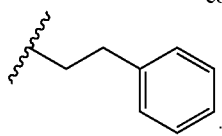

3. The compound of claim 1, where $R^{2a}$ is

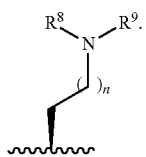

4. The compound of claim 3, where $R^8$ and $R^9$ are independently selected from H and methyl.

5. The compound of claim 3, where $R^{2a}$ is

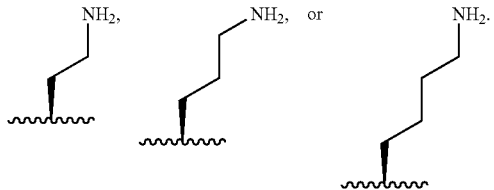

6. The compound of claim 3, where $R^{2a}$ is

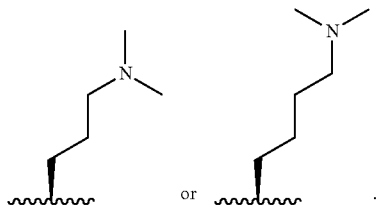

7. The compound of claim 1, wherein $R^{2a}$ a

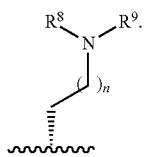

8. The compound of claim 7, wherein $R^{2a}$ is

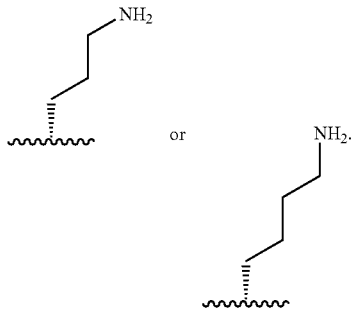

9. The compound of claim 1, wherein $AA_2$ is

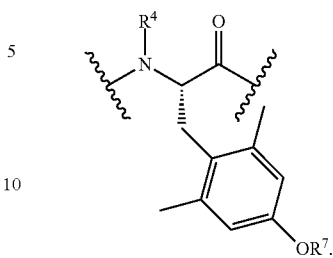

10. The compound of claim 9, wherein $R^7$ is H.

11. The compound of claim 1, wherein $AA_1$ is

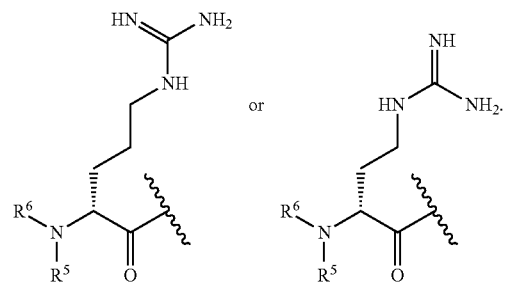

12. The compound of claim 1, wherein $R^{2b}$ is H.
13. The compound of claim 1, wherein $R^5$ is H.
14. The compound of claim 1, wherein $R^6$ is H.
15. The compound of claim 1, wherein X is

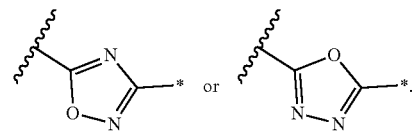

16. The compound of claim 1, wherein $R^3$ and $R^4$ are H.
17. The compound of claim 1, wherein the compound is selected from
D-Arg-DMT-(5-((S)-1',5'-diaminopent-1'-yl)-3-benzyl)-1,2,4-oxadiazole;
D-Arg-DMT-(5-((R)-1',5'-diaminopent-1'-yl)-3-benzyl)-1,2,4-oxadiazole;
D-Arg-DMT-(5-((S)-2',6'-diaminohex-2'-yl)-3-benzyl)-1,2,4-oxadiazole;
D-Arg-DMT-(5-((S)-5'-dimethylamino-1'-aminopent-1'-yl)-3-benzyl)-1,2,4-oxadiazole;
D-Arg-DMT-(5-((R)-1',5'-diaminopent-1'-yl)-3-(2',3',4',5',6'-pentafluorobenzyl)-1,2,4-oxadiazole;
D-Arg-DMT-(5-((S)-1',5'-diaminopent-1'-yl)-3-(4-tert-butylbenzyl)-1,2,4-oxzdiazole;
D-Arg-DMT-(5-((R)-1',5'-diaminopent-1'-yl)-3-(4-tert-butylbenzyl)-1,2,4-oxzdiazole;
D-Arg-DMT-(5-((S)-1',5'-diaminopent-1'-yl)-3-(4'-trifluoromethylbenzyl)-1,2,4-oxadiazole;
D-Arg-DMT-(5-((S)-1',5'-diaminopent-1'-yl)-3-(4-phenylbenzyl))-1,2,4-oxadiazole;
D-Arg-DMT-(5-((S)-1',5'-diaminopent-1'-yl)-3-(4'-cyclohexylbenzyl))-1,2,4-oxadiazole;
D-Arg-DMT-(5-((S)-1',5'-diaminopent-1'-yl)-3-phenethyl))-1,2,4-oxadiazole;

D-Arg-DMT-(5-((S)-1',5'-diaminopent-1'-yl)-3-cyclohexylmethyl)-1,2,4-oxadiazole;
D-Arg-DMT-(5-((S)-1',5'-diaminopent-1'-yl)-3-cyclohexylmethyl)-1,2,4-oxadiazole;
D-Arg-DMT-(5-((S)-1',5'-diaminopent-1'-yl)-3-cycloheptylmathyl)-1,2,4-oxadiazole;
D-Arg-DMT-(5-((S)-1',5'-diaminopent-1'-yl)-3-bicyclo[2,2,2]pentanylmethyl)-1,2,4-oxadiazole;
D-Arg-DMT-(5-((S)-1',5'-diaminopent-1'-yl)-3-bicyclo[2,2,2] octanylmethyl)-1,2,4-oxadiazole;
D-Arg-DMT-(5-((1 S)-(5-(1',5'-diaminopent-1'-yl-3-adamant-1'-yl)-1,2,4-oxadiazole;
D-Arg-DMT-(5-((1R)-(5-(1',5'-diaminopent-1'-yl-3-adamant-1'-yl)-1,2,4-oxadiazole;
D-Arg-DMT-(5-((S)-1',5'-diaminopent-1'-yl)-3-admantylmethyl)-1,2,4-oxzadiazole;
D-Arg-DMT-(5-(α-(S)-histamine)-3-phenyl)-1,2,4-oxadiazole;
D-Arg-DMT-(5-(α-(S)-histamine)-3-benzyl)-1,2,4-oxadiazole;
D-Arg-DMT-(5-(α-(S)-histamine)-3-phenethyl)-1,2,4-oxadiazole;
D-Arg-DMT-(5-(α-(S)-histamine)-3-cyclopentylmethyl)-1,2,4-oxadiazole;
D-Arg-DMT-(5-(α-(S)-histamine)-3-cyclohexylmethyl)-1,2,4-oxadiazole;
D-Arg-DMT-(5-(α-(S)-t-methylhistamine)-3-cyclohexylmethyl)-1,2,4-oxadiazole;
D-Arg-DMT-(5-(α-(S)-p-methylhistamine)-3-cyclohexylmethyl)-1,2,4-oxadiazole;
D-Arg-DMT-(5-(α-(S)-histamine)-3-cycloheptylmethyl)-1,2,4-oxadiazole;
D-Arg-DMT-(5-(α-(S)-histamine)-3-bicyclo[2,2,2]pentanylmethyl)-1,2,4-oxadiazole;
D-Arg-DMT-(5-(α-(S)-histamine)-3-bicyclo[2,2,2] octanylmethyl)-1,2,4-oxadiazole;
D-Arg-DMT-(5-(α-(S)-histamine)-3-admantyl)-1,2,4-oxadiazole;
D-Arg-DMT-(5-(α-(S)-histamine)-3-admantylmethyl)-1,2,4-oxadiazole;
D-Arg-DMT-(5-((S)-(2-(1H-indol-3-yl)-1-aminoethyl)-3-benzyl)-1,2,4-oxadiazole;
D-Arg-DMT-(5-((1 S)-2-(pyridin-4-yl)-1-aminoethyl-3-admantylmethyl)-1,2,4-oxadiazole;
D-Agb-DMT-(5-((S)-1',5'-diaminopent-1'-yl)-3-benzyl)-1,2,4-oxadiazole;
D-Agb-DMT-(5-((S)-1',4'-diaminobut-1'-yl)-3-benzyl)-1,2,4-oxadiazole;
D-Agb-DMT-(5-((S)-4'-dimethylamino-1'-aminobut-1'-yl)-3-benzyl)-1,2,4-oxadiazole;
D-Agb-DMT-(5-(2'-(S)-4-histamine)-3-admantylmethyl)-1,2,4-oxadiazole;
(N,N-diMe)-D-Agb-DMT-(5-(2'-(S)-4-histamine)-3-admantyl)-1,2,4-oxadiazole;
D-Agb-DMT-(5-((S)-(2-(1H-indol-3-yl)-1-aminoethyl)-3-benzyl)-1,2,4-oxadiazole;
D-Agb-DMT-(5-((S)-(2-(1H-indol-3-yl)-1-aminoethyl)-3-admantylmethyl)-1,2,4-oxadiazole;
D-(δ-2-amino-1H-imidazol-1-yl)-Nva-DMT-(5-((S)-1',4'-diaminopropan-1'-yl)-3-benzyl)-1,2,4-oxadiazole;
D-(δ-2-amino-1H-imidazol-1-yl)-Nva-DMT-(5-((S)-1',4'-diaminobut-1'-yl)-3-cyclohexylmethyl)-1,2,4-oxadiazole;
D-(δ-2-amino-1H-imidazol-1-yl)-Nva-DMT-(5-((S)-1',4'-diaminobut-1'-yl)-3-admantyl)-1,2,4-oxadiazole;
D-(δ-2-amino-1H-imidazol-1-yl)-Nva-DMT-(5-((S)-1',4'-diaminobut-1'-yl)-3-admantylmethyl)-1,2,4-oxadiazole;
D-(δ-2-amino-1H-imidazol-1-yl)-Nva-DMT-(5-((R)-1',4'-diaminobut-1'-yl)-3-admantylmethyl)-1,2,4-oxadiazole;
D-(δ-2-amino-1H-imidazol-1-yl)-Nva-DMT-(5-((R)-1',4'-diaminobut-1'-yl)-3-(bicyclo[2.2.2] octanylmethyl)-1,2,4-oxadiazole;
D-(δ-2-amino-1H-imidazol-1-yl)-Nva-DMT-(5-((S)-4'-dimethylamino-1'-aminobut-1'-yl)-3-admantylmethyl)-1,2,4-oxadiazole;
D-(δ-2-amino-1H-imidazol-1-yl)-Nva-DMT-(5-((S)-1',5'-diaminopent-1'-yl)-3-cyclohexylmethyl)-1,2,4-oxadiazole;
D-(δ-2-amino-1H-imidazol-1-yl)-Nva-DMT-(5-((S)-5'-dimethylamino-1'-aminopent-1'-yl)-3-cyclohexylmethyl)-1,2,4-oxadiazole;
D-(δ-2-amino-1H-imidazol-1-yl)-Nva-DMT-(5-(α-(S)-histamine)-3-benzyl)-1,2,4-oxadiazole;
D-(δ-2-amino-1H-imidazol-1-yl)-Nva-DMT-(5-(α-(S)-histamine)-3-(4-phenylbenzyl))-1,2,4-oxadiazole;
D-(δ-2-amino-1H-imidazol-1-yl)-Nva-DMT-(5-(α-(S)-histamine)-3-cyclopentylmethyl)-1,2,4-oxadiazole;
D-(δ-2-amino-1H-imidazol-1-yl)-Nva-DMT-(5-(α-(S)-histamine)-3-cyclohexylmethyl)-1,2,4-oxadiazole;
D-(δ-2-amino-1H-imidazol-1-yl)-Nva-DMT-(5-(α-(S)-histamine)-3-cycloheptylmethyl)-1,2,4-oxadiazole;
D-(δ-2-amino-1H-imidazol-1-yl)-Nva-DMT-(5-(α-(S)-t-methylhistamine)-3-cyclohexylmethyl)-1,2,4-oxadiazole;
D-(δ-2-amino-1H-imidazol-1-yl)-Nva-DMT-(5-(α-(S)-histamine)-3-cyclohexylmethyl)-1,2,4-oxadiazole;
D-(δ-2-amino-1H-imidazol-1-yl)-Nva-DMT-(5-(α-(S)-histamine)-3-admantylmethyl)-1,2,4-oxadiazole;
D-(δ-2-amino-1H-imidazol-1-yl)-Nva-DMT-(5-(α-(S)-t-methylhistamine)-3-admantylmethyl)-1,2,4-oxadiazole;
D-(δ-2-amino-1H-imidazol-1-yl)-Nva-DMT-(5-((1S)-(2-(1H-indol-3-yl)-1-aminoethyl)-3-(4-phenylbenzyl))-1,2,4-oxadiazole;
D-(δ-2-amino-1H-imidazol-1-yl)-Nva-DMT-(5-((1 S)-(2-(1-methyl-indol-3-yl)-1-aminoethyl)-3-(4-phenylbenzyl))-1,2,4-oxadiazole;
D-(δ-2-amino-1H-imidazol-1-yl)-Nva-DMT-(5-((1 S)-(2-(1H-indol-3-yl)ethyl)-3-admantylmethyl)-1,2,4-oxadiazole;
D-(δ-2-amino-1H-imidazol-1-yl)-Nva-DMT-(5-((1S)-(2-(6-fluoro-1H-indol-3-yl)ethyl)-3-admantylmethyl)-1,2,4-oxadiazole;
D-(δ-2-amino-1H-imidazol-1-yl)-Nva-DMT-(5-((1 S)-(2-(1-methyl-indol-3-yl)-1-aminoethyl)-3-admantylmethyl)-1,2,4-oxadiazole;
D-(δ-2-amino-1H-imidazol-1-yl)-Nva-(O-Me)-DMT-(5-(α-histimine)-3-(4-phenylbenzyl))-1,2,4-oxadiazole;
D-(δ-2-amino-1H-imidazol-1-yl)-Nva-(O-Me)-DMT-(5-(α-(S)-t-methylhistamine)-3-(4-phenylbenzyl))-1,2,4-oxadiazole
(Carbamimidoyl)-D-Dab-DMT-(5-((S)-1',5'-diaminopent-1'-yl)-3-benzyl)-1,2,4-oxadiazole;
(Carbamimidoyl)-D-Dab-DMT-(5-((S)-1',5'-diaminobutan-1'-yl)-3-benzyl)-1,2,4-oxadiazole;
(Carbamimidoyl)-D-Dab-DMT-(5-(2'-(S)-4-histamine)-3-admantylmethyl)-1,2,4-oxadiazole;
D-Arg-DMT-(5-(α-histimine))-3-benzyl)-1,3,4-oxadiazole;

D-Arg-DMT-(2-((S)-1',5'-diaminopent-1'-yl)-4-benzyl)-1,3-oxazole;
D-Arg-DMT-(2-((S)-1',5'-diaminopent-1'-yl)-5-benzyl)-1,3-oxazole;
D-Arg-DMT-(2-((S)-1',5'-diaminopent-1'-yl)-4-benzyl)-1,3-thiazole;
D-Arg-DMT-(2-((S)-1',5'-diaminopent-1'-yl)-5-benzyl)-1,3-thiazole;
D-Arg-DMT-(2-((S)-1',5'-diaminopent-1'-yl)-4-benzyl)-furan;
D-Arg-DMT-(2-((S)-1',5'-diaminopent-1'-yl)-5-benzyl)-furan;
D-Arg-DMT-(1-((S)-1',5'-diaminopent-1'-yl)-3-phenoxy)-benzene;
D-Arg-DMT-(1-((S)-1',5'-diaminopent-1'-yl)-4-phenoxy)-benzene;
D-Arg-DMT-(2-((S)-1',5'-diaminopent-1'-yl)-4-phenoxy)-pyridine;
D-Arg-DMT-(2-((S)-1',5'-diaminopent-1'-yl)-5-phenoxy)-pyridine;
D-Arg-DMT-(2-((S)-1',5'-diaminopent-1'-yl)-6-benzyl)-pyridine; and
D-Arg-DMT-(2-((S)-1',5'-diaminopent-1'-yl)-4-benzyl)-pyrimidine.

18. The compound of claim 1, wherein the compound has the following structure:

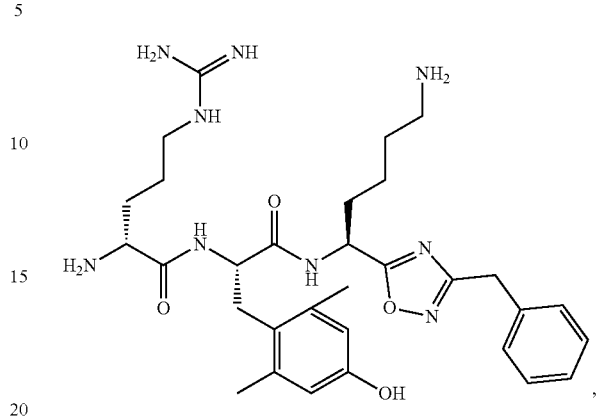

or a pharmaceutically acceptable salt thereof.

* * * * *